(12) United States Patent
Nakasuji et al.

(10) Patent No.: US 7,417,236 B2
(45) Date of Patent: Aug. 26, 2008

(54) SHEET BEAM-TYPE TESTING APPARATUS

(75) Inventors: Mamoru Nakasuji, Kanagawa (JP); Nobuharu Noji, Kanagawa (JP); Tohru Satake, Kanagawa (JP); Toshifumi Kimba, Kanagawa (JP); Hirosi Sobukawa, Kanagawa (JP); Tsutomu Karimata, Kanagawa (JP); Shin Oowada, Kanagawa (JP); Shoji Yoshikawa, Tokyo (JP); Mutsumi Saito, Kanagawa (JP)

(73) Assignee: Ebara Corporation, Tokyo (JP)

( * ) Notice: Subject to any disclaimer, the term of this patent is extended or adjusted under 35 U.S.C. 154(b) by 32 days.

(21) Appl. No.: 11/360,704

(22) Filed: Feb. 24, 2006

(65) Prior Publication Data

US 2006/0138343 A1   Jun. 29, 2006

Related U.S. Application Data

(63) Continuation of application No. 09/891,612, filed on Jun. 27, 2001, now Pat. No. 7,049,585.

(30) Foreign Application Priority Data

| Jul. 27, 2000 | (JP) | ............................. 2000-227132 |
| Nov. 2, 2000 | (JP) | ............................. 2000-335756 |
| Dec. 8, 2000 | (JP) | ............................. 2000-374164 |
| Jan. 31, 2001 | (JP) | ............................. 2001-22931 |
| Feb. 8, 2001 | (JP) | ............................. 2001-31901 |
| Feb. 8, 2001 | (JP) | ............................. 2001-31906 |
| Feb. 9, 2001 | (JP) | ............................. 2001-33599 |
| Feb. 13, 2001 | (JP) | ............................. 2001-36088 |
| Mar. 12, 2001 | (JP) | ............................. 2001-68301 |
| Apr. 13, 2001 | (JP) | ............................. 2001-115013 |
| May 28, 2001 | (JP) | ............................. 2001-158662 |

(51) Int. Cl.
*H01J 37/20* (2006.01)

(52) U.S. Cl. ............... 250/440.11; 250/310; 250/492.2; 361/234

(58) Field of Classification Search ................ None
See application file for complete search history.

(56) References Cited

U.S. PATENT DOCUMENTS

| 2,452,893 | A |  | 11/1948 | Bachman |  |
| 3,983,401 | A |  | 9/1976 | Livesay |  |
| 4,180,738 | A |  | 12/1979 | Smith et al. |  |
| 4,412,133 | A | * | 10/1983 | Eckes et al. | ............... 250/492.2 |
| 4,584,479 | A |  | 4/1986 | Lamattina et al. |  |
| 4,607,167 | A |  | 8/1986 | Petric |  |
| 4,911,103 | A |  | 3/1990 | Davis et al. |  |
| 4,912,052 | A |  | 3/1990 | Miyoshi et al. |  |
| 4,944,645 | A |  | 7/1990 | Suzuki |  |
| 5,047,646 | A |  | 9/1991 | Hattori et al. |  |
| 5,359,197 | A |  | 10/1994 | Komatsu et al. |  |
| 5,362,968 | A |  | 11/1994 | Miyoshi et al. |  |
| 5,444,256 | A |  | 8/1995 | Nagai et al. |  |
| 5,576,833 | A | * | 11/1996 | Miyoshi et al. | ............. 250/310 |
| 5,747,819 | A |  | 5/1998 | Nakasuji et al. |  |
| 5,751,538 | A |  | 5/1998 | Nakasuji |  |
| 5,763,863 | A |  | 6/1998 | Grosfeld et al. |  |
| 5,770,863 | A |  | 6/1998 | Nakasuji |  |
| 5,822,171 | A | * | 10/1998 | Shamouilian et al. | ........ 361/234 |
| 5,892,224 | A |  | 4/1999 | Nakasuji |  |
| 5,981,947 | A |  | 11/1999 | Nakasuji et al. |  |
| 5,994,704 | A |  | 11/1999 | Nakasuji |  |
| 6,025,600 | A |  | 2/2000 | Archie et al. |  |
| 6,087,667 | A |  | 7/2000 | Nakasuji et al. |  |
| 6,125,522 | A |  | 10/2000 | Nakasuji |  |
| 6,265,719 | B1 |  | 7/2001 | Yamazaki et al. |  |
| 6,268,606 | B1 |  | 7/2001 | Abe et al. |  |
| 6,315,512 | B1 | * | 11/2001 | Tabrizi et al. | ............... 414/217 |
| 6,344,750 | B1 |  | 2/2002 | Lo et al. |  |
| 6,476,390 | B1 |  | 11/2002 | Murakoshi et al. |  |
| 6,583,634 | B1 |  | 6/2003 | Nozoe et al. |  |
| 6,603,130 | B1 |  | 8/2003 | Bisschops et al. |  |

FOREIGN PATENT DOCUMENTS

| EP | 0999572 A2 | 5/2000 |
| JP | 52-115161 | 9/1977 |
| JP | 52-117567 | 10/1977 |
| JP | 57-072326 | 5/1982 |
| JP | 57-125871 | 8/1982 |

| | | |
|---|---|---|
| JP | 60-000741 | 1/1985 |
| JP | 62-100936 A | 10/1985 |
| JP | 61-239624 A | 10/1986 |
| JP | 62-195838 | 8/1987 |
| JP | 63-6737 A | 1/1988 |
| JP | 1-95456 A | 4/1989 |
| JP | 03-022339 | 1/1991 |
| JP | 03-053439 | 3/1991 |
| JP | 03-102814 | 4/1991 |
| JP | 03-266350 | 11/1991 |
| JP | 03-276548 | 12/1991 |
| JP | 04-266350 | 9/1992 |
| JP | 05-047649 A | 2/1993 |
| JP | 05-063261 | 3/1993 |
| JP | 05-251316 | 9/1993 |
| JP | 07-065766 | 3/1995 |
| JP | 07-249393 | 9/1995 |
| JP | 08-138611 | 5/1996 |
| JP | 9-73872 A | 3/1997 |
| JP | 09-073872 A | 3/1997 |
| JP | 09-311112 | 12/1997 |
| JP | 10-062503 | 3/1998 |
| JP | 10-073424 A | 3/1998 |
| JP | 10-125271 A | 5/1998 |
| JP | 10-177952 | 6/1998 |
| JP | 10302697 A | 11/1998 |
| JP | 11-132975 | 5/1999 |
| JP | 2000-3692 A | 1/2000 |
| JP | 2000-67798 A | 3/2000 |
| JP | 2000-067798 A | 3/2000 |
| JP | 2000-090868 | 3/2000 |
| JP | 2000-100369 A | 4/2000 |
| JP | 2000-133565 A | 5/2000 |
| WO | WO 9950651 A1 | 10/1999 |
| WO | WO 00/25352 A1 | 5/2000 |

OTHER PUBLICATIONS

Mamoru Nakasuji et al., *Low Voltage and high speed operating electrostatic wafer chunk using sputtered tantalum oxide membrane*, J. Vac. Sci. Technol. A 12(5), Sep./Oct. 1994, American Vacuum Society pp. 2834-2839.

Mamoru Nakasuji et al., *High-Emittance and Low-Brightness Electron Gun for Reducing-Image Projection system: Computer Simulation*, Jpn. J. Appl. Phys. vol. 36 (1997) pp. 2404-2408.

H. Hayashi, et al., LSI Testing Symposium 1998, *Minutes of the meeting*, P160 (1998) (partial translation).

B. Lischke et al., *Multi beam Concepts for Nanometer Devices*, Japanese Journal of Applied Physics, vol. 28, No. 10, Oct. 1989, pp. 2058-2064.

P. Sandland et al., *A electron-beam inspecting system for x-ray mask production*, J. Vac. Sci. Technol. B9 (b), Nov./Dec. 1991, American Vacuum Society, pp. 3005-3009.

W.D. Meisburger, et al., *Requirements and performance of an electron-beam column designed for x-ray mask inspection*, J. Vac. Soc. Technol., B9 (6), Nov./Dec. 1991, American Vacuum Society, pp. 3010-3014.

Table 5-1 *work Finction in Metals* p. 116.

\* cited by examiner

*Primary Examiner*—Jack I Berman
(74) *Attorney, Agent, or Firm*—Westerman, Hattori, Daniels & Adrian, LLP.

(57) ABSTRACT

An electron beam apparatus such as a sheet beam based testing apparatus has an electron-optical system for irradiating an object under testing with a primary electron beam from an electron beam source, and projecting an image of a secondary electron beam emitted by the irradiation of the primary electron beam, and a detector for detecting the secondary electron beam image projected by the electron-optical system; specifically, the electron beam apparatus comprises beam generating means 2004 for irradiating an electron beam having a particular width, a primary electron-optical system 2001 for leading the beam to reach the surface of a substrate 2006 under testing, a secondary electron-optical system 2002 for trapping secondary electrons generated from the substrate 2006 and introducing them into an image processing system 2015, a stage 2003 for transportably holding the substrate 2006 with a continuous degree of freedom equal to at least one, a testing chamber for the substrate 2006, a substrate transport mechanism for transporting the substrate 2006 into and out of the testing chamber, an image processing analyzer 2015 for detecting defects on the substrate 2006, a vibration isolating mechanism for the testing chamber, a vacuum system for holding the testing chamber at a vacuum, and a control system 2017 for displaying or storing positions of defects on the substrate 2006.

18 Claims, 49 Drawing Sheets

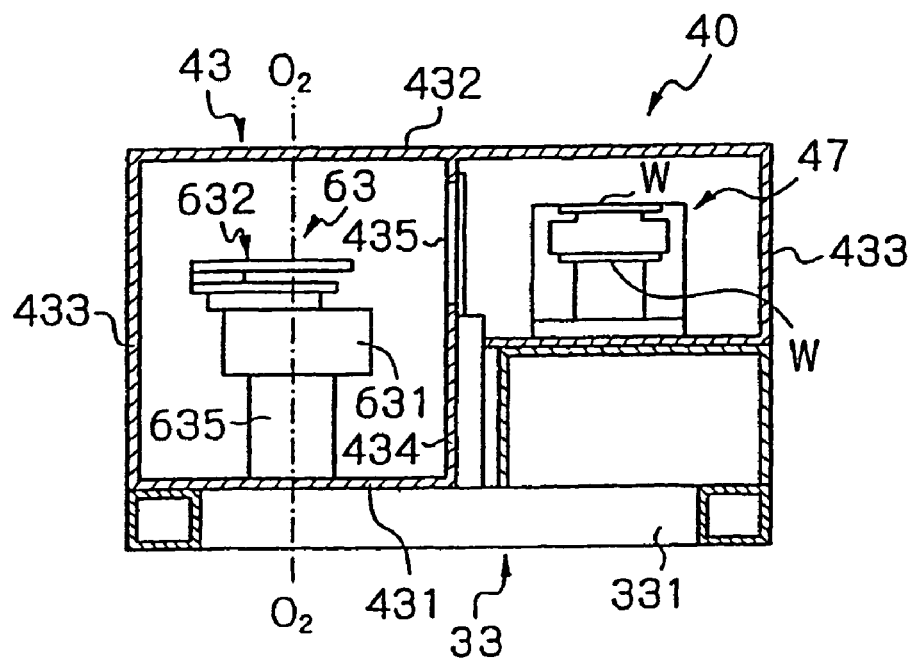
FIG. 8
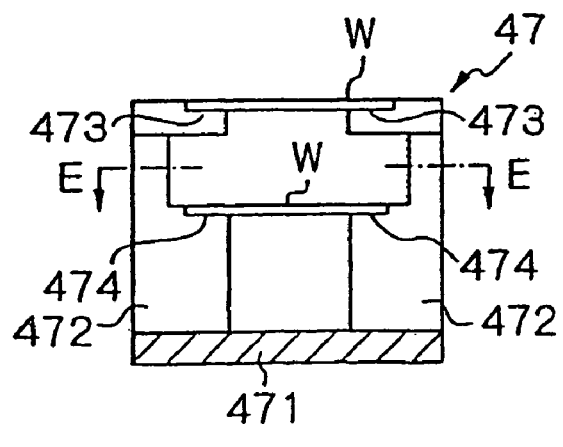
FIG. 9 [A]
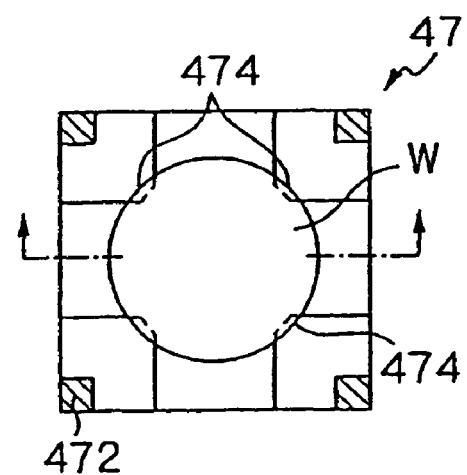
FIG. 9 [B]

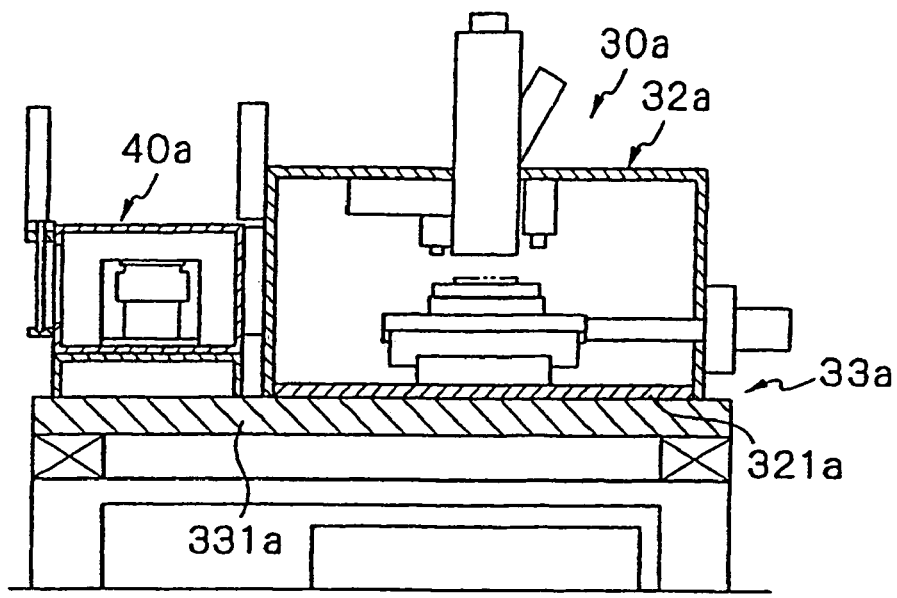
FIG. 10 [A]
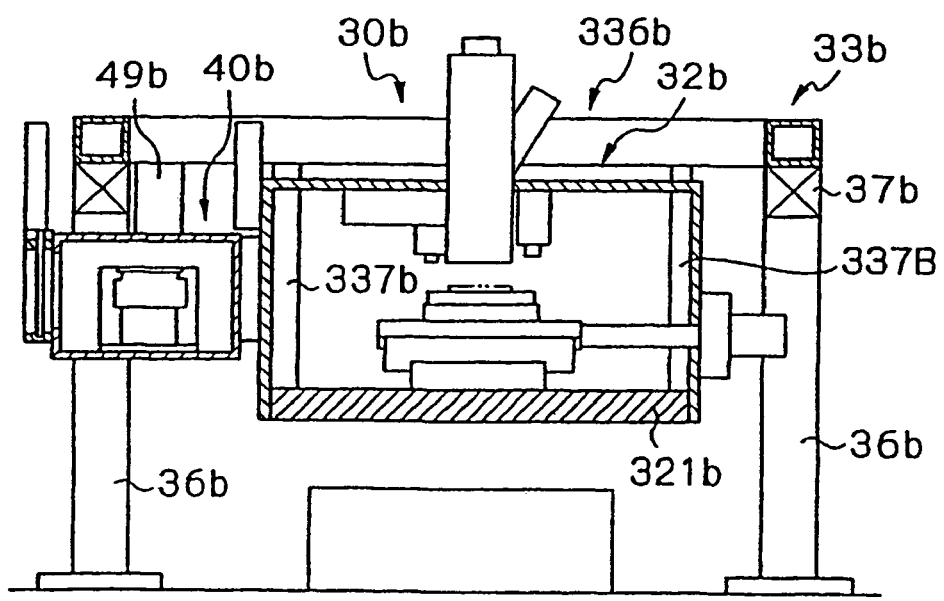
FIG. 10 [B]

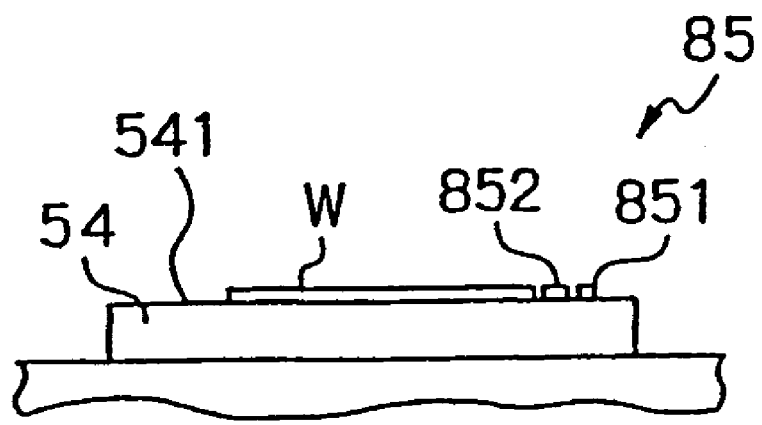
FIG. 13 [A]
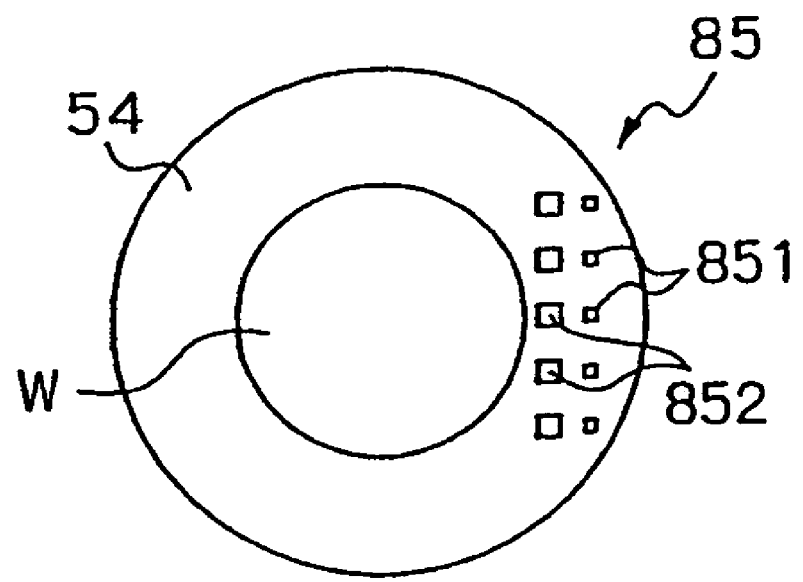
FIG. 13 [B]

BREAKDOWN OCCURRENCE
PROBABILITY FOR EACH METAL

| METAL | WORK FUNCTION [eV] | BREAKDOWN OCCURRENCE PROBABILITY |
|---|---|---|
| ALUMINUM | 4.2 | HIGH |
| GOLD | 4.9 | MIDDLE |
| PLATINUM | 5.3 | LOW |

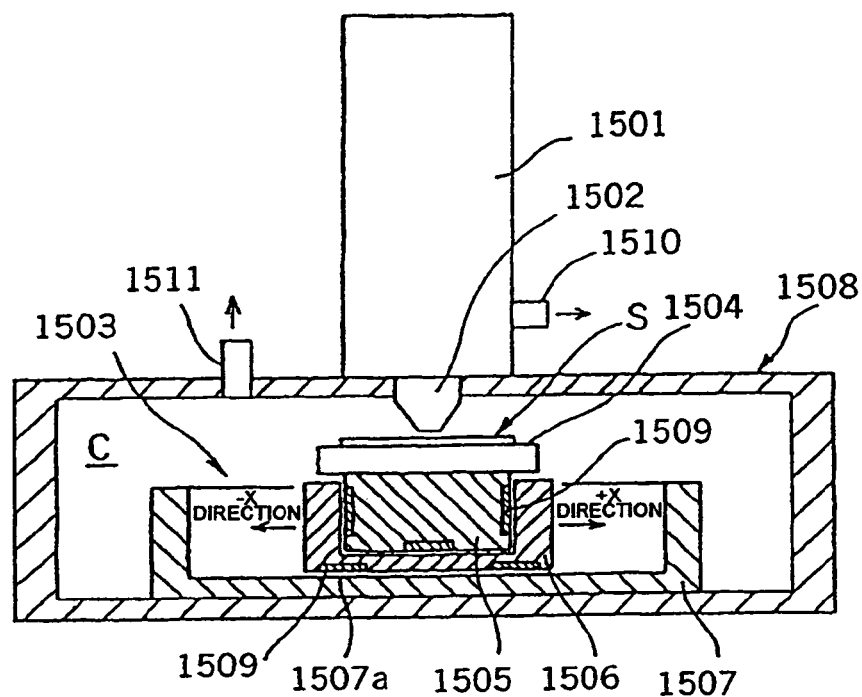
FIG. 36 [A]
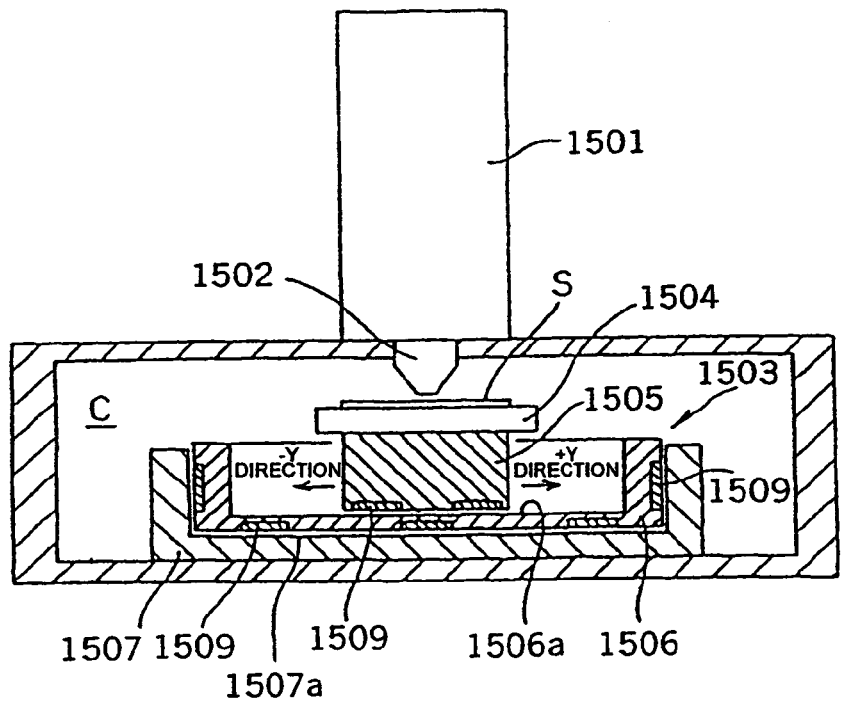
FIG. 36 [B]

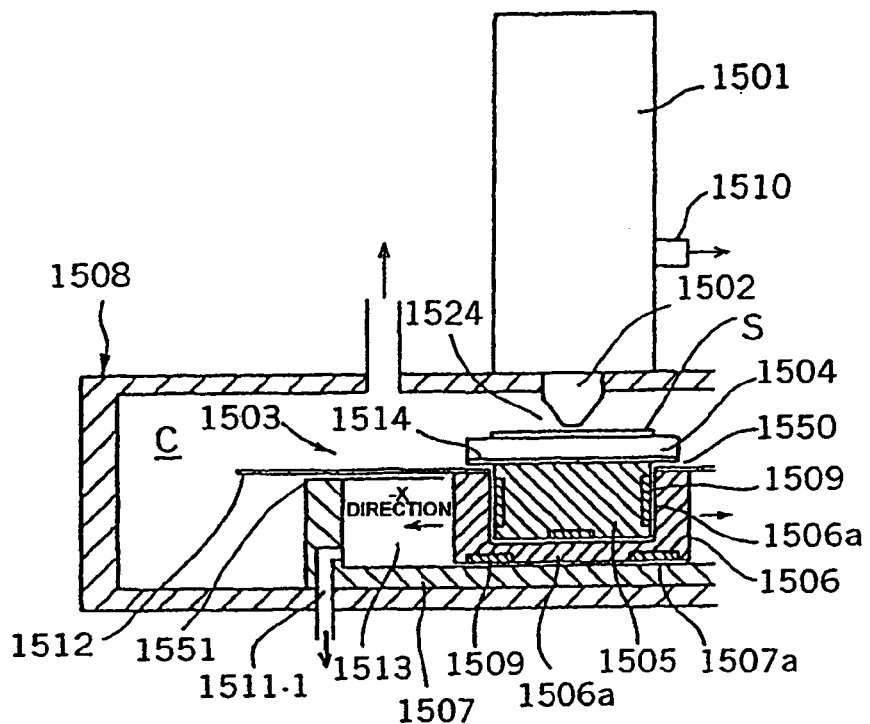
FIG. 38 [A]
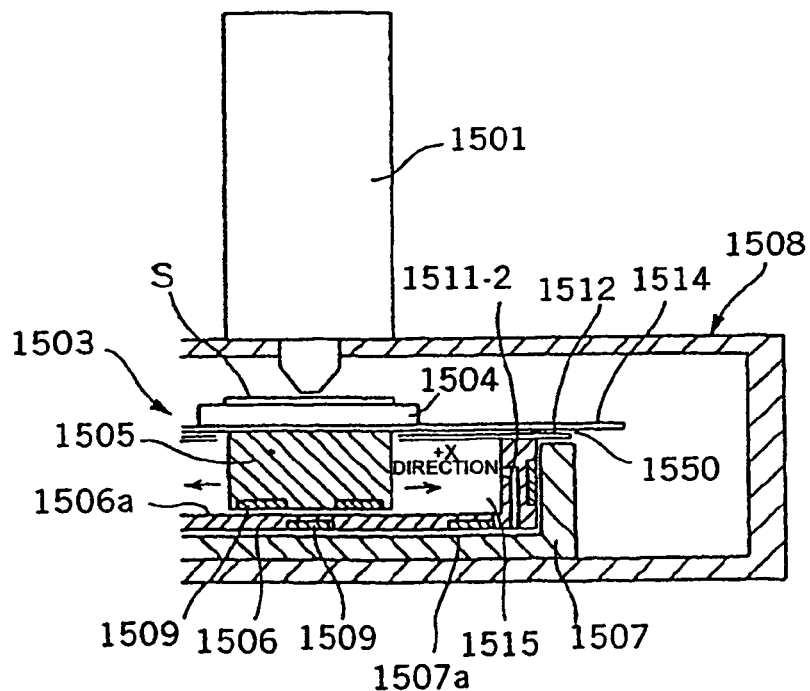
FIG. 38 [B]

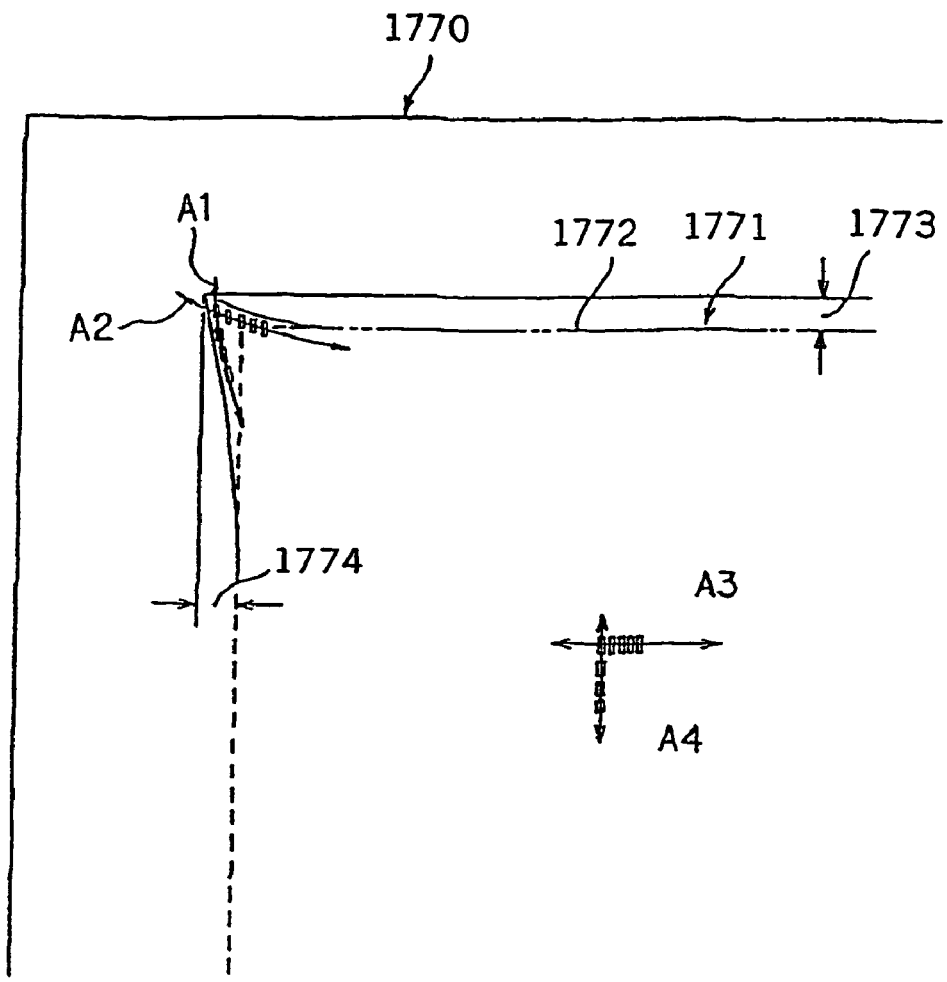
FIG. 49 [A]
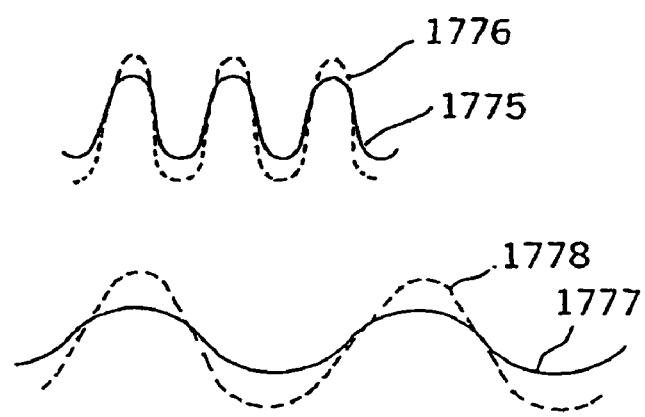
FIG. 49 [B]

SHEET BEAM-TYPE TESTING APPARATUS

CROSS-REFERENCE TO RELATED APPLICATION

This application Continuation of U.S. application Ser. No. 09/891,612, filed Jun. 27, 2001, now U.S. Pat. No. 7,049,585.

TECHNICAL FIELD

In semiconductor processes, design rules are now going to enter the era of 100 nm, and the production scheme is shifting from small-kind mass production represented by DRAM to a multi-kind small production such as SOC (silicon on chip). Associated with this shifting, the number of manufacturing steps has been increased, and an improved yield of each process is essential, so that testing for defects caused by the process becomes important. The present invention relates to a charged particle beam suitable for a sheet beam-type testing apparatus for testing a wafer after each of steps in a semiconductor process, and more particularly, to a sheet beam-type testing apparatus using a charged particle beam such as an electron beam, and a semiconductor device manufacturing method and an exposure method using the testing apparatus.

BACKGROUND ART

With the trend of increasingly higher integration of semiconductor devices and finer patterns, a need exists for high resolution, high throughput testing apparatuses. A resolution of 100 nm or less is required for examining defects on a wafer substrate of 100 nm design rule. Also, as the amount of testing is increased to cause an increase in manufacturing steps resulting from higher integration of devices, a higher throughput is required. Further, as devices are formed of an increased number of layers, testing apparatuses are required to have the ability to detect defective contacts (electric defect) of vias which connect wires between layers. While optical defect testing apparatuses are mainly used at present, it is anticipated that electron beam based defect testing apparatuses will substitute for optical defect testing apparatus as a dominant testing apparatus in the future from a viewpoint of the resolution and defective contact testing capabilities. However, the electron beam based defect testing apparatus also has a disadvantage in that it is inferior to the optical one in the throughput.

For this reason, a need exists for the development of a high resolution, high throughput testing apparatus which is capable of detecting electric defects. It is said that the resolution of an optical defect testing apparatus is limited to one half of the wavelength of used light, and the limit is approximately 0.2 µm in an example of practically used optical defect detecting apparatus which uses visible light. On the other hand, in electron beam based systems, scanning electron microscopes (SEM) have been commercially available. The scanning electron microscope has a resolution of 0.1 µm and takes a testing time of eight hours per 20 cm wafer. The electron beam based system also has a significant feature that it is capable of testing electric defects (broken wires, defective conduction, defective conduction of vias, and so on). However, it takes so long testing time that it is expected to develop a defect testing apparatus which can rapidly conduct a test.

Generally, a testing apparatus is expensive and low in throughput as compared with other process apparatuses, so that it is presently used after critical steps, such as after etching, deposition, CMP (chemical-mechanical polishing) planarization processing, and so on. Now, describing a testing apparatus in accordance with an electron beam based scanning (SEM) scheme, an SEM based testing apparatus narrows down an electron beam which is linearly irradiated to a sample for scanning. The diameter of the electron beam corresponds to the resolution. On the other hand, by moving a stage in a direction perpendicular to a direction in which the electron beam is scanned, a region under observation is tow-dimensionally irradiated with the electron beam. The width over which the electron beam is scanned generally extends over several hundred µm. A secondary electron beam generated from the sample by the irradiation of the narrowed electron beam (called the "primary electron beam") is detected by a combination of a scintillator and a photomultiplier (photomultiplier tube) or a semiconductor based detector (using PIN diodes). The coordinates of irradiated positions and the amount of the secondary electron beam (signal strength) are combined to generate an image which is stored in a storage device or output on a CRT (Braun tube).

The foregoing is the principle of SEM (scanning electron microscope). From an image generated by this system, defects on a semiconductor (generally, Si) wafer is detected in the middle of a step. A scanning speed, corresponding to the throughput, is determined by the amount of primary electron beam (current value), diameter of the beam, and a response speed of a detector. Currently available maximum values are 0.1 µm for the beam diameter (which may be regarded as the same as the resolution), 100 nA for the current value, and 100 MHz for the response speed of the detector, in which case it is said that a testing speed is approximately eight hours per wafer of 20 cm diameter.

In the SEM based testing apparatus described above, the cited testing speed is considered substantially as a limit. Therefore, a new scheme is required for increasing the testing speed, i.e., the throughput.

DISCLOSURE OF THE INVENTION

The present invention relates to an electron beam apparatus suitable for a sheet beam based testing apparatus, and a semiconductor device manufacturing method and an exposure method using the apparatus.

A first embodiment of the present invention provides a map projection type electron beam apparatus. For this purpose, the first embodiment provides a substrate testing apparatus, a substrate testing method and a device manufacturing method using such a substrate testing apparatus, characterized by comprising:

beam generating means for irradiating an electron beam having a particular width;

a primary electron-optical system for leading the charged particle beam to reach the surface of a substrate under testing;

a secondary electron-optical system for trapping a secondary electron beam generated from the substrate and leading the same to an image processing system;

a stage having for transportably holding the substrate with a continuous degree of freedom equal to at least one;

a testing chamber for the substrate;

a substrate transport mechanism for transporting the substrate into and out of the testing chamber;

an image processing analyzer for detecting defects on the substrate;

a vibration isolation mechanism for the testing chamber;

a vacuum system for holding the testing chamber at a vacuum; and a control system for displaying or storing positions of defects on the substrate.

A second embodiment of the present invention provides an electron beam apparatus suitable for a testing apparatus for testing an object under testing by irradiating the object with an electron beam, and a device manufacturing method using the electron beam apparatus.

A second embodiment of the present invention provides a testing apparatus comprising:

an electron-optical device having an electron-optical system for irradiating the object under testing with a primary electron beam from an electron source to project an image of secondary electrons emitted by the irradiation of the primary electron beam, and a detector for detecting the secondary electron image projected by the electron-optical system;

a stage device for holding the object under testing and moving the object under testing relative to the electron-optical system;

a mini-environment device for supplying a clean gas to the object under testing to prevent dust from attaching to the object under testing;

a working chamber for accommodating the stage device, said working chamber being controllable in a vacuum atmosphere;

at least two loading chambers disposed between the mini-environment device and the working chamber, and adapted to be independently controllable in a vacuum atmosphere;

a loader having a carrier unit capable of transferring the object under testing between the mini-environment device and one of the loading chambers, and another carrier unit capable of transferring the object under testing between the one loading chamber and the stage device; and a vibration isolator through which the working chamber and the loading chamber are supported.

Further, the second embodiment of the present invention provides a testing apparatus comprising:

an electron-optical device having an electron-optical system for irradiating the object under testing with a primary electron beam from an electron source, and for accelerating secondary electrons emitted by the irradiation of the primary electron beam with a deceleration electric field type objective lens to project an image of the secondary electrons, a detector for detecting the secondary electron image projected by the electron-optical system, and electrodes disposed between the deceleration electric field type objective lens and the object under testing for controlling a field intensity on the surface of the object under testing which is irradiated with the primary electron beam;

a stage device for holding the object under testing and moving the object under testing relative to the electron-optical system;

a working chamber for accommodating the stage device, said working chamber being controllable in a vacuum atmosphere;

a loader for supplying the object under testing onto the stage device within the working chamber;

a precharge unit for irradiating a charged particle beam to the object under testing placed in the working chamber to reduce variations in charge on the object under testing;

a potential applying mechanism for applying a potential to the object under testing; and a supporting device supported through a vibration isolator for supporting the working chamber.

In the testing apparatus described above, the loader may include a first loading chamber and a second loading chamber capable of independently controlling an atmosphere therein, a first carrier unit for carrying the object under testing between the first loading chamber and the outside of the first loading chamber, and a second carrier unit disposed in the second loading chamber for carrying the object under testing between the first loading chamber and the stage device. The electron beam apparatus may further comprise a partitioned mini-environment space for supplying a clean gas flowing to the object under testing carried by the loader to prevent dust from attaching to the object under testing, wherein the supporting device may support the loading chamber and the working chamber through the vibration isolator.

Also, the testing apparatus may further comprise an alignment controller for observing the surface of the object under testing for an alignment of the object under testing with respect to the electron-optical system to control the alignment, and a laser interference range finder for detecting coordinates of the object under testing on the stage device, wherein the coordinates of the object under testing is determined by the alignment controller using patterns formed on the object under testing. In this event, the alignment of the object under testing may include rough alignment performed within the mini-environment space, and alignment in XY-directions and alignment in a rotating direction performed on the stage device.

Further, the second embodiment of the present invention provides a method of manufacturing a device comprising the step of detecting defects on a wafer using the foregoing testing apparatus in the middle of a process or subsequent to the process.

A third embodiment of the present invention provides an electron beam apparatus for focusing electron beams emitted from a plurality of electron beam sources on the surface of a sample through an electron-optical system, characterized by comprising:

a partition wall for separating the electron beam sources from the electron-optical system, wherein the partition wall has holes in a large aspect ratio for the electron beams to pass therethrough.

The holes are provided two or more for each of the electron beam sources. Each of the holes is formed at a position which swerves from the irradiating axis of the beam source. Preferably, the partition wall is formed of a material having a high rigidity, and the electron beam source and the electron-optical system are attached to the partition wall.

The third embodiment of the present invention also provides a device manufacturing method for evaluating a wafer in the middle of a process using the electron beam apparatus.

A fourth embodiment of the present invention provides an evaluation apparatus for directing an electron beam into a sample using an electrostatic optical system including an electrostatic lens, detecting a secondary electron beam generated from the sample by the irradiation of the electron beam to form data, and evaluating the sample based on the data, characterized in that:

electrodes in the electron-optical system are coated with a metal having a work function of 5 eV or higher.

According to this evaluation apparatus, since the electrodes or some of the electrodes are coated with a metal having a work function of 5 eV or higher, no secondary electron beam will be emitted from the electrodes, a discharge will be less likely to occur between electrodes, and a breakdown will occur between electrodes less frequently.

Preferably, the metal coated on the electrodes in the electrostatic optical system is platinum or an alloy which includes platinum as a main material. In this case, as the electrodes or some of the electrodes are coated with platinum (work function: 5.3 [eV]) or an alloy which includes platinum as a main material, a smaller amount of secondary electron beam will be emitted from the electrodes, so that a discharge will be less likely to occur between the electrodes, and a breakdown will occur between electrodes less frequently. Also, even with the sample being a semiconductor wafer, the platinum coated on the electrodes, if attached on a pattern of the semiconductor wafer, will not deteriorate transistors, so that it is suitable for testing a semiconductor wafer.

The fourth embodiment of the present invention provides an evaluation apparatus for directing an electron beam into a sample using an electrostatic optical system including an electrostatic lens, detecting a secondary electron beam generated from the sample by the irradiation of the electron beam to form data, and evaluating the sample based on the data, characterized in that:

the electrostatic lens includes at least two electrodes having potential differences, and insulating materials positioned between the two electrodes for holding the at least two electrodes;

at least one of the at least two electrodes has a first electrode surface having a minimum inter-electrode distance between the at least two electrodes, a second electrode surface having an inter-electrode distance longer than the first electrode surface, and a step between the first electrode surface and the second electrode surface in a direction along the at least two electrodes; and the insulating material substantially vertically supports the second electrode surface and an electrode surface of the other electrode between the at least two electrodes, and a minimum creeping distance of the insulating material between the at least two electrodes is substantially equal to an inter-electrode distance in the supported electrode portion.

According to this evaluation apparatus, the electrodes are supported by the insulating material which has long creeping distance, so that a discharge between electrodes, and hence a breakdown between electrodes can be made less probable. Further, at least one of the electrodes is shaped to have the first electrode surface, the second electrode surface and the step between these electrode surfaces, so that the surface of the insulating material need not be formed with crimps, resulting in a lower manufacturing cost.

Also, since the minimum creeping distance of the insulating material between the electrodes is substantially equal to the distance between the electrodes in the supported electrode portion, the surface of the insulating material is substantially free from ruggedness between the electrodes, and a gas exhausted from the insulating material will not be increased. Therefor the degree of vacuum will not be lowered in a beam path of the apparatus.

Preferably, the metal coated on the electrodes in the electrostatic optical system is platinum or an alloy which includes platinum as a main material. In this case, as the electrodes or some of the electrodes are coated with platinum or an alloy which includes platinum as a main material, a discharge between electrodes, and hence a breakdown between electrodes will occur less frequently. Also, even with the sample being a semiconductor wafer, the platinum coated on the electrodes, if attached on a pattern of the semiconductor wafer, will not deteriorate transistors, so that it is suitable for testing a semiconductor wafer.

Further, the fourth embodiment of the present invention also provides a device manufacturing method using the evaluation apparatus, characterized by evaluating patterns on a semiconductor wafer, which is the sample, using the evaluation apparatus in the middle of device manufacturing.

According to this device manufacturing method, by using the evaluation apparatus in the middle of device manufacturing, even if patterns on the semiconductor wafer, which is a sample, are evaluated, the evaluation can be made without breakdown between electrodes in the electrostatic optical system.

A fifth embodiment of the present invention provides an electron beam apparatus for irradiating a sample with a primary electron beam using a primary optical system, and separating a secondary electron beam emitted from the sample from the primary optical system by an ExB separator for introduction into a secondary optical system, characterized in that:

the amount of deflection of the secondary electron beam by a magnetic field of the ExB separator is twice the amount of deflection by an electric field, and the direction of deflection by the magnetic field is opposite to the direction of deflection by the electric field.

This electron beam apparatus is characterized in that, in the electron beam apparatus for irradiating the sample with the primary electron beam using a primary optical system, and separating the secondary electron beam emitted from the sample from the primary optical system by the ExB separator for introduction into the secondary optical system, the amount of deflection of the secondary electron beam by the magnetic field of the ExB separator is twice the amount of deflection by an electric field, and the directions of deflection are opposite to each other.

The fifth embodiment of the present invention also provides an electron beam apparatus for irradiating a sample with a primary electron beam using a primary optical system, and separating a secondary electron beam emitted from the sample from the primary optical system by an ExB separator for introduction into a secondary optical system, characterized in that the amount of deflection of the primary electron beam by a magnetic field of the ExB separator is twice the amount of deflection by an electric field, and the direction of deflection by the magnetic field is opposite to the direction of deflection by the electric field.

This electron beam apparatus is characterized in that the amount of deflection of the first electron beam by the magnetic field of the ExB separator is twice the amount of deflection by the electric field, and the directions of deflection are opposite to each other in the electron beam apparatus for irradiating the sample with the primary electron beam using a primary optical system, and separating the secondary electron beam emitted from the sample from the primary optical system by the ExB separator for introduction into the secondary optical system.

In this event, preferably, the primary electron beam comprised of a plurality of beams is formed by the primary optical system for irradiating the surface of the sample, and secondary electron beams emitted from the samples by the irradiation of the primary electron beam comprised of the plurality of beams are detected by a plurality of secondary electron beam detectors.

The aforementioned electron beam apparatus can be available in any of a defect testing apparatus, a line width measuring apparatus, an alignment accuracy measuring apparatus, and a high time resolution potential contrast measuring apparatus.

Also, the fifth embodiment of the present invention provides a device manufacturing method for testing a wafer in the middle of a process using the electron beam apparatus.

A sixth embodiment of the present invention provides an electron beam apparatus, characterized by comprising:

a measuring mechanism for measuring first data indicative of rising of a secondary charged particle beam signal waveform when a pattern edge parallel in a first direction is moved in a second direction in regard to an excitation voltage of an objective lens, and second data indicative of rising of the secondary charged particle beam signal waveform when a pattern edge parallel in the second direction is moved in the first direction;

means for approximating each of the first data and the second data using quadratics, finding an excitation condition for the objective lens indicative of a minimum value of each quadratic; and means for fitting the objective lens to an algebraic mean of the found excitation condition.

A plurality of the electron beam apparatuses may be positioned opposite to the sample such that respective ones of the plurality of primary electron beams are converged by corresponding ones of the objective lens simultaneously on different locations on the sample.

Further, preferably, the electron beam apparatus comprises means for correcting astigmatism after exciting the objective lens using the exciting means with a voltage equal to the algebraic average with the pattern being charged, and then evaluating the pattern.

Also, the sixth embodiment provides an electron beam apparatus for converging an electron beam using an electron-optical system including an objective lens, and scanning a pattern with the electron beam to evaluate the pattern, characterized in that:

the objective lens comprises a first electrode applied with a voltage close to a ground, and a second electrode applied with a voltage remote from the ground;

a focal distance of the objective lens can be changed by changing the voltage applied to the first electrode; and the exciting means comprises means for changing the voltage applied to the second electrode to largely change the focal distance of the objective lens, and means for changing the voltage applied to the first electrode to change the focal distance of the objective lens in a short time.

The sixth embodiment of the present invention also provides a device manufacturing method for evaluating a wafer in the middle of a process using the electron beam apparatus.

A seventh embodiment of the present invention provides an electron beam apparatus for irradiating an object with an electron beam to perform at least one of working, manufacturing, observation and testing of the object, comprises:

a mechanical construction for determining a position of an electronic beam with respect to the object, a piezoelectric element attached to the mechanical construction for receiving a force from vibrations of the mechanical construction; and a vibration attenuating circuit electrically connected to the piezoelectric element to attenuate electric energy output from the piezoelectric element.

When an object is irradiated with an electron beam to perform at least one of working, manufacturing, observation and testing of the object, an external force including a vibration component at a resonant frequency of proper vibration applied to a mechanical construction causes the mechanical construction to amplify the vibration component at a resonant magnification determined by its transfer function, and to vibrate. This vibration applies a force to the piezoelectric element. The piezoelectric element transduces the vibration energy of the mechanical construction into electric energy which is output. However, since the vibration attenuating circuit attenuates this electric energy, the piezoelectric element generates a force to cancel the external force applied to the piezoelectric element. In this way, the vibrations generated by the mechanical resonance can be canceled to reduce the resonant magnification.

The mechanical construction is a portion or entirety of an electron beam applied apparatus which generates problematic vibrations, and an arbitrary mechanical construction for aligning the electron beam. For example, the mechanical construction may be optics in an optical system for focusing an electron beam on an object, a barrel for containing such an optical system, a supporting stand for carrying an object, or optics in an optical system for focusing a secondary electron beam generated by irradiating the object with the electron beam on a detector, a barrel for containing such an optical system, a barrel for containing the detector, and so on.

The vibration attenuating circuit comprises at least inductive means as an element having an inductance or an equivalent circuit of the element, and the inductive means is connected to the piezoelectric element having a static capacitance to form a resonant circuit. The inductance of the inductive means is determined with respect to the static capacitance of the piezoelectric element such that a resonant frequency of the resonant circuit substantially matches a resonant frequency of the mechanical construction.

Preferably, a resistive element is included in the vibration attenuating circuit. In this event, the capacitive impedance of the piezoelectric element and the inductive impedance of the inductive means cancel each other at the resonant frequency, so that the impedance of the resonant circuit virtually has only a resistive element. Therefore, during resonance, the electric energy output from the piezoelectric element is substantially fully consumed by the resistive element.

The seventh embodiment of the present invention also provides a semiconductor manufacturing method which comprises a step of executing at least one of working and manufacturing of semiconductor devices, and observation and testing of semiconductor devices during working or finished ones, using the electron beam apparatus.

According to an eighth embodiment of the present invention, an electrostatic chuck for electrostatically sucking and holding a wafer is applied with a voltage which increases or decreases between zero volt to a predetermined voltage over time. The electrostatic chuck is comprised of a laminate of a substrate, an electrode plate, and an insulating layer. A voltage associated with a voltage applied to a wafer is applied to the electrode plate to generate an attractive force between the wafer and the chuck. The electrode plate is divided into a first electrode comprised of a central portion thereof and some of a peripheral portion thereof, and a second electrode comprised of the remaining portion. The first electrode is first applied with a voltage, the wafer is then placed at a low potential or a ground potential, and subsequently the second electrode is applied with a voltage.

According to the eighth embodiment of the present invention, in a combination of a wafer and the electrostatic chuck for electrostatically sucking and holding the wafer, the electrostatic chuck is formed of the laminate of the substrate, electrode plate and insulating layer, the wafer is applied with a voltage through a predetermined resistor or a contact, and the contact is in the shape of a needle, the leading end of which comes in contact with the back surface of the wafer, or in the shape of a knife edge, the edge of which comes in contact with the side surface of the wafer.

The eighth embodiment of the present invention also provides a device manufacturing method for sucking and holding a wafer using the electrostatic chuck or the combination.

A ninth embodiment of the present invention provides an apparatus for carrying a sample on an XY stage, moving the sample to an arbitrary position in a vacuum, and irradiating the surface of the sample with an electron beam, characterized in that:

the XY stage comprises a non-contact supporting mechanism by means of static pressure bearings, and a vacuum sealing mechanism through differential pumping;

a partition is disposed between a location of the sample which is irradiated with the beam and a static pressure bearing support of the stage for reducing a conductance; and a pressure difference is produced between an electron beam irradiating region and the static pressure bearing support.

According to the ninth embodiment, the non-contact supporting mechanism by means of the static pressure bearings is applied to a supporting mechanism for the XY stage for carrying a sample thereon, and the vacuum sealing mechanism through differential exhaust is provided around the static pressure bearings such that a high pressure gas used for the static pressure bearing does not leak into a vacuum chamber, so that the stage device can demonstrate highly accurate positioning performance in vacuum. Further, by forming the partition between the electron beam irradiated position and the static pressure bearing support for reducing the conductance, even if a gas adsorbed on the surface of a sliding part of the stage is released each time the sliding part of the stage is moved from a high pressure gas section to a vacuum environment, the exhausted gas hardly reaches the electron beam irradiated position, thereby preventing the pressure at the electron beam irradiated position from rising. In other words, the employment of the foregoing configuration can stabilize the degree of vacuum at the electron beam irradiated position on the surface of the sample, and highly accurately drive the stage, thereby making it possible to accurately process the sample with the electron beam without contaminating the surface of the sample.

The partition may contain a differential exhaust structure. In this event, the partition is placed between the static pressure bearing support and the electron beam irradiating region, and a vacuum evacuation path is routed within the partition to provide a differential pumping function, so that a gas released from the static pressure bearing support cannot pass through the partition into the electron beam irradiating region. In this way, the degree of vacuum at the electron beam irradiated position can be further stabilized.

The partition may have a cold trap function. In this event, in a region at a pressure of $10^{-7}$ Pa or higher, main components of a residual gas in the vacuum and a gas released from the surface of the material are water molecules. Therefore, if the water molecules can be efficiently exhausted, a high degree of vacuum can be readily maintained with stability. Therefore, a cold trap cooled at approximately $-100°$ C. to $-200°$ C., if provided in the partition, enables the released gas generated on the static pressure bearing side to be frozen and trapped by the cold trap, so that the released gas pass into the electron beam irradiating region with difficulty, and the degree of vacuum is readily maintained stable in the electron beam irradiating region. It goes without saying that the cold trap is effective not only for the water molecules but also for removing organic gas molecules such as a oil group which is a factor of hampering a clean vacuum.

Further, the partitions may be disposed at two locations, i.e., near the electron beam irradiated position and near the static pressure bearing. In this event, since the partitions which reduce the conductance are disposed at two locations, i.e., near the electron beam irradiated position and near the static pressure bearing, the vacuum chamber is divided into three chambers consisting of an electron beam irradiating chamber, a static pressure bearing chamber, and an intermediate chamber through small conductance. Then, a vacuum evacuation system is configured to set lower pressures from the charged particle beam irradiation chamber to the intermediate chamber and to the static pressure bearing chamber in this order. By doing so, even if the released gas causes a rise in pressure in the static pressure bearing chamber, a pressure fluctuating rate can be suppressed since this is a chamber in which the pressure has been initially set high. Therefore, fluctuations in pressure to the intermediate chamber are suppressed by the partition, thereby making it possible to reduce the fluctuations in pressure to a level at which substantially no problem arises.

The gas supplied to the static pressure bearings is preferably dry nitrogen or inert gas. Also preferably, at least surfaces of parts facing the static pressure bearings are applied with a surface treatment for reducing a released gas. As described above, on the sliding parts of the stage exposed to a high pressure gas atmosphere in the static pressure bering chamber, gas molecules included in the high pressure gas are adsorbed on their surfaces, and as the sliding parts are exposed to a vacuum environment, the adsorbed gas molecules are desorbed from the surfaces and act as a released gas which deteriorates the degree of vacuum. It is therefore necessary, for preventing the deterioration of the degree of vacuum, to reduce the amount of gas molecules to be adsorbed, and promptly exhaust adsorbed gas molecules.

For this purpose, it is effective that the static pressure bearings are supplied with a high pressure gas which is dry nitrogen, from which moisture has been sufficiently removed, or a highly pure inert gas (for example, a highly pure nitrogen gas) to remove gas components which are adsorbed to a surface with ease and desorbed therefrom with difficulty (organic substances, moisture and so on) from the high pressure gas. An inert gas such as nitrogen has a significantly low surface coverage to a surface and a significantly high desorbing speed from the surface, as compared with moisture and organic substance. Therefore, when a highly pure inert gas, from which moisture and organic components have been maximally removed, is used for the high pressure gas, a small amount of gas is released even when the sliding parts are moved from the static pressure bearing chamber to the vacuum environment. Also, since the released gas promptly attenuates, the deterioration of the degree of vacuum can be reduced. It is therefore possible to suppress a rise in pressure when the stage is moved.

Also effectively, at least surfaces of components, particularly, surfaces of parts which reciprocate between a high pressure gas atmosphere and a vacuum environment are applied with a surface treatment for reducing a released gas. As the surface treatment, when a base material is a metal, Tic (titanium carbide), TiN (titanium nitride), nickel plating, passivation, electrolytic polishing, composite electrolytic polishing, glass bead shot, and so on are contemplated. When a base material is Sic ceramics, coating of concise SiC layer by CVD and so on are contemplated. It is therefore possible to further suppress a rise in pressure when the stage is moved.

Also, the ninth embodiment of the present invention provides a wafer defect testing apparatus for testing the surface of a semiconductor wafer for defects using the electron beam apparatus. Since this can realize the testing apparatus which is highly accurate in stage positioning performance and stable in the degree of vacuum in the electron beam irradiating region, a testing apparatus which has high testing performance and is free from fear of contaminating the sample is provided.

In addition, the ninth embodiment of the present invention also provides an exposure apparatus for drawing a circuit pattern of a semiconductor device on the surface of a semiconductor wafer or a reticle using the electron beam apparatus. Since this can realize the exposure apparatus which is highly accurate in stage positioning performance and stable in the degree of vacuum in the electron beam irradiating region, an exposure apparatus which has high testing performance and is free from fear of contaminating the sample is provided.

Furthermore, the ninth embodiment of the present invention also provides a semiconductor manufacturing method for manufacturing semiconductors using the electron beam apparatus. Since this results in manufacturing semiconductors using the apparatus which is highly accurate in stage positioning performance and stable in the degree of vacuum in the electron beam irradiating region, fine semiconductor circuits can be formed.

A tenth embodiment of the present invention provides an apparatus for irradiating an electron beam to a sample carried on an XY stage, characterized in that:

the XY stage is contained in a housing and supported by static pressure bearings with respect to the housing in a non-contact manner;

the housing containing the stage is evacuated to vacuum; and a differential exhaust mechanism is disposed around a portion of the electron beam apparatus for irradiating an electron beam to the surface of the sample for evacuating a region on the surface of the sample in which the electron beam is irradiated.

In this way, a high pressure gas for the static pressure bearings leaking into a vacuum chamber is first exhausted through a pipe for vacuum evacuation connected to the vacuum chamber. Then, by disposing the differential exhaust mechanism around the portion in which an electron beam is irradiated for evacuating a region in which the electron beam is irradiated, the pressure in the electron beam irradiating region is made largely lower than the pressure in the vacuum chamber, thereby making it possible to stably achieve a degree of vacuum at which the sample can be processed with the electron beam without problem. In other words, the sample on the stage can be stably processed with the electron beam using the stage having a structure similar to a static pressure bearing type stage which is generally used in the atmosphere (a stage supported by static pressure bearings, which does not have a differential exhaust mechanism).

The gas supplied to the static pressure bearings of the XY stage is preferably dry nitrogen or a highly pure inert gas. The highly pure inert gas is preferably pressurized after exhausted from the housing which contains the stage, and again supplied to the static pressure bearings. In this way, the remaining gas component in the vacuum housing is a highly pure inert gas, so that the surface of the construction within the vacuum chamber is not susceptible to contamination by moisture, oil component and so on. In addition, even if inert gas molecules are adsorbed on the surface of the sample, they are promptly desorbed from the surface of the sample if they are exposed to the differential exhaust mechanism or a high vacuum in the electron beam irradiating region, thereby making it possible to minimize the influence on the degree of vacuum in the electron beam irradiating region and stabilize the processing on the sample with the electron beam.

The tenth embodiment of the present invention provides a wafer defect testing apparatus for testing the surface of a semiconductor wafer for defects using the electron beam apparatus. It is therefore possible to provide a testing apparatus, at a low cost, which is highly accurate in stage positioning performance and stable in the degree of vacuum in the electron beam irradiating region.

The tenth embodiment of the present invention provides an exposure apparatus for drawing a circuit pattern of a semiconductor device on the surface of a semiconductor wafer or a reticle using the electron beam apparatus. It is therefore possible to provide an exposure apparatus, at a low cost, which is highly accurate in stage positioning performance and stable in the degree of vacuum in the electron beam irradiating region.

The tenth embodiment of the present invention provides a semiconductor manufacturing method for manufacturing semiconductors using the electron beam apparatus. Since this results in manufacturing semiconductors using the apparatus which is highly accurate in stage positioning performance and stable in the degree of vacuum in the electron beam irradiating region, fine semiconductor circuits can be formed.

An eleventh embodiment of the present invention provides an electron beam apparatus which comprises a plurality of optical systems each for generating a primary electron beam, converging the primary electron beam, scanning the primary electron beam on a sample for irradiation, and detecting a secondary electron beam emitted from an electron beam irradiated portion of the sample using a detector, characterized by comprising a retarding voltage applying unit for applying the sample with a retarding voltage, and a function for applying an optimal retarding voltage depending on the sample, wherein the optical system comprises at least one axially symmetric lens produced by working a bulk of insulating material, and having the surface applied with a metal coating.

The eleventh embodiment of the present invention also provides an electron beam apparatus which has a primary optical system for generating a primary electron beam, converging the primary electron beam, and scanning the primary electron beam on a sample for irradiation, wherein a secondary electron beam emitted from an electron beam irradiated portion of the sample is accelerated, separated from the primary optical system by an ExB separator, and detected by a detector, characterized by comprising a retarding voltage applying unit for applying the sample with a retarding voltage, a charge-up checking function unit for checking a charge-up state of the sample, and a function for determining an optimal retarding voltage based on information output from the charge-up checking function unit to apply the retarding voltage to the sample or to change it to an optimal beam current.

The eleventh embodiment of the present invention also provides an electron beam apparatus which is characterized by having an optical system for irradiating an electron beam to a sample, and a charge-up checking function, wherein the charge-up checking function evaluates a distorted pattern or a blurred pattern at a particular site of the sample, when the secondary electron beam generated from the sample irradiated with the primary electron beam is detected to form an image, and evaluates that charge-up is large when the result shows that the distorted pattern or the blurred pattern is large.

The charge-up checking function can apply the sample with a variable retarding voltage, and forms an image near a boundary where a pattern density largely varies on the sample which is applied with at least two retarding voltages, and may have a device for displaying the image such that an operator can evaluate the distorted pattern or the blurred pattern.

Also, the eleventh embodiment of the present invention provides a device manufacturing method characterized by detecting defects on a wafer in the middle of a process using the electron beam apparatus.

A twelfth embodiment of the present invention provides a defect testing apparatus for testing a sample for defects, characterized by comprising:

image capturing means for capturing each of images of a plurality of regions under testing displaced from one another while partially overlapping on the object under testing on the sample;

means for storing a reference image; and defect determining means for comparing the images of the plurality of regions under testing captured by the image capturing means with the reference image stored in the storage means to determine defects on the sample. Here, while the sample under testing may be selected from arbitrary ones for which defects can be detected, the present invention can produce a distinct effect when a semiconductor wafer is intended.

In this embodiment, the image capturing means operates to capture each of the images of the plurality of regions under testing displaced from one another while partially overlapping on the object under testing on the sample, and the defect determining means operates to compare the images of the plurality of regions under testing captured by the image capturing means with the reference image stored in the storage means to determine defects on the sample.

In this way, since the twelfth embodiment of the present invention can capture a plurality of images of regions under testing at different positions, an image under testing with less discrepancy in position with the reference image can be selectively utilized in a subsequent process, thereby making it possible to prevent a degraded defect detecting accuracy due to misalignment. Moreover, even if the sample and the image capturing means is in such a positional relationship that a portion of a pattern under testing is normally lost from the image region under testing, it is highly likely that the entire pattern under testing lies in any of regions covered by the plurality of images of the regions under testing displaced from one another, thereby making it possible to prevent erroneous detection of defect due to such partial loss of the pattern.

The comparing means performs a so-called matching operation between each of the captured images of the plurality of regions under testing and the reference image, and operates to determine that the sample is non-defective if there is substantially no difference between at least one image of the plurality of regions under testing and the reference image. Conversely, if there is a substantial difference between all the images of the regions under testing and the reference image, the sample is determined as defective, thereby detecting defects at a higher accuracy.

In the twelfth embodiment, electron irradiating means is further provided for irradiating a primary electron beam to each of a plurality of regions under testing to emit secondary electron beams from the sample, wherein the image capturing means detects the secondary electron beams emitted from the plurality of regions under testing, thereby making it possible to sequentially capture the images of the plurality of regions under testing.

Further, the electron irradiating means preferably comprises a particle beam source for emitting primary electrons, and deflecting means for deflecting the primary electrons, such that a primary electron beam emitted from the particle beam source is deflected by the deflecting means to sequentially irradiate the primary electron beam to the plurality of regions under testing. In this event, since the position of an input image can be readily changed by the deflecting means, a plurality of images under testing at different positions can be captured at a high speed.

The twelfth embodiment of the present invention also provides a semiconductor device manufacturing method which includes a step of testing a wafer during working or a finished one for defects, using the electron beam apparatus.

BRIEF DESCRIPTION OF THE DRAWINGS

FIG. 8 is a diagram illustrating a loader housing in FIG. 5, viewed along a line D-D in FIG. 6(a);

FIGS. 9[A] and 9[B] are an enlarged view of a wafer rack, wherein FIG. 9[A] is a side view and FIG. 9[B] is a cross-sectional view taken along a line E-E in FIG. 9[A];

FIGS. 10[A] and 10[B] are diagrams illustrating exemplary modifications to a method of supporting a main housing;

FIGS. 13[A] and 13[B] show diagrams for explaining an electron beam calibration mechanism, where FIG. 13[A] is a side view and FIG. 13[B] is a plan view;

FIG. 27(a) shows the relationship between the electron beam testing apparatus and coordinate axes; FIG. 27(b) shows the proper vibration of a barrel; and FIG. 27(c) shows an actuator attached to cancel the proper vibrations;

FIG. 37(a) shows pattern defect detection; FIG. 37(b) line width measurement; and FIG. 37(c) potential contrast measurement, respectively;

FIGS. 36[A] and 36[B] are diagrams illustrating a vacuum chamber and an XY stage of a conventional electron beam apparatus, where FIG. 36[A] is a front view and FIG. 36[B] is a side view;

FIGS. 38[A] and 38[B] are diagrams illustrating a vacuum chamber and an XY stage in a ninth embodiment of the charged particle beam apparatus according to the present invention, where FIG. 38[A] is a front view and FIG. 38[B] is a side view;

FIG. 49 is a diagram for explaining a site at which charge-up is evaluated, and an evaluation method;

BEST MODE FOR IMPLEMENTING THE INVENTION

In the following, a variety of embodiments of a charged particles beam apparatus according to the present invention will be described for an electron beam based apparatus which is taken as an example. Any embodiment is suitable for use in a sheet beam based testing apparatus.

Embodiment Relating to Overall Structure of Apparatus (First Embodiment)

A first embodiment of the charged particle beam apparatus according to the present invention relates to an electron beam based projection system, so that the projection system will be described first.

The projection system involves collectively irradiating a region under observation on a sample with a primary electron beam, i.e., irradiating a fixed area without scanning, and focusing a secondary electron beam from the irradiated region collectively on a detector (a combination of a microchannel plate and a fluorescent plate) through a lens system as an image of the secondary electron beam. This image is transduced into an electric signal by a two-dimensional CCD (solid-state imager device) or TDI-CCD (line image sensor) to output on a CRT or to store in a storage device. From this image information, defects on the sample wafer (a semiconductor (Si) wafer in the middle of a process) are detected. With a CCD, a stage is moved in the minor axis direction or major axis direction, and movements are made on a step-and-repeat basis. With TDI-CCD, the stage is continuously moved in an integrating direction. Since the TDI-CCD can sequentially capture images, the TDI-CCD is used when a defect testing is conducted continuously. The resolution is determined by a scaling factor, accuracy and so on of a focusing optical system (secondary optical system), and the resolution of 0.05 µm has been achieved, by way of example. In this event, with the resolution of 0.1 µm, when 1.6 µA is applied to an area of 200 µm×50 µm as an electron beam irradiating condition, approximately one hour of testing time is required for every 20 cm wafer, which is faster than the SEM system by a factor of eight. The specifications of the TDI-CCD used herein define 2048 pixels×512 stages, and a line rate at 3.3 microseconds (line frequency at 300 kHz). While the irradiated area in this example is fitted to the specifications of the TDI-CCD, the irradiated area may be changed depending on an object under irradiation.

Figure 1:
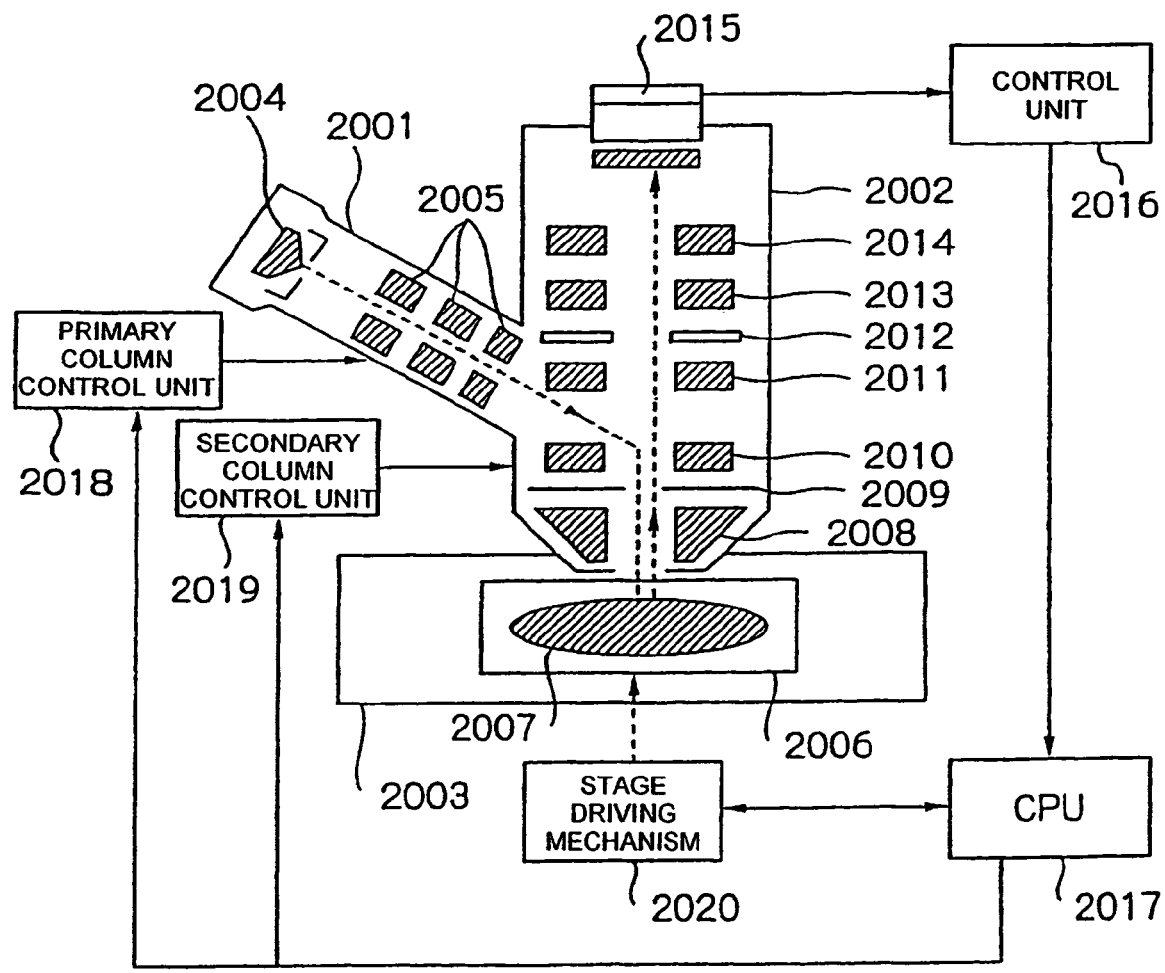
FIG. 1 is a diagram generally illustrating the configuration of a testing apparatus which is a first embodiment of a charged particle beam apparatus according to the present invention.

Now, the relationship between main functions of the map projection system, and its general figure will be described with reference to FIG. 1. In FIG. 1, the testing apparatus has a primary column 2001, a secondary column 2002, and a chamber 2003. In the primary column 2001, an electronic gun 2004 is arranged, and a primary optical system 2005 is positioned on the optical axis of an electron beam (primary electron beam) emitted from the electron gun 2004. In the chamber 2003, in turn, a stage 2006 is arranged, and a sample 2007 is carried on the stage 2006.

On the other hand, in the secondary column 2002, a cathode lens 2008, a numerical aperture (NA) 2009, a Wien filter (ExB filter) 2010, a second lens 2011, a field aperture 2012, a third lens 2013, a fourth lens 2014, and a detector 2015 are positioned on the optical axis of a secondary electron beam generated from the sample 2007. The numerical aperture 2009, which corresponds to a diagram, is made of a thin plate of metal (Mo or the like) formed with a circular hole extending therethrough, and is positioned such that its opening is at a convergence position of the primary electron beam as well as a focus position of the cathode lens 2008. Therefore, the cathode lens 2008 and the numerical aperture 2009 constitute a telecentric electron-optical system.

The output of the detector 2015 is input to a control unit 2016, while the output of the control unit 2016 is input to a CPU 2017. A control signal of the CPU 2017 is input to a primary column control unit 2018, a secondary column control unit 2019, and a stage driving mechanism 2020. The primary column control unit 2018 controls a lens voltage for the primary optical system 2005, while the secondary column control unit 2019 controls lens voltages for the cathode lens 2008 and second lens 2011-fourth lens 2014, as well as controls an electromagnetic field applied to the Wien filter 2010.

The stage driving mechanism 2020 transfers stage position information to the CPU 2017. Also, the primary column 2001, secondary column 2002 and chamber 2003 are connected to a vacuum exhaust system (not shown), such that they are evacuated by a turbo molecular pump in the vacuum exhaust system to maintain a vacuum state therein.

A primary electron beam emitted from the electron gun 2004 impinges on the Wien filter 2010 while receiving a lens action by the primary optical system 2005. As a chip for the electron gun, $L_aB_6$, capable of drawing a large current with a rectangular cathode, is preferably used.

The primary optical system 2005 uses quadrupole or octpole electrostatic (or electromagnetic) lenses which are asymmetric about the optical axis. This can give rise to convergence and divergence on each of the X-axis and Y-axis, similarly to a so-called cylindrical lens. The lenses are configured in two stages or in three stages to optimize conditions for the respective lenses, thereby making it possible to shape an electron beam irradiated region on the surface of a sample into an arbitrary rectangle or ellipse without losing the irradiated electron beam. Specifically, when electro-static lenses are used, four cylindrical rods are used to place opposing electrodes (a and b, c and d) at an equal potential and impart them opposite voltage characteristics. Instead of cylindrical ones, a lens having a shape resulting from dividing a circular plate generally used in an electrostatic deflector into four may be used as the quadrupole lens. In this event, the lenses can be reduced in size.

The primary electron beam passing through the primary optical system 2005 has its trajectory deflected by a deflecting action of the Wien filter 2010. As described later, the Wien filter 2010 can generate a magnetic field and an electric field orthogonal to each other. Assuming now that an electric field is E, a magnetic field is B, and the velocity of electrons is v, the Wien filter allows only electrons which satisfy the Wien condition E=vB to go straight, and deflects the trajectories of the remaining electrons. For the primary electron beam, a force FB is generated from the magnetic field and a force FE is generated from the electric field to deflect the beam trajectory. On the other hand, for the secondary electron beam, since the forces FB and FE act in the opposite directions, they cancel each other, allowing the secondary electron beam to go straight therethrough as it is.

A lens voltage for the primary optical system 2005 has been previously set such that the primary electron beam is focused on the opening of the numerical aperture 2009. The numerical aperture 2009 acts to prevent excessive electron beams dispersed within the apparatus from reaching the surface of the sample, and to prevent the sample 2007 from charging and contamination. Further, since the numerical aperture 2009 and the cathode lens 2008 constitute a telecentric electron-optical system, the primary electron beam transmitting the cathode lens 2008 is transformed into a parallel beam which is uniformly and evenly irradiated to the sample 2007. In other words, Koehler illumination, so called in the optical microscope, is implemented.

As the sample 2007 is irradiated with the primary electron beam, secondary electrons, reflected electrons or back-scattered electrons are emitted from the beam irradiated surface of the sample 2007 as a secondary electron beam. The secondary electron beam transmits the cathode lens 2008 while receiving a lens action thereof. The cathode lens 2008 comprises three electrodes. The lowermost electrode is designed to form a positive electric field between itself and a potential close to the sample 2007 to draw electrons (particularly, less directional secondary electrons) and efficiently introduce the electrons into the lens. The lens action is generated by applying voltages to the first and second electrodes of the cathode lens 2008, and placing the third electrode at a zero potential.

On the other hand, the numerical aperture 2009 is placed at a focus position of the cathode lens 2008, i.e., a back focus position from the sample 2007. Therefore, light flux of an electron beam emitted out of the center of the view field (out of axis) is transformed into a parallel beam which passes through the central position of the numerical aperture 2009 without eclipse. The numerical aperture 2009 serves to reduce lens aberration of the second lens 2011-fourth lens 2014 for the secondary electron beam.

The secondary electron beam passing through the numerical aperture 2009 goes straight as it is without receiving a deflecting action of the Wien filter 2010. By changing the electromagnetic field applied to the Wien filter 2010, electrons having particular energy (for example, secondary electrons, reflected electrons or back-scattered electrons) alone can be introduced into the detector 2015 from the secondary electron beam.

If the secondary electron beam is focused only with the cathode lens 2008, aberration is more likely to occur due to a stronger lens action. Therefore, image formation is performed once in combination of the second lens 2011. The secondary electron beam provides intermediate image formation on the field aperture 2012 by the cathode lens 2008 and second lens 2011. In this event, generally, the magnification required as the secondary optical system is often insufficient, so that the third lens 2013 and forth lens 2014 are added to the configuration as lenses for enlarging the intermediate image. The secondary electron beam is enlarged by the third lens 2013, fourth lens 2014 and forms an image. Here, the secondary electron beam forms images a total of three times. Alternatively, the third lens 2013 and fourth lens 2014 may be combined to force the secondary electron beam to form an image once (a total of two times).

All of the second lens 2011, third lens 2013 and fourth lens 2014 are lenses symmetric about the optical axis, which are called uni-potential lenses or Einzel lenses. Each of the lenses comprises three electrodes, where the two outer electrodes are generally placed at zero potential, and a voltage applied to the central electrode generates a lens action for controlling. Also, the field aperture 2012 is positioned at an intermediate image formation point. While the field aperture 2012 limits the field of view to a required range, similar to a viewing diaphragm of an optical microscope, it blocks excessive beams together with the third lens 2013 and fourth lens 2014, for electronic beams, to prevent the detector 2015 from charging and contamination. The magnification is set by changing lens conditions (focal lengths) of the third lens 2013 and fourth lens 2014.

The secondary electron beam is enlarged and projected by the secondary optical system, and is focused on a detecting face of the detector 2015. The detector 2015 is comprised of a micro-channel plate (MCP) for amplifying electrons; a fluorescent plate for transducing electrons into light; a lens and other optics for relaying a vacuum system to the outside to transmit an optical image; and an imager device (CCD or the like). The secondary electron beam is focused on the MCP detecting face, amplified, transduced into an optical signal by the fluorescent plate, and opto-electrically transduced into an electric signal by the imager device.

The control unit 2016 reads an image signal of the sample from the detector 2015 for transmission to the CPU 2017. The CPU 2017 conducts a pattern defect testing from the image signal through template matching or the like. The stage 2006 is movable in the XY directions by the stage driving mechanism 2020. The CPU 2017 reads the position of the stage 2006, outputs a driving control signal to the stage driving mechanisms 2020 to drive the stage 2006, and sequentially detects an image and conducts the testing.

In this way, in the testing apparatus in the first embodiment, the numerical aperture 2009 and the cathode lens 2008 constitute a telecentric electron-optical system, so that the sample can be uniformly irradiated with the primary electron beam. In other words, the Koehler illumination can be readily implemented. Further, for the secondary electron beam, an overall primary beam from the sample 2007 impinges perpendicularly on the cathode lens 2008 (parallel with the optical axis of the lens) and passes through the numerical aperture 2009, so that peripheral light will not eclipsed or the luminance of an image will not be degraded in a peripheral portion of the sample. In addition, although so-called magnification chromatism, i.e., difference in the position of image formation due to variations in energy possessed by electrons, occurs (particularly, large magnification chromatism occurs since the secondary electron beam has largely varying energy), the numerical aperture 2009 is placed at the focus position of the cathode lens 2008, so that this magnification chromatism can be suppressed.

Since the magnification is changed after the passage through the numerical aperture 2009, a uniform image can be generated over the entire field of view on the detection side, even if set magnifications are changed in the lens conditions for the third lens 2013 and fourth lens 2014.

While an even and uniform image can be captured in this embodiment, generally, as the magnification is increased, a problem arises that the brightness of image is reduced. To improve this, the lens conditions for the primary optical system may be designed such that when the magnification is changed by modifying the lens conditions for the secondary optical system, an effective field of view on the surface of a sample determined thereby is identical in size to an electron beam irradiated onto the surface of the sample. Specifically, while the field of view becomes narrower as the magnification is larger, the irradiated energy density of the electron beam is increased simultaneously with this, so that a signal density of detected electrons is held constant at all times to avoid the reduced brightness of image even if the field of view is enlarged and projected in the secondary optical system.

Also, in the testing apparatus of the first embodiment, the Wien filter 2010 is used to deflect the trajectory of the primary electron beam and allow the secondary electron beam to go straight therethrough, the present invention is not limited to that, but a Wien filter may be used for allowing the primary electron beam to go straight therethrough while deflecting the trajectory of the secondary electron beam. Further, while a rectangular beam is formed from a rectangular cathode and a quadrupole lens in this embodiment, the present invention is not limited to this. For example, a rectangular beam or an elliptic beam may be created from a circular beam, or a circular beam may be passed through a slit to extract a rectangular beam. Also, a plurality of beams may be scanned such that electron beams are generally irradiated uniformly to an irradiated region. The scanning in this event may be performed such that the plurality of beams arbitrarily scan respective regions allocated thereto (however with a uniform amount of irradiation).

Explaining now the electron gun as an electron beam source, a thermal electron beam source may be used as the electron beam source in this embodiment. An electron emitter (cathode) is made of $L_aB_6$. However, another material may be used as long as it is refractory (the vapor pressure is low at high temperatures) and small in work function. Preferably, the tip is formed in the shape of cone or truncated cone resulting from cutting off the tip of a cone. The tip of the truncated cone may have a diameter of approximately 100 μm. While an field emission type or thermal field emission type electron beam source may be used as another system, an $L_aB_6$ based thermal electron source is optimal for this embodiment in which a relatively wide region (for example, 100×25-400×100 μm$^2$) is irradiated with a large current (approximately 1 μA). (In the SEM system, a thermal electric field electron beam source is generally used).

The thermal electron beam source is based on a method of emitting electrons by heating an electron emitting material, while the thermal field emission electron beam source means a method for emitting electrons by applying the electron emitting material with a high electric field, and stabilizing the emission of electrons by heating the electron beam emitter.

As will be understood from the description with reference to FIG. 1, the functions of main components in the projection system are as follows. First, as to the primary electron-optical system, a section for forming electron radiations emitted from an electron gun into a beam shape and irradiating a wafer surface with a rectangular or circular (elliptic) electron beam is called the "primary electron-optical system." The size and current density of the electron beam can be controlled by controlling the lens conditions for the primary electron-optical system. Also, the primary electron beam is directed perpendicular to the wafer by a Wien filter positioned at a junction of the primary/secondary electron-optical systems.

Thermal electrons emitted from an $L_aB_6$ cathode of the electron gun is focused as a cross-over image on a gun diaphragm by a Wehnelt, triple anode lens. An electron beam with an incident angle adapted to the lens with an illumination field diagram is focused on a numerical aperture diagram in the form of rotational asymmetry by controlling the primary electrostatic lens, and subsequently two-dimensionally irradiated onto a wafer surface. A rear stage of the primary electrostatic lens is comprised of a three-stage quadrupole (QL) and a one-stage electrode for correcting geometrical aberration. While the quadrupole lens has limitations such as strict alignment accuracy, it characteristically has a strong converging action as compared with a rotationally symmetrical lens, so that it can correct the geometrical aberration corresponding to spherical aberration of a rotationally symmetric lens by applying an appropriate voltage to the geometrical aberration correcting electrode. In this way, a uniform surface beam can be irradiated to a predetermined region.

Next, as to the secondary electron-optical system, a focusing/projection optical system for focusing a two-dimensional secondary electron image produced by processing a secondary electron beam generated from a wafer irradiated with a primary electron beam at the position of a field diaphragm by electrostatic lenses (CL, TL) corresponding to an objective lens, and enlarging and projecting the secondary electron image using a lens (PL) at a rear stage, is called the "secondary electron-optical system." In this event, the wafer is applied with a minus bias voltage (decelerating electric field voltage). A decelerating electric field has a decelerating effect for an irradiated beam, and also has effects of reducing a damage on a wafer (sample), accelerating the secondary electron beam generated from the surface of the sample due to a potential difference between CL and the wafer, and reducing chromatism. Electrons converged by CL is focused on FA by TL, and the resulting image is enlarged and projected by PL, and formed on a secondary electron beam detector (MCP). In the secondary electron-optical system, NA is positioned between CL-TL and optimized to constitute an optical system which is capable of reducing off-axis aberration.

In addition, for correcting errors caused by the manufacturing of the electron-optical system, and astigmatism and anisotropic magnification of an image produced by passing a Wien filter, an electrostatic octpole (STIG) is disposed for correction, and preferably, a deflector (OP) positioned between respective lenses may be used to correct misalignment. In this way, a projection optical system can be achieved with a uniform resolution in the field of view.

The Wien filter 2010 is a unit based on an electromagnetic prism optical system which has electrodes and magnetic poles positioned in orthogonal directions to generate an electric field and a magnetic field in an orthogonal relationship. As an electromagnetic field is selectively applied, an electron beam incident from one direction into the field is deflected, while an electron beam incident from the opposite direction is allowed to go straight. This is achieved because of the ability to create conditions (Wien conditions) for canceling a force received by electrons from the electric field and a force received thereby from the magnetic field, whereby the primary electron beam is deflected and irradiated perpendicularly onto a wafer, while the secondary electron beam goes straight toward the detector.

The detailed structure of the Wien filter 2010 as an electron beam deflector will be described with reference to FIGS. 2(a) and 2(b). As illustrated in these figures, a field generated by the electron beam deflector has a structure in which an electric field is oriented orthogonal to a magnetic field in a plane perpendicular to the optical axis of he aforementioned projection optical system, i.e., an ExB structure.

Here, the electric field is generated by electrodes 2030a, 2030b which have concave curved surfaces. The electric fields generated by the electrodes 2030a, 2030b are controlled by controllers 2031a, 2031b, respectively. Electromagnetic coils 2032a, 2032b are arranged orthogonal to the electrodes 2030a, 2030b for generating the magnetic field. In this event, for improving the uniformity of the magnetic field, a pole piece having a parallel flat plate shape is provided to form a magnetic path. While the electrodes 2030a, 2030b for generating the electric field may be arranged symmetric about a point 2034, they may be concentrically arranged.

FIG. 2(b) is a vertical cross-sectional view on a plane which passes the point 2034 in FIG. 2(a) and perpendicular to the electrodes 2030a, 2030b. Referring to FIG. 2(b), behaviors of electron beams will be described. Irradiated electron beams 2035a, 2035b are deflected by an electric field generated by the electrodes 2030a, 2030b and a magnetic field generated by the electromagnetic coils 2031a, 2031b, and then impinge on the surface of a sample in a direction perpendicular thereto. Here, incident positions and angles of the irradiated electron beams 2035a, 2035b to the Wien filter 2010 are uniquely determined as the energy of electrons is determined. Further, by controlling conditions of the electric field and magnetic field, i.e., the electric field generated by the electrodes 2030a, 2030b and the magnetic field generated by the electromagnetic coils 2031a, 2031b by their respective controllers 2031a, 2031b, 2033a, 2033b such that the secondary electron beams 2036a, 2036b go straight, i.e., vB=E stands, secondary electron beams go straight through the Wien filter 2010 and impinges on the projection optical system, where v is the velocity of electrons (m/s), B is the magnetic field (T), e is the amount of charge (C), and E is the electric field (V/m).

Finally, the detector will be described. The image of the secondary electron beam from the wafer, focused by the secondary optical system is first amplified by the microchannel plate (MCP), then strikes the fluorescent screen, and transduced into a light image. The MCP is comprised of several millions of very thin conductive glass capillaries of 6-25 μm in diameter and 0.24-1.0 mm in length which are bundled and shaped into a thin plate. Each of the capillaries acts as an independent secondary electron amplifier, when a predetermined voltage is applied, to form, as a whole, the secondary electron amplifier. An image transduced into light by this detector is projected through a vacuum transmission window onto TDI-CCD on a one-to-one basis in an FOP system which is placed in the atmosphere.

As will be understood from the foregoing description, the testing apparatus, which is the first embodiment, can improve the throughput of the electron beam based testing apparatus.

Figure 3:
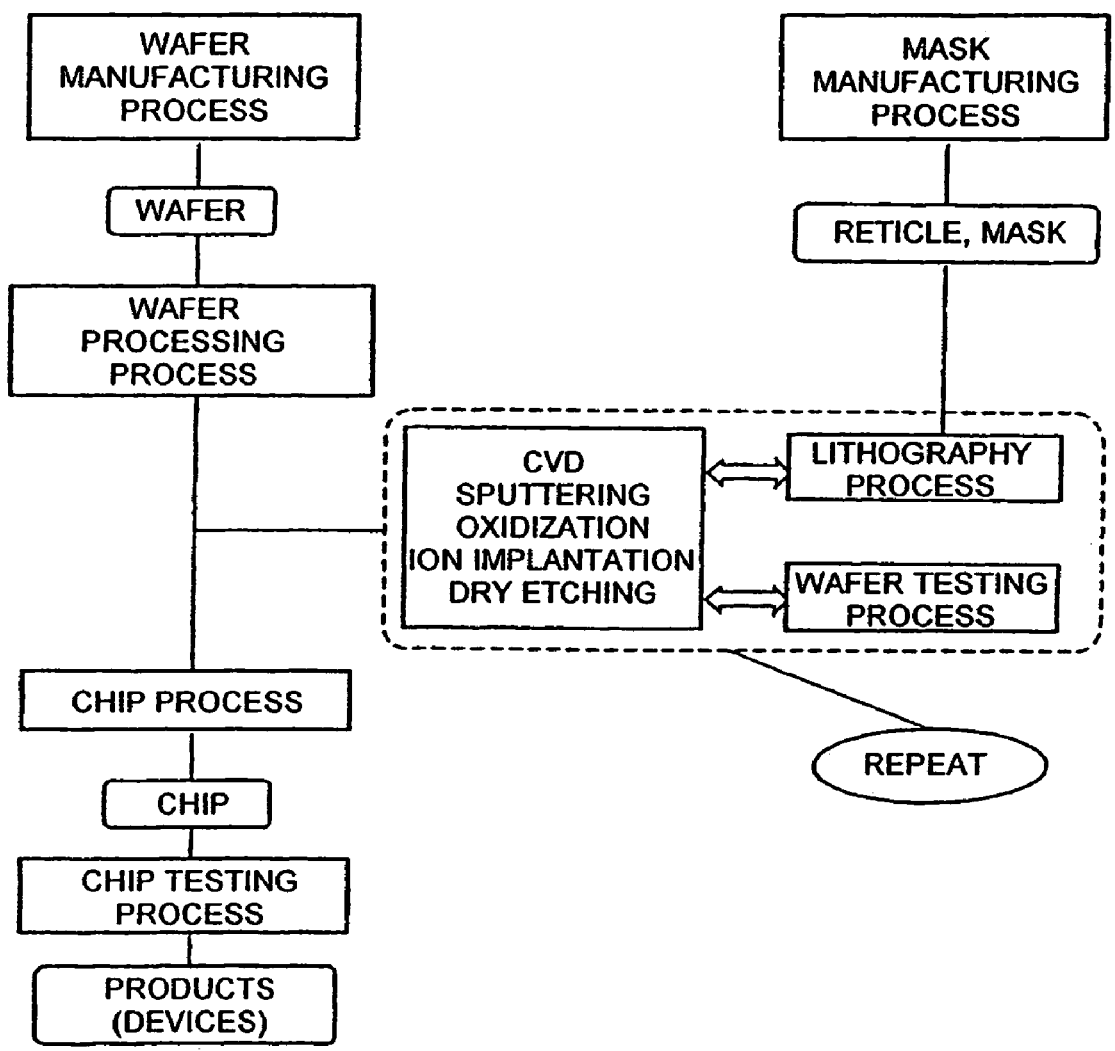
FIG. 3 is a flow chart illustrating an embodiment of a semiconductor device manufacturing method according to the present invention.

FIG. 3 illustrates an example of a semiconductor device manufacturing method which uses the first embodiment of the present invention, and includes the following main processes.

(1) a wafer manufacturing process for manufacturing a wafer (or a wafer preparing process for preparing a wafer);

(2) a mask manufacturing process for manufacturing masks for use in exposure (or mask preparing process for preparing masks);

(3) a wafer processing process for performing processing required to the wafer;

(4) a chip assembling process for excising one by one chips formed on the wafer and making them operable; and (5) a chip testing process for testing complete chips.

The respective main processes are further comprised of several sub-processes.

Among these main processes, the wafer processing process set forth in (3) exerts critical affections to the performance of resulting semiconductor devices. This process involves sequentially laminating designed circuit patterns on the wafer to form a large number of chips which operate as memories, MPUs and so on. The wafer processing process includes the following sub-processes:

(A) a thin film forming sub-process for forming dielectric thin films serving as insulating layers, metal thin films for forming wirings or electrodes, and so on (using CVD, sputtering and so on);

(B) an oxidization sub-process for oxidizing the thin film layers and the wafer substrate;

(C) a lithography sub-process for forming a resist pattern using masks (reticles) for selectively processing the thin film layers and the wafer substrate;

(D) an etching sub-process for processing the thin film layers and the substrate in conformity to the resist pattern (using, for example, dry etching techniques);

(E) an ion/impurity injection/diffusion sub-process;

(F) a resist striping sub-process; and (G) a sub-process for testing the processed wafer.

The wafer processing process is repeated a number of times equal to the number of required layers to manufacture semiconductor devices which operate as designed.

Figure 4A:
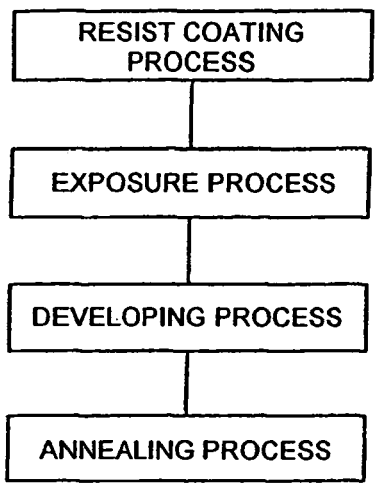
FIG. 4(a) is a flow chart illustrating a lithography step which forms the core of wafer processing steps in FIG. 3.

FIG. 4(a) is a flow chart illustrating the lithography process (C) which forms the core of the wafer processing process in FIG. 3. The lithography process includes the following steps:

(a) a resist coating step for coating a resist on the wafer on which circuit patterns have been formed in the previous process;

(b) a step of exposing the resist;

(c) a developing step for developing the exposed resist to produce a resist pattern; and (d) an annealing step for stabilizing the developed resist pattern.

When the defect testing apparatus of the present invention is used in the testing sub-process set forth in (G), any semiconductor devices even having miniature patterns can be tested at a high throughput, so that a total inspection can also be conducted, thereby making it possible to improve the yield rate of products and prevent defective products from being shipped. In this respect, description will be made with reference to FIG. 4(b).

Generally, an electron beam based testing apparatus is expensive and low in throughput as compared with other process apparatuses, so that such a defect testing apparatus is presently used after critical steps for which testing is most required (for example, etching, deposition or CMP (chemical-mechanical polishing) planarization processing). In this event, a wafer under testing is aligned on a super precise X-Y stage through an atmosphere transport system and a vacuum transport system, and fixed by an electrostatic chuck mechanism or the like. Subsequently, testing for defects and so on is conducted in accordance with a procedure illustrated in FIG. 4(b).

Figure 4B:
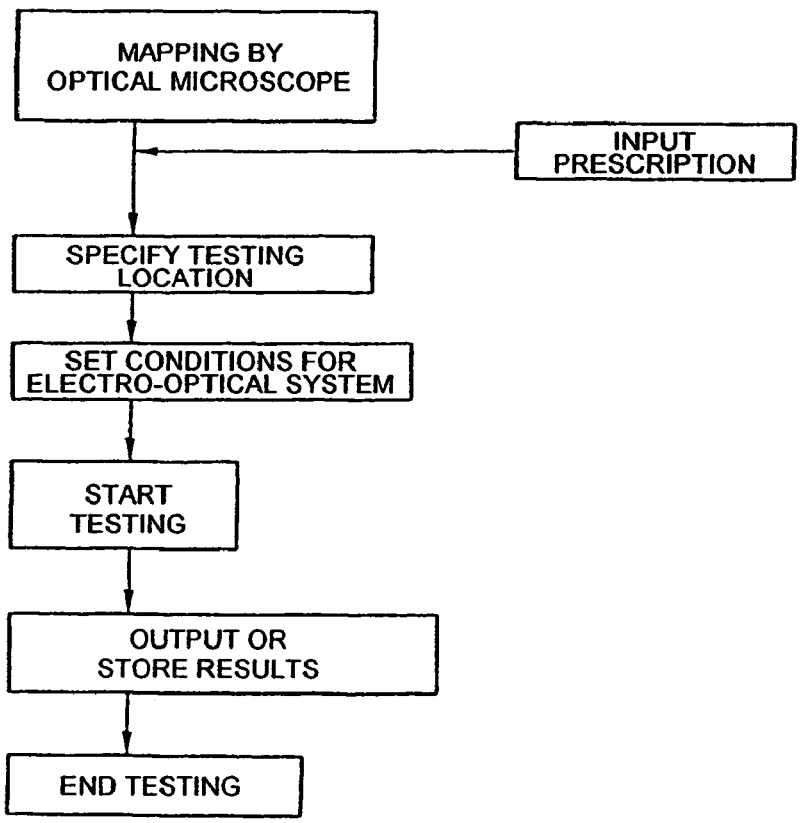
FIG. 4(b) is a flow chart illustrating a wafer testing step in the wafer processing steps in FIG. 3.

In FIG. 4(b), first, an optical microscope is used to confirm the position of each die, and detect the height of each location for storage as required. Other than this, the optical microscope is used to capture an optical microscopic image of a desired site such as defects for comparison with an electron beam image. Next, information on prescription is input to the apparatus in accordance with the type of a wafer (after which process, whether the size of the wafer is 20 cm or 30 cm, and so on) to specify a testing location, set electron-optical systems, set testing conditions, and so on. Subsequently, the defect testing is conducted generally in real time while images are captured. Through comparison of cells with one another, comparison of dies, and so on, a high speed information processing system installed with algorithms conducts the testing to output the result to a CRT and so on and stores the result in a memory as required.

Defects include particle defect, anomalous shape (pattern defect), electrical defects (disconnected wires or vias, defective conduction and the like), and so on. Distinction of these defects, and classification of the defects by size, and identification of killer defects (critical defects which disable chips to be used) may be automatically performed in real time.

The detection of electrical defects can be carried out by detecting anomalous potential contrasts. For example, a defectively conducted location is generally charged in positive by irradiation of electron beams (at approximately 500 eV) and presents a lower contrast, so that it can be distinguished from normal locations. An electron beam irradiating means in this case refers to a low potential (energy) electron beam generating means (generation of thermal electrons, UV/photoelectrons) which is separately provided for emphasizing the contrast caused by a potential difference, other than the normal electron beam irradiating means for testing. Before irradiating a region under testing with a testing electron beam, a low potential (energy) electron beam is generated for irradiation. For the projection system which can positively charge a sample by irradiating the same with a testing electron beam, the low potential electron beam generating means need not be provided in separation depending on specifications. Also, defects can be detected from a difference in contrast which is produced by applying a sample such as a wafer with a positive or a negative potential with respect to a reference potential (due to a difference in the ease of flow in a forward direction or a backward direction of the device). Such a defect testing apparatus can be utilized as well in a line width measuring apparatus and an alignment precision measurement.

A method of testing electrical defects of a sample under testing may take advantage of the fact that a voltage at an essentially electrically insulated portion is different from a voltage when this portion is conducted. For this purpose, charges are previously supplemented to a sample under testing to produce a difference in potential between the essentially electrically insulated portion and a portion which should have been electrically insulated but is conducted by some cause. Subsequently, a charged particle beam is irradiated from the charged particle beam apparatus according to the present invention to acquire data with the difference in potential, and the acquired data is analyzed to detect the conducted state.

Embodiment Relating to Testing Apparatus (Second Embodiment)

The second embodiment of the present invention relates to an electron beam apparatus suitable for testing, using an electron beam, defects in patterns formed on the surface of an object under testing, and more particularly, to an electron beam apparatus suitable for a testing apparatus useful, for example, in detecting defects on a wafer in a semiconductor manufacturing process, which includes irradiating an object under testing with an electron beam, capturing secondary electrons which vary in accordance with the properties of the surface thereof to form image data, and testing patterns formed on the surface of the object under testing based on the image data at a high throughput, and a method of manufacturing devices at a high yield rate using such an electron beam apparatus.

As an apparatus for testing defects of a wafer using an electron beam, an apparatus using a scanning electron microscope (SEM) already commercially available is known. This apparatus involves raster scanning an object under testing with a narrowed electron beam at very narrow intervals of raster width, detecting secondary electrons emitted from the object under testing associated with the scanning to form a SEM image, and comparing such SEM images of different dies at the same locations to extract defects of the object under testing.

Conventionally, however, there has been no electron beam based defect testing apparatus which is completed as a general system.

A defect testing apparatus to which an SEM is applied requires a long time for defect testing due to a small beam dimension, a resulting small pixel dimension and a small raster width. In addition, a beam current increased for purposes of improving the throughput would cause charging on a wafer having an insulating material formed on the surface thereof, thereby failing to produce satisfactory SEM images.

Hitherto, clarification has hardly been made for the overall structure of a testing apparatus which takes into account the relevancy of an electron-optical device for irradiating an object under testing with an electron beam for testing, and other subsystems associated therewith for supplying the object under testing to an irradiating position of the electron-optical device in a clean state and for aligning the object under testing. Further, with the trend of increasingly larger diameters of wafers which would be subjected to testing, the subsystems are also required to support larger diameter wafers.

In view of the problems mentioned above, the second embodiment of the present invention has been proposed. It is an object of the present invention to provide an electron beam apparatus which employs an electron beam based electron-optical system, and achieves harmonization of the electron-optical system with other components, which constitute the testing apparatus, to improve the throughput;

an electron beam apparatus which is capable of efficiently and accurately testing an object under testing by improving a loader for carrying the object under testing between a cassette for storing objects under testing and a stage device for aligning the object under testing with respect to the electron-optical system, and devices associated therewith;

an electron beam apparatus which is capable of solving the problem of charging, experienced in the SEM, to accurately test an object under testing; and a method of manufacturing a device at a high yield rate by testing an object under testing such as a wafer, using the electron beam apparatus described above.

In the following, the second embodiment of a charged particle beam apparatus according to the present invention will be described with reference to the accompanying drawings, in connection with an overall structure and operation of a semiconductor testing apparatus for testing, as an object under testing, a substrate, i.e., a wafer which has patterns formed on the surface thereof, as well as in connection with a device manufacturing method using the semiconductor testing apparatus.

Figure 5:
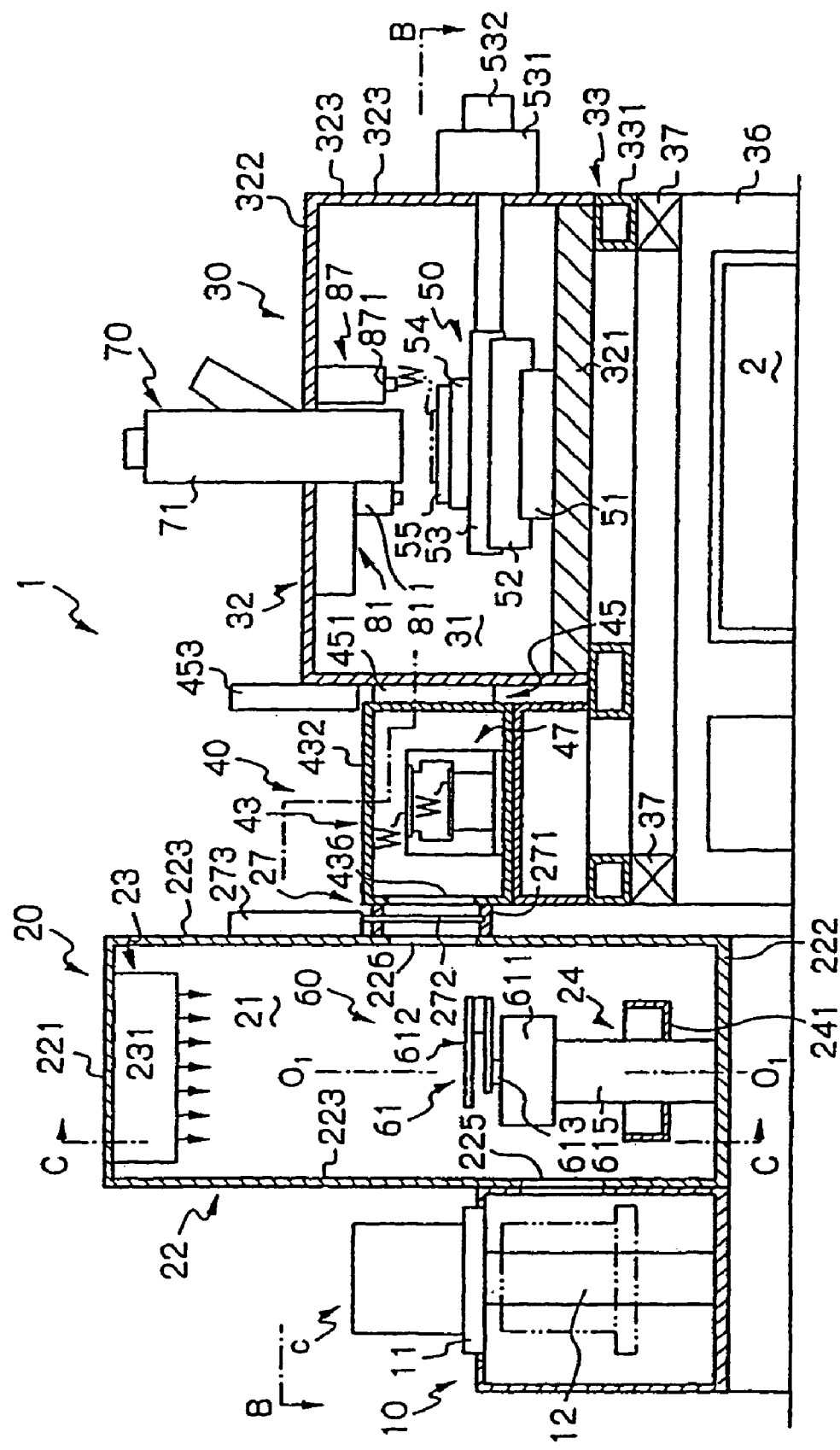
FIG. 5 is an elevation illustrating the main components of a testing apparatus which is a second embodiment of the charged particle beam apparatus according to the present invention, viewed along a line A-A in FIG. 6.
Figure 6A:
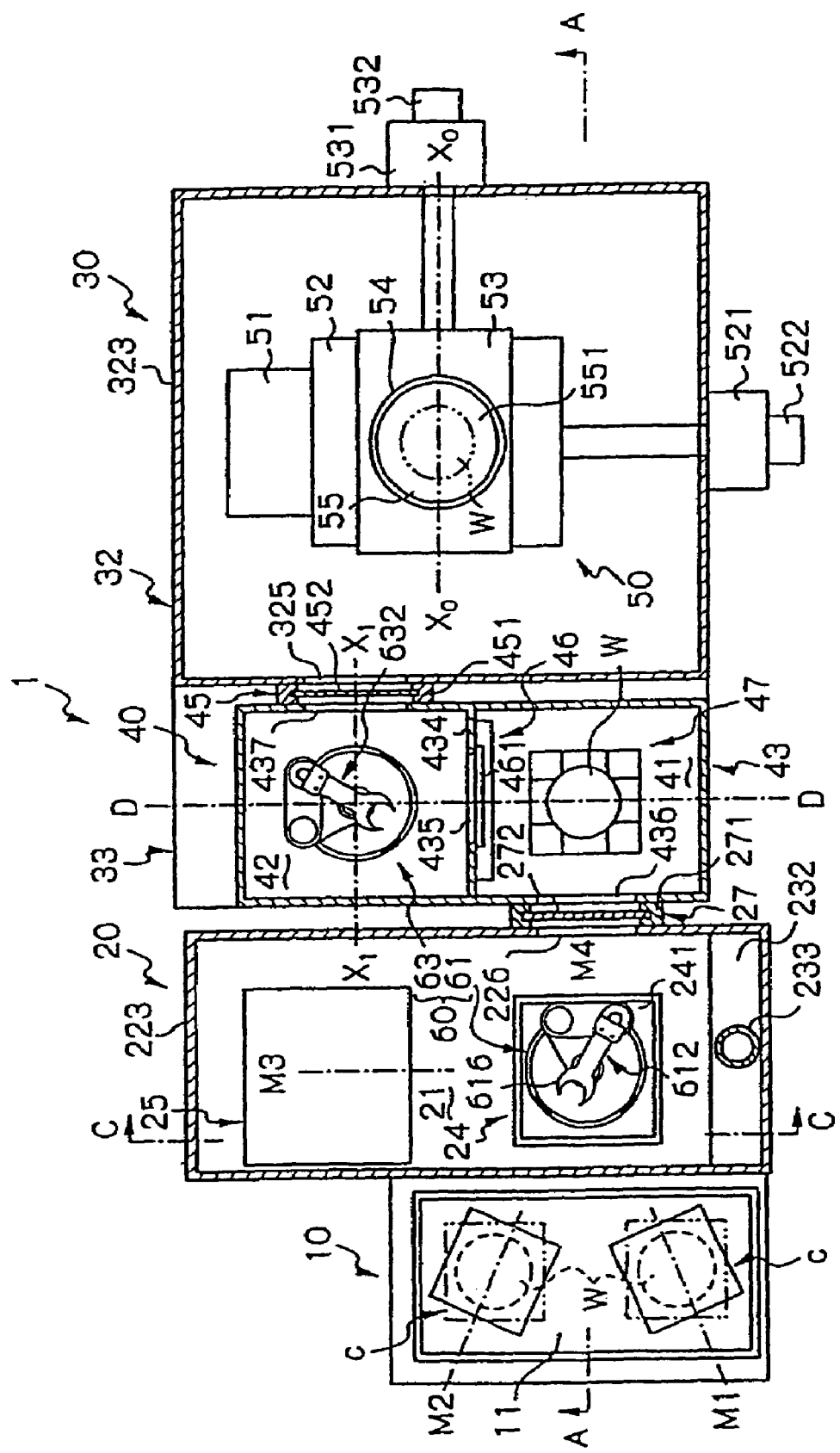
FIG. 6(a) is a plan view of the main components of the testing apparatus illustrated in FIG. 5, viewed along a line B-B in FIG. 5.
Figure 6B:
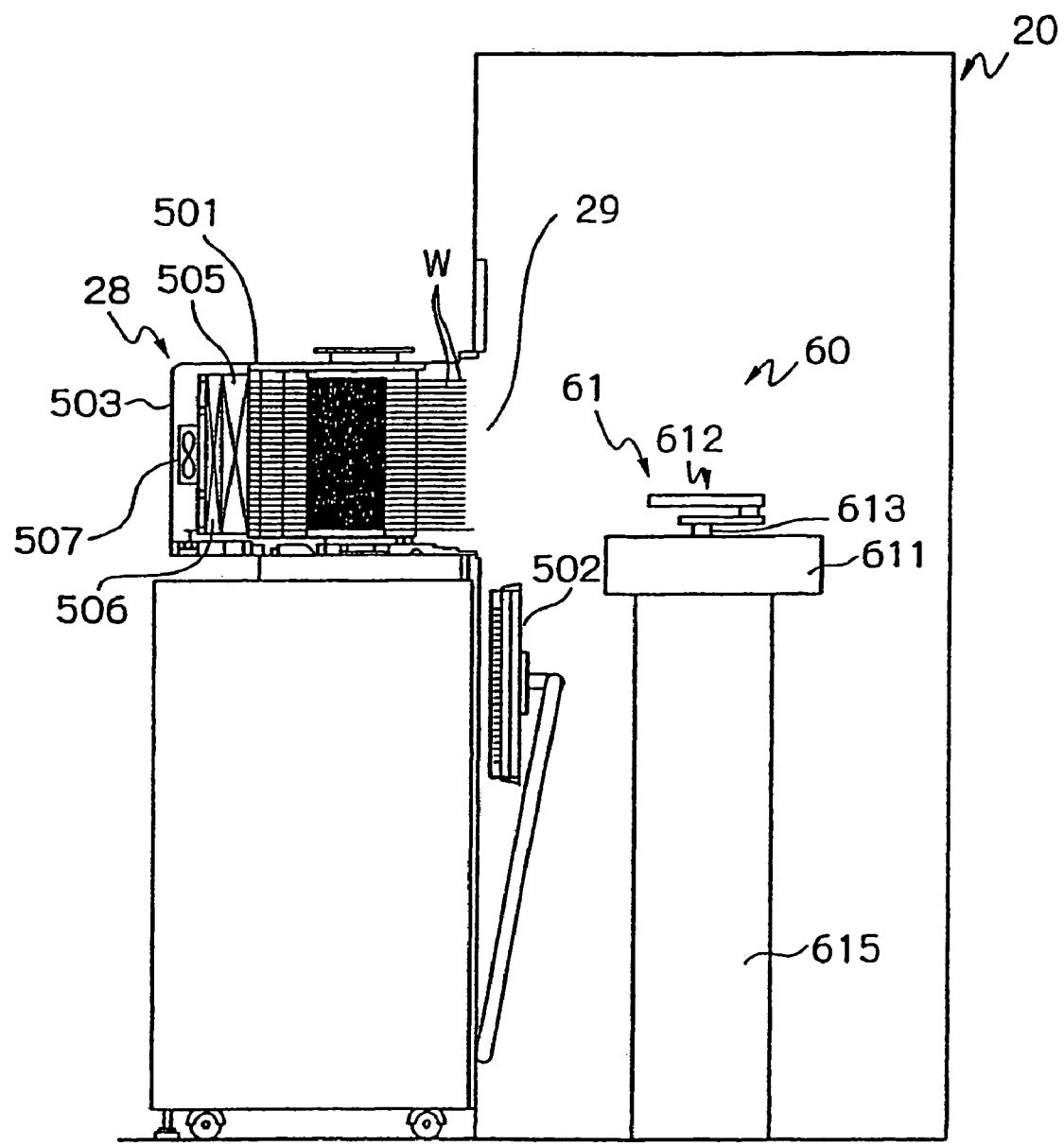
FIG. 6(b) is a diagram illustrating an exemplary modification to the configuration illustrated in FIG. 6(a)

In FIGS. 5 and 6(*a*), a semiconductor testing apparatus 1 comprises a cassette holder 10 for holding cassettes which stores a plurality of wafers; a mini-environment chamber 20; a main housing 30 which defines a working chamber; a loader housing 40 disposed between the mini-environment chamber 20 and the main housing 30 to define two loading chambers; a loader 60 for loading a wafer from the cassette holder 10 onto a stage system 50 disposed in the main housing 30; and an electron-optical system 70 installed in the vacuum main housing 30. These components are arranged in a positional relationship as illustrated in FIGS. 5 and 6(*a*). The semiconductor testing apparatus 1 further comprises a precharge unit 81 disposed in the vacuum main housing 30; a potential applying mechanism 83 (see in FIG. 12) for applying a wafer with a potential; an electron beam calibration mechanism 85 (see in FIG. 13); and an optical microscope 871 which forms part of an alignment controller 87 for aligning the wafer on the stage system 50.

The cassette holder 10 is configured to hold a plurality (two in this embodiment) of cassettes c (for example, closed cassettes such as FOUP manufactured by Assist Co.) in which a plurality (for example, twenty-five) wafers are placed side by side in parallel, oriented in the vertical direction. The cassette holder 10 can be arbitrarily selected for installation adapted to a particular loading mechanism. Specifically, when a cassette, carried to the cassette holder 10, is automatically loaded into the cassette holder 10 by a robot or the like, the cassette holder 10 having a structure adapted to the automatic lading can be installed. When a cassette is manually loaded into the cassette holder 10, the cassette holder 10 having an open cassette structure can be installed. In this embodiment, the cassette holder 10 is a type adapted to the automatic cassette loading, and comprises, for example, an up/down table 11, and an elevating mechanism 12 for moving the up/down table 11 up and down. The cassette c can be automatically set onto the up/down table 11 in a state indicated by chain lines in FIG. 6(*a*). After the setting, the cassette c is automatically rotated to a state indicated by solid lines in FIG. 6(*a*) so that it is directed to the axis of pivotal movement of a first carrier unit within the mini-environment chamber 20. In addition, the up/down table 11 is moved down to a state indicated by chain lines in FIG. 5. In this way, the cassette holder 10 for use in automatic loading, or the cassette holder 10 for use in manual loading may be both implemented by those in known structures, so that detailed description on their structures and functions are omitted.

FIG. 6(*b*) shows a modification to a mechanism for automatically loading a cassette. A plurality of 300 mm wafers W are contained in a slotted pocket (not shown) fixed to the inner surface of a box body 501 for carriage and storage. This wafer carrying box 28 comprises a box body 501 of a squared cylinder, a wafer carrying in/out door 502 provided at an aperture 29 of a side surface of the box body 501 for communicate with an automatic door opening apparatus and capable of being opened and closed mechanically, a cap 503 positioned in opposite to the aperture 29 to cover the aperture 29 for the purpose of detachably mounting filers and fan motors, a slotted pocket (not shown), an ULPA filter 505, a chemical filter 506 and a fan motor 507. In this modification, wafers W are carried in and out by means of a first carrying unit 612 of a robot type loader 60.

It should be noted that substrates, i.e., wafers accommodated in the cassette c are wafers subjected to testing which is generally performed after a process for processing the wafers or in the middle of the process within semiconductor manufacturing processes. Specifically, accommodated in the cassette are substrates or wafers which have undergone a deposition process, CMP, ion implantation and so on; wafers each formed with wiring patterns on the surface thereof; or wafers which have not been formed with wiring patterns. Since a large number of wafers accommodated in the cassette c are spaced from each other in the vertical direction and arranged side by side in parallel, the first carrier unit has an arm which is vertically movable such that a wafer at an arbitrary position can be held by the first carrier unit, as described later in detail.

Figure 7:
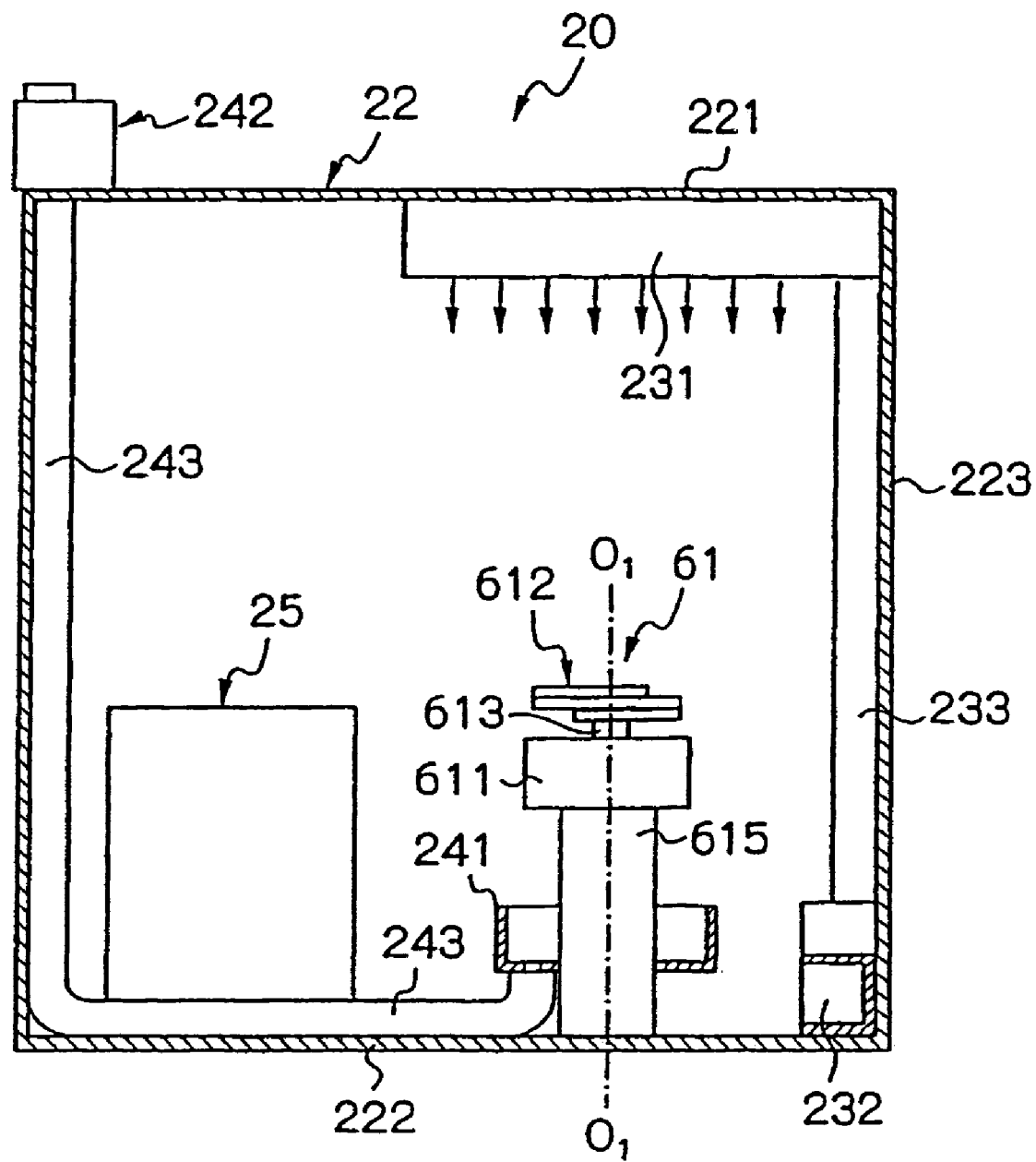
FIG. 7 is a cross-sectional view illustrating an mini-environment device in FIG. 5, viewed along a line C-C.

In FIGS. 5 through 7, the mini-environment device 20 comprises a housing 22 which defines a mini-environment space 21 that is controlled for the atmosphere; a gas circulator 23 for circulating a gas such as clean air within the mini-environment space 21 for the atmosphere control; a discharger 24 for recovering a portion of air supplied into the mini-environment space 21 for discharging; and a pre-aligner 25 for roughly aligning a substrate, i.e., a wafer under testing, which is placed in the mini-environment space 21.

The housing 22 has a top wall 221, a bottom wall 222, and peripheral wall 223 which surrounds four sides of the housing 22 to provide a structure for isolating the mini-environment space 21 from the outside. For controlling the atmosphere in the mini-environment space 21, the gas circulator 23 comprises a gas supply unit 231 attached to the top wall 221 within the mini-environment space 21 as illustrated in FIG. 7 for cleaning a gas (air in this embodiment) and delivering the cleaned gas downward through one or more gas nozzles (not shown) in laminar flow; a recovery duct 232 disposed on the bottom wall 222 within the mini-environment space for recovering air which has flown down to the bottom; and a conduit 233 for connecting the recovery duct 232 to the gas supply unit 231 for returning recovered air to the gas supply unit 231.

In this embodiment, the gas supply unit 231 takes about 20% of air to be supplied, from the outside of the housing 22 for cleaning. However, the percentage of gas taken from the outside may be arbitrarily selected. The gas supply unit 231 comprises an HEPA or ULPA filter in a known structure for creating cleaned air. The laminar downflow of cleaned air is mainly supplied such that the air passes a carrying surface formed by the first carrier unit, later described, disposed within the mini-environment space 21 to prevent dust particles, which could be produced by the carrier unit, from attaching to the wafer. Therefore, the downflow nozzles need not be positioned near the top wall as illustrated, but is only required to be above the carrying surface formed by the carrier unit. In addition, the air need not either be supplied over the entire mini-environment space 21.

It should be noted that an ion wind may be used as cleaned air to ensure the cleanliness as the case may be. Also, a sensor may be provided within the mini-environment space 21 for observing the cleanliness such that the apparatus is shut down when the cleanliness is degraded.

An access port 225 is formed in a portion of the peripheral wall 223 of the housing 22 that is adjacent to the cassette holder 10. A shutter device in a known structure may be provided near the access port 225 to shut the access port 225 from the mini-environment device 20. The laminar downflow near the wafer may be, for example, at a rate of 0.3 to 0.4 m/sec. The gas supply unit 231 may be disposed outside the mini-environment space 21 instead of within the mini-environment space 21.

The discharger 24 comprises a suction duct 241 disposed at a position below the wafer carrying surface of the carrier unit and below the carrier unit; a blower 242 disposed outside the housing 22; and a conduit 243 for connecting the suction duct 241 to the blower 242. The discharger 24 aspires a gas flowing down around the carrier unit and including dust, which could be produced by the carrier unit, through the suction duct 241, and discharges the gas outside the housing 22 through the conduits 243, 244 and the blower 242. In this event, the gas may be discharged into an exhaust pipe (not shown) which is laid to the vicinity of the housing 22.

The aligner 25 disposed within the mini-environment space 21 optically or mechanically detects an orientation flat (which refers to a flat portion formed along the outer periphery of a circular wafer and hereunder called as ori-fla) formed on the wafer, or one or more V-shaped notches formed on the outer peripheral edge of the wafer to previously align the position of the waver in a rotating direction about the axis O-O at an accuracy of approximately ±one degree. The pre-aligner forms part of a mechanism for determining the coordinates of an object under testing, which is a feature of the claimed invention, and is responsible for rough alignment of an object under testing. Since the pre-aligner itself may be of a known structure, description on its structure and operation is omitted.

Though not shown, a recovery duct for the discharger 24 may also be provided below the prealigner such that air including dust, discharged from the prealigner, is discharged to the outside.

In FIGS. 5 and 6(a), the main housing 30, which defines the working chamber 31, comprises a housing body 32 that is supported by a housing supporting device 33 carried on a vibration isolator 37 disposed on a base frame 36. The housing supporting device 33 comprises a frame structure 331 assembled into a rectangular form. The housing body 32 comprises a bottom wall 321 mounted on and securely carried on the frame structure 331; a top wall 322; and a peripheral wall 323 which is connected to the bottom wall 321 and the top wall 322 and surrounds four sides of the housing body 32, and isolates the working chamber 31 from the outside. In this embodiment, the bottom wall 321 is made of a relatively thick steel plate to prevent distortion due to the weight of equipment carried thereon such as the stage device 50. Alternatively, another structure may be employed.

In this embodiment, the housing body 32 and the housing supporting device 33 are assembled into a rigid construction, and the vibration isolator 37 blocks vibrations from the floor, on which the base frame 36 is installed, from being transmitted to the rigid structure. A portion of the peripheral wall 323 of the housing body 32 that adjoins the loader housing 40, later described, is formed with an access port 325 for introducing and removing a wafer. The vibration isolator may be either of an active type which has an air spring, a magnetic bearing and so on, or a passive type likewise having these components. Since any known structure may be employed for the vibration isolator, description on the structure and functions of the vibration isolator itself is omitted. The working chamber 31 is held in a vacuum atmosphere by a vacuum system (not shown) in a known structure.

A controller 2 for controlling the operation of the overall apparatus is disposed below the base frame 36, and mainly comprises a main controller, a control controller and a stage controller.

The main controller has a man-machine interface through which the operation by an operator (input of various instructions/commands and menus, instruction to start a test, switch between automatic and manual test modes, input of all commands necessary when the manual test mode) is performed. Further, the main controller performs a communication to a host computer in a factory, control of a vacuum discharge system, carriage of a sample such as a wafer, control of alignment, transmission of commands to the control controller and the stage controller and receipt of information. Moreover, the main controller has a function of obtaining an image signal from the optical microscope, a stage vibration correcting function for feeding back a vibration signal of the stage to the electron-optical system to correct a deteriorated image, and an automatic focus correcting function for detecting a Z-direction (the direction of the axis of the secondary optical system) displacement of a sample observing position to feed back the displacement to the electron-optical system so as to automatically correct the focus. Reception and transmission of a feedback signal to the electron-optical system and a signal from the stage can be performed through the control controller and the stage controller.

The control controller is mainly responsible for control of the electron-optical system (control of an a highly accurate voltage source for electron gun, lenses, alighners and Wien filter). Specifically, the control controller effects control (gang control) of automatic voltage setting to each lens system and the alighners in correspondence with each operation mode, for example, causes a region to be irradiated by a constant electron current even if the magnification is changed, and automatically sets a voltage applied to each lens system and the alighners in correspondence with each magnification.

The stage controller is mainly responsible for control regarding the movement of the stage and enables the achievement of accurate X- and Y-direction movement of micrometer order. Further, the stage controller achieves control of rotation (θ control) of the stage within an error accuracy of ±0.3 seconds.

In FIGS. 5, 6(a) and 8, the loader housing 40 comprises a housing body 43 which defines a first loading chamber 41 and a second loading chamber 42. The housing body 43 comprises a bottom wall 431; a top wall 432; a peripheral wall 433 which surrounds four sides of the housing body 43; and a partition wall 434 for partitioning the first loading chamber 41 and the second loading chamber 42 such that both the loading chambers can be isolated from the outside. The partition wall 434 is formed with an opening, i.e., an access port 435 for passing a wafer between both the loading chambers. Also, a portion of the peripheral wall 433 that adjoins the mini-environment device 20 and the main housing 30 is formed with access ports 436, 437. The housing body 43 of the loader housing 40 is carried on and supported by the frame structure 331 of the housing supporting device 33. This prevents the vibrations of the floor from being transmitted to the loader housing 40 as well.

The access port 436 of the loader housing 40 is in alignment with the access port 226 of the housing 22 of the mini-environment device 20, and a shutter device 27 is provided for selectively blocking a communication between the mini-environment space 21 and the first loading chamber 41. The shutter device 27 has a sealing material 271 which surrounds the peripheries of the access ports 226, 436 and is fixed to the side wall 433 in close contact therewith; a door 272 for blocking air from flowing through the access ports in cooperation with the sealing material 271; and a driver 273 for moving the door 272. Likewise, the access port 437 of the loader housing 40 is in alignment with the access port 325 of the housing body 32, and a shutter 45 is provided for selectively blocking a communication between the second loading chamber 42 and the working chamber 31 in a hermetic manner. The shutter 45 comprises a sealing material 451 which surrounds the peripheries of the access ports 437, 325 and is fixed to side walls 433, 323 in close contact therewith; a door 452 for blocking air from flowing through the access ports in cooperation with the sealing material 451; and a driver 453 for moving the door 452.

Further, the opening formed through the partition wall 434 is provided with a shutter 46 for closing the opening with the door 461 to selectively blocking a communication between the first and second loading chambers in a hermetic manner. These shutter devices 27, 45, 46 are configured to provide air-tight sealing for the respective chambers when they are in a closed state. Since these shutter devices may be implemented by known ones, detailed description on their structures and operations is omitted. It should be noted that a method of supporting the housing 22 of the mini-environment chamber 20 is different from a method of supporting the loader housing 40. Therefore, for preventing vibrations from being transmitted from the floor through the mini-environment chamber 20 to the loader housing 40 and the main housing 30, a vibration-absorption cushion material may be disposed between the housing 22 and the loader housing 40 to provide air-tight sealing for the peripheries of the access ports.

Within the first loading chamber 41, a wafer rack 47 is disposed for supporting a plurality (two in this embodiment) of wafers spaced in the vertical direction and maintained in a horizontal state. As illustrated in FIG. 9, the wafer rack 47 comprises posts 472 fixed at four corners of a rectangular substrate 471, spaced from one another, in an upright state. Each of the posts 472 is formed with supporting devices 473, 474 in two stages, such that peripheral edges of wafers W are carried on and held by these supporting devices. Then, leading ends of arms of the first and second carrier units, later described, are brought closer to wafers from adjacent posts and grab the wafers.

The loading chambers 41, 42 can be controlled for the atmosphere to be maintained in a high vacuum state (at a vacuum degree of $10^{-5}$ to $10^{-6}$ Pa) by a vacuum evacuator (not shown) in a known structure including a vacuum pump, not shown. In this event, the first loading chamber 41 may be held in a low vacuum atmosphere as a low vacuum chamber, while the second loading chamber 42 may be held in a high vacuum atmosphere as a high vacuum chamber, to effectively prevent contamination of wafers. The employment of such a structure allows a wafer, which is accommodated in the loading chamber and is next subjected to the defect testing, to be carried into the working chamber without delay. The employment of such a loading chambers provides for an improved throughput for the defect testing, and the highest possible vacuum state around the electron source which is required to be kept in a high vacuum state, together with the principle of a multi-beam type electron device, later described.

The vacuum exhaust system comprises a vacuum pump, a vacuum valve, a vacuum gauge and a vacuum pipe for performing vacuum exhaust of the electron-optical system, the detectors, the sample chamber and the load lock chamber in accordance with a predetermined sequence. The vacuum valve is controlled so as to achieve the degree of vacuum required by the respective units. For this end, the degree of vacuum is monitored at any time, and an emergency control of a separation valve by an interlocking mechanism is performed to maintain the degree of vacuum, if any abnormality is found. As the vacuum pump, a turbo molecular pump is used for the main exhaust and a Roots dry pump is used for rough exhaust. The pressure at a test location (electron beam irradiated region) is $10^{-3}$ to $10^{-5}$ Pa. Preferably, pressure of $10^{-4}$ to $10^{-6}$ Pa is practical.

The first and second loading chambers 41, 42 are connected to a vacuum exhaust pipe and a vent pipe for an inert gas (for example, dried pure nitrogen) (neither of which are shown), respectively. In this way, the atmospheric state within each loading chamber is attained by an inert gas vent (which injects an inert gas to prevent an oxygen gas and so on other than the inert gas from attaching on the surface). Since an apparatus itself for implementing the inert gas vent is known in structure, detailed description thereon is omitted.

In the testing apparatus according to the present invention which uses an electron beam, when representative lanthanum hexaborate ($LaB_6$) used as an electron source for an electron-optical system, later described, is once heated to such a high temperature that causes emission of thermal electrons, it should not be exposed to oxygen within the limits of possibility so as not to shorten the lifetime. The exposure to oxygen can be prevented without fail by carrying out the atmosphere control as mentioned above at a stage before introducing a wafer into the working chamber in which the electron-optical system is disposed.

The stage device 50 comprises a fixed table 51 disposed on the bottom wall 301 of the main housing 30; a Y-table 52 movable in a Y-direction on the fixed table 51 (the direction vertical to the drawing sheet in FIG. 5); an X-table 53 movable in an X-direction on the Y-table 52 (in the left-to-right direction in FIG. 1); a turntable 54 rotatable on the X-table; and a holder 55 disposed on the turntable 54. A wafer is releasably held on a wafer carrying surface 551 of the holder 55. The holder 55 may be of a known structure which is capable of releasably grabbing a wafer by means of a mechanical or electrostatic chuck feature.

The stage device 50 uses servo motors, encoders and a variety of sensors (not shown) to operate a plurality of tables as mentioned above to permit highly accurate alignment of a wafer held on the carrying surface 551 by the holder 55 in the X-direction, Y-direction and Z-direction (in the up-down direction in FIG. 5) with respect to an electron beam irradiated from the electron-optical system, and in a direction about the axis normal to the wafer supporting surface (θ direction). The alignment in the Z-direction may be made such that the position on the carrying surface 551 of the holder 55, for example, can be finely adjusted in the Z-direction. In this event, a reference position on the carrying surface 551 is sensed by a position measuring device using a laser of an extremely small diameter (a laser interference range finder using the principles of interferometer) to control the position by a feedback circuit, not shown. Additionally or alternatively, the position of a notch or an orientation flat of a wafer is measured to sense a plane position or a rotational position of the wafer relative to the electron beam to control the position of the wafer by rotating the turntable 54 by a stepping motor which can be controlled in extremely small angular increments.

In order to maximally prevent dust produced within the working chamber, servo motors 531, 531 and encoders 522, 532 for the stage device 50 are disposed outside the main housing 30. Since the stage system 50 may be of a known structure used, for example, in steppers and so on, detailed description on its structure and operation is omitted. Likewise, since the laser interference range finder may also be of a known structure, detailed description on its structure and operation is omitted.

It is also possible to establish a basis for signals which are generated by previously inputting a rotational position, and X-, Y-positions of a wafer relative to the electron beam in a signal detecting system or an image processing system, later described. The wafer chucking mechanism provided in the holder 55 is configured to apply a voltage for chucking a wafer to an electrode of an electrostatic chuck, and the alignment is made by pinning three points on the outer periphery of the wafer (preferably spaced equally in the circumferential direction). The wafer chucking mechanism comprises two fixed aligning pins and a push-type clamp pin. The clamp pin can implement automatic chucking and automatic releasing, and constitutes a conducting spot for applying the voltage.

Figure 2:
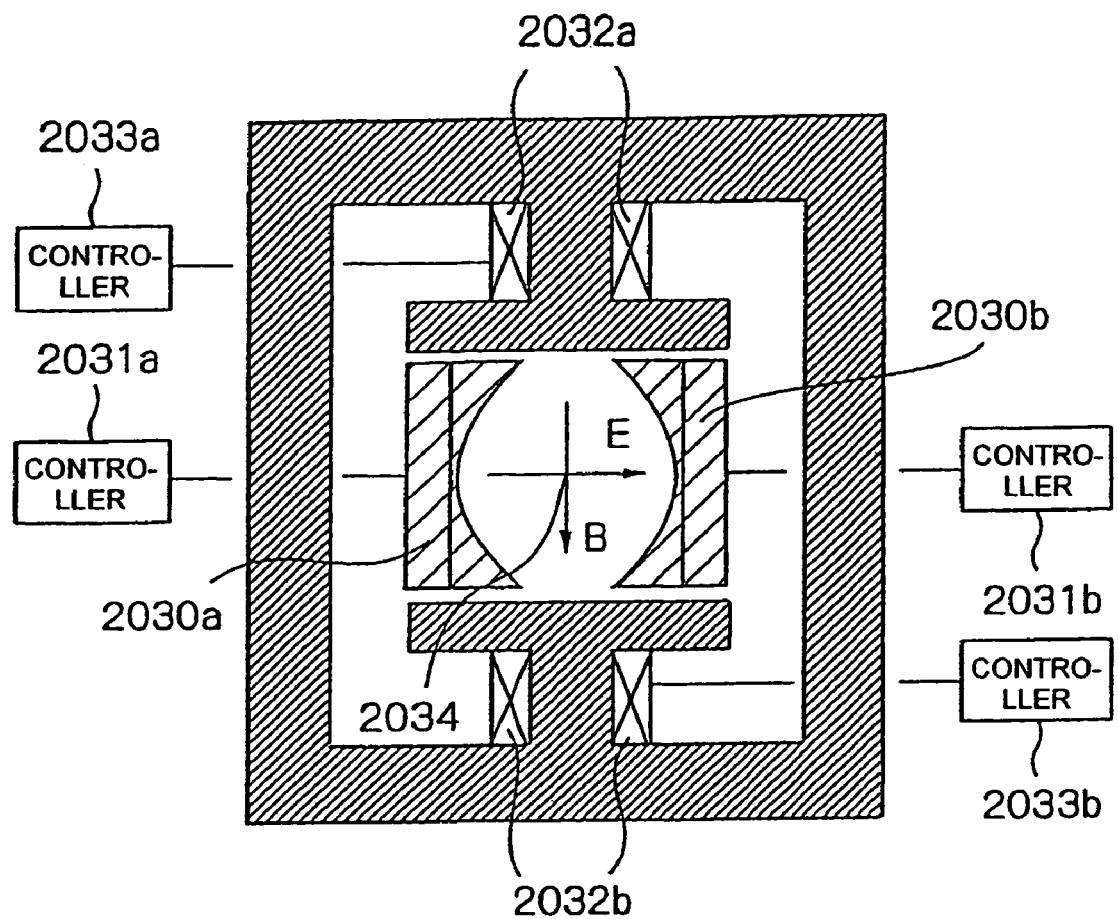
FIG. 2(a) is a plan view of an electron deflection system.
FIG. 2(b) is a cross-sectional view of the same.
Figure 2:
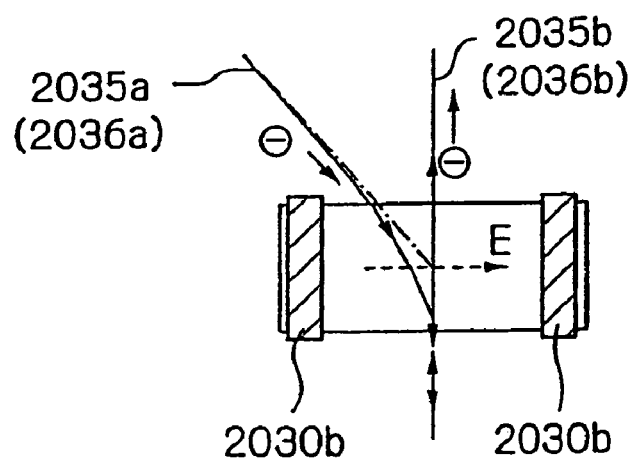

While in this embodiment, the X-table is defined as a table which is movable in the left-to-right direction in FIG. 6(a); and the Y-table as a table which is movable in the up-down direction, a table movable in the left-to-right direction in FIG. 2 may be defined as the Y-table; and a table movable in the up-down direction as the X-table.

The loader 60 comprises a robot-type first carrier unit 61 disposed within the housing 22 of the mini-environment chamber 20; and a robot-type second carrier unit 63 disposed within the second loading chamber 42.

The first carrier unit 61 comprises a multi-node arm 612 rotatable about an axis $O_1$-$O_1$ with respect to a driver 611. While an arbitrary structure may be used for the multi-node arm, the multi-node arm in this embodiment has three parts which are pivotably attached to each other. One part of the arm 612 of the first carrier unit 61, i.e., the first part closest to the driver 611 is attached to a rotatable shaft 613 by a driving mechanism (not shown) of a known structure, disposed within the driver 611. The arm 612 is pivotable about the axis $O_1$-$O_1$ by means of the shaft 613, and radially telescopic as a whole with respect to the axis $O_1$-$O_1$ through relative rotations among the parts. At a leading end of the third part of the arm 612 furthest away from the shaft 613, a grabber 616 in a known structure for grabbing a wafer, such as a mechanical chuck or an electrostatic chuck, is disposed. The driver 611 is movable in the vertical direction by an elevating mechanism 615 of a known structure.

The first carrier unit 61 extends the arm 612 in either a direction M1 or a direction M2 within two cassettes c held in the cassette holder 10, and removes a wafer accommodated in a cassette c by carrying the wafer on the arm or by grabbing the wafer with the chuck (not shown) attached at the leading end of the arm. Subsequently, the arm is retracted (in a state as illustrated in FIG. 6(a)), and then rotated to a position at which the arm can extend in a direction M3 toward the prealigner 25, and stopped at this position. Then, the arm is again extended to transfer the wafer held on the arm to the prealigner 25. After receiving a wafer from the prealigner 25, contrary to the foregoing, the arm is further rotated and stopped at a position at which it can extend to the second loading chamber 41 (in the direction M4), and transfers the wafer to a wafer receiver 47 within the second loading chamber 41.

For mechanically grabbing a wafer, the wafer should be grabbed on a peripheral region (in a range of approximately 5 mm from the peripheral edge). This is because the wafer is formed with devices (circuit patterns) over the entire surface except for the peripheral region, and grabbing the inner region would result in failed or defective devices.

The second carrier unit 63 is basically identical to the first carrier unit 61 in structure except that the second carrier unit 63 carries a wafer between the wafer rack 47 and the carrying surface of the stage device 50, so that detailed description thereon is omitted.

In the loader 60, the first and second carrier units 61, 63 each carry a wafer from a cassette held in the cassette holder 10 to the stage device 50 disposed in the working chamber 31 and vice versa, while remaining substantially in a horizontal state. The arms of the carrier units are moved in the vertical direction only when a wafer is removed from and inserted into a cassette, when a wafer is carried on and removed from the wafer rack, and when a wafer is carried on and removed from the stage device 50. It is therefore possible to smoothly carry a larger wafer, for example, a wafer having a diameter of 30 cm.

Next, how a wafer is carried will be described in sequence from the cassette c held by the cassette holder 10 to the stage device 50 disposed in the working chamber 31.

As described above, when the cassette is manually set, the cassette holder 10 having a structure adapted to the manual setting is used, and when the cassette is automatically set, the cassette holder 10 having a structure adapted to the automatic setting is used. In this embodiment, as the cassette c is set on the up/down table 11 of the cassette holder 10, the up/down table 11 is moved down by the elevating mechanism 12 to align the cassette c with the access port 225.

As the cassette is aligned with the access port 225, a cover (not shown) provided for the cassette is opened, and a cylindrical cover is applied between the cassette c and the access port 225 of the mini-environment to block the cassette and the mini-environment space 21 from the outside. Since these structures are known, detailed description on their structures and operations is omitted. When the mini-environment device 20 is provided with a shutter for opening and closing the access port 225, the shutter is operated to open the access port 225.

On the other hand, the arm 612 of the first carrier unit 61 remains oriented in either the direction M1 or M2 (in the direction M1 in this description). As the access port 225 is opened, the arm 612 extends to receive one of wafers accommodated in the cassette at the leading end. While the arm and a wafer to be removed from the cassette are adjusted in the vertical position by moving up or down the driver 611 of the first carrier unit 61 and the arm 612 in this embodiment, the adjustment may be made by moving up and down the up/down table 11 of the cassette holder 10, or made by both.

As the arm 612 has received the wafer, the arm 621 is retracted, and the shutter is operated to close the access port (when the shutter is provided). Next, the arm 612 is pivoted about the axis $O_1$-$O_1$ such that it can extend in the direction M3. Then, the arm 612 is extended and transfers the wafer carried at the leading end or grabbed by the chuck onto the prealigner 25 which aligns the orientation of the rotating direction of the wafer (the direction about the central axis vertical to the wafer plane) within a predetermined range. Upon completion of the alignment, the carrier unit 61 retracts the arm 612 after a wafer has been received from the prealigner 25 to the leading end of the arm 612, and takes a posture in which the arm 612 can be extended in a direction M4. Then, the door 272 of the shutter device 27 is moved to open the access ports 223, 236, and the arm 612 is extended to place the wafer on the upper stage or the lower stage of the wafer rack 47 within the first loading chamber 41. It should be noted that before the shutter device 27 opens the access ports to transfer the wafer to the wafer rack 47, the opening 435 formed through the partition wall 434 is closed by the door 461 of the shutter 46 in an air-tight state.

In the process of carrying a wafer by the first carrier unit, clean air flows (as downflow) in laminar flow from the gas supply unit 231 disposed on the housing of the mini-environment chamber to prevent dust from attaching on the upper surface of the wafer during the carriage. A portion of the air near the carrier unit (in this embodiment, about 20% of the air supplied from the supply unit 231, mainly contaminated air) is aspirated from the suction duct 241 of the discharger 24 and discharged outside the housing. The remaining air is recovered through the recovery duct 232 disposed on the bottom of the housing and returned again to the gas supply unit 231.

As the wafer is placed into the wafer rack 47 within the first loading chamber 41 of the loader housing 40 by the first carrier unit 61, the shutter device 27 is closed to seal the loading chamber 41. Then, the first loading chamber 41 is filled with an inert gas to expel air. Subsequently, the inert gas is also discharged so that a vacuum atmosphere dominates within the loading chamber 41. The vacuum atmosphere within the loading chamber 41 may be at a low vacuum degree. When a certain degree of vacuum is provided within the loading chamber 41, the shutter 46 is operated to open the access port 434 which has been sealed by the door 461, and the arm 632 of the second carrier unit 63 is extended to receive one wafer from the wafer receiver 47 with the grabber at the leading end (the wafer is carried on the leading end or grabbed by the chuck attached to the leading end). Upon completion of the receipt of the wafer, the arm 632 is retracted, followed by the shutter 46 again operated to close the access port 435 by the door 461.

It should be noted that the arm 632 has previously taken a posture in which it can extend in the direction N1 of the wafer rack 47 before the shutter 46 is operated to open the access port 435. Also, as described above, the access ports 437, 325 have been closed by the door 452 of the shutter 45 before the shutter 46 is operated to block the communication between the second loading chamber 42 and the working chamber 31 in an air-tight state, so that the second loading chamber 42 is evacuated.

As the shutter 46 is operated to close the access port 435, the second loading chamber 42 is again evacuated at a higher degree of vacuum than the first loading chamber 41. Meanwhile, the arm 632 of the second carrier unit 63 is rotated to a position at which it can extend toward the stage device 50 within the working chamber 31. On the other hand, in the stage device 50 within the working chamber 31, the Y-table 52 is moved upward, as viewed in FIG. 6(*a*), to a position at which the center line $O_0$-$O_0$ of the X-table 53 substantially matches an X-axis $X_1$-$X_1$ which passes a pivotal axis $O_2$-$O_2$ of the second carrier unit 63. The X-table 53 in turn is moved to the position closest to the leftmost position in FIG. 6(*a*), and remains awaiting at this position.

When the second loading chamber 42 is evacuated to substantially the same degree of vacuum as the working chamber 31, the door 452 of the shutter 45 is moved to open the access ports 437, 325, allowing the arm 632 to extend so that the leading end of the arm 632, which holds a wafer, approaches the stage device 50 within the working chamber 31. Then, the wafer is placed on the carrying surface 551 of the stage device 50. As the wafer has been placed on the carrying surface 551, the arm 632 is retracted, followed by the gate 45 operated to close the access ports 437, 325.

The foregoing description has been made on the operation until a wafer in the cassette c is carried and placed on the stage device 50. For returning a wafer, which has been carried on the stage device 50 and processed, from the stage device 50 to the cassette c, the operation reverse to the foregoing is performed. Since a plurality of wafers are stored in the wafer rack 47, the first carrier unit 61 can carry a wafer between the cassette and the wafer rack 47 while the second carrier unit 63 is carrying a wafer between the wafer rack 47 and the stage device 50, so that the testing operation can be efficiently carried out.

Specifically, if a wafer A and a wafer B, both processed already, are placed on the wafer rack 47 of the second carrier unit, the wafer B not processed is moved to the stage device 50 and a process starts. In the middle of the process, the processed wafer A is moved to the wafer rack 47 from the stage device 50. A unprocessed wafer C is likewise extracted from the wafer rack 47 by the arm and is aligned by the prealighner. Then, the wafer C is moved to the wafer rack 47 of the loading chamber 41. By doing so, it is possible to replace the wafer A with the unprocessed wafer C in the wafer rack 47 during the wafer B is being processed.

Depending upon how such an apparatus for performing a test or evaluation is utilized, a plurality of the stage devices 50 can be disposed causing a wafer to be transferred from one wafer rack 47 to each stage device, making it possible to process a plurality of wafers in a similar manner.

FIG. 10 illustrates an exemplary modification to the method of supporting the main housing. In an exemplary modification illustrated in FIG. 10[A], a housing supporting device 33a is made of a thick rectangular steel plate 331a, and a housing body 32a is carried on the steel plate. Therefore, the bottom wall 321a of the housing body 32a is thinner than the bottom wall 222 of the housing body 32 in the foregoing embodiment.

In an exemplary modification illustrated in FIG. 10[B], a housing body 32b and a loader housing 40b are suspended by a frame structure 336b of a housing supporting device 33b. Lower ends of a plurality of vertical frames 337b fixed to the frame structure 336b are fixed to four corners of a bottom wall 321b of the housing body 32b, such that the peripheral wall and the top wall are supported by the bottom wall. A vibration isolator 37b is disposed between the frame structure 336b and a base frame 36b. Likewise, the loader housing 40 is suspended by a suspending member 49b fixed to the frame structure 336. In the exemplary modification of the housing body 32b illustrated in FIG. 10[B], the housing body 32b is supported in suspension, the general center of gravity of the main housing and a variety of devices disposed therein can be brought downward. The methods of supporting the main housing and the loader housing, including the exemplary modifications described above, are configured to prevent vibrations from being transmitted from the floor to the main housing and the loader housing.

In another exemplary modification, not shown, the housing body of the main housing is only supported by the housing supporting device from below, while the loader housing may be placed on the floor in the same way as the adjacent mini-environment chamber. Alternatively, in a further exemplary modification, not shown, the housing body of the main housing is only supported by the frame structure in suspension, while the loader housing may be placed on the floor in the same way as the adjacent mini-environment device.

Figure 11:
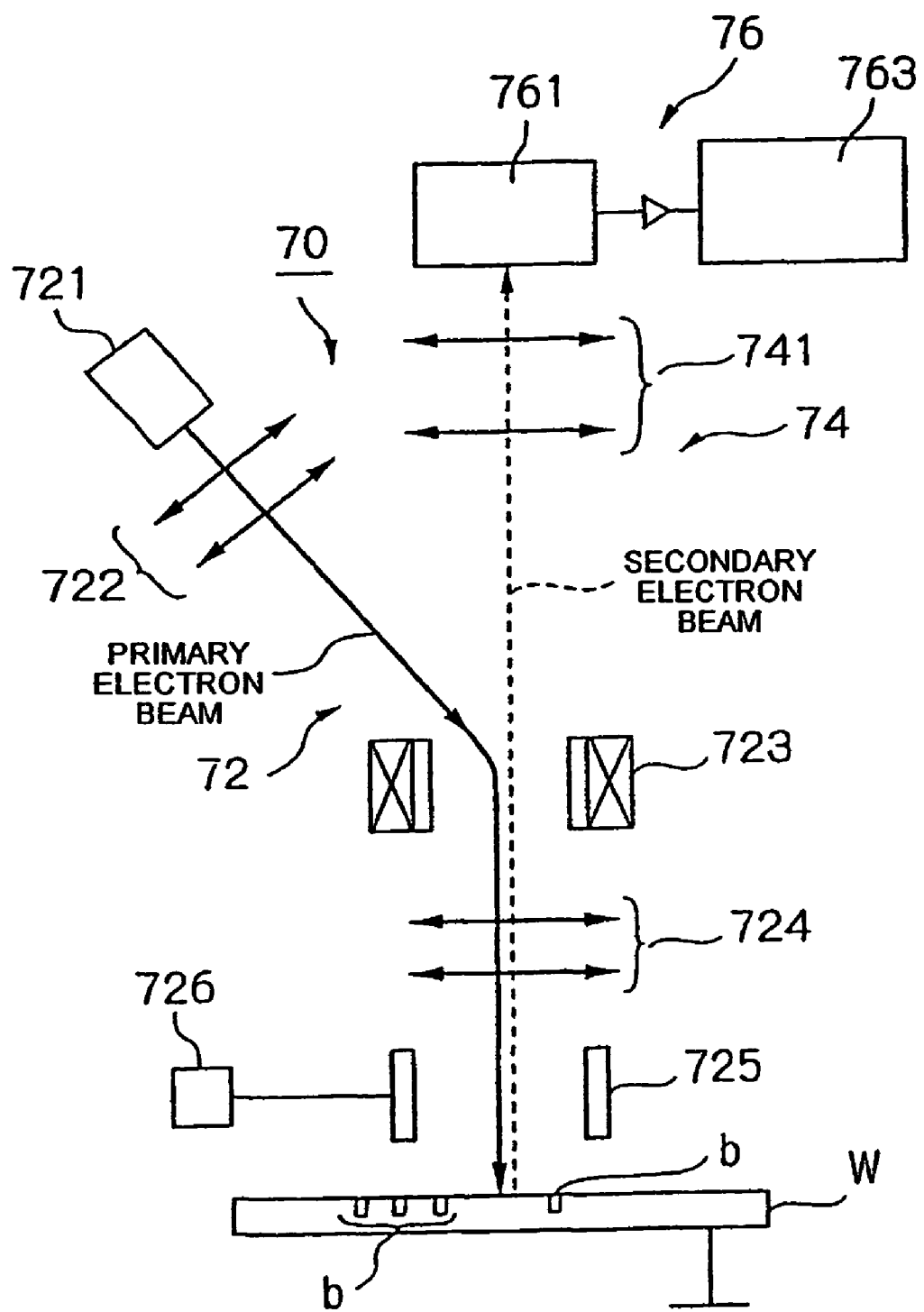
FIG. 11 is a schematic diagram illustrating a general configuration of an electron-optical device in the testing apparatus of FIG. 5.

The electron-optical device 70 comprises a column 71 fixed on the housing body 32. Disposed within the column 71 are an electron-optical system comprised of a primary electron-optical system (hereinafter simply called the "primary optical system") 72 and a secondary electron-optical system (hereinafter simply called the "secondary optical system") 74, and a detecting system 76, as illustrated generally in FIG. 11. The primary optical system 72, which is an optical system for irradiating the surface of a wafer W under testing with an electron beam, comprises an electron gun 721 for emitting an electron beam; a lens system 722 comprised of electrostatic lenses for converging a primary electron beam emitted from the electron gun 721; a Wien filter (i.e., an ExB separator or an ExB filter) 723; and an objective lens system 724. These components are arranged in order with the electron gun 721 placed at the top, as illustrated in FIG. 11. The lenses constituting the objective lens system 724 in this embodiment are deceleration electric field type objective lenses. In this embodiment, the optical axis of the primary electron beam emitted from the electron gun 721 is oblique to the optical axis of irradiation along which the wafer W under testing is irradiated with the electron beam (vertical to the surface of the wafer). Electrodes 725 are disposed between the objective lens system 724 and the wafer W under testing. The electrodes 27 are axially symmetric about the optical axis of irradiation of the primary electron beam, and controlled in voltage by a power supply 726.

The secondary optical system 74 comprises a lens system 741 comprised of electrostatic lenses which pass secondary electrons separated from the primary optical system by an ExB deflector 723. This lens system 741 functions as a magnifier for enlarging a secondary electron image.

The detecting system 76 comprises a detector 761 and a detector 763 which are disposed on a focal plane of the lens system 741.

Next, the operation of the electron-optical device 70 configured as described above will be described.

The primary electron beam emitted from the electron gun 721 is converged by the lens system 722. The converged primary electron beam impinges on the ExB deflector 723, is deflected so that it is irradiated vertical to the surface of the wafer W, and focused on the surface of the wafer W by the objective lens system 724.

The secondary electrons emitted from the wafer by the irradiation of the primary electron beam are accelerated by the objective lens system 724, impinge on the ExB deflector 723, travels straight through the deflector 723, and are lead to the detector 761 by the lens system 741 of the secondary optical system. Then, the secondary electrons are detected by the detector 761 which generates a detection signal to an image processing unit 763.

Assume in this embodiment that the objective lens system 724 is applied with a high voltage in a range of 10 to 20 kV, and a wafer has been prepared in place.

Here, when the electrodes 725 are applied with a voltage of −200 V if the wafer W includes a via b, an electric field of 0 to −0.1 V/mm ("−" indicates that the wafer W has a higher potential) is produced on the surface of the wafer W irradiated with the electron beam. In this state, although the wafer W can be tested for defects without causing a discharge between the objective lens system 724 and the wafer W, a slight degradation is experienced in the efficiency of detecting the secondary electrons. Therefore, a sequence of operations involving irradiating the electron beam and detecting the secondary electrons is performed, for example, four times, such that the results of the four detections are applied with processing such as accumulative addition, averaging and so on to obtain a predetermined detection sensitivity.

On the other hand, when the wafer is free from the via b, no discharge is caused between the objective lens system 724 and the wafer even if the electrodes 725 are applied with a voltage of +350, so that the wafer W can be tested for defects. In this event, since the secondary electrons are converged by the voltage applied to the electrodes 725 and further converged by the objective lens 724, the detector 761 has an improved efficiency of detecting the secondary electrons. Consequently, the processing as the wafer defect detector is performed at a higher speed, so that the testing can be made at a higher throughput.

The precharge unit 81, as illustrated in FIG. 5, is disposed adjacent to the barrel 71 of the electron-optical device 70 within the working chamber 31. Since this testing apparatus is configured to test a substrate or a wafer under testing for device patterns or the like formed on the surface thereof by irradiating the wafer with an electron beam, so that the secondary electrons emitted by the irradiation of the electron beam are used as information on the surface of the wafer. However, the surface of the wafer may be charged up depending on conditions such as the wafer material, energy of the irradiated electrons, and so on. Further, even on the surface of a single wafer, some region may be highly charged, while another region may be lowly charged. Variations in the amount of charge on the surface of the wafer would cause corresponding variations in information provided by the resulting secondary electrons, thereby failing to acquire correct information.

For preventing such variations, in this embodiment, the precharge unit 81 is provided with a charged particle irradiating unit 811. Before testing electrons are irradiated to a predetermined region on a wafer under testing, charged particles are irradiated from the charged particle irradiating unit 811 of the precharge unit 81 to eliminate variations in charge. The charges on the surface of the wafer previously form an image of the surface of the wafer under testing, which image is evaluated to detect possible variations in charge to operate the precharge unit 81 based on the detection.

Alternatively, the precharge unit 81 may irradiate a blurred primary electron beam.

Figure 12:
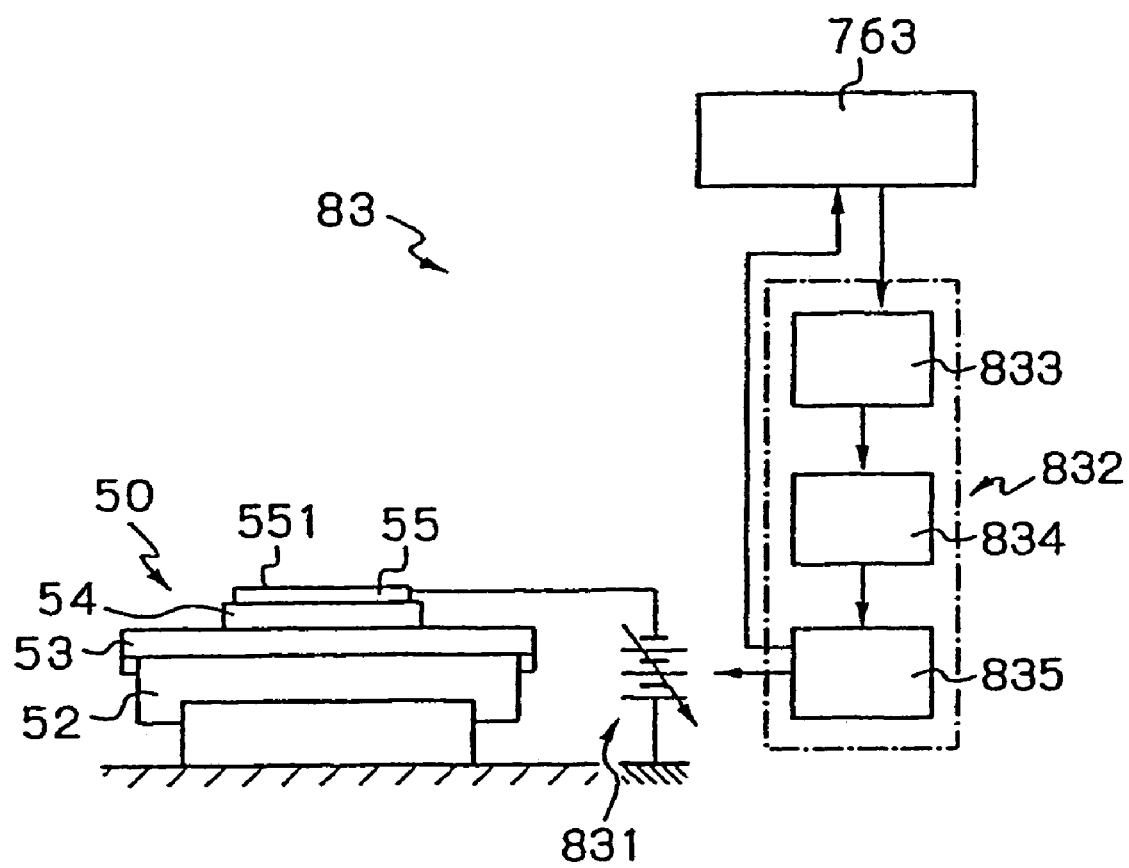
FIG. 12 is a diagram illustrating a potential applying mechanism.
Figure 14:
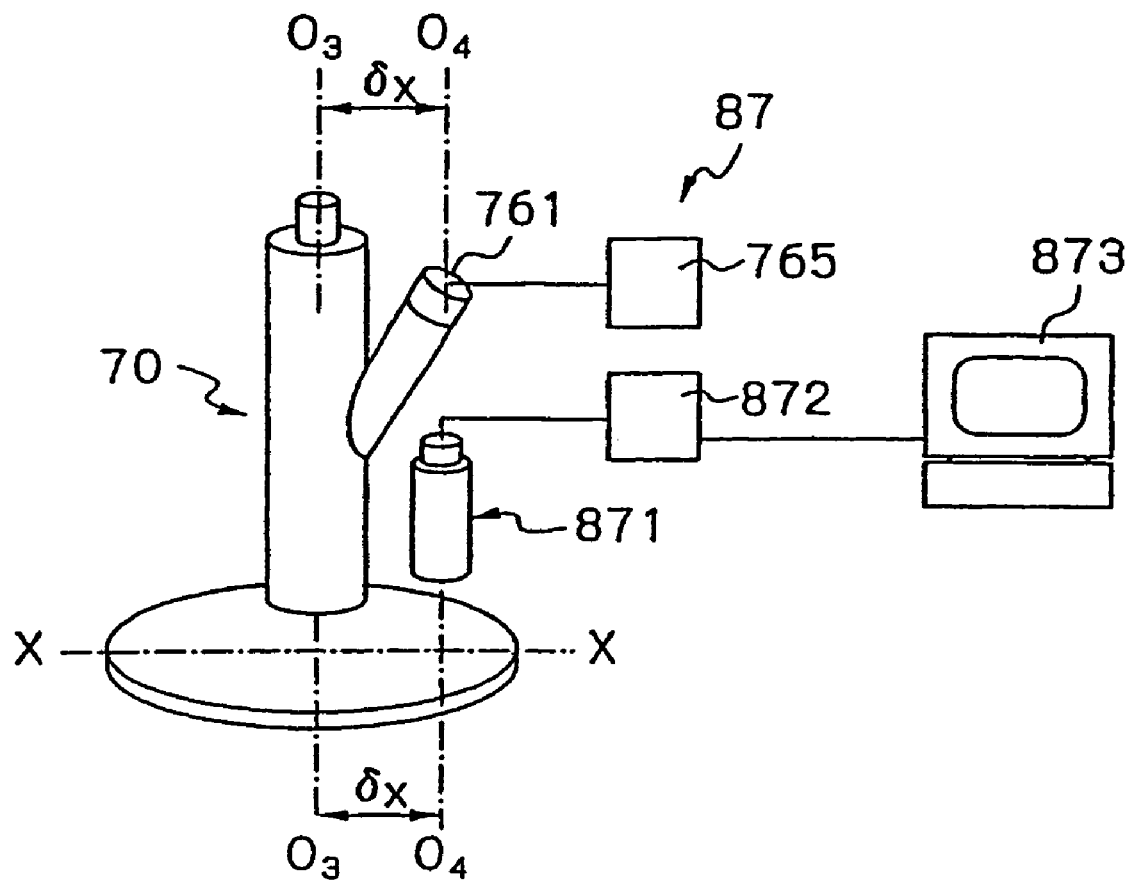
FIG. 14 is a schematic explanatory view of a wafer alignment controller.

Referring next to FIG. 12, the potential applying mechanism 83 applies a potential of ±several volts to a carrier of a stage, on which the wafer is placed, to control the generation of secondary electrons based on the fact that the information on the secondary electrons emitted from the wafer (secondary electron generating rate) depend on the potential on the wafer. The potential applying mechanism 83 also serves to decelerate the energy originally possessed by irradiated electrons to provide the wafer with irradiated electron energy of approximately 100 to 500 eV.

As illustrated in FIG. 12, the potential applying mechanism 83 comprises a voltage applying device 831 electrically connected to the carrying surface 541 of the stage device 50; and a charging examining/voltage determining system (hereinafter examining/determining system) 832. The examining/determining system 832 comprises a monitor 833 electrically connected to an image forming unit 763 of the detecting system 76 in the electron-optical device 70; an operator 834 connected to the monitor 833; and a CPU 835 connected to the operator 834. The CPU 835 supplies a signal to the voltage applying device 831.

The potential applying mechanism 83 is designed to find a potential at which the wafer under testing is hardly charged, and to apply such potential to the carrying surface 541.

Referring next to FIG. 13, the electron beam calibration mechanism 85 comprises a plurality of Faraday cups 851, 852 for measuring a beam current, disposed at a plurality of positions in a lateral region of the wafer carrying surface 541 on the turntable 54. The Faraday cups 851 are provided for a narrow beam (approximately φ2 μm), while the Faraday cups 852 for a wide beam (approximately φ30 μm). The Faraday cuts 851 for a narrow beam measure a beam profile by driving the turntable 54 step by step, while the Faraday cups 852 for a wide beam measure a total amount of currents. The Faraday cups 851, 852 are mounted on the wafer carrying surface 541 such that their top surfaces are coplanar with the upper surface of the wafer W carried on the carrying surface 541. In this way, the primary electron beam emitted from the electron gun 721 is monitored at all times. This is because the electron gun 721 cannot emit a constant electron beam at all times but varies in the emission current as it is used over time.

The alignment controller 87, which aligns the wafer W with the electron-optical device 70 using the stage device 50, performs the control for rough alignment through wide field observation using the optical microscope 871 (a measurement with a lower magnification than a measurement made by the electron-optical system); high magnification alignment using the electron-optical system of the electron-optical device 70; focus adjustment; testing region setting; pattern alignment; and so on. The wafer is tested at a low magnification using the optical system in this way because an alignment mark must be readily detected by an electron beam when the wafer is aligned by observing patterns on the wafer in a narrow field using the electron beam for automatically testing the wafer for patterns thereon.

The optical microscope 871 is disposed on the housing 30 (alternatively, may be movably disposed within the housing 30), with a light source, not shown, being additionally disposed within the housing 30 for operating the optical microscope. The electron-optical system for observing the wafer at a high magnification shares the electron-optical systems (primary optical system 72 and secondary optical system 74) of the electron-optical device 70. The configuration may be generally illustrated in FIG. 12. For observing a point of interest on a wafer at a low magnification, the X-stage 53 of the stage device 50 is moved in the X-direction to move the point of interest on the wafer into a view field of the optical microscope 871. The wafer is viewed in a wide field by the optical microscope 871, and the point of interest on the wafer to be observed is displayed on a monitor 873 through a CCD 872 to roughly determine a position to be observed. In this event, the magnification of the optical microscope may be changed from a low magnification to a high magnification.

Next, the stage device 50 is moved by a distance corresponding to a spacing δx between the optical axis of the electron-optical device 70 and the optical axis of the optical microscope 871 to move the point on the wafer under observation, previously determined by the optical microscope 871, to a point in the view field of the electron-optical device 70. In this event, since the distance δx between the axis $O_3$-$O_3$ of the electron-optical device and the axis $O_4$-$O_4$ of the optical microscope 871 is previously known (while it is assumed that the electron-optical device 70 is deviated from the optical microscope 871 in the direction along the X-axis in this embodiment, they may be deviated in the Y-axis direction as well as in the X-axis direction), the point under observation can be moved to the viewing position by moving the stage device 50 by the distance δx. After the point under observation has been moved to the viewing position of the electron-optical device 70, the point under observation is imaged by the electron-optical system at a high magnification for storing a resulting image or displaying the image on the monitor 765 through the CCD 761.

After the point under observation on the wafer imaged by the electron-optical system at a high magnification is displayed on the monitor 765, misalignment of the stage device 50 with respect to the center of rotation of the turntable 54 in the wafer rotating direction, and misalignment δθ of the stage device 50 with respect to the optical axis $O_3$-$O_3$ of the electron-optical system in the wafer rotating direction are detected in a known method, and misalignment of a predetermined pattern with respect to the electron-optical device in the X-axis and Y-axis is also detected. Then, the operation of the stage device 50 is controlled to align the wafer based on the detected values and data on a testing mark attached on the wafer or data on the shape of the patterns on the wafer which have been acquired in separation.

The testing apparatus as described with reference to FIGS. 5 to 14, used in the wafer testing process (G) in the device manufacturing method described with reference to FIGS. 3 and 4(*a*) and 4(*b*), can detect semiconductor devices having fine patterns with high throughput, thereby enabling all wafers to be tested, the yield rate of the products to be improved and defective products to be prevented from being shipped. In this regards, the description made with reference to FIGS. 3, 4(*a*) and 4(*b*) is incorporated herewith by reference and is omitted here accordingly.

Embodiment Relating to Column (Third Embodiment)

Now, an electron beam apparatus, which is a third embodiment of the electron beam apparatus according to the present invention, will be described with reference to FIG. 15. This electron beam apparatus is suitable for evaluating and testing samples such as wafers, masks and so on which have patterns with a minimum line width of 0.1 micron or less at a high throughput and high reliability, and can be used for manufacturing of devices.

An electron beam apparatus using multi-beams is already known. For example, a known electron beam apparatus emits one or more electron beams converged to a predetermined diameter from an electron beam source which is focused on the surface of a sample under testing, moves the sample under testing to scan the electron beams on the surface of the sample under testing, detects secondary electron beams emitted from the sample under testing and reflected electron beams using a plurality of detecting devices, and simultaneously or parallelly processes outputs of the detecting devices to reduce a time required for evaluating miniature patterns.

Also, a known miniature pattern evaluation apparatus irradiates a sample under testing with a plurality of primary electron beams, detects secondary electron beams emitted as the result and reflected electron beams for each primary electron beam, and adjusts voltages on electrodes and excitation currents for each primary electron beam, in order to eliminate variations in the spot shapes of electron beams emitted from a plurality of electron beam sources to improve the precision of the evaluation on miniature patterns.

In such a multi-beam based electron beam apparatus, the electron beam source section requires a different degree of vacuum from a lens/deflection system. For example, in a multi-emitter or thermal field emission type electron beam source, a safe operation is not ensured unless the degree of vacuum higher than $10^{-8}$ torr is provided near a cathode of the electron beam source, while the lens/deflection system can sufficiently operate if the degree of vacuum on the order of $10^{-6}$ torr is achieved even in case an electrostatic lens and an electrostatic deflector are used. There is therefore a problem that a predetermined degree of vacuum must be maintained for each component of the electron beam apparatus.

Also, since an extremely large number of ions exist on the optical axis of the electron beam within a column of an electron microscope, another problem is that positive ions collide with the cathode of the electron beam source to perforate the cathode. Further, actually, no clear solution has been given to a problem of how respective columns are fixed when a multi-beam and multi-column electron beam apparatus is to be manufactured.

Figure 15:
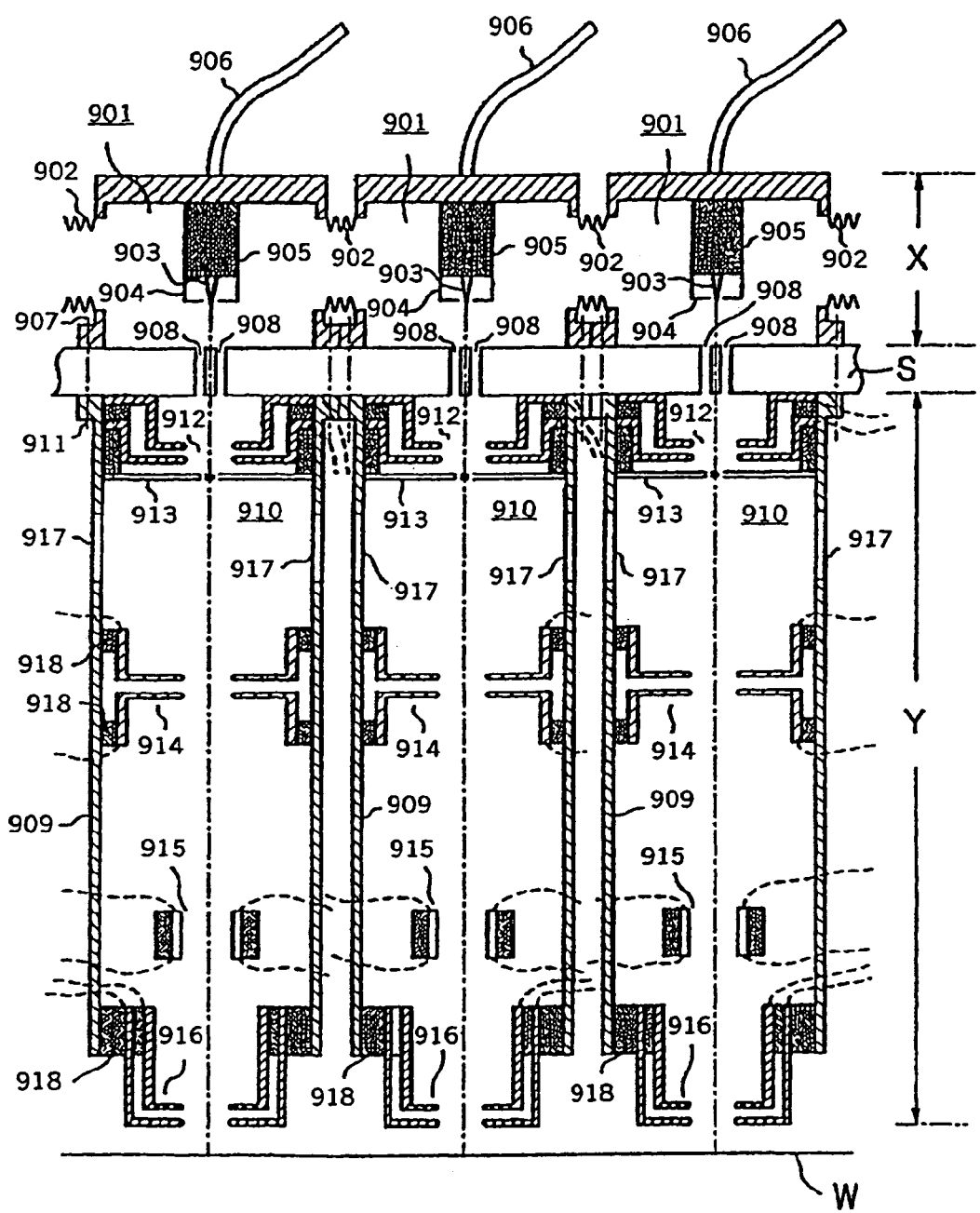
FIG. 15 is a cross-sectional view generally illustrating a third embodiment of the charged electron beam apparatus according to the present invention.

An electron beam apparatus illustrated in FIG. 15, which has been proposed to solve the problems mentioned above, is characterized by holding a high degree of vacuum in an electron beam source section even when the degree of vacuum is low in a lens/deflection system, thereby preventing damages of the cathode of the electron beam source and making itself resistant to vibrations.

In FIG. 15, the electron beam apparatus has a multi-beam/multi-column structure, wherein an electron beam source section X and an electron-optical system Y are separated by a thick partition wall S which has both ends fixed to a column (not shown). The electron beam source section X comprises a plurality of electron beam source chambers 901, each in a cylindrical shape, mutually coupled by a bellows 902. Each of the electron beam source chambers 901 comprises a thermal field emission type electron beam source 905 which is comprised of a TFE cathode 903 and a Schottky shield 904. Each of the electron beam sources 905 is powered through a high voltage cable 906, and emits an electron beam from the TFE cathode 903. TFE is an acronym of thermal field emission.

Each of the electron beam source chamber 901 is fixed to the partition wall S with a screw 907. Therefore, the partition wall S needs to have a predetermined thickness to have a sufficient rigidity. If the partition wall S is not sufficient in rigidity, a reinforcing rib is desirably disposed between adjacent electron beam source chambers 901. Each of the electron beam source chambers 901 is connected to an ion pump (not shown) for evacuation.

The partition wall S is formed with a predetermined number, for example, four of holes 908 on a circumference about the optical axis of the electron beam source 905 of each electron beam source chamber 901 such that electron beams emitted from surfaces of tungsten <301> or <100> orientation surface of the TFE cathode 3 in the respective electron beam sources 905 can fully pass through the partition wall S. These holes 908 each have a large aspect ratio (ratio of the diameter of the hole to the length of the hole) so as not to deteriorate the degree of vacuum in the electron beam source chamber, and is formed to have a larger diameter as it is further away from the TFE cathode 903. Alternatively, each of the holes 908 may be obliquely formed in a direction away from the optical axis at a lower location. Generally, the aspect ratio may preferably be 10 or more.

On the other hand, the electron-optical system Y has a lens/deflection system 910 arranged corresponding to each of the electron beam source chambers 901 in order to reshape each of electron beams emitted from the plurality of electron beam source chambers 901 such that a sample W such as a wafer is irradiated with the plurality of electron beams. Each of the lens/deflection system 910 comprises an elongated pipe 909 fixed to the partition wall S with a screw 911 so as to surround, for example, the four holes 908 which allow electron beams from corresponding electron beam sources 905 to pass therethrough. In each of the pipes 909, a required lens and deflector are arranged for reshaping electron beams, which have passed through, for example, the four holes 908 of the partition wall S, and for directing them perpendicular to the sample W. In this way, the multi-column electron-optical system Y is configured.

Thus, each lens/deflection system 910 has, within the pipe 909, a condenser lens 912, a multi-aperture plate 913, a reduction lens 914, a deflector 915 and an objective lens 916 arranged in order. The condenser lenses 912 converge electron beams which have passed through the respective holes 908 formed through the partition wall S. The multi-aperture plates 913 comprise a number of small holes equal to the holes 908 in the portion of the partition wall S surrounded by the pipe 909 so as to pass therethrough the electron beams converged by the condenser lenses 912. The reduction lenses 914 reduce the dimension and interval of the electron beams, which have passed through the multi-aperture plate 913, so that they pass through the deflectors 915. The deflector 915 changes the direction in which the electron beam travels such that the electron beam reduced by the reduction lens 914 scans on the sample. The objective lens 916 focuses the electron beam passing through the deflector 915 on the sample W.

Each of the pipes 909 is provided with an exhaust hole 917 through which the interior of each pipe 909 is held at a vacuum by a pump for maintaining the interior of the column (not shown), which houses the partition wall S, electron beam source section Y and electron-optical system Y at a vacuum. Also, the condenser lens 912, multi-aperture plate 913, reduction lens 914, deflector 915 and objective lens 916 are applied with required voltages through lead lines illustrated by dotted lines in FIG. 15. The condenser lens 912, multi-aperture plate 913, reduction lens 914, deflector 915 and objective lens 916 are attached on the inner wall of the pipe 909 through an insulating spacer 918, as required.

The electron beam apparatus illustrated in FIG. 15 can be used in the testing process (G) described with reference to FIG. 3 and FIGS. 4(a), 4(b) as an evaluation apparatus for testing for defects, measurement of line widths, measurement of alignment precision, measurement of potential contrast, defect review, or strobe SEM in order to evaluate a wafer in the middle of the process. In this regard, the description related to FIG. 3 and FIGS. 4(a), 4(b) is incorporated herewith by reference and is omitted here accordingly.

Embodiment Relating to Structure of Electrodes
(Fourth Embodiment)

A fourth embodiment of the present invention relates to an electron beam apparatus which comprises an electrode structure for preventing the breakdown in an electron-optical system which uses an electrostatic lens for irradiating a sample with an electron beam, and a device manufacturing method using this apparatus.

Up to now, studies have been made for applying a high sensitivity, high resolution electron beam apparatus which utilizes electron beams in order to test a surface state of a fine pattern for which optical testing alone cannot be relied on to provide sufficient sensitivity and resolution.

Such an electron beam apparatus emits an electron beam from an electron beam source, accelerates and converges the emitted electron beam by an electrostatic optical system such as an electrostatic lens, and directs the electron beam to a sample or an object under testing. Next, a secondary electron beam emitted from the sample by the incident electron beam is detected to generate a signal corresponding to the detected secondary electron beam, and data on the sample, for example, is formed from this signal. The surface state of the sample is tested using the formed data.

In an electron-optical system using an electrostatic lens such as an electrostatic lens for use in such an electron beam apparatus, electrodes for generating an electric field for accelerating or converging an electron beam are arranged in the direction of the optical axis of the electron beam at multiple stages. These electrodes are each applied with a predetermined voltage, such that the electron beam is accelerated or converged at a predetermined point on the optical axis by the electric field generated due to a difference in potential on the electrodes.

In a conventional electron beam apparatus, a portion of electron beams emitted from an electron beam source may collide with electrodes irrespective of an electric field in an electron-optical system using an electrostatic lens. In this event, the electron beams collide with electrodes to emit secondary electron beams from the electrodes themselves. The amount of secondary electron beams emitted from the electrodes depends on the material of the electrodes or a material coated on the electrodes. As a larger number of secondary electron beams are emitted from the electrodes, the secondary electron beams are accelerated by the electric field of the electrodes to ionize a residual gas within the apparatus. Then, the ions collide with the electrodes, causing further secondary electron beams to be emitted from the electrodes. Therefore, as a large amount of secondary electron beams are emitted, a discharge is more likely to occur between electrodes, resulting in an increased probability of breakdown between electrodes.

For example, comparing the probability of breakdown between an electrode coated with aluminum and an electrode coated with gold, the probability of breakdown is slightly higher with the aluminum coated electrode. Aluminum has a work function of 4.2 [eV], while gold has a work function of 4.9 [eV]. Here, the work function refers to minimum energy required to draw out one electron within the metal into a vacuum (unit: eV).

Also, when an electrode is coated with gold, and a sample in the electron beam apparatus is a semiconductor wafer, the gold is sputtered by electron beams colliding with the coated gold, resulting in the gold attached on the surface of the semiconductor wafer. The gold attached on the surface of the semiconductor would be diffused into silicon crystals in subsequent thermal processes, resulting in deteriorated performance of transistors. Therefore, in this case, the electron beam apparatus is not suitable for testing a semiconductor wafer.

On the other hand, in an electrostatic lens, for example, of an electron-optical system using the electrostatic lens, the distance between electrodes is reduced to provide an electrostatic lens with a short focal distance. A shorter focal distance reduces an aberration coefficient of the electrostatic lens and is of low aberration, with the result that the electrostatic lens has a high resolution and that the evaluation apparatus is improved in resolution.

Alternatively, an electrostatic lens with a short focal distance can be provided by increasing potential differences applied between electrodes of the electrostatic lens. Thus, as is the case of reducing the distance between electrodes, the electrostatic lens exhibits low aberration and high resolution, so that the electron beam apparatus is improved in resolution. As such, with a reduced distance between electrodes and larger potential differences between electrodes, the electrostatic lens can be synergistically provided with lower aberration and higher resolution. However, a shorter distance between electrodes and a larger potential difference between the electrodes would result in a problem of higher susceptibility to a discharge between the electrodes and an increased probability of breakdown between the electrodes.

Conventionally, an insulating material is inserted between electrodes which are supported by the insulating material, to hold insulation between the electrodes. Also, the insulating performance on the surface of the insulating material is improved by increasing a minimum creeping distance (insulating surface length) of the insulating material between the electrodes. For example, the minimum creeping distance between electrodes is increased, for example, by forming the surface of an insulating material in the shape of crimps in the direction along the electrodes.

However, the surface of an insulating material is generally difficult in working as compared with a metal, so that the working cost becomes higher. Also, the surface of the insulating material formed in a crimp shape or the like results in a larger surface area of the insulating area, so that gases emitted from the insulating material may increase when a vacuum is held in the electron beam apparatus. Therefore, in many cases, the degree of vacuum is reduced, resulting in a lower resistance voltage between electrodes on the contrary.

The fourth embodiment of the present invention has been proposed to solve such problems. In the following, the configuration and operation of a projection type evaluation apparatus having an electrostatic optical system, and a device manufacturing method using the apparatus will be described for the case where the projection type evaluation apparatus is applied with the electron beam apparatus which is capable of preventing the breakdown between electrodes in the electrostatic optical system according to the present invention.

Figures 16, 17:
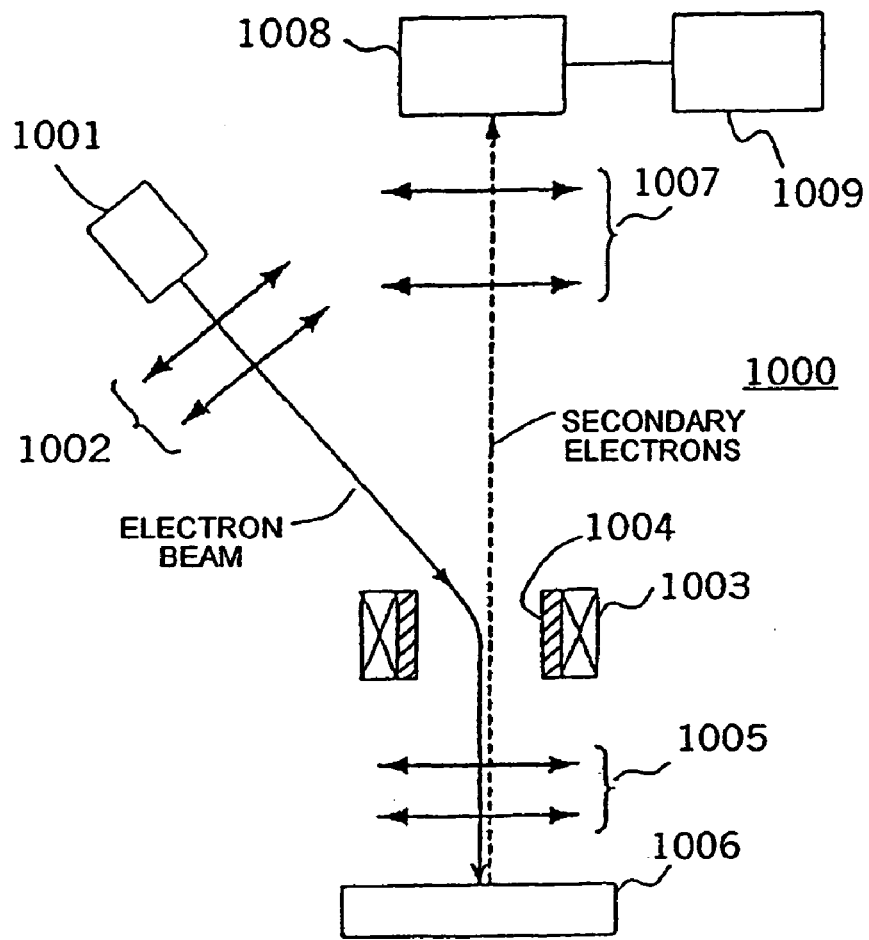
FIG. 16 is a configuration diagram schematically illustrating an evaluation apparatus which is a fourth embodiment of the charged electron beam apparatus according to the present invention.
FIG. 17 is a table showing a breakdown occurrence probability for each metal.

In FIG. 16, in a projection type evaluation apparatus 1000, an electron beam irradiated to a sample has a predetermined irradiation face, and a secondary electron beam radiated from the sample irradiated with the electron beam also has a predetermined radiation face. From an electron beam source 1001, an electron beam having a two-dimensional region, for example, a rectangular radiation face is irradiated and deflected by an electrostatic lens system 1002 in a predetermined direction. The deflected electron beam is directed to an ExB deflector 1003 diagonally from above, and is deflected in the direction of a semiconductor wafer 1006, which is a sample, by a field in which an electric and magnetic field of the ExB deflector 1003 are produced orthogonal to each other (a solid line in FIG. 16).

The electron beam deflected toward the semiconductor wafer 1006 by the ExB deflector 1003 is decelerated by an electric field generated by voltages applied to electrodes within the electrostatic objective lens system 1005, and focused on the semiconductor wafer 1006 by the electrostatic objective lens 1005.

Next, a secondary electron beam generated by the irradiation of the electron beam to the semiconductor wafer 1006 is accelerated by the electric field of the electrostatic objective lens system 1005 in the direction of a detector 1008 (a dotted line in FIG. 16), and directed into the ExB deflector 1003. The ExB deflector 1003 redirects the accelerated secondary electron beam toward an electrostatic intermediate lens system 1007. Next, the electrostatic intermediate lens system 1007 directs the secondary electron beam into the detector 1008 to detect the secondary electron beam. The secondary electron beam detected by the detector 1008 is converted into data which is transmitted to a display device 1009, and an image of the secondary electron beam is displayed on the display device 1009 for testing patterns on the semiconductor wafer 1006.

Next, described in detail will be the configuration of the electrostatic lens system 1002, electrostatic objective lens 1005, electrostatic intermediate lens system 1007 and ExB deflector 1003 in the projection type evaluation apparatus 1000. The electrostatic lens system 1002 and electrostatic objective lens system 1005, through which an electron beam passes, and the electrostatic intermediate lens system 1007, through which a secondary electron beam passes, include a plurality of electrodes for generating predetermined electric fields. Also, all of these electrodes are coated with platinum on their surfaces. Further, electrodes 1004 of the ExB deflector 1003 are also coated with platinum on their surfaces.

Now, a breakdown occurrence probability will be described for each of metals coated on electrodes with reference to FIG. 17. The breakdown occurrence probability is represented by a relative hierarchical relationship for each metal. Also, it is assumed that in the projection type evaluation apparatus, other testing conditions are identical except for the type of metal coated on electrodes.

First, comparing the probability of producing the breakdown between an electrode coated with aluminum and an electrode coated with gold, the electrode coated with gold exhibited a slightly lower probability of breakdown. Therefore, the gold is more effective in preventing the breakdown. Further, comparing the probability of producing the breakdown between an electrode coated with gold and an electrode coated with platinum, the electrode coated with platinum exhibited a yet lower probability of breakdown.

Here, in regard to the work function of each metal, aluminum has a work function of 4.2 [eV]; gold 4.9 [eV], and platinum 5.3[eV]. Here, the work function refers to minimum energy required to draw out one electron beam within the metal into a vacuum (unit:eV). In other words, as the value of work function is larger, an electron beam is more difficult to draw out.

Therefore, in the map projection type evaluation apparatus 1000, when an electron beam emitted from the electron beam source 1001 collides with an electrode, a less amount of secondary electron beam will be emitted from the electrode if the electrode is coated with a metal having a large value of work function (including an alloy made of a metal having a large value of work function as a main material), so that the probability of producing the breakdown of the electrode is reduced. For this reason, a metal having a large work function is preferable to certain extent. Specifically, when an electrode is coated with a metal having a work function equal to 5 [eV], it is possible to suppress the probability of producing the breakdown of the electrode.

Also, when a sample under testing is the semiconductor 1006 and an electrode is coated with gold, as in this embodiment, an electron beam may collide with gold in some cases to result in the gold attached on patterns of the semiconductor wafer 1006. Therefore, if the electrode is coated with platinum in this embodiment, no platinum will be attached on patterns of the semiconductor wafer 1006. Even attachment of platinum would not deteriorate the device performance. In addition, the occurrence of producing the breakdown of the electrode is reduced, so that the electrode coated with platinum is more preferable.

Figure 18:
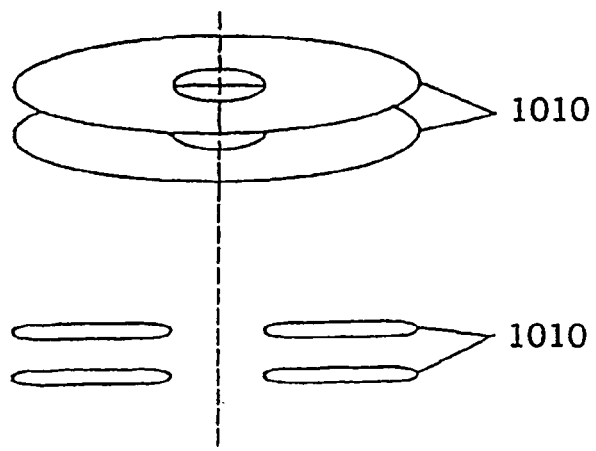
FIG. 18 is a perspective view and a cross-sectional view of an electrode.

Next, an example of the shape and structure of electrodes will be described with reference to FIGS. 18 and 19. In FIG. 18, electrodes 1010 are electrodes of an electrostatic lens included in the electrostatic lens system 1002, electrostatic objective lens system 1005 and electrostatic intermediate lens system 1007.

The electrodes 1010 are in the shape of disk formed with a throughhole substantially at the center thereof, through which an electron beam and a secondary electron beam can pass. In the projection type evaluation apparatus 1000 of this embodiment, the electrodes 1010 are applied with a predetermined voltage by a power supply, not shown.

Figure 19:
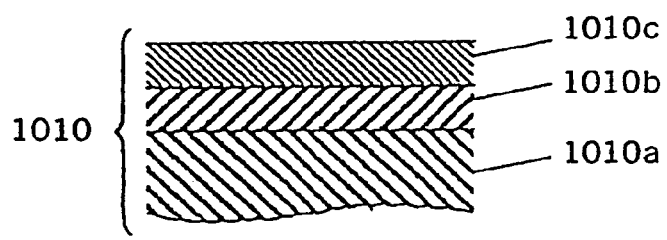
FIG. 19 is a partial cross-sectional view of the electrode illustrated in FIG. 18.

FIG. 19 is a partial cross-sectional view of a surface portion of an electrode 1010. The surface of the electrode 1004 in the ExB deflector 1003 may have an equivalent structure to the surface of the electrode 1010. A material for the electrodes 1010 comprises silicon bronze 1010a. Titanium 1010b is sputter coated in a thickness of 50 nm on the silicon bronze 1010a worked into a required dimensional shape, and platinum 1010c is further sputter coated in a thickness of 200 nm on the titanium 1010b to form the electrode 1010.

Figure 20:
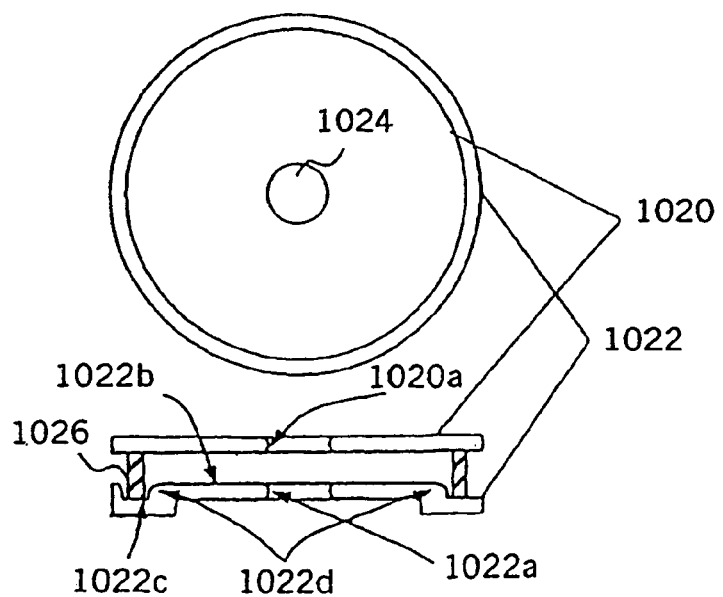
FIG. 20 is a top plan view and a cross-sectional view of the electrode illustrated in FIG. 18.
Figure 21:
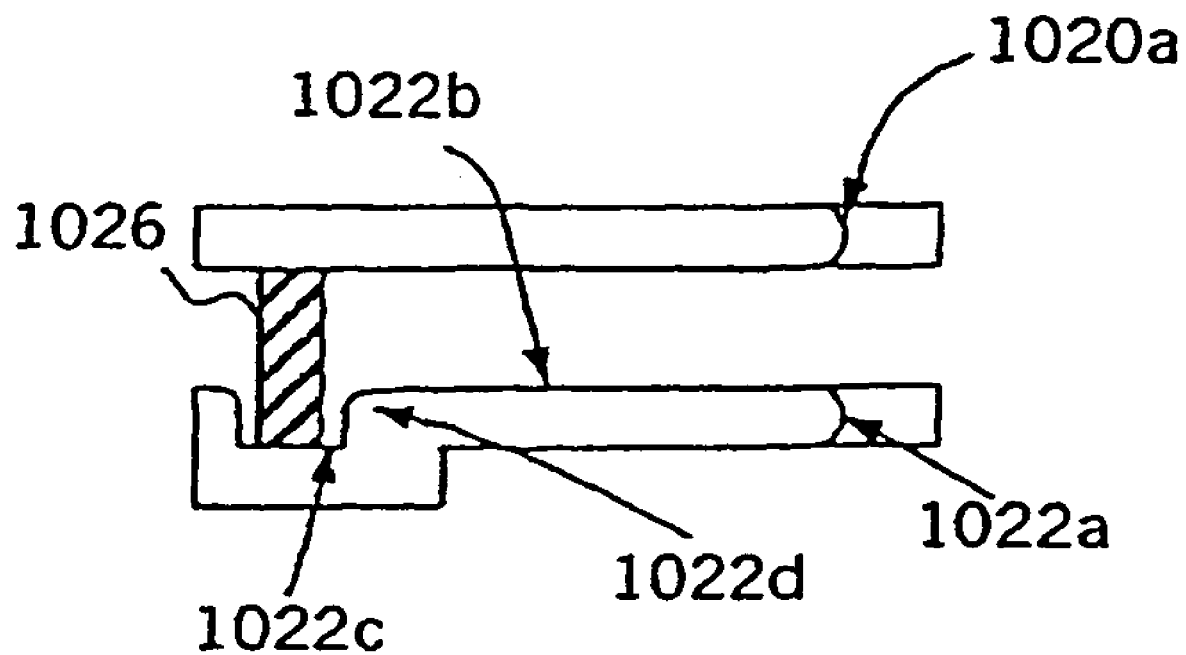
FIG. 21 is an enlarged cross-sectional view of a main portion of the electrode illustrated in FIG. 20.

Now, the structure of electrodes for preventing a breakdown between the electrodes when a large potential difference is present between the electrodes in this embodiment will be described in detail with reference to FIGS. 20 and 21. Electrodes 1020, 1022 in FIG. 20 are electrodes included, for example, in the electrostatic objective lens system 1005, and platinum is coated on the electrodes, as mentioned above. Also, the electrodes 1020, 1022 are applied with predetermined voltages by a power supply, not shown. In this embodiment, the electrode 1022 on the semiconductor wafer 1006 side is applied with a high voltage, for example, a voltage of 15 kV, while the electrode 1020 is applied with a voltage of 5 kV.

Throughholes 1024, through which the electron beam and secondary electron beam pass, are formed in central portions of the electrodes 1020, 1022, and an electric field is formed within the throughhole 1024 by a potential difference between the electrodes 1020, 1022. Electron beams are decelerated and converged by this electric field, and irradiated to the semiconductor wafer 1006. In this event, since the potential difference between the electrodes is large, an electrostatic objective lens having a short focal distance can be used for the electrostatic objective lens system 1005. Consequently, the electrostatic objective lens system 1005 exhibits low aberration and high resolution.

An insulating spacer 1026 is inserted between the electrodes 1020 and 1022, where the insulating spacer 1026 substantially vertically supports the electrodes 1020, 1022. A minimum creeping distance of the insulating spacer 1026 between the electrodes is substantially the same as the distance between portions of the electrodes supported by the insulating spacer 1026. In other words, the surface of the insulating spacer 1026 between the electrodes is not formed in the shape of crimps in the direction along the electrodes but substantially in a linear shape.

The electrode 1022 has a first electrode surface 1022b at a minimum distance between the electrodes, a second electrode surface 1022c having an inter-electrode distance longer than the first electrode surface 1022b, and a step 1022d (FIG. 21) between the first electrode surface 1022b and the second electrode surface 1022c in the direction along these two electrodes. The insulating spacer 1026 supports the electrode 1022 on the second electrode surface 1022c.

Since the electrode 1022 is shaped as described, it is possible to make the minimum creeping distance of the insulating spacer 1026 longer than the minimum distance between the electrodes while holding the minimum distance between the electrodes at a predetermined distance, without creating crimps or the like on the surface of the insulating spacer 1026 in the direction along the electrodes. Also, since the surface of the insulating spacer 1026 is not applied with a large electric field, the resulting structure is less susceptible to a creeping discharge.

Consequently, the electrostatic objective lens system 1005 can be an electrostatic objective lens with a short focal distance, low aberration and high resolution, and the insulating performance of the insulating spacer 1026 is not degraded between the electrodes, so that the breakdown between the electrodes can be prevented. Further, since the metal-made electrode 1022 is worked to have the step 1022d, a working cost is less expensive than working the insulating spacer 1026. In addition, the surface of the insulating spacer 1026 is substantially free of ruggedness in the direction along the electrodes, so that gases emitted from the insulating spacer 1026 will not be increased. Furthermore, since corner portions between an open end 1020a of the through hole 1024 of the electrode 1020 and an open end 1022a of the throughhole 1024 of the electrode 1022 are formed with curvatures, no electric field will be concentrate on both corner portions, so that the breakdown between the electrodes can be more reliably prevented. Moreover, since a corner portion of the step 1022d of the electrode 1022 between the electrodes is formed with a curvature, no electric field will be concentrate on both corner portions, so that the breakdown between the electrodes can be more reliably prevented.

While in the fourth embodiment, the step 1022d is formed in the electrode 1022, the electrode 1020 may also be worked to have a step toward the electrode 1022, or in place of the electrode 1022, the electrode 1020 alone may be worked to have a step toward the electrode 1022. Also, while the electrodes having the insulating spacer 1026 inserted therebetween has been described in the electrostatic objective lens system 1005, the insulating spacer may be applied to another electrostatic lens system, if it includes electrodes with a large potential difference generated therebetween, thereby making it possible to prevent a breakdown between the electrodes.

The fourth embodiment described with reference to FIGS. 16-21 can be used in the testing process (G) in the device manufacturing method previously described with reference to FIG. 3 and FIGS. 4(a), 4(b) to evaluate a semiconductor wafer without causing a breakdown between electrodes in any electrostatic lens system. In this regard, the description related to FIG. 3 and FIGS. 4(a), 4(b) is cited, so that description herein is omitted.

Embodiment Relating to Deflection (Fifth Embodiment)

A fifth embodiment of the present invention relates to an electron beam apparatus which is capable of performing testing for defects on patterns with a minimum line width of 0.2 micrometers or less, measurement of line widths, measurement of alignment precision, stopgap measurement, high time resolution potential contrast measurement, and so on at a high throughput and high reliability, and a device manufacturing method using the apparatus.

A known electron beam apparatus employs a Wien filter to separate a primary electron beam from a secondary electron beam emitted from a sample irradiated with the primary electron beam. For example, a known electron beam apparatus emits a primary electron beam from an electron beam source such that it forms a predetermined angle with respect to the optical axis perpendicular to a sample, deflects the travelling direction of the primary electron beam by a Wien filter so as to go along the optical axis such that the primary electron beam impinges perpendicularly on the sample, and separates a secondary electron beam emitted from the sample from the primary electron beam by the Wien filter to force the secondary electron beam to travel along the optical axis and impinge on a detector. Also, another known electron beam apparatus directs a primary electron beam perpendicularly into a sample, separates a secondary electron beam emitted thereby from the sample by an ExB separator from the primary electron beam and inputs the secondary electron beam to a detector.

Such conventional electron beam apparatuses have a problem of inability to narrow down a beam comprised of primary electron radiations since the primary electron beams having a large energy width are deflected at different angles by the ExB separator depending on the magnitude of energy possessed by the primary electron radiations, causing chromatism in the primary electron beams. The problem of chromatism is also found in an electron beam apparatus which forces a secondary electron beam emitted from a sample irradiated with a primary electron beam to linearly impinge on a detector along the optical axis. When the secondary electron beam emitted from a sample has a wide energy width, chromatism is generated when the secondary electron beam passes through a secondary optical system, thereby adversely affecting accurate detection of the secondary electron beam.

The fifth embodiment of the present invention has been proposed to solve the problems of the conventional electron beam apparatuses as mentioned above, and provides a means for largely reducing the effect of chromatism on a Wien filter in an electron beam apparatus which narrows down the primary electron beam for scanning a sample, or for largely reducing chromatism caused by the energy width of the secondary electron beam in an electron beam apparatus which projects an image of the secondary electron beam for detection.

Also, the fifth embodiment of the present invention is suitable for a defect testing apparatus and so on which use the electron beam apparatus which achieves a reduction in chromatism as mentioned. Further, a wafer in the middle of a process can be tested using such a defect testing apparatus and so on in a device manufacturing method.

Figure 22:
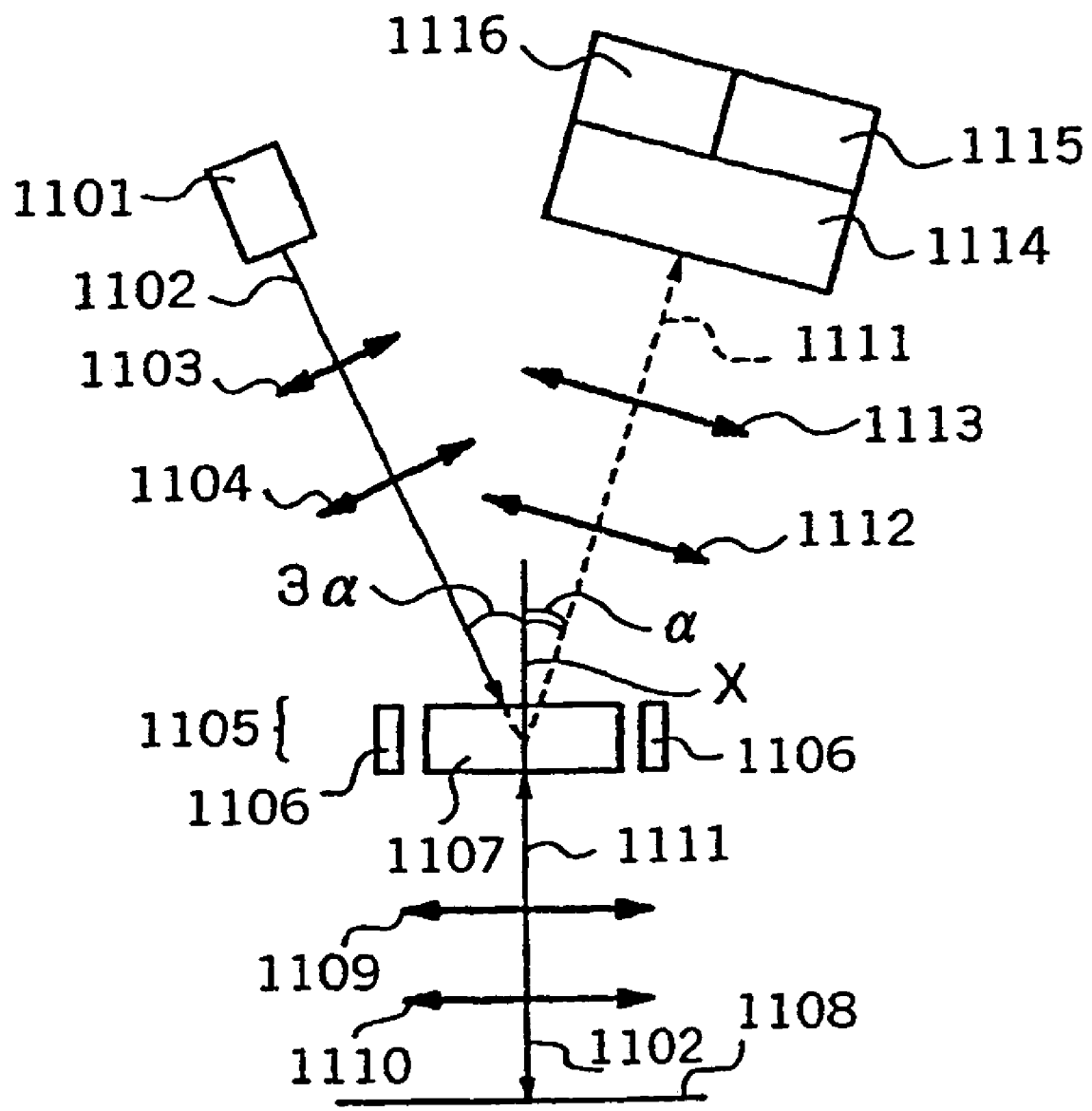
FIG. 22 is a diagram generally illustrating a fifth embodiment of the charged particle beam apparatus according to the present invention.

In FIG. 22, a primary system including an electron beam source, and a secondary system including a detector are arranged opposite to each other with respect to the optical axis X perpendicular to a sample, at a predetermined angle formed therebetween. In FIG. 22, a primary electron beam 1102 emitted from the electron beam source 1101 is reshaped into a rectangle by an opening (not shown), reduced by lenses 1103, 1104, and impinges on a Wien filter 1105. In this event, assume that the angle formed by the primary electron beam 1012 to the optical axis X is 3α. Specifically, the Wien filter 1105 comprises electrodes 1106 for creating an electric field for electrostatic deflection, and a magnet 1107 for creating a magnetic field for electromagnetic deflection. The Wien filter 1105 deflects the primary electron beams 1102 incident thereon to the left, i.e., closer to the optical axis X by an angle α by an electrostatic deflecting action of the electrodes 1106, and deflects the primary electron beam 1102 to the left by an angle 2α by an electromagnetic deflecting action of the magnet 1107, i.e., deflects the primary electron beam 1102 to the left totally by the angle 3☐, and forces the deflected primary electron beam 1102 to travel along the optical axis X perpendicular to a sample 1108. Subsequently, the primary electron beam 1102 impinges on the sample 1108 through lens systems 1109, 1110 and is irradiated to the sample 1108. The angle α is, for example, 10 degrees.

A secondary electron beam 1111 emitted from the sample 1108 by the irradiation of the primary electron beam 1102 is enlarged by the lens systems 1109, 1110, and then impinges on the Wien filter 1105 which deflects the secondary electron beam 1111 to the right by α degrees from the optical axis X, i.e., further away from the optical axis by the action of its electrode 1106 and magnet 1107. The secondary electron beam 1111 separated from the primary electron beams by the Wien filter 1105 is enlarged by a secondary optical system including lens systems 1112, 1113, and focused on a detector 1114. The output of the detector 1114 is processed as appropriated by an image processing unit 1115 and stored in an image memory 1116.

In the fifth embodiment, chromatism caused by the Wien filter 1105 is more problematic in the secondary optical system for processing the secondary electron beams 1111. Thus, for eliminating the influence of the chromatism caused by the Wien filter 1105 on the secondary electron beam 1111, the Wien filter 1105 is arranged such that its electrostatic deflecting action and electromagnetic deflecting action deflect the secondary electron beams in direction opposite to each other, and such that a predetermined relationship is established between an angle by which the secondary electron beam is deflected by the electrostatic deflecting action and an angle by which the secondary electron beam is deflected by the electromagnetic deflecting action. In this way, the secondary electron beam 1111 emitted from the sample 1108 and traveling along the optical axis X is deflected by a predetermined angle in the direction opposite to the primary electron beams 1102 with respect to the optical axis X, and in this event, the chromatism due to an energy width possessed by the secondary electron beam 1111 can be reduced to a neglectable magnitude.

Thus, when the secondary electron beams 1111 impinges on the Wien filter 1105, the electrode 1106 of the Wien filter 1105 deflects the secondary electron beam 1111 to the left, i.e., closer to the optical axis X by an angle ☐ by the electrostatic deflecting action, while the magnet 1107 deflects the secondary electron beam 1111 to the right, i.e., further away from the optical axis X by an angle 2☐. In this event, assuming that the beam energy of the secondary electron beams incident on the Wien filter 1105 is Vo, a secondary electron beam having energy smaller than Vo by ΔV is deflected by the electrodes 1106 by an angle:

$$\alpha/(1-\Delta V/Vo)=\beta$$

to the left from the optical axis, i.e., closer to the optical axis X. Simultaneously, the secondary electron beam 1111 having energy smaller than Vo by ΔV is deflected by the magnet 1107 by an angle:

$$2\alpha/\{1-(\Delta V/Vo)\}^{1/2}=\gamma$$

to the right with respect to the optical axis X, i.e., further away from the optical axis X. In a primary approximation:

$$(1-\Delta V/Vo)^{-1}=(1+\Delta V/Vo); \text{ and}$$

$$2\{(1-\Delta V/Vo)\}^{-1/2}=2\{1+(\tfrac{1}{2})(\Delta V/Vo)\}$$

are derived, so that the following equation is established:

$$\gamma-\beta=2\alpha\{1+(\tfrac{1}{2})(\Delta V/Vo)\}-\alpha(1+\Delta V/Vo)=\alpha$$

Stated another way, a term related to the energy width of the secondary electron beam is erased by canceling the electrostatic deflecting action and the electromagnetic deflecting action of the Wien filter 1105, so that the secondary electron beam 111 is deflected by the Wien filter 1105 to the right with respect to the optical axis X, i.e., further away from the optical axis X by the angle α, thereby making it possible to neglect the chromatism caused by the Wien filter 1105.

Figure 23:
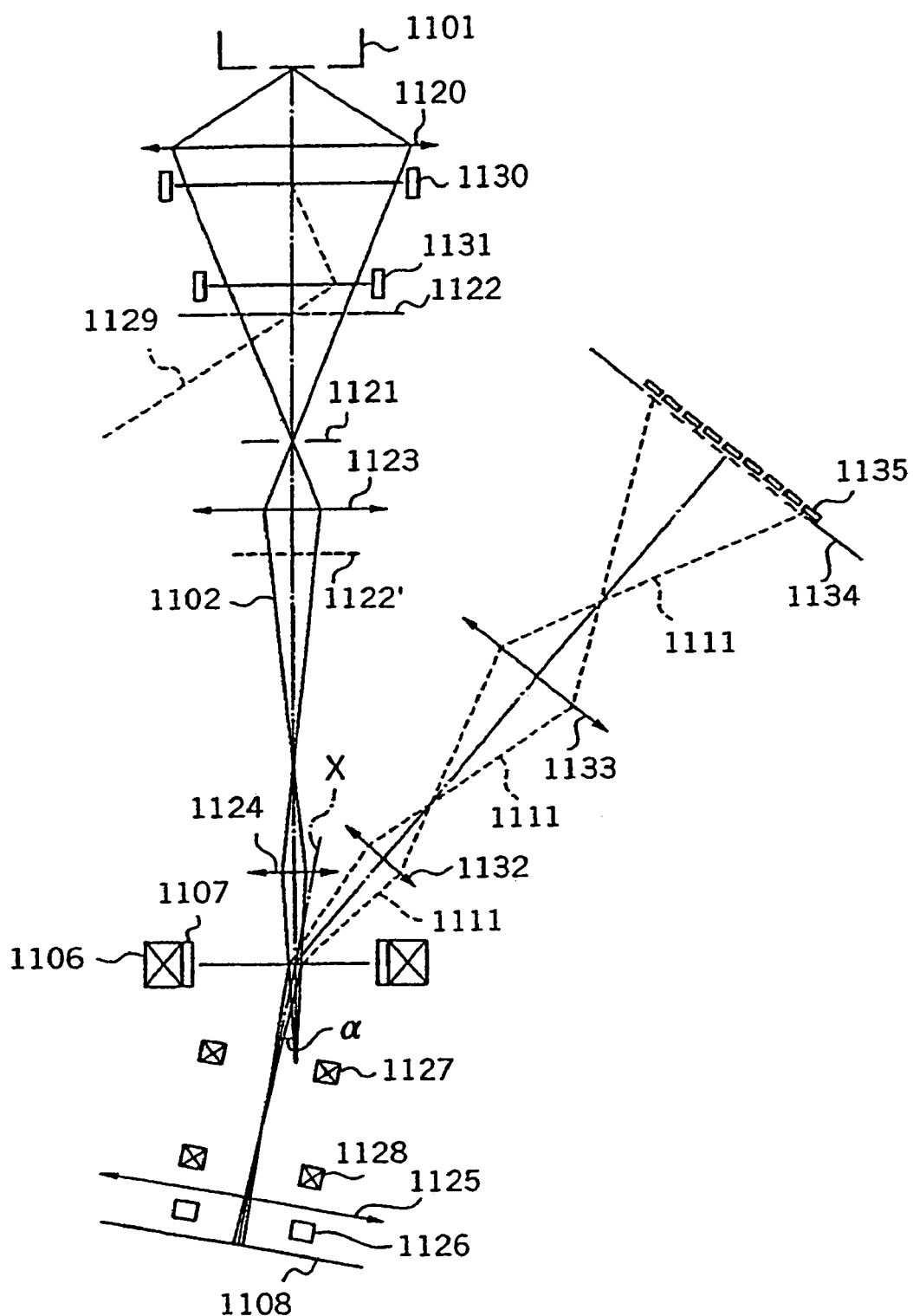
FIG. 23 is a diagram illustrating in detail the configuration of the electron beam apparatus illustrated in FIG. 22.

FIG. 23 is a diagram illustrating in detail the configuration of the fifth embodiment of the present invention. In FIG. 23, a primary electron beam 1102 emitted from an electron beam source 1101 is converged to an opening of a blanking opening plate 1121 by a condenser lens 1120. The primary electron beam 1102 passes an opening plate 1122 having a large number of openings before traveling to the opening plate 1121, whereby the primary electron beam 1102 is transformed into multiple beams having a desired number of thin beams. The multiple primary electron beams 1102 pass through the opening plate 1121, are reduced to beams of a predetermined dimension by reduction lenses 1123, 1124 to form a reduced image 1122', and then enter the Wien filter 1105. In this event, the angle of the primary electron beams 1102 formed with the optical axis X is α. The primary electron beams 1102 are deflected by the Wien filter 1105 by the angle α, travel along the optical axis X perpendicular to the sample 1108, and are reduced by an objective lens 1125 and symmetric electrodes 1126 and irradiated to the sample 1108.

For scanning the sample 1108 in a direction perpendicular to a direction in which openings are arranged on the opening plate 1122 (in FIG. 23, the direction perpendicular to the sheet) with the primary electron beams 1102 exiting the Wien filter 1105, scanning electrodes 1127, 1128 are placed along the optical path of the primary electron beams 1102. Also, blanking deflectors 1130, 11131 are arranged for deviating the traveling direction of the primary electron beams 1102 from a normal traveling direction during a blanking period such that the primary electron beams 1102 travel along an optical path 1129.

The sample 1108 emits secondary electron beams 1111 from respective locations irradiated respectively with a plurality of thin beams which constitute the primary electron beams 1102. The multiple secondary electron beams 1111 thus emitted are separated from the primary electron beams by the Wien filter 1105, enlarged by focusing electron-optical systems 1132, 1133, pass through an opening plate 1134 having openings corresponding to the openings of the opening plate 1122, and impinge on multiple detectors 1135. Here illustrated in FIG. 23 is that the opening plate 1122 and opening plate 1134 are rotated by 90° about the optical axis.

While the chromatism caused by the Wien filter 1105 is also problematic for the primary electron beams and secondary electron beams in this case, the influence of the chromatism generated in the secondary optical system can be reduced by extending mutual intervals of the plurality of beams which constitute the multiple beams.

On the other hand, for eliminating the influence exerted by the chromatism caused by the Wien filter 1105 on the primary electron beams 1102, in FIG. 23, the Wien filter 1105 is arranged such that its electrostatic deflecting action and electromagnetic deflecting action deflect the primary electron beams in direction opposite to each other, and such that a predetermined relationship is established between an angle by which the primary electron beams are deflected by the electrostatic deflecting action and an angle by which the primary electron beams are deflected by the electromagnetic deflecting action. In this way, the primary electron beams 1112 emitted from the electron beam source 1101 and traveling obliquely with respect to the optical axis X are deflected by a predetermined angle to the left with respect to the optical axis X, i.e., closer to the optical axis X, and in this event, the chromatism due to an energy width possessed by the primary electron beams 1102 can be reduced to a neglectable magnitude.

Specifically describing the foregoing, the Wien filter 1105 deflects the primary electron beams 1102 to the right, i.e., further away from the optical axis by an angle α by the electrostatic deflecting action of the electrodes 1106, and deflects the primary electron beams 1102 to the left, i.e., closer to the optical axis X by an angle 2α by the electromagnetic deflecting action of the magnet 1107. As a result, the primary electron beams 1102, which have impinged on the Wien filter 1105, are deflected to the left by an angle α as a whole. In this event, it is possible to neglect the influence of an energy width possessed by the primary electron beams 1102. Specifically, the chromatism caused by an extended energy width of the primary electron beams 1102 is eliminated.

Explaining in a mathematical point of view, assuming that the beam energy of the secondary electron beams incident on the Wien filter 1105 is Vo, a primary electron beam having energy smaller than Vo by ΔV is deflected by the electrodes 1106 by an angle:

$$\alpha/(1-\Delta V/Vo)=\delta$$

Since this value is larger than α, the primary electron beam is deflected additionally to the right, i.e., further away from the optical axis X. Simultaneously, the primary electron beam having energy smaller than Vo by ΔV is deflected by the magnet 1107 by an angle:

$$2\alpha\{1-(\Delta V/Vo)\}^{-1/2}=\theta$$

Since this value is larger than 2α, the primary electron beams are deflected additionally to the left, i.e., closer to the optical axis X. Thus, the difference between these angles is calculated as follows:

$$\theta-\delta=2\alpha\{1-(\Delta V/Vo)\}^{-1/2}-\alpha(1-\Delta V/Vo)^{-1}$$

Since ΔV is extremely smaller than Vo:

$$(1-\Delta V/Vo)^{-1/2}=(1+\Delta V/2Vo)$$

is established as a primary approximation, so that eventually, $$\theta-\delta=2\alpha(1-\Delta V/2Vo)-\alpha(1-\Delta V/Vo)=\alpha$$

is established. In this way, when the primary electron beams 1102 are deflected by the Wien filter 1105 by an angle α closer to the optical axis X, the energy width possessed by the primary electron beams can be neglected, thereby making it possible to eliminate the chromatism caused by the Wien filter 1105.

When a plurality of beams constituting the primary electron beams 1102 are arranged on a single column and are deflected by the Wien filter 1105 in a direction perpendicular to a direction in which these beams are arranged, the chromatism generated in the secondary optical system appears in the direction perpendicular to the beam arranged direction, so that crosstalk between the plurality of beams will not be increased by the chromatism.

The electron beam apparatus described with reference to FIGS. 22 and 23 can be applied to a variety of apparatuses such as a defect detecting apparatus, an alignment precision measuring apparatus, a line width measuring apparatus, a high time resolution potential contrast measuring apparatus, a defect review apparatus, and strobe SEM apparatus. Also, the electron beam apparatus of the fifth embodiment can be used in the testing process (G) in the device manufacturing method described in FIGS. 3 and 4(a), 4(b) in order to evaluate a wafer in the middle of a process. In this regard, the description related to FIG. 3 and FIGS. 4(a), 4(b) is incorporated herewith by reference and is omitted herein.

While the fifth embodiment of the present invention has been described, the present invention is not limited to such an embodiment. For example, a plurality of electron beam irradiation/detection systems, each comprised of an electron beam source, a primary optical system, a secondary optical system and a detector may be provided in order to simultaneously irradiate different locations on the sample 1108, wherein the sample is irradiated with a plurality of primary electron beams emitted from the plurality of electron beam sources, and a plurality of secondary electron beams emitted from the sample are received by a plurality of detectors. This can largely reduce a time required for the testing and measurements.

Embodiment Relating to Driving of Objective Lens (Sixth Embodiment)

A sixth embodiment of the present invention relates to an electron beam apparatus which is capable of performing a variety of evaluations for testing for defects on patterns having line widths of 0.1 micron or less, CD measurements, alignment precision measurement, potential measurement at a high time resolution, and so on at a high throughput, high accuracy and high reliability, and a device manufacturing method using this apparatus.

When patterns formed on the surface of a sample such as a semiconductor wafer is evaluated at a high accuracy using the result of scanning by an electron beam, it is necessary to take into consideration variations in the height of the sample. This is because the varying height of the sample results in a change in the distance between patterns on the surface of the sample and an objective lens for converging the electron beam on the patterns to cause a lower resolution due to dissatisfaction of a focusing condition, thereby failing to provide correct evaluation.

To eliminate this problem, a known electron beam apparatus directs light obliquely into the surface of a sample, measures the height of the sample by use of the reflected light, feeds back the result of measurement to an electron-optical system for converging an electron beam to the sample to control currents and voltages supplied to components of the electron-optical system, and thereby focuses the electron-optical system.

However, a system which directs light obliquely into a sample requires optics mainly made of an insulating material which should be placed in a space between the surface of the sample and the lower surface of the electron-optical system for reflecting incident light. For this purpose, the spacing between the surface of the sample and the lower surface of the electron-optical system must be ensured more than necessity, which however makes the problems such as the aberration of the electron-optical system unneglectable. Presently, however, there is no means which simultaneously focuses the electron-optical system and eliminates the problems such as the aberration of the electron-optical system.

The focusing of the electron-optical system must be performed in consideration of not only the distance between the surface of the sample and the lower surface of the electron-optical system but also a charging state on the surface of the sample, and space charge effect of electron beams, so that errors might occur unless parameters related to the focusing of the electron-optical system are electron-optically measured.

Further, when the electron-optical system is focused by adjusting an excitation current for a magnetic lens included in the electron-optical system, it is necessary to take a long time period from setting of the excitation current to a predetermined value to stable establishment of the focal distance of the electron-optical system, i.e., a long settling time, thereby presenting a problem that it is difficult to perform the focusing at a high speed. Otherwise, when the electron-optical system is focused by changing an excitation voltage for an electrostatic lens, a high voltage applied to the electrostatic lens must be changed, thereby similarly presenting a problem that a long settling time is required.

The sixth embodiment of the present invention provides an electron beam apparatus which is capable of electron-optically focusing the electron-optical system in a short time, and a device manufacturing method using this apparatus for solving the foregoing problems.

Figure 24:
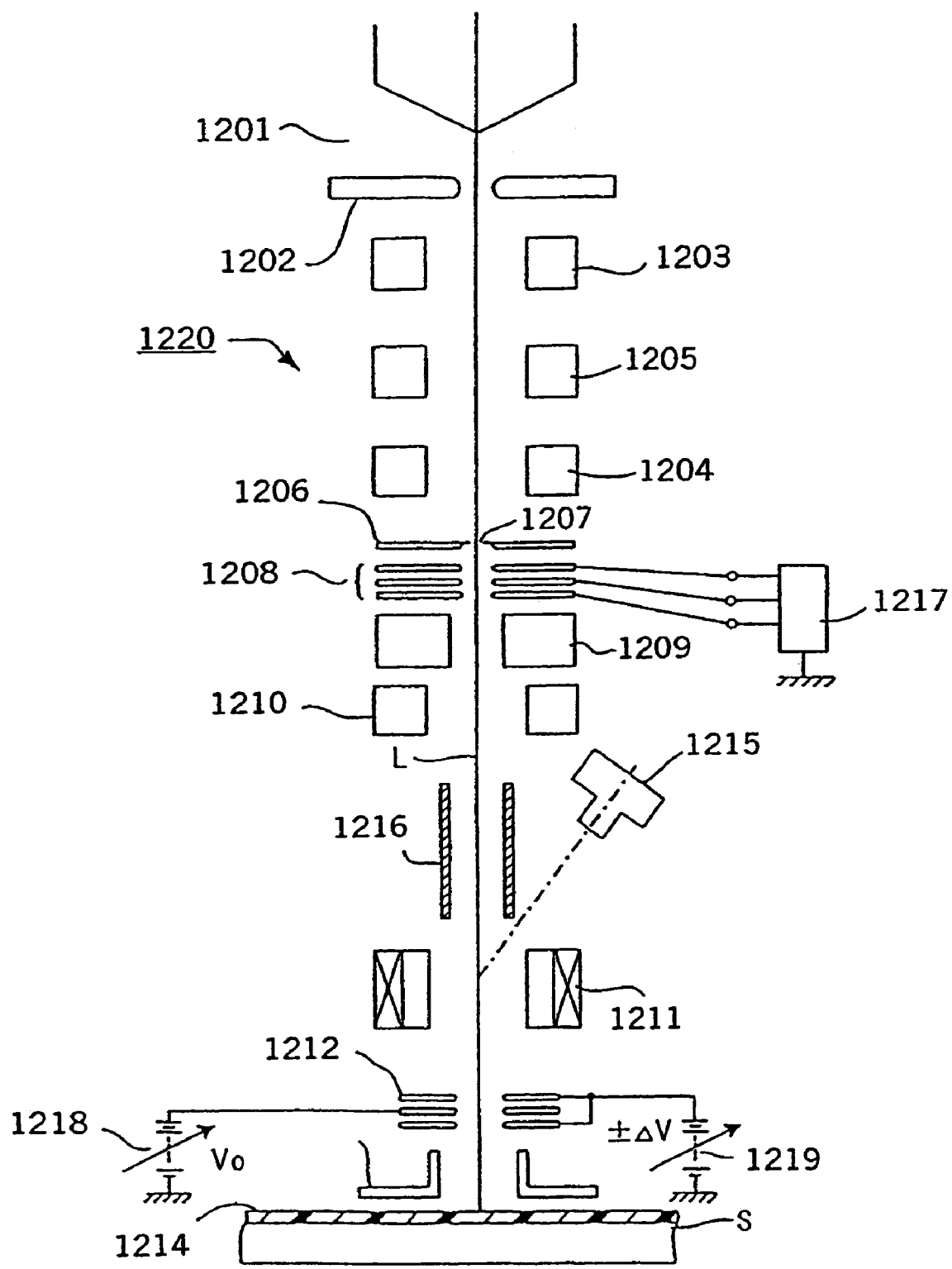
FIG. 24 is a diagram generally illustrating a sixth embodiment of the charged particle beam apparatus according to the present invention.

FIG. 24 generally illustrates the configuration of the sixth embodiment of the present invention. In FIG. 24, an electron beam source 1201 comprises an anode 1202. An emitted primary electron beam is accelerated by the anode 1202 and passes through a small hole 1207 of an opening plate 1206 by way of deflectors 1203, 1204 for alignment, and astigmatism correcting lens 1205. The primary electron beam passing through the opening plate 1206 is converged by a condenser lens 1208, passes through a Wien filter 1211 by way of deflectors 1209, 1210, is reduced by an objective lens 1212, passes through axially symmetric electrodes 1213, and is focused on one of a plurality of rectangular circuit patterns, for example, formed on the surface of a sample 1214 carried on a stage S. The axially symmetric electrodes 1213 are placed with substantially no space between itself and the sample 1214. The stage S is movable in a second direction perpendicular to a first direction in which the primary electron beam is deflected, so that the circuit patterns are scanned by the deflection of the primary electron beam and movements of the stage S.

As a result of the scanning using the primary electron beam, a secondary electron beam emitted from a circuit pattern on the sample 1214 is attracted and accelerated by an electric field of the objective lens 1212, and deflected by the Wien filter 1211 such that it deviates from an optical axis L, so that the secondary electron beam is separated from the primary electron beam. Eventually, the secondary electron beam is detected by a secondary electron beam detector 1085. The secondary electron beam detector 1215 outputs an electric signal indicative of the intensity of the incident secondary electron beam. This electric signal is amplified by a corresponding amplifier (not shown), and processed for generating an image.

For the condenser lens 1208 to reduce the primary electron beam, respective electrodes forming part of the condenser lens 1208 are applied with required voltages from a first power supply 1217. The objective lens 1212 in turn is a uni-potential lens. For converging the primary electron beam on the surface of the sample 1214, a central electrode of the objective lens 1212 is applied with a positive high voltage Vo (volts) from a second power supply 1218, while an upper electrode and a lower electrode of the objective lens 1212 are applied with small voltages ±ΔVo from a third power supply 1219.

The electron beam source 1201, anode 1202, deflectors 1203, 1204 for alignment, astigmatism correcting lens 1205, aperture plate 1206, condenser lens 1208, deflectors 1209, 1210, Wien filter 1211, objective lens 1212, axially symmetric electrode 1213, and secondary electron beam detector 1215 are housed in a column 1216 of a suitable size to constitute a single electron beam scanning/detection system 1220. Initial focusing of the electron beam scanning/detection system 1220 can be performed by changing the positive voltage Vo while fixing the voltages ±ΔVo, for example, at −10 volts.

As described above, the electron beam scanning/detection system 1220 scans one of chip patterns on the sample 1214, detects a secondary electron beam emitted from the sample 1214 as the result of the scanning, and outputs an electric signal indicative of its intensity. Actually, since the sample 1214 is formed with a plurality of chip patterns on its surface, electron beam scanning/detection systems (not shown) similar in configuration to the electron beam scanning/detection system 1220 are arranged in parallel with the electron beam scanning/detection system 1220 such that the mutual distance is equal to an integer multiple of the dimension of one chip on the sample 1214.

Describing further on the electron beam scanning/detection system 1220, the electric signal output from the secondary electron beam detector 1215 is converted into binary information, and this binary information is converted to image data. As a result, image data representative of the circuit pattern formed on the surface of the sample 1214 can be acquired. The acquired image data is stored in a suitable storage means and is compared with a reference pattern. In this way, defects on the circuit pattern formed on the sample 1214 can be detected.

A variety of reference circuit patterns may be used for comparison with the image data representative of a certain circuit pattern on the sample 1214. For example, it is possible to use image data produced from CAD data for fabricating the circuit patterns which have been scanned to generate the image data.

In the electron beam apparatus illustrated in FIG. 24, the values of voltages ±Vo applied to the upper electrode and lower electrode of the objective lens 1212 are determined under control of a controller (not shown) such as a CPU in the following manner. First, a location at which a pattern edge parallel to a first direction in which the primary electron beam is deflected and a pattern edge parallel to a second direction perpendicular to the first direction exist on an arbitrary circuit pattern formed on the surface of the sample 1214 is read, for example, from pattern data.

Next, using the deflectors 1209, 1210 and the Wien filter 1211, the pattern edge parallel to the first direction is scanned by the primary electron beam in the second direction, and an electric signal indicative of the intensity of a secondary electron beam emitted as the result is obtained from the secondary electron beam detector 1215 to measure a rising width (unit: microns) of the electric signal. Similarly, the pattern edge parallel to the second direction is also scanned in the first direction by the primary electron beam using the deflectors 1209, 1210 and the Wien filter 1211, and an electric signal indicative of the intensity of a secondary electron beam emitted as the result is obtained from the secondary electron beam detector 1215 to measure a rising width of the secondary electron beam. This operation is performed each time the values of the voltages ±ΔVo are changed. In this way, graphs A and B shown in FIG. 25(*a*) are derived.

Figure 25:
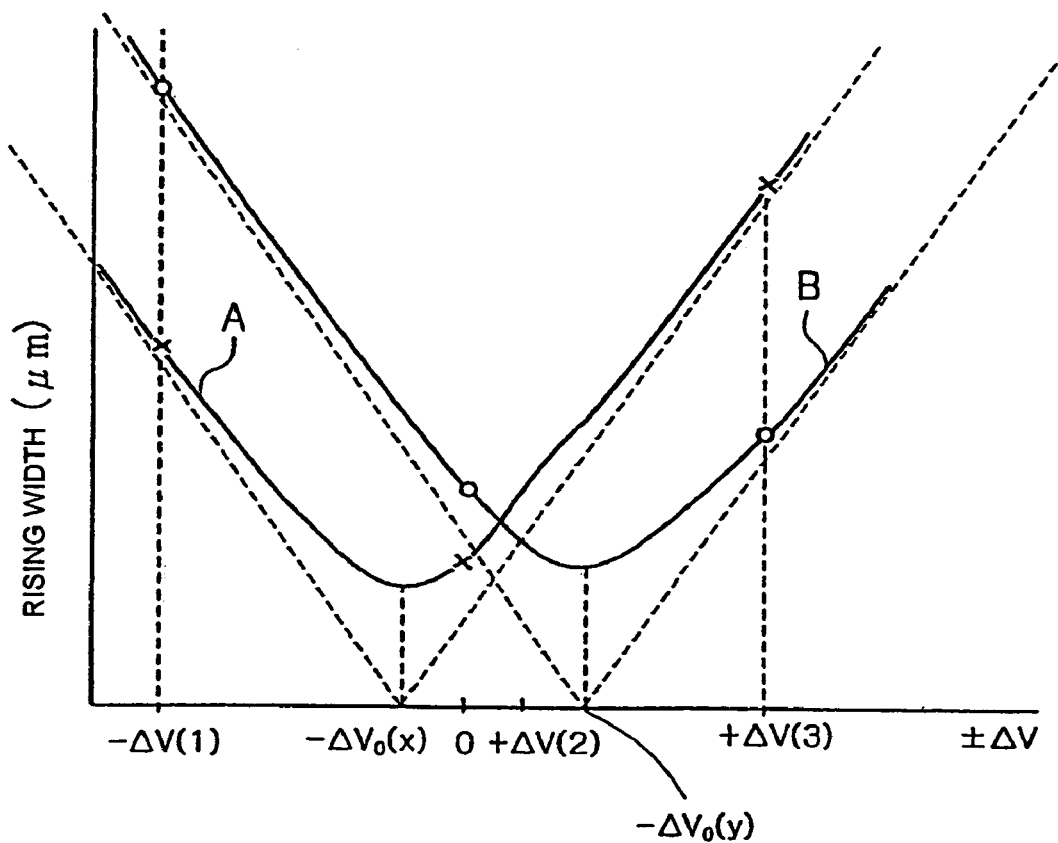
FIG. 25(a) is a graph showing the relationship between a negative voltage applied to an objective lens and a rising width of an electric signal.
FIG. 25(b) is a diagram for explaining the rising width of the electric signal.
Figure 25:
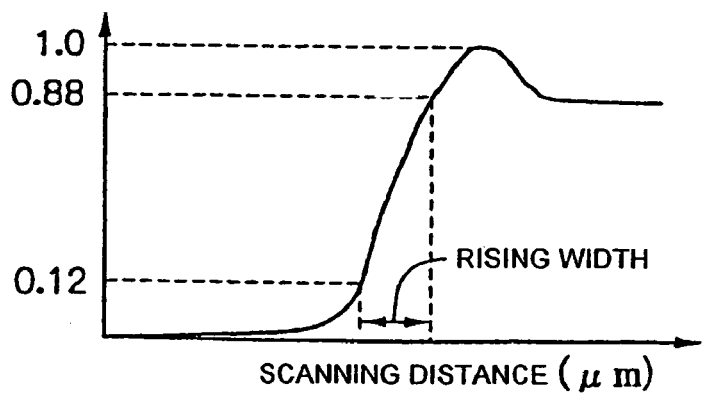

The aforementioned "rising width of the electric signal" refers to a scanning distance (in units of microns) in the second direction required for the electric signal measured when the pattern edge parallel to the first direction is scanned in the second direction to change from 12% to 88% of its maximum value, with the voltage ±ΔVo fixed at a certain value, as shown in FIG. 25(*b*).

In FIG. 25(*a*), the graph A shows that the voltage ΔVo is minimum at −ΔVo(x), i.e., the rising is the sharpest. Similarly, the graph B shows that the voltage ΔVo is minimum at +ΔVo (x), i.e., the rising is the sharpest. Therefore, the focusing condition for the objective lens 1212, i.e., the values of the voltages ±ΔVo applied to the upper electrode and lower electrode are preferably set to $\{-\Delta Vo(x)+\Delta Vo(y)\}/2$.

Actually, since the voltages ±ΔVo change only from 0 to ±20 volts, the objective lens 1212 can be settled at a high speed, specifically, in 10 microseconds. As such, only 150 microseconds were required to acquire the graphs A and B in FIG. 25(*a*).

Alternatively, such a large number of measurements need not be performed for measuring the curves A, B. As shown in FIG. 25(*a*), a rising width may be measured by setting −ΔV (1), +ΔV(2), +ΔV(3) as the values of ±ΔVo to derive the graphs A, B through hyperbolic approximation to find minimum values +ΔVo(y), −ΔVo(x) for the rising. In this case, the measurement can be made on the order of 45 microseconds.

A, B in FIG. 25(*a*) have the shape of hyperbola. Assuming that the rising width is p (mm), and objective lens voltages ±ΔVo are q (volts), the curves A, B can be expressed by:

$$(p^2/a^2)-(q-c)^2/b^2=1$$

where a, b and c are constants. Therefore, substituting three values $q_1$, $q_2$, $q_3$ for q and values $p_1$, $p_2$, $p_3$ corresponding thereto into the above equation, the following three equations are derived:

$$(p_1^2/a^2)-(q_1-c)^2/b^2=1 \quad (1)$$

$$(p_2^2/a^2)-(q_2-c)^2/b^2=1 \quad (2)$$

$$(p_3^2/a^2)-(q_3-c)^2/b^2=1 \quad (3)$$

The values of a, b, c are calculated from these equations (1)-(3), where they have minimum values when q=c. In other words, the voltage −xVo(x) at the objective lens which results in a minimum rising width can be found from three lens conditions. Completely in a similar manner, +ΔVo(y) can be found.

As in the graphs A, B in FIG. 25(*a*), the rising width is generally different when a pattern edge is scanned in a first direction and when it is scanned in a second direction. In such a case, for example, a voltage applied to the octpole astigmatism correcting lens 1205 must be adjusted to correct the astigmatism so as to further reduce the rising of the electric signal from the secondary electron beam detector 1215 when the pattern edge is scanned in the first direction and in the second direction perpendicular thereto.

As described above, electron beam scanning/detection systems (not shown) similar in configuration to the electron beam scanning/detection system 1220 are arranged in parallel with the electron beam scanning/detection system 1220 such that the mutual distance is equal to an integer multiple of the dimension of one chip on the sample 1214, and the focusing operation must be performed such that the primary electron beam is focused on the sample 1214 in each of the electron beam scanning/detection systems. However, such focusing can be substantially simultaneously performed, so that the throughput budget is merely a slight value.

Since this method attempts to satisfy the focusing condition not with an optical Z sensor but with an electron-optical means, this method can advantageously satisfy the correct focusing condition even if a sample is charged.

As described above, the focusing operation is performed in the electron beam scanning/detection system before a transition to a process for evaluating the sample 1214.

When a defect testing apparatus using the sixth embodiment of the present invention is used in the testing process (G) in the device manufacturing method described with reference to FIGS. 3 and 4(*a*), 4(*b*), semiconductor devices even having miniature patterns can be tested at a high throughput, so that a total inspection can also be conducted, thereby making it possible to improve the yield rate of products and prevent defective products from being shipped. In this regard, the description related to FIG. 3 and FIGS. 4(*a*), 4(*b*) is incorporated herewith by reference and is omitted herein.

Embodiment Relating to Anti-Vibration Apparatus
(Seventh Embodiment)

A seventh embodiment of the present invention relates to an electronic beam apparatus which irradiates a target position on an object with an electronic beam to perform at least one of working, manufacturing, observation and testing for the object, and more particularly, to an electronic beam apparatus which reduces unwanted mechanical vibrations occurring in a mechanical construction for aligning an electron beam, a method of reducing vibrations, and a semiconductor manufacturing process which comprises a step of performing at least one of working, manufacturing, observation and testing for semiconductor devices using the apparatus.

Generally, an electron beam based approach for observing a micro-structure of an object employs a testing apparatus for testing for defects on patterns formed on a wafer or the like, a scanning electronic microscope (SEM) and so on. However, due to its observation resolution ranging from μm to several tens of nm, observation must be made after external vibrations are sufficiently removed. Also, in an apparatus which uses an electron beam for exposure, a vibration isolator should be used to sufficiently remove external vibrations, and the rigidity must be enhanced to minimize stagger due to mechanical resonance caused by the structure of a barrel section, in order to deflect an electron beam to precisely irradiate the beam to a target position. To enhance the rigidity of a construction, a reduction in size is not compatible with an enhanced rigidity due to physical constraints on dimensions associated with the electron-optical system, so that the rigidity is often enhanced by increasing the thickness of the wall of the barrel portion, increasing the size of the same, and so on. However, the enhancement in rigidity by this method experiences quite a few disadvantages including an economical aspect, such as a limited freedom in the design including an increase in the weight of the apparatus, limitations on the shape, larger size of vibration isolation stand.

In view of the foregoing fact, the seventh embodiment of the present invention provides an electron beam apparatus which can appropriately attenuate unwanted vibrations due to the resonance of a mechanical construction for aligning a beam so as to highly accurately maintain an aligned beam, without necessarily enhancing the rigidity of the mechanical construction, to realize mitigation of constraints in designing, reduction in size and weight of the apparatus, and improved economy, as well as a semiconductor manufacturing process which uses the apparatus in a semiconductor device manufacturing step to enable efficient manufacturing, testing, working, observation, and so on.

Figure 26:
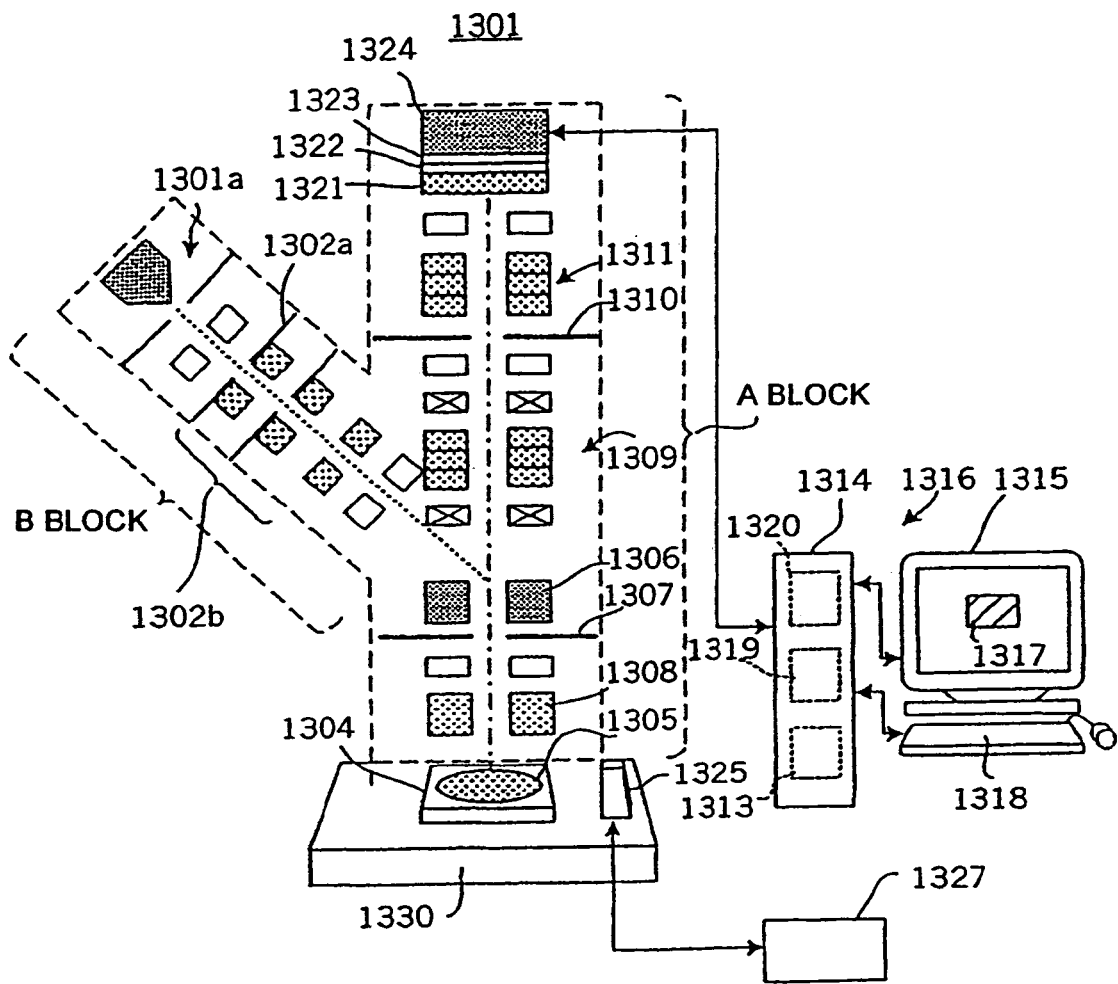
FIG. 26 is a configuration diagram of an electron beam testing apparatus which is a seventh embodiment of the charged particle beam apparatus according to the present invention.

FIG. 26 illustrates the configuration of the seventh embodiment of the present invention when it is applied to an electron beam testing apparatus for testing a semiconductor wafer for defects using electron beams. The electron beam testing apparatus 1301 illustrated in FIG. 26 is of a so-called projection type, and has a mechanical construction comprised of an A block and a B block projecting diagonally upward from the A block. A primary electron beam irradiating means is arranged in the B block for irradiating a primary electron beam, while a projection optical system for projecting a secondary electron beam, and an imaging means for detecting the intensity of the secondary electron beam are included in the A block. The A block is coupled to the lowermost fixing stand 1330.

The primary electron beam irradiating means arranged in the B block comprises an electron beam source 1301a including a cathode and an anode for emitting and accelerating a primary electron beam; a rectangular opening 1302a for reshaping the primary electron beam into a rectangle; and a quadrupole lens 1302b for reducing and focusing the primary electron beam. Disposed below the A block are an ExB deflector 1306 for deflecting the reduced primary electron beam such that it substantially perpendicularly impinges on a semiconductor wafer 1305 in a field in which an electric field E is orthogonal to a magnetic field B; a numerical aperture (NA) 1307; and an objective lens 1308 for focusing the primary electron beam passing through the numerical aperture on the wafer 1305.

Here, the primary electron beam reduced by the quadrupole lens 1302b forms an image of 500 μm×250 μm, for example, on a deflection main surface of the ExB deflector 1306, and simultaneously forms a crossover image of the electron beam source 1301a on the numerical aperture 1307 such that the Koehler's illumination condition is satisfied. The objective lens 1308 causes an image of 100 μm×50 μm, for example, to be formed on the wafer 1305, and this region is illuminated.

The wafer 1305 is placed within a sample chamber, not shown, which can be evacuated to vacuum, and carried on a stage 1304 which is movable in an X-Y horizontal plane. Here, the relationship between the A block and B block and an XYZ orthogonal coordinate system is shown in FIG. 27(a). The surface of the wafer lies on an X-Y horizontal plane, and the Z-axis is substantially parallel to the optical axis of the projection optical system. As the stage 1304 having the wafer 1305 carried thereon is moved in the X-Y horizontal plane, a surface under testing of the wafer 1305 is sequentially scanned by the primary electron beam. The stage 1304 is carried on the fixing stand 1330.

The projection optical system disposed above the A block comprises an intermediate electrostatic lens 1309, a projection electrostatic lens 1311, and a diaphragm 1310 positioned between these lenses. A secondary electron beam emitted from the wafer 1305 due to the irradiation with the primary electron beam, a reflected electron beam, and a scattered electron beam are enlarged and projected by this projection optical system at a predetermined magnification (for example, 200-300 times), and focused on a lower surface of a multi-channel plate 1321, later described.

The imaging means placed at the top of the A block comprises the multi-channel plate 1321, a fluorescent screen 1322, a relay lens 1323, and an imager unit 1324. The multi-channel plate 1321 comprises a large number of channels in the plate for generating a larger number of electron beams when the secondary electron beam focused by the electrostatic lenses 1309 and 1311 passes through the channels. In other words, the secondary electron beam is amplified. The fluorescent screen 1322 is illuminated by the amplified secondary electron beam to generate fluorescent light of intensity corresponding to the intensity of the secondary electron beam. In other words, the intensity of the secondary electron beam is transduced into the intensity of light. The relay lens 1323 is positioned to introduce the fluorescent light to the imager unit 1324. The imager unit 1324 is comprised of a large number of CCD imager devices for transducing the light introduced by the relay lens 1323 into electric signals. A so-called TDI (Time Delay Integral) detector is preferably used in order to improve the S/N ratio of detected signals. While the irradiation with the primary electron beam causes the generation of scattered electron beam and reflected electron beam as well as the secondary electron beam, these electron beams are collectively called the "secondary electron beam" here.

Figure 29:
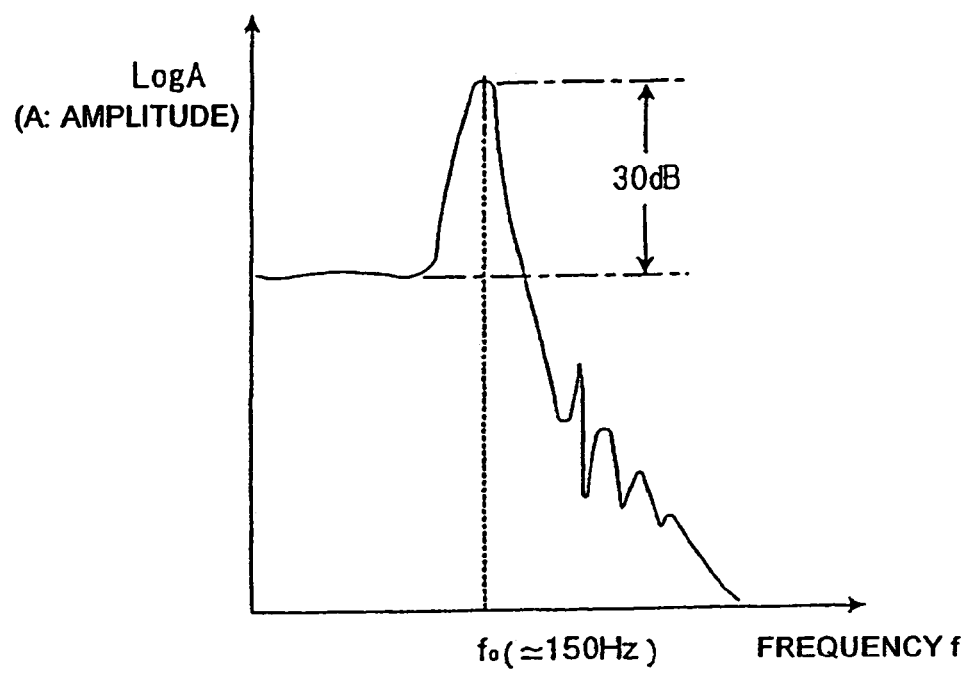
FIG. 29 is a graph showing a transfer function of the barrel in the electron beam testing apparatus illustrated in FIG. 26.

A column 1346 comprised of the mechanical construction of the A block and the B block coupled thereto, generally has one or more fundamental vibration modes. A resonant frequency and resonance direction in each fundamental vibration mode are determined by the shape, mass distribution, size, placement of machines inside the construction, and so on. For example, as illustrated in FIG. 27(b), the column 1346 has at least mode 1 of fundamental vibration 1388. In this mode 1, the column 1346 vibrates at frequency of 150 Hz, for example, substantially along the Y-direction. An example of transfer function for the barrel in this event is shown in FIG. 29. In FIG. 29, the horizontal axis represents the frequency, and the vertical axis represents a logarithmic vibration amplitude A. With this transfer function, the barrel has a gain of resonance magnification 30 dB (approximately 30 times) at resonant frequency of 150 Hz. Therefore, even with small vibrations applied from the outside, if the vibrations include a frequency component near 150 Hz, this frequency component is amplified approximately by a factor of 30 in this example to vibrate the barrel. This results in harmful events such as a blurred image.

In the prior art, for preventing this, large scaled countermeasures have been taken, such as the entire barrel carried on an vibration isolation stand to prevent vibrations from the outside, and/or reviewing the thickness and structure of the barrel to reduce a resonance magnification.

Figure 27:
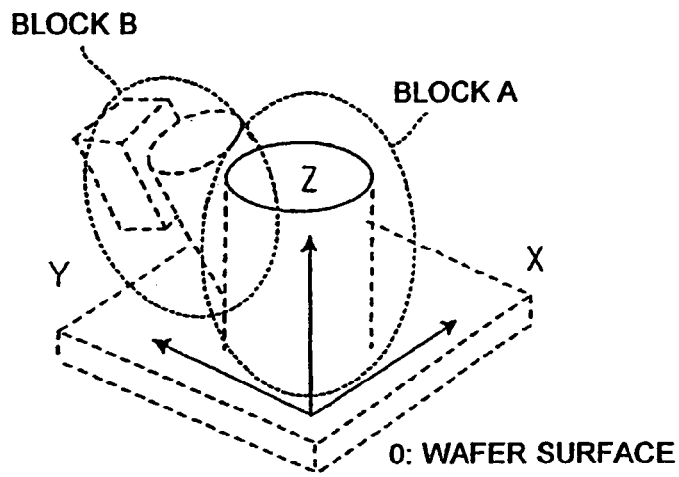
FIGS. 27 (a) to 27(c) are diagrams generally illustrating blocks in a mechanical construction of the electron beam testing apparatus illustrated in FIG. 26, where
Figure 27:
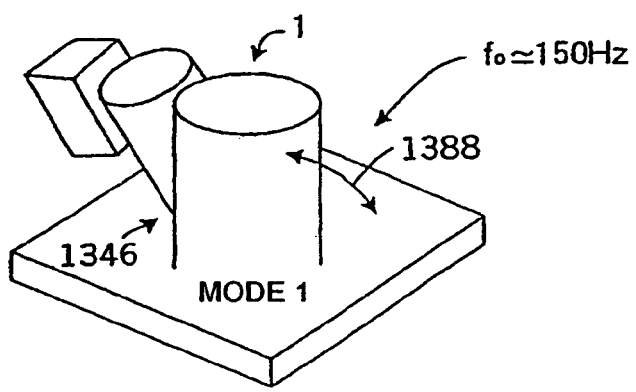
Figure 27:
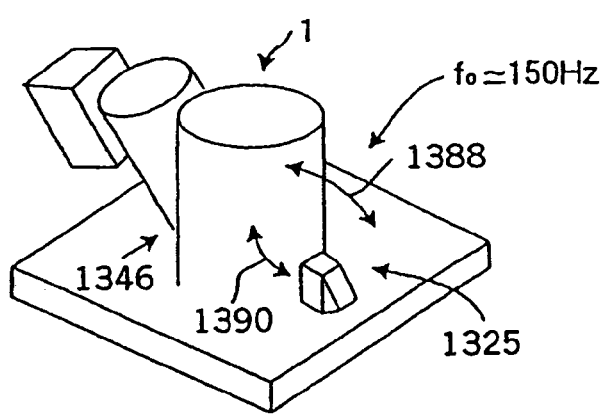

In the seventh embodiment of the present invention, to avoid this, an actuator 1325 is installed on the base of the A block for applying pressure vibrations 1390 to the barrel to cancel vibrations 1388, as illustrated in FIG. 27(*c*). This actuator 1325 is electrically connected to a vibration attenuating circuit 1327, as illustrated in FIG. 28.

Figure 28:
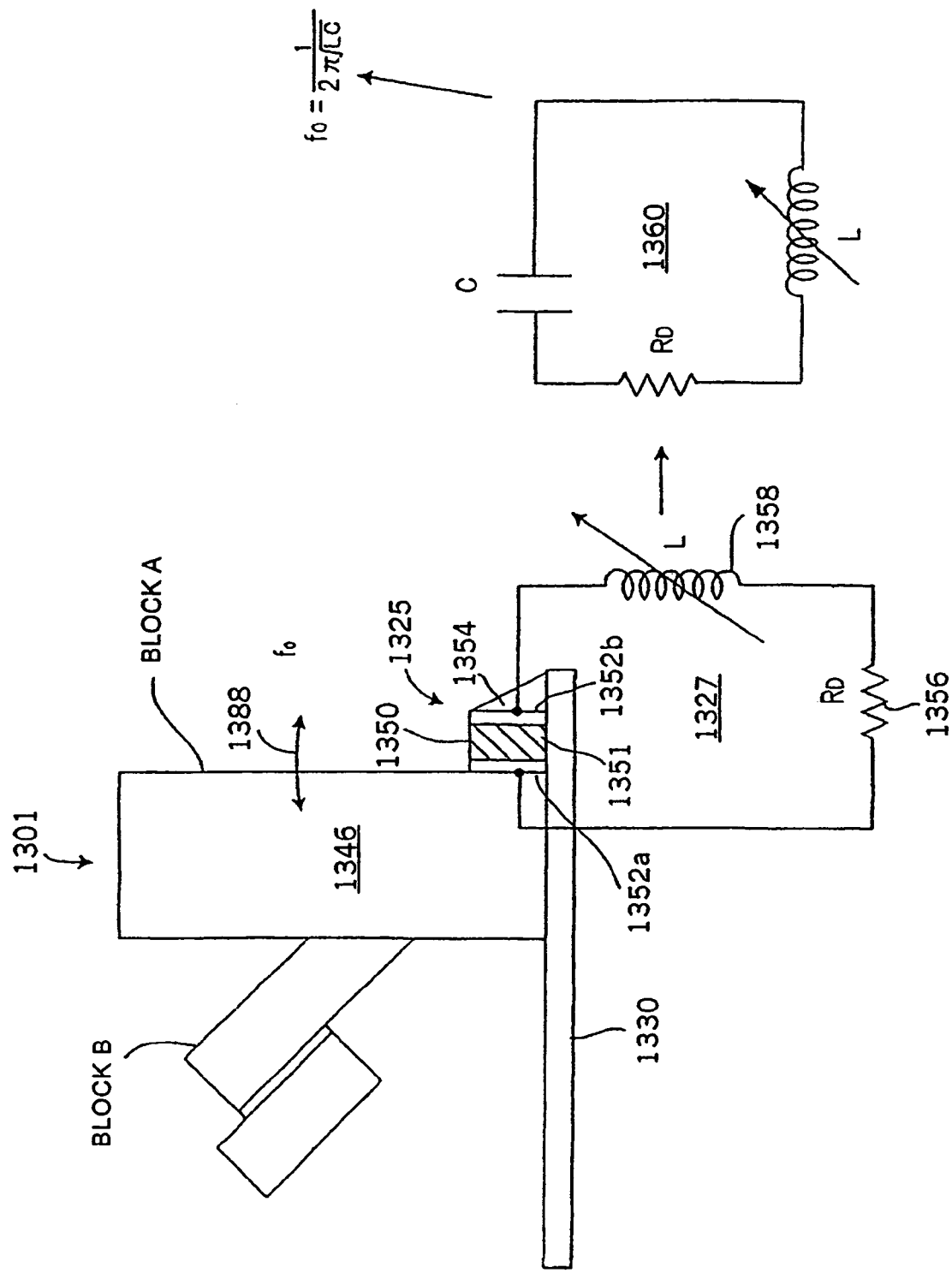
FIG. 28 is a schematic diagram illustrating an actuator and a vibration attenuating circuit used in the electron beam testing apparatus illustrated in FIG. 26, as well as the configuration of an equivalent circuit of a formed series resonant circuit.

FIG. 28 illustrates the general configuration of the actuator 1325 and the vibration attenuating circuit 1327. As illustrated in FIG. 28, the actuator 1325 has a piezoelectric element 1350 comprised of a dielectric material 1351 having a piezoelectric effect sandwiched by electrodes 1352*a* and 1352*b*; and a supporting stand 1354 fixed on the fixing stand 1330 for supporting the piezoelectric element 1350 from the electrode 1352*b* side. The piezoelectric element 1350 is sandwiched between the A block of the barrel 1346 and the supporting stand 1354, and the electrode 1352*a* is bonded to the outer wall of the A block, while the electrode 1352*b* to the supporting stand 1354. In this way, the piezoelectric element 1350 receives a positive pressure when the barrel 1346 comes closer by reciprocal vibrations 1388, and a negative pressure when the barrel 1346 goes away. The piezoelectric element 1350 is installed at a position which is effective in suppressing the vibrations 1388 of the barrel 1346. For example, it is preferably installed such that the directions of the vibration 1388 are orthogonal to the electrodes 1352*a* and 1352*b*.

The vibration attenuating circuit 1327 comprises a variable inductance 1358 and a resistor 1356 connected in series between both electrodes 1352*a*, 1352*b* of the piezoelectric element 1350. Since the variable inductance 1358 has an inductance L, the resistor 1356 has a resistance value $R_D$, and the piezoelectric element 1350 has an electric capacitance C, the serially connected piezoelectric element 1350 and vibration attenuating circuit 1327 are equivalent to a series resonant circuit designated by reference numeral 1360. The resonant frequency fo' of this series resonant circuit is expressed by:

$$fo'=1/\{2\pi(LC)^{1/2}\}$$

In the present invention, respective parameters are set such that the resonant frequency $f_0'$ of the resonant circuit is substantially equal to the resonant frequency $f_0$ of the barrel 1346. Specifically, the inductance L of the variable inductance 1358 is tuned to establish:

$$fo=1/\{2\pi(LC)^{1/2}\}$$

for the electric capacitance C of the given piezoelectric element 1350. Actually, the capacitance C of the piezoelectric element 1350 is small for forming a resonant circuit to have the same mechanical resonant frequency, so that a very large inductance L is often required, in which case, however, a resonant circuit can be realized by using an operational amplifier or the like to form an equivalently large inductance.

Also, the value $R_D$ of the resistor 1356 is selected such that the Q value of a resonant frequency component of the series resonant circuit substantially matches the Q value of a resonant component having a peak in the transfer function shown in FIG. 29. The series resonant circuit 1360 thus created has electric frequency characteristics designated by reference numeral 1384 in FIG. 29.

The electron beam testing apparatus 1301 illustrated in FIG. 26 is controlled and managed by a controller 1316. As illustrated in FIG. 26, the controller 1316 may comprise a general-purpose personal computer or the like. This computer comprises a controller body 1314 for executing a variety of control and operational processing in accordance with predetermined programs; a CRT 1315 for displaying results of processing by the body 1314; and an input device 1318 such as a keyboard and a mouse for the operator to enter instructions. Of course, the controller 1316 may be built by hardware dedicated to the electron beam testing apparatus, a workstation, or the like.

The controller body 1314 comprises a CPU, RAM, ROM, a hard disk, all not shown, a variety of control boards such as a video board, and so on. On a memory such as RAM and hard disk, a secondary electron beam image storage region 1320 is allocated for storing an electric signal received from the imager unit 1324, i.e., digital image data representing a secondary electron beam image of the wafer 1305. Also, on the hard disk, a reference image storage 1313 exists for previously storing reference image data of the wafer which is free from defects. Further, the hard disk stores a defect detecting program 1319 in addition to a control program for controlling the overall electron beam testing apparatus. This defect detecting program 1319 has functions of controlling movements of the stage 1304 in the XY plane, performing a variety of operational processing such as addition for digital image data received from the imager unit 1324 in the meantime, and reproducing a secondary electron beam image on the storage region 1320 from the resulting data. Further, this defect detecting program 1319 reads secondary electron beam image data created on the storage region 1320, and automatically detects defects on the wafer 1305 in accordance with a predetermined algorithm based on the image data.

Next, the action of this embodiment will be described. A primary electron beam is emitted from the electron beam source 1301*a*, and is irradiated to the surface of the set wafer 1305 through the rectangular opening 1302*a*, quadrupole lens 1302*b*, ExB deflector 1306 and objective lens 1308. As described above, a region under testing over 100 μm×50 μm is illuminated on the wafer 1305 from which a secondary electron beam is emitted. This secondary electron beam is enlarged by the intermediate electrostatic lens 1309, the projection electrostatic lens 1311 and projected onto the lower surface of the multi-channel plate 1321, and imaged by the imager unit 1324 to capture a secondary electron beam image of the projected region on the wafer 1305. The stage 1304 is driven to sequentially move the wafer 1305 every predetermined width in X-Y horizontal plane, and the foregoing procedure is executed to capture an image of the whole surface under testing.

While the enlarged secondary electron beam image is being imaged, if the barrel 1346 is applied with an external force including a vibration component at the resonant frequency $f_0$ (150 Hz), the barrel 1346 amplifies this vibration component at a resonant magnification (30 dB) determined by its transfer function to produced proper vibrations. The vibrations 1388 apply the piezoelectric element 1350 with positive and negative pressures. The piezoelectric element 1350 once transduces vibration energy of the barrel 1346 into electric energy which is output. Since both electrodes 1352a, 1352b of the piezoelectric element 1350 are connected to the inductance 1358 (L) and the resistor 1356 ($R_D$) in series to form a resonant circuit, the capacitive impedance of the piezoelectric element 1350 and the inductive impedance L of the inductance 1358 cancel each other at the resonant frequency $f_0$, so that the impedance of the resonant circuit virtually has only the resistor 2056 ($R_D$). Therefore, during resonance, the electric energy output from the piezoelectric element 1350 is substantially fully consumed by the resistor 1356 (RD).

Consequently, the piezoelectric element 1350 generates a force to cancel an external force applied to the piezoelectric element 1350 from the barrel 1346, thereby making it possible to cancel the vibrations 1388 generated by mechanical resonance and reduce the resonant magnification. Since the secondary electron beam is enlarged and mapped, fluctuations in the map due to the vibration are further increased. However, this embodiment can obviate a blurred map caused by such fluctuations.

Figure 30:
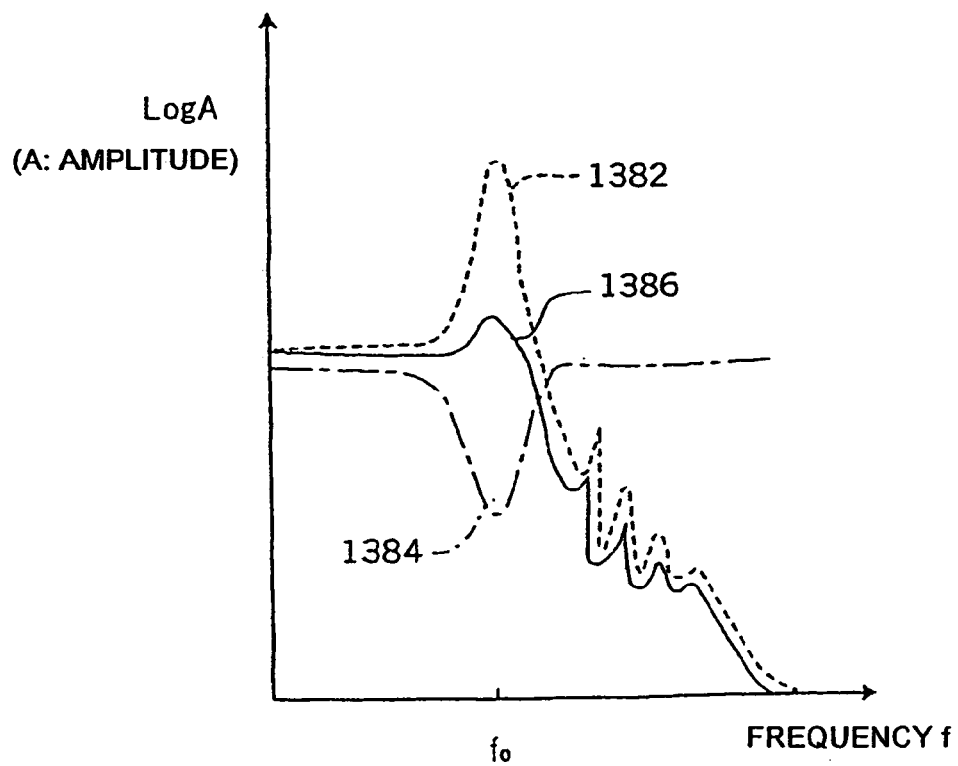
FIG. 30 is a graph showing the transfer function of the barrel, electric frequency characteristic of the series resonant circuit, and a total transfer function in the electron beam testing apparatus illustrated in FIG. 26.

As shown in FIG. 30, a resonant component in the transfer function 1382 of the barrel 1346 as a mechanical construction (corresponding to FIG. 29) is canceled by the resonant component of the series resonant circuit 1360 having the electric frequency characteristic 1384, so that the barrel 1346 has an aggregate transfer function 1386 which is low in resonant magnification as a whole.

As described above, as a satisfactory secondary electron beam image free from blurred image is provided, the electron beam testing apparatus 1301 of this embodiment performs processing for testing the wafer 1305 for defects from the image. As this defect testing processing, a so-called pattern matching method or the like may be used. This method matches a reference image read from the reference image storage 1313 with an actually detected secondary electron beam image to calculate a distance value indicative of the similarity of both. When this distance value is smaller than a predetermined threshold, the testing apparatus 1301 determines "non-defective" as the similarity is high. On the other hand, when the distance value is equal to or larger than the predetermined threshold value, the testing apparatus 1301 determines "defective" as the similarity is low. When determining "defective," the testing apparatus 1301 may display a warning to the operator. In this event, the CRT 1315 may display the secondary electron beam image 1317 on its display screen. In addition, the pattern matching method may be used for each fractional region of the secondary electron beam image.

Figure 31:
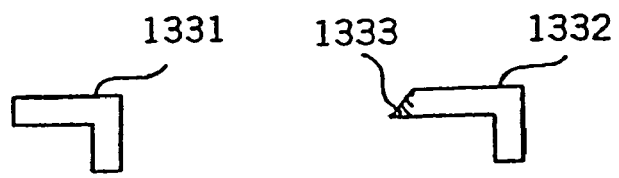
FIGS. 31(a) to 31(c) are diagrams for explaining a wafer testing method according to the present invention, where
Figure 31:
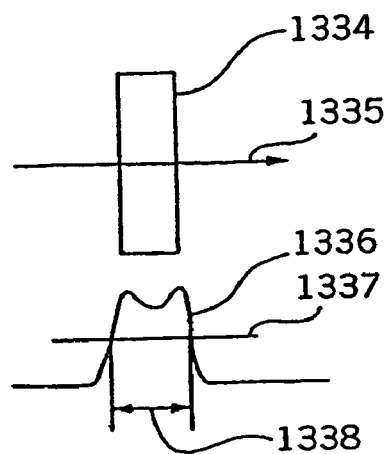
Figure 31:
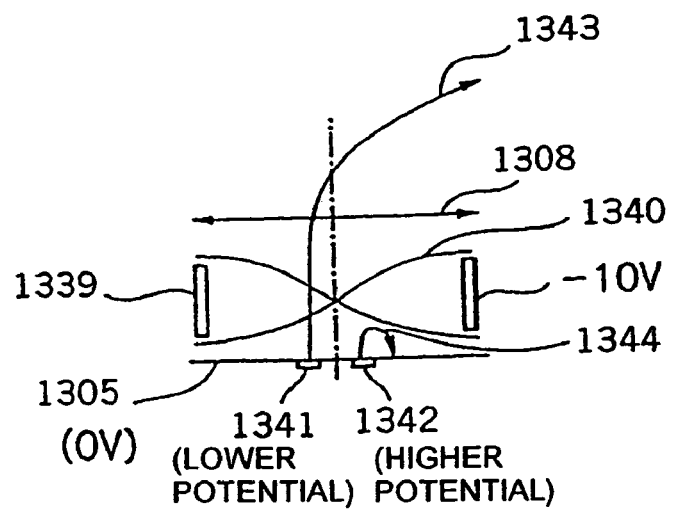

Other than the pattern matching method, there are defect testing methods, for example, as illustrated in FIGS. 31(*a*)-31(*c*). FIG. 31(*a*) illustrates an image 1331 of the first detected die, and an image of 1332 of another die which is detected second time. If an image of another die, detected third time, is determined to be identical or similar to the first image 1331, a portion 1333 in the second die image 1332 is determined to have a defect, so that the defective portion can be detected.

FIG. 31(*b*) illustrates an example of measuring a line width of a pattern formed on a wafer. 1336 designates a signal indicative of the intensity of an actual secondary electron beam when an actual pattern 1334 on a wafer is scanned in a direction 1335. The width 1338 of a portion of this signal which continuously exceeds a previously calibrated and determined threshold level 1337 can be measured as a line width of the pattern 1334. If the thus measured line width is not within a predetermined range, this pattern can be determined to have a defect.

FIG. 31(*c*) illustrates an example of measuring a potential contrast for a pattern formed on a wafer. In the configuration illustrated in FIG. 26, axially symmetric electrodes 1339 are disposed above the wafer 1305, and are applied, for example, with a potential of −10 V with respect to the potential on the wafer at 0 V. An equi-potential plane at −2 V in this event is shaped as indicated by 1340. Assume herein that patterns 1341 and 1342 formed on the wafer are at potentials of −4 V and 0 V, respectively. In this event, since a secondary electron beam emitted from the pattern 1341 has an upward speed corresponding to motion energy of 2 eV on the −2 equi-potential plane 1340, so that the secondary electron beam jumps over a potential barrier 1340, escapes from the electrode 1339 as indicated by a trajectory 1343, and detected by the detector. On the other hand, a secondary electron beam emitted from the pattern 1342 cannot jump over the potential barrier of −2 V, and is driven back to the surface of the wafer, as indicated by a trajectory 1344, so that it is not detected. Therefore, an image of the detected pattern 1341 is bright, while an image of the detected pattern 1342 is dark. Consequently, the potential contrast is can be ontained. If the brightness of a detected image and potential are previously calibrated, the potential of a pattern can be measured from a detected image. Then, a defected portion on a pattern can be evaluated from this potential distribution.

As described above, the testing for defects can be realized at a higher accuracy by making respective measurements as described above for a satisfactory secondary electron beam image free from blurred image, captured by the seventh embodiment of the present invention.

When the electron beam testing apparatus so far described as the seventh embodiment of the present invention is used in the wafer testing process (G) in the device manufacturing method described with reference to FIGS. 3 and 4(*a*), 4(*b*), highly accurate testing can be efficiently made since detected images can be obviated from deterioration due to vibrations of the mechanical construction, making it possible to prevent defective products from being shipped. In this regard, the description related to FIG. 3 and FIGS. 4(*a*), 4(*b*) is incorporated herewith by reference and is omitted herein.

The seventh embodiment of the present invention is not limited to the foregoing, but may be arbitrarily modified in a preferred manner within the gist of the present invention. For example, the mechanical resonant frequency and mode are not necessarily single, but generally, a plurality of resonant frequencies and modes occur, in which case a required number of actuators 1325 may be installed at required locations of the barrel to support them. For example, when the mechanical construction block A illustrated in FIG. 27(*b*) has vibrations in the X-direction as well as the vibrations 1388 in the Y-direction, another actuator may be installed to cancel the vibrations in the X-direction. Further, when the B block and D block also have independent proper vibrations, actuators may be installed for these blocks as well.

The vibration attenuating circuit 1327 need not be equivalent to the series resonant circuit 1360, but may be implemented by a circuit, the electric frequency characteristics of which have a plurality of resonant frequencies when the mechanical proper vibrations have a plurality of resonant frequencies in the same vibration direction.

The actuator may be installed not only in the barrel, but also in a part required to precisely align the beam position, for example, the X-Y state 1304, or in optics of a variety of optical devices.

While the semiconductor wafer 1305 has been taken as an example of a sample under testing for the electron beam testing apparatus of the seventh embodiment, the sample under testing is not limited to this, but arbitrary one may be selected as long as defects thereon can be detected by electron beams. For example, a mask formed with an exposure pattern for a wafer may be chosen as an object under testing.

Further, the seventh embodiment can be applied to the entirety of apparatuses which apply electron beams for irradiate a beam to a target position on an object. In this event, the seventh embodiment can be extended not only to the testing of the object but also to an apparatus which performs at least some of working, manufacturing and observation thereof. Of course, the concept of the object herein referred to encompasses not only the wafer and mask as mentioned, but also an arbitrary object for which at least some of testing, working, manufacturing and observation thereof can be conducted with the beam. The device manufacturing method may also be applied not only to the testing during a semiconductor device manufacturing step but also to a process itself for manufacturing semiconductor devices with beams.

While the configuration illustrated in FIG. 26 has been shown as an electron beam testing apparatus of the seventh embodiment, the electron-optical system and so on can be arbitrarily modified as required. For example, while the electron beam irradiating means of the electron beam testing apparatus 1301 is the type that directs the primary electron beam vertically to the surface of the wafer 1305 from above, the ExB deflector 1306 may be omitted such that the primary electron beam is directed diagonally into the surface of the wafer 1305.

Embodiment Relating to Holding of Wafer (Eighth Embodiment)

An eighth embodiment of the present invention relates to an electrostatic chuck for electrostatically sucking and holding a wafer in an electron beam apparatus, a combination of the wafer and the electrostatic shuck, particularly, a combination of an electrostatic chuck usable in an electron beam apparatus using decelerating electric field objective lenses, and a wafer, and a device manufacturing method which uses an electron beam apparatus that comprises a combination of an electrostatic chuck and a wafer.

A known electrostatic chuck for electrostatically chucking and fixing a wafer comprises electrode layers disposed on a substrate, formed of a plurality of electrodes insulated from each other, and a power supply for sequentially applying a voltage from one electrode to another. Also, an electron beam apparatus using decelerating electric field objective lens is known.

For evaluating a wafer in the middle of a process with an electron beam apparatus using decelerating electric field objective lens, it is necessary to apply a negative high voltage to the wafer. In this event, sudden application of a high negative voltage would break devices in the middle of the process, so that the voltage must be gradually applied.

On the other hand, a majority of wafers are coated with an insulating film such as $SiO_2$, a nitride film or the like on side surfaces and back surfaces, so that when a zero potential or a low potential is to be applied to the wafer, no voltage is applied to the wafer. Further, although a wafer centrally bowed in convex toward the electrostatic chuck can be relatively easily chucked and fixed, a wafer centrally bowed in concave toward the chuck presents a problem that, with a single-pole electrostatic chuck, only a peripheral portion is chucked but a central portion is held unchucked.

The eighth embodiment of the present invention, for solving the above problems, provides an electrostatic chuck for use with decelerating electric field objective lens, which is capable of chucking a wafer coated with an insulating film on its side surface and back surface and centrally bowed in concave toward the chuck, a combination of a wafer and an electrostatic chuck, and a device manufacturing method for evaluating a wafer in the middle of a process using such a combination of an electrostatic chuck and a wafer.

Figure 32:
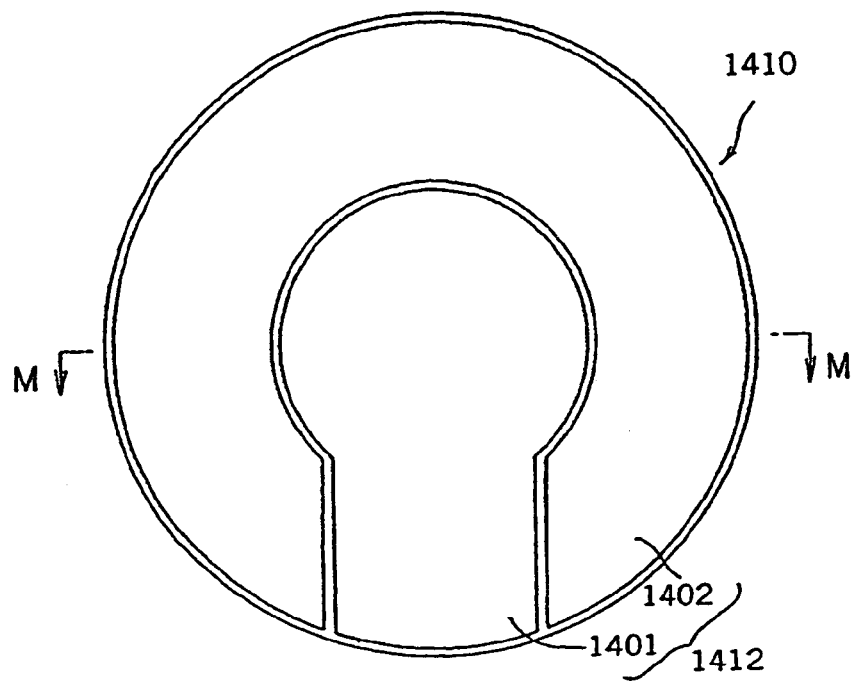
FIG. 32 is a schematic plan view of an electrostatic chuck in an eighth embodiment of the electron beam apparatus according to the present invention, i.e., a plan view with a wafer removed to show electrodes.
Figure 33:
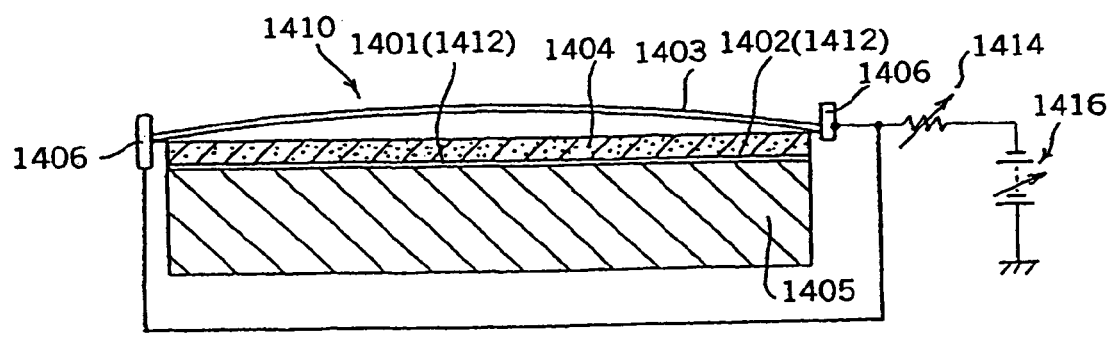
FIG. 33 is a schematic vertical cross-sectional view taken along a straight line M-M in FIG. 32, a cross-sectional view showing a state in which a wafer is carried but not applied with a voltage.

FIG. 32 is a plan view of an electrostatic chuck 1410 in the eighth embodiment of the present invention, removing a wafer to show an electrode plate 1412. FIG. 33 is a schematic cross-sectional view in the vertical direction along a line M-M of the electrostatic chuck of FIG. 32, showing that a wafer is carried but not applied with a voltage. The electrostatic chuck 1410 has a laminate structure comprised of a substrate 1405, an electrode plate 1412 and an insulating layer 1404, as illustrated in FIG. 33. The electrode plate 1412 includes a first electrode 1401 and a second electrode 1402. The first electrode 1401 and second electrode 1402 are separated such that they can be separately applied with voltages, and are formed of thin films such that they can be moved at a high speed without generating eddy currents in a magnetic field.

The first electrode 1401 is comprised of a central portion and some of a peripheral portion of the circular electrode plate 1412 on the plan view, while the second electrode 1402 is comprised of the remaining horseshoe-shaped peripheral portion. The insulating layer 1404 is disposed on the electrode plate 1412. The insulating layer 1404 is formed of a sapphire substrate of 1 mm in thickness. Sapphire is single crystal of alumina and has a high breakdown voltage since it is completely free of bore as in alumina ceramics. For example, a sapphire substrate of 1 mm in thickness can sufficiently withstand a potential difference of $10^4$ V or higher.

The wafer 1403 is applied with a voltage through contacts 1406 having a knife-edge shaped metal portion. As illustrated in FIG. 33, two contacts 1406 are brought into contact with the side surface of the wafer 1403. The two contacts 1406 are used in order to avoid a possible failure of conduction and a force generated to urge the wafer 1403 to one side, as could be otherwise experienced if only one contact was used. The insulating layer 1404 is broken for making the conduction. However, since particles could be scattered upon discharging, the contacts 1406 are connected to a power supply 1416 through a resistor 1414 to prevent a large discharge from occurring. Since this resistor 1414 prevents the formation of a conduction hole if it is too large, and causes a large discharge to scatter particles if it is too small, an allowable value for the resistor is determined for each insulating layer 1404.

Figure 34:
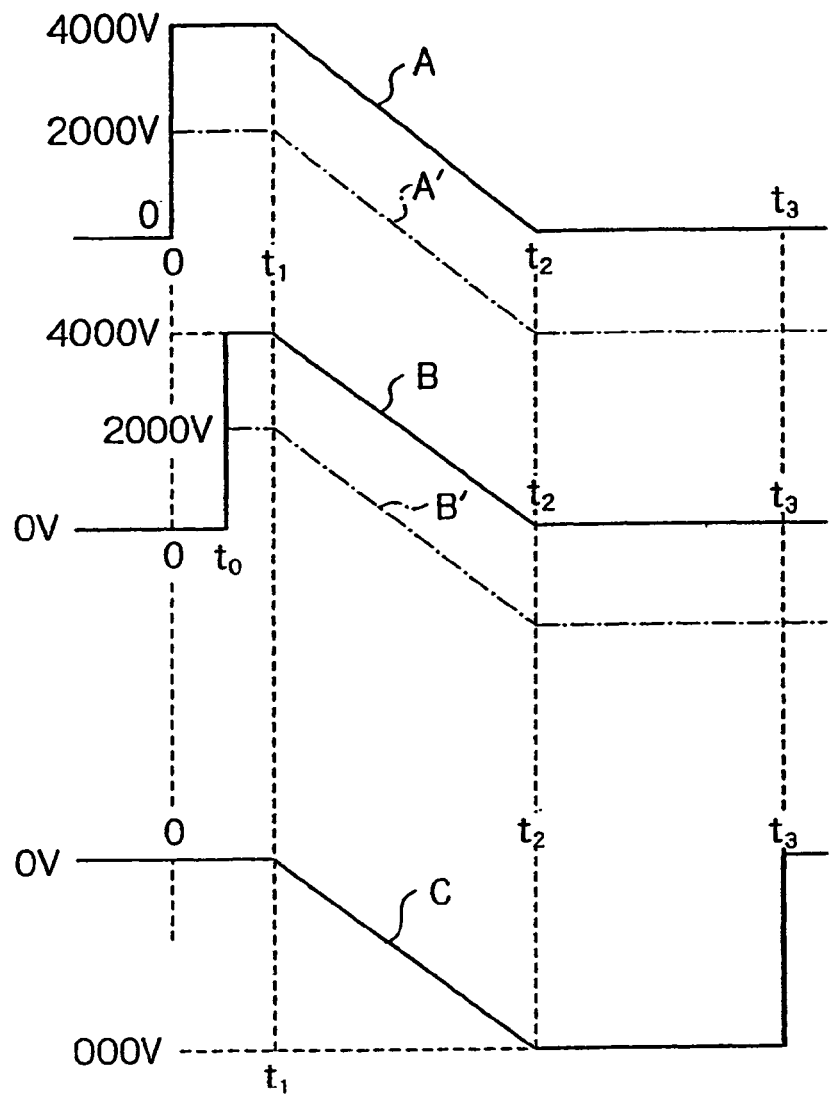
FIGS. 34(a) and 34(b) are time charts of voltages applied to electrodes and a wafer.
Figure 34:
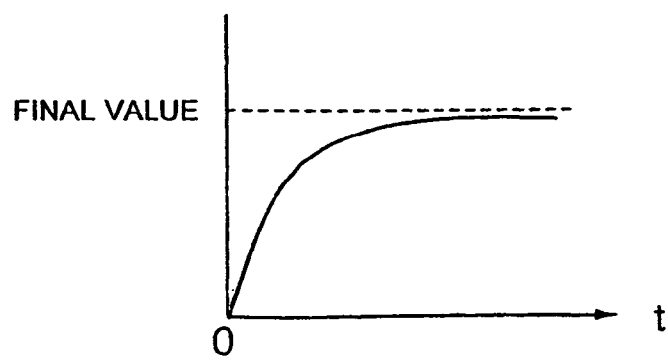

FIG. 34(*a*) shows a time chart of applied voltages. The first electrode is applied with 4 kV at time t=0, as indicated by a line A. At time $t=t_0$, at which the wafer is chucked both in the central portion and in the peripheral portion, the second electrode is applied with 4 kV, as indicated by a line B. At time $t=t_1$, a voltage C across the wafer is controlled to be gradually deepened (lowered) to reach −4 kV at time $t=t_2$. The first electrode and the second electrode are applied with gradually reduced voltages from time $t=t_1$ to time $t=t_2$, and with 0 V at $t=t_2$.

At time t=t₃ at which evaluation has been made for the wafer chucked and held by the chuck, the voltage C across the wafer is reduced to 0 V, and the wafer is removed to the outside.

When the electrostatic chuck holds a wafer with a potential difference of 2 kV, rather than a potential difference of 4 kV, the first electrode and the second electrode are applied with voltages A', B' at 2 kV, respectively, as indicated by one-dot chain lines in FIG. 34. When the wafer is applied with −4 kV, the first electrode and the second electrode are applied with −2 kV, respectively. In this way, the insulating layer 2104 is prevented from being applied with a voltage more than necessity, by the application of voltages, so that the insulating layer can be prevented from breakdown.

Figure 35:
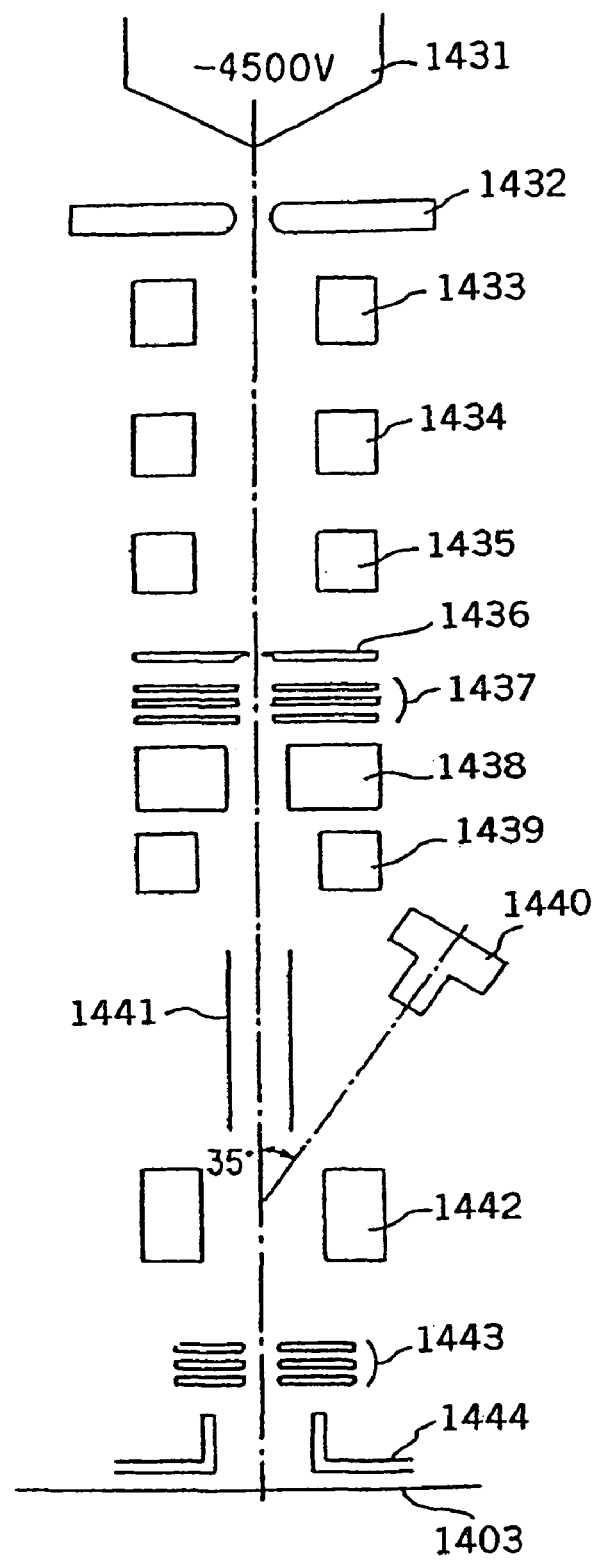
FIG. 35 is a block diagram illustrating an exemplary configuration of an electron beam apparatus which uses the electrostatic chuck illustrated in FIG. 32.

FIG. 35 is a block diagram illustrating an electron beam apparatus which comprises the electrostatic chuck described above. Unnecessary beams are removed from electron beams emitted from an electron beam source 1431 by an aperture of an anode 1432 which determine the numerical aperture (NA). The electron beam is reduced by a condenser lens 1437 and an objective lens 1443, and focused on a wafer 1403 applied with −4 kV, and scans on the wafer 1403 with deflectors 1438 and 1442. A secondary electron beam emitted from the wafer 1403 is collected by the objective lens 1443, deflected to the right by approximately 35° by an ExB separator 1442, and detected by a secondary electron beam detector 1440 to capture an SEM image on the wafer. In the electron beam apparatus of FIG. 35, reference numerals 1433, 1435 designate alignment tools; 1434 an astigmatism correcting tool; 1436 an opening plate; 1441 a shield; and 1444 an electrode. The electrostatic chuck described in FIGS. 33 and 34 is disposed below the wafer 1403.

When the eighth embodiment of the present invention is used in the testing process (G) in the device manufacturing method described with reference to FIGS. 3 and 4(a), 4(b), semiconductor devices even having miniature patterns can be tested at a high throughput, so that a total inspection can also be conducted, thereby making it possible to improve the yield rate of products and prevent defective products from being shipped. In this regard, the description related to FIG. 3 and FIGS. 4(a), 4(b) is incorporated herewith by reference and is omitted herein.

The manner of increasing or decreasing the voltages applied to the electrostatic chuck is not limited to that shown in FIG. 34. For example, as shown in FIG. 34(b), an exponentially changing voltage may also be used. In essence, any voltage may be used as long as it reaches a predetermined voltage without delay.

Embodiment Relating to Stage for Carrying Sample
(Ninth Embodiment)

A ninth embodiment of the present invention relates to an apparatus for irradiating an electron beam to a sample carried on an XY stage, a defect testing apparatus or an exposure apparatus utilizing the apparatus, and a device manufacturing method using these apparatuses.

A stage for accurately positioning a sample in a vacuum is used in an apparatus which irradiates an electron beam to the surface of a sample such as a semiconductor wafer, or the like to expose the surface of the wafer with a pattern such as a semiconductor circuit or to test patterns formed on the surface of the sample, or in an apparatus which irradiates an electron beam to perform ultra-precision working on the sample.

When highly accurate positioning is required to such a stage, a structure of supporting a stage with static pressure bearings in a non-contact manner is employed. In this event, a degree of vacuum is maintained in a vacuum chamber by forming a differential pumping mechanism for exhausting a high pressure gas in a range of the hydorstatic pressure bearing such that the high pressure gas supplied from the static pressure bearings will not be exhausted directly to the vacuum chamber.

An example of such a stage according to the prior art is illustrated in FIG. 36. In the structure of FIG. 36, a leading end of a barrel 1501 of an electron beam apparatus for generating an electron beam for irradiating a sample, i.e., an electron beam irradiating tip 1502 is attached to a housing 1508 which constitutes a vacuum chamber C. The inside of the barrel is evacuated to vacuum by a vacuum pipe 1510, and the chamber C is evacuated to a vacuum by a vacuum pipe 1511. Then, electron beam is irradiated from the leading end 1502 of the barrel 1501 to a sample S such as a wafer placed therebelow.

Figure 37:
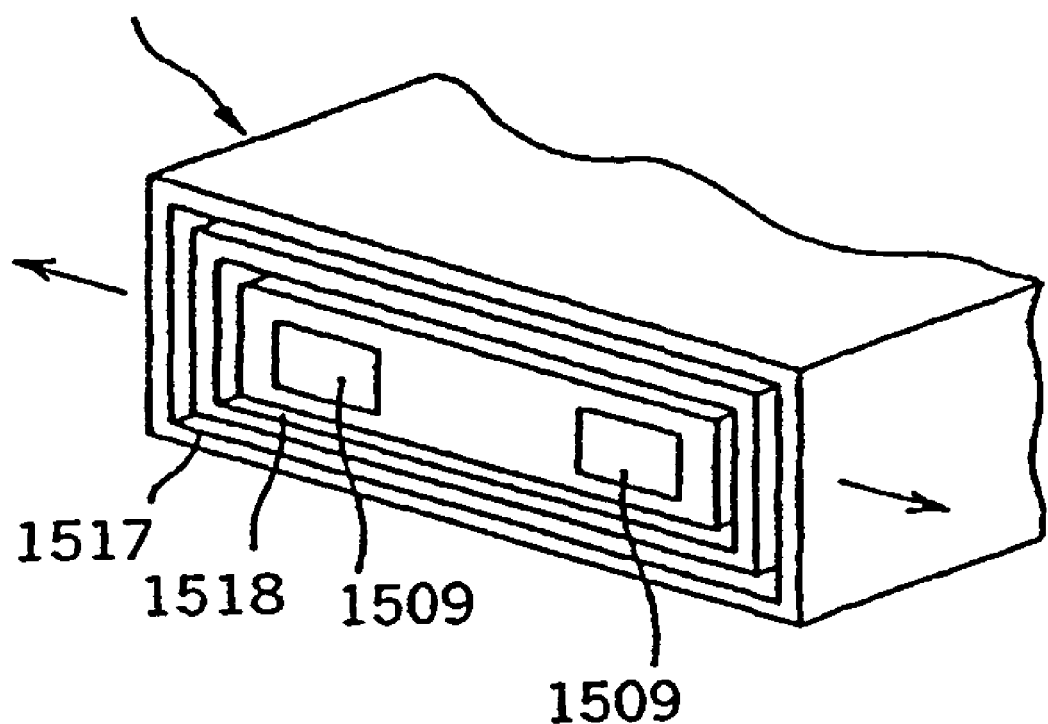
FIG. 37 is a diagram for explaining a differential pumping mechanism in FIG. 36.

The sample S is removably held on a sample base 1504 in a known method. The sample base 1504 is mounted on the top surface of a Y-direction movable section 1505 of an XY stage (hereinafter simply called the "stage") 1503. The Y-direction movable section 1505 has a plurality of static pressure bearings 1509 attached on surfaces (both left and right side surfaces and a lower surface in FIG. 36[A]) opposite to a guide surface 1506a of an X-direction movable section 1506 of the stage 1503. The Y-direction movable section is movable in the Y-direction (in the left-to-right direction in FIG. 36[B]) while maintaining a small gap between the guide surface and the opposite surfaces by the action of the static pressure bearings 1509. Further, around the hydrostatic pressure bearings, a differential pumping mechanism is disposed to prevent a high pressure gas supplied to the static pressure bearings from leaking into the inside of the vacuum chamber C. This situation is shown in FIG. 37. Double grooves 1518 and 1517 are formed around the static pressure bearings 1509, and these grooves are evacuated to vacuum at all times by a vacuum pipe and a vacuum pump, not shown. With such a structure, the Y-direction movable section 1505 is supported in a non-contact state in vacuum so that it is freely movable in the Y-direction. These double grooves 1518 and 1517 are formed to surround the static pressure bearings 1509 of the movable section 1505 on the surface on which the static pressure bearings are disposed. Since the static pressure bearing may have a known structure, detailed description thereon is omitted.

The X-section movable section 1506, which carries the Y-direction movable section 1505 has a concave shape open to above, as is apparent from FIG. 36. The X-direction movable section 1506 is also provided with completely similar hydrostatic pressure bearings and grooves, such that the X-direction movable section 1506 is supported to a stage stand 1507 in a non-contact manner, and is freely movable in the X-direction.

By combining movements of these Y-direction movable section 1505 and X-direction movable section 1506, it is possible to move the sample S to an arbitrary position in the horizontal direction with respect to the leading end of the barrel, i.e., the electron beam irradiating tip 1502 to irradiate electron beams to a desired position of the sample.

In the stage having a combination of the static pressure bearings and the differential pumping mechanism, the guide surfaces 1506a and 1507a opposing the static pressure bearings 1509 reciprocate between a high pressure gas atmosphere of the static pressure bearings and a vacuum environment within the chamber as the stage is moved. In this event, while the guide surfaces are exposed to the high pressure gas atmosphere, the gas is adsorbed to the guide surfaces, and the adsorbed gas is released as the guide surfaces are exposed to the vacuum environment. Such states are repeated. Therefore, as the stage is moved, the degree of vacuum within the chamber C is degraded, giving rise to a problem that the aforementioned processing such as exposure, testing and working, by use of the electron beam cannot be stably performed and that the sample is contaminated.

To solve such problem, the ninth embodiment of the present invention provides:

an electron beam apparatus which prevents the degree of vacuum from degrading to permit stable processing such as testing and working by use of an electron beam;

an electron beam apparatus which has a non-contact supporting mechanism by means of static pressure bearings and a vacuum sealing mechanism by means of differential pumping to generate a pressure difference between an electron beam irradiation region and a supporter of the static pressure bearings;

an electron beam apparatus for reducing a gas released from the surface of parts facing the static pressure bearings;

a defect testing apparatus using the electron beam apparatus to test the surface of a sample, or an exposure apparatus for delineating patterns on the surface of the sample; and a semiconductor manufacturing method for manufacturing semiconductor devices using the electron beam apparatus as described above.

In the following, the ninth embodiment of the present invention will be described with reference to the drawings. In FIG. 38, a partition plate 1514 largely extending substantially horizontally in the +Y direction and in the −Y direction (in the left and right directions in FIG. 38[B]) is attached on the top surface of a Y-direction movable section 1505 of a stage 1503, such that a reducer 1550 having a small conductance is formed at all times between the top surface of the X-direction movable section 1506 and the partition plate 1514. Also, on the top surface of an X-direction movable section 6, a similar partition plate 1512 is placed to extend in the ±X-directions (in the left and right directions in FIG. 38[A]), such that a reducer 1551 is formed at all time between the top surface of a stage stand 1507 and the partition plate 1512. The stage stand 1507 is fixed on a bottom wall in a housing 1508 in a known manner.

Thus, the reducers 1550 and 1551 are formed at all times when the sample base 1504 is moved to whichever position, so that even if a gas is released from the guide surfaces 1506a and 1507a while the movable sections 1505 and 1506 are moved, the movement of the released gas is prevented by the reducers 1550 and 1551, thereby making it possible to significantly suppress an increase in pressure in a space 1524 near the sample irradiated with electron beams.

The side surface and the lower surface of the movable section 1505 and the lower surface of the movable section 1506 of the stage are formed with grooves around the static pressure bearings 1509 for differential pumping, as illustrated in FIG. 37. Since evacuation to vacuum is performed through these grooves, the released gas from the guide surfaces are mainly exhausted by these differential pumping unit when the reducers 1550, 1551 are formed. Therefore, the pressures in the spaces 1513 and 1515 within the stage are higher than the pressure within the chamber C. Therefore, if locations which are evacuated to vacuum are separately provided, not only the spaces 1513 and 1515 are evacuated through the differential pumping grooves 1517 and 1518, but also the pressures in the spaces 1513 and 1515 can be reduced to further suppress an increase in pressure near the sample 1524. Vacuum evacuation passages 1511-1 and 1511-2 are provided for this purpose. The evacuation passages extend through the stage stand 1507 and the housing 1508 and communicate with the outside. Also, the evacuation passage 1511-2 is formed in the X-direction movable section 1506, and is open to the lower surface of the X-direction movable section 1506.

While the provision of the partition plates 1512 and 1514 results in a requirement of increasing the size of the chamber C such that the chamber C does not interfere with the partition walls, this aspect can be improved by making the partition plates of a retractile material or in a telescopical structure. In this embodiment, the partition wall is made of rubber or in bellows form, and its end in the moving direction is fixed to the X-direction moving section 1506 for the partition plate 1514, and to an inner wall of the housing 1508 for the partition plate 1512, respectively.

Figure 39:
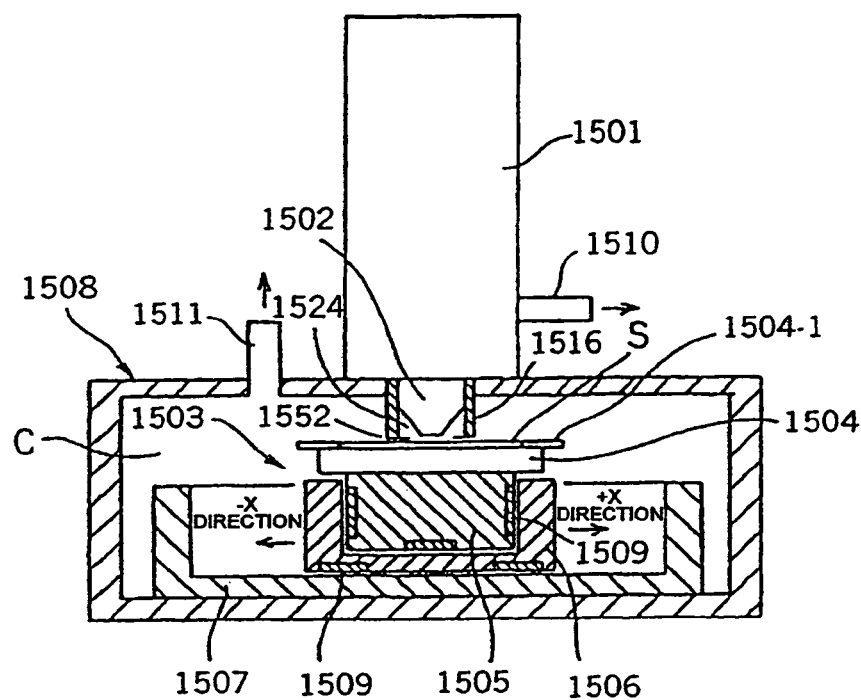
FIG. 39 is a diagram illustrating a vacuum chamber and an XY stage in a first exemplary modification to the ninth embodiment of the present invention.

FIG. 39 illustrates a first exemplary modification in the ninth embodiment of the present invention. In this example, a cylindrical partition 1516 is formed around the leading end of the barrel, i.e., the electron beam irradiating tip 1502 to provide a reducer between the top surface of the sample S and the electron beam irradiating tip 1502. In such a configuration, even if a gas is released from the XY stage to cause an increased pressure within the chamber C, the inside 1524 of the partition is partitioned by the partition 1516 and the gas is exhausted through the vacuum pipe 1510, so that a pressure difference is produced between the inside of the chamber C and the inside 1524 of the partition to suppress an increased pressure within the space 1524 in the partition. While a gap between the partition 1516 and the surface of the sample varies depending on the pressure maintained within the chamber C and around the irradiating tip 1502, approximately several tens of μm to several mm are proper. The inside of the partition 1516 is communicated with the vacuum pipe by a known method.

Also, some electron beam apparatus may apply a sample S with a high voltage of approximately several kV, so that a conductive material placed near the sample can give rise to a discharge. In this case, the partition 1516 may be made of an insulating material such as ceramics to prevent a discharge between the sample S and the partition 1516.

A ring member 1504-1 disposed around the sample S (wafer) is a plate-shaped adjusting part fixed to the sample base 1504, which is set at the same level as the wafer such chat a small gap 1525 is formed over the entire periphery of the leading end of the partition 1516 even if an end portion of a sample such as a wafer is irradiated with an electron beam. In this way, even when an electron beam is irradiated to whichever position of the sample S, the constant small gap 1552 is formed at all times at the leading end of the partition 1516, thereby making it possible to stably maintain the pressure in the space 1524 around the leading end of the barrel.

Figure 40:
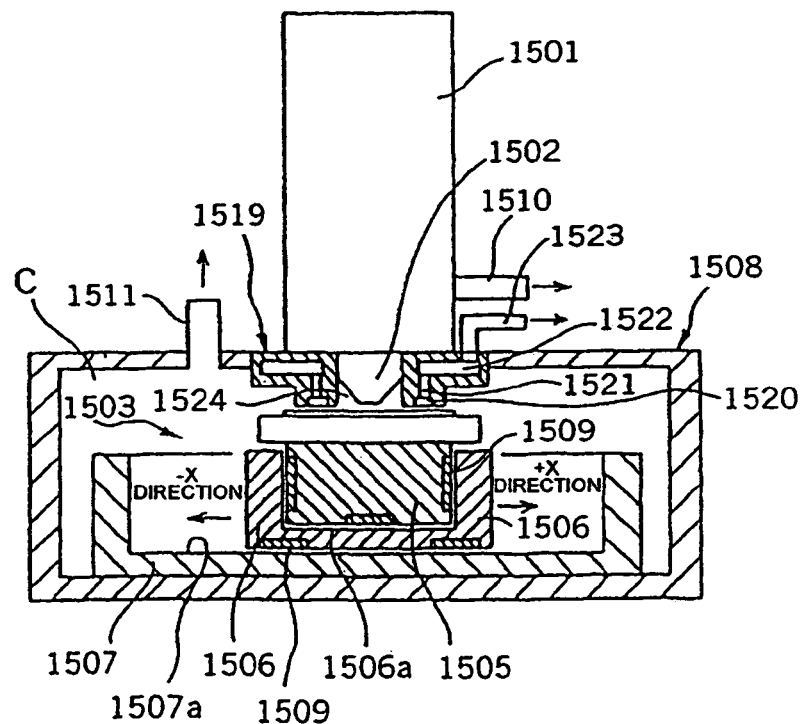
FIG. 40 is a diagram illustrating a vacuum chamber and an XY stage in a second exemplary modification to the ninth embodiment of the present invention.

FIG. 40 illustrates a second exemplary modification in the ninth embodiment of the present invention. A partition 1519 containing a differential pumping structure is disposed around an electron beam irradiating tip 2 of the barrel 1501. The partition 1519 has a cylindrical shape, and a circumferential groove 1520 is formed inside. An exhaust passage 1521 extends upward from the circumferential grove. The exhaust passage is connected to a vacuum pipe 1523 through an internal space 1522. There is a small gap ranging from several tens of μm to several mm between the lower end of the partition wall 1519 and the upper surface of the sample S.

In such a configuration, even if a gas is released from the stage in association with a movement of the stage to cause an increased pressure within the chamber C, and the gas is going to flow into the leading end, i.e., the electron beam irradiating tip 1502, the partition 1519 reduces the gap between the sample S and the leading end to make the conductance extremely small, so that the gas is impeded from flowing into the electron beam irradiating tip 1502 and the amount of flowing gas is reduced. Further, the introduced gas is exhausted from the circumferential groove 1520 to the vacuum pipe 1523, so that substantially no gas flows into the space 1524 around the electron beam irradiating tip 1502, thereby making it possible to maintain the pressure at the electron beam irradiating tip 1502 at a desired high vacuum.

Figure 41:
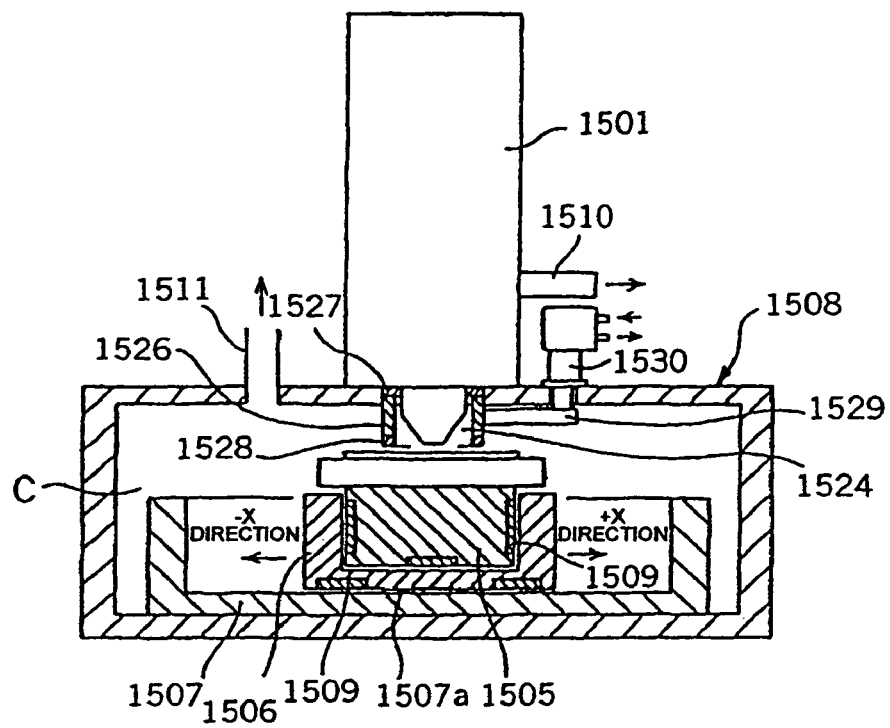
FIG. 41 is a diagram illustrating a vacuum chamber and an XY stage in a third exemplary modification to the ninth embodiment of the present invention.

FIG. 41 illustrates a third exemplary modification in the ninth embodiment of the present invention. A partition 1526 is formed around the chamber C and the electron beam irradiating tip 1502 to separate the electron beam irradiating tip 1502 from the chamber C. This partition 1526 is coupled to a freezer 1530 through a supporting member 1529 made of a high thermally conductive material such as copper and aluminum, and is cooled at −100° C. to −200° C. A member 1527 is provided for preventing thermal conduction between the cooled partition 1526 and the barrel, and is made of a low thermally conductive material such as ceramics and resin material. Also, a member 1528, which is made of a non-insulating material such as ceramics, is formed at a lower end of the partition 1526 and is responsible for preventing the sample S and the partition 1526 from discharging.

In such a configuration, gas molecules which are going to flow from the chamber C into the electron beam irradiating tip are impeded by the partition 1526 from flowing toward the electron beam irradiating tip, and even if the molecules flow, they are frozen and trapped on the surface of the partition 1526, thereby making it possible to maintain low the pressure in the space 1524 in which the electron beam irradiating tip 1502 is positioned.

As the freezer, a variety of freezers can be used such as a liquid nitrogen based freezer, an He freezer, a pulse tube type freezer, and so on.

Figure 42:
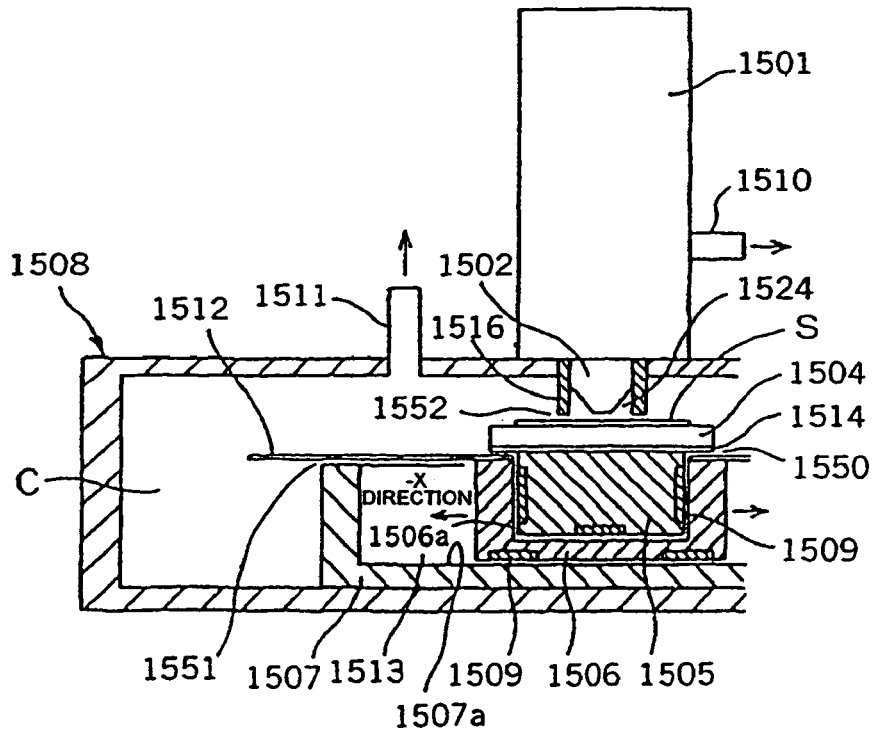
FIG. 42 is a diagram illustrating a vacuum chamber and an XY stage in a fourth exemplary modification to the ninth embodiment of the present invention.

FIG. 42 illustrates a fourth exemplary modification in the ninth embodiment of the present invention. Partition plates 1512, 1514 similar to that illustrated in FIG. 38 are disposed on both movable sections of the stage 1503, so that even if the sample base 1504 is moved to an arbitrary position, the space 1513 within the stage and the inside of the chamber C are partitioned by these partitions through reducers 1550, 1551. Further, a partition 1516 similar to that illustrated in FIG. 39 is formed around the electron beam irradiating tip 1502 to partition the inside of the chamber C and the space 1524, in which the electron beam irradiating tip 1502 is positioned, through a reducer 1552. Therefore, even if a gas adsorbed on the stage is released into the space 1513 while the stage is moved to increase the pressure in this space, an increased pressure in the chamber C is suppressed, and an increased pressure in the space 1524 is further suppressed. In this way, the pressure in the electron beam irradiation space 1524 can be maintained in a low state. In addition, the space 1524 can be stably maintained at a yet lower pressure by providing the partition 1519 which contains a differential pumping mechanism as illustrated in the partition 1516, or the partition 1526 cooled by a freezer, as illustrated in FIG. 40.

Figure 43:
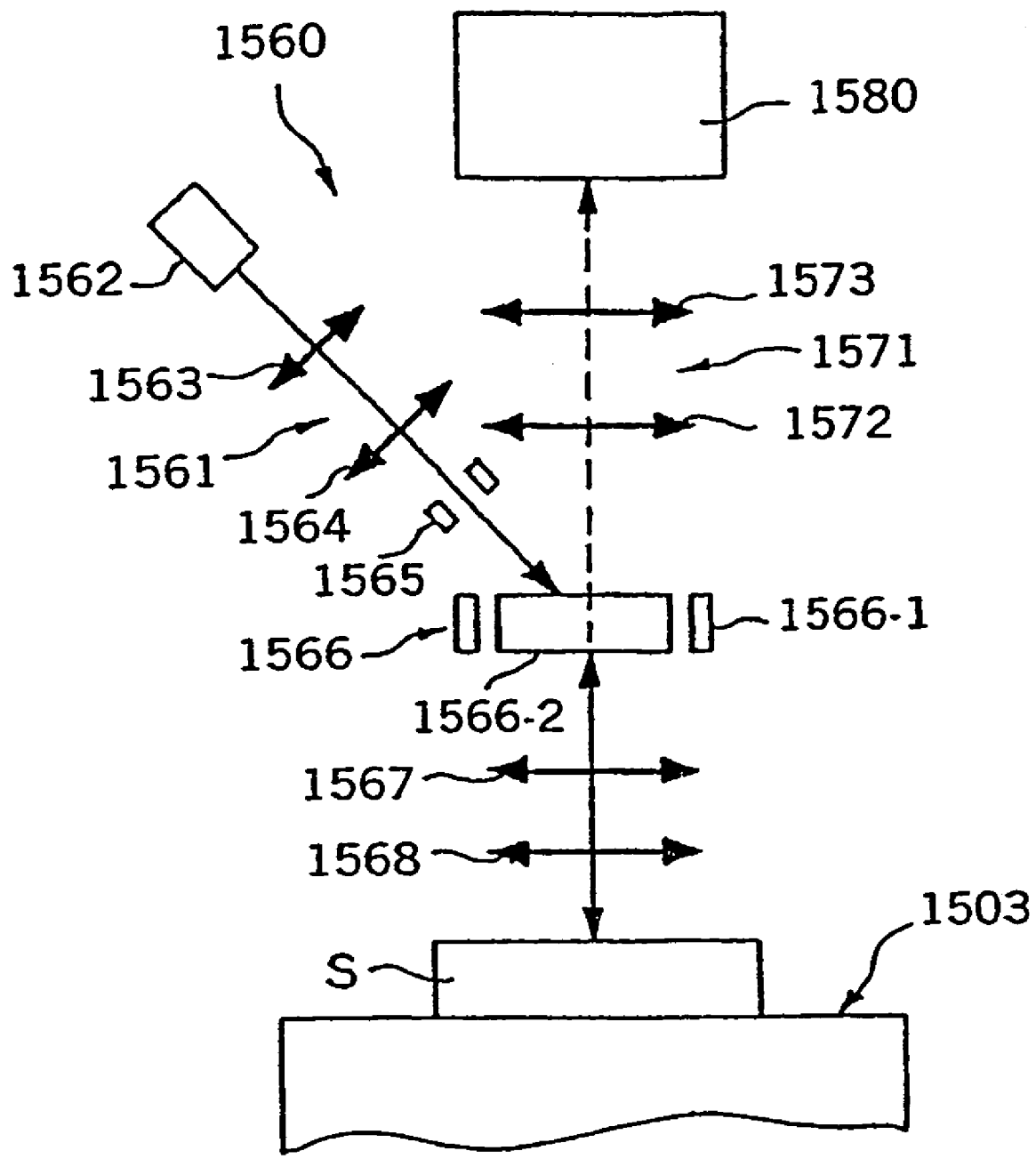
FIG. 43 is a schematic diagram showing an example of an optical system and a detection system disposed in a barrel illustrated in FIGS. 38-42.

FIG. 43 schematically illustrates an optical system and a detection system of the electron beam apparatus according to the ninth embodiment. While the optical system is disposed within the barrel 1501, these optical system and detector are illustrative in all sense, and arbitrary optical system and detector may be used as required. An optical system 1560 of the electron beam apparatus comprises a primary optical system 1561 for irradiating an electron beam to a sample S carried on the stage 1503; and a secondary optical system 1571 into which a secondary electron beam emitted from the sample is introduced. The primary optical system 1561 comprises an electron beam source 1562 for emitting an electron beam; a lens system 1563, 1564 comprised of two-stage electrostatic lenses for converging an electron beam emitted from the electron beam source 1562; a deflector 1565; a Wien filter 1566 for deflecting an electron beam such that its optical axis is oriented perpendicular to the surface of an object; and a lens system 1567, 1568 comprised of two-stage electrostatic lenses. These components are positioned in order obliquely with respect to the optical axis of the electron beam vertical to the surface of the sample S (sample surface) with the electron beam source 1562 placed at the top, as illustrated in FIG. 36. The Wien filter 1566 comprises an electrode 1566-1 and a magnet 1566-2.

The secondary optical system 1571, which is an optical system into which a secondary electron beam emitted from the sample S is introduced, comprises a lens system 1572, 1573 comprised of two-stage electrostatic lenses disposed above the Wien filter 1566 in the primary optical system. A detector 1580 detects a secondary electron beam sent through the secondary optical system 1571. Since the structure and function of the respective components in the optical system 1560 and the detector 1580 are identical to conventional ones, detailed description thereon is omitted.

An electron beam emitted from the electron beam source 1562 is reshaped by a square aperture of the electron beam source, reduced by the two-stage lens systems 1563 and 1564, has its optical axis adjusted by the deflector 1565, and focused on a deflection central surface of the Wien filter 1566 in a square having one side of 1.25 mm. The Wien filter 1566 is arranged such that an electric field and a magnetic field are orthogonal to each other in a plane perpendicular to the normal of the sample, and allows an electron beam to go straight therethrough when the relationship among the electric field, magnetic field, and energy of the electron beam satisfies a predetermined condition, and otherwise deflects the electron beam in a predetermined direction depending on the mutual relationship among these electric field, magnetic field, and energy of the electric field. In FIG. 43, the Wien filter is set to allow an electron beam from the electron beam source to impinge perpendicularly to the sample S, and a secondary electron beam emitted from the sample to go straight therethrough in the direction of the detector 1580. The reshaped beam deflected by the Wien filter 1566 is reduced by the lens systems 1567, 1568 by a factor of five, and projected onto the sample S. A secondary electron beam having information on a pattern image emitted from the sample S is enlarged by lens systems 1567, 1568 and 1572, 1573 to form a secondary electron beam image on the detector 1580. The four-stage enlarging lenses constitute distortion-free lenses since the lens system 1567 and 1568 forms a symmetric tablet lens, and the lens system 1572 and 1573 also forms a symmetric tablet lens.

When the ninth embodiment of the present invention is used in the testing process (G) or the exposure process (c) in the device manufacturing method described with reference to FIGS. 3 and 4(*a*), 4(*b*), miniature patterns can be stably-tested or exposed at a high accuracy, thereby making it possible to improve the yield rate of products and prevent defective products from being shipped. In this regard, the description related to FIG. 3 and FIGS. 4(*a*), 4(*b*) is incorporated herewith by reference and is omitted herewith.

Embodiment Relating to Stage for Carrying Sample
(Tenth Embodiment)

A tenth embodiment of the present invention relates to an apparatus for irradiating an electron beam to a sample carried on an XY stage, and more particularly, to an electron beam apparatus which comprises a differential pumping mechanism around a barrel without containing the differential pumping mechanism in an XY stage, a defect testing apparatus or an exposure apparatus utilizing the apparatus, and a device manufacturing method using these apparatuses.

As previously described with reference to FIGS. 36 and 37, a conventional XY stage which has a combination of static pressure bearings and a differential pumping mechanism, because of the inclusion of the differential pumping mechanism, is complicated in structure and large as compared with a static pressure bearing type stage used in the atmosphere, and also has a problem in low reliability as a stage and a high cost. In this embodiment, FIGS. 36, 37, and the previous description thereon are incorporated herewith by reference as description of the prior art.

The tenth embodiment of the present invention, to solve the above problem, provides:

an electron beam apparatus which eliminates a differential exhaust mechanism from an XY stage to enable simplification of structure and reduction in size;

an electron beam apparatus which comprises a differential pumping mechanism for evacuating a housing which contains the XY stage to vacuum and evacuating a region on the surface of a sample irradiated with an electron beam;

a defect testing apparatus for testing the surface of the sample using the electron beam apparatus, or an exposure apparatus for drawing patterns on the surface of the sample; and a semiconductor manufacturing method for manufacturing semiconductor devices using the electron beam apparatus as mentioned above.

In the tenth embodiment, a term "vacuum" is used in a normal meaning in the art.

Figure 44:
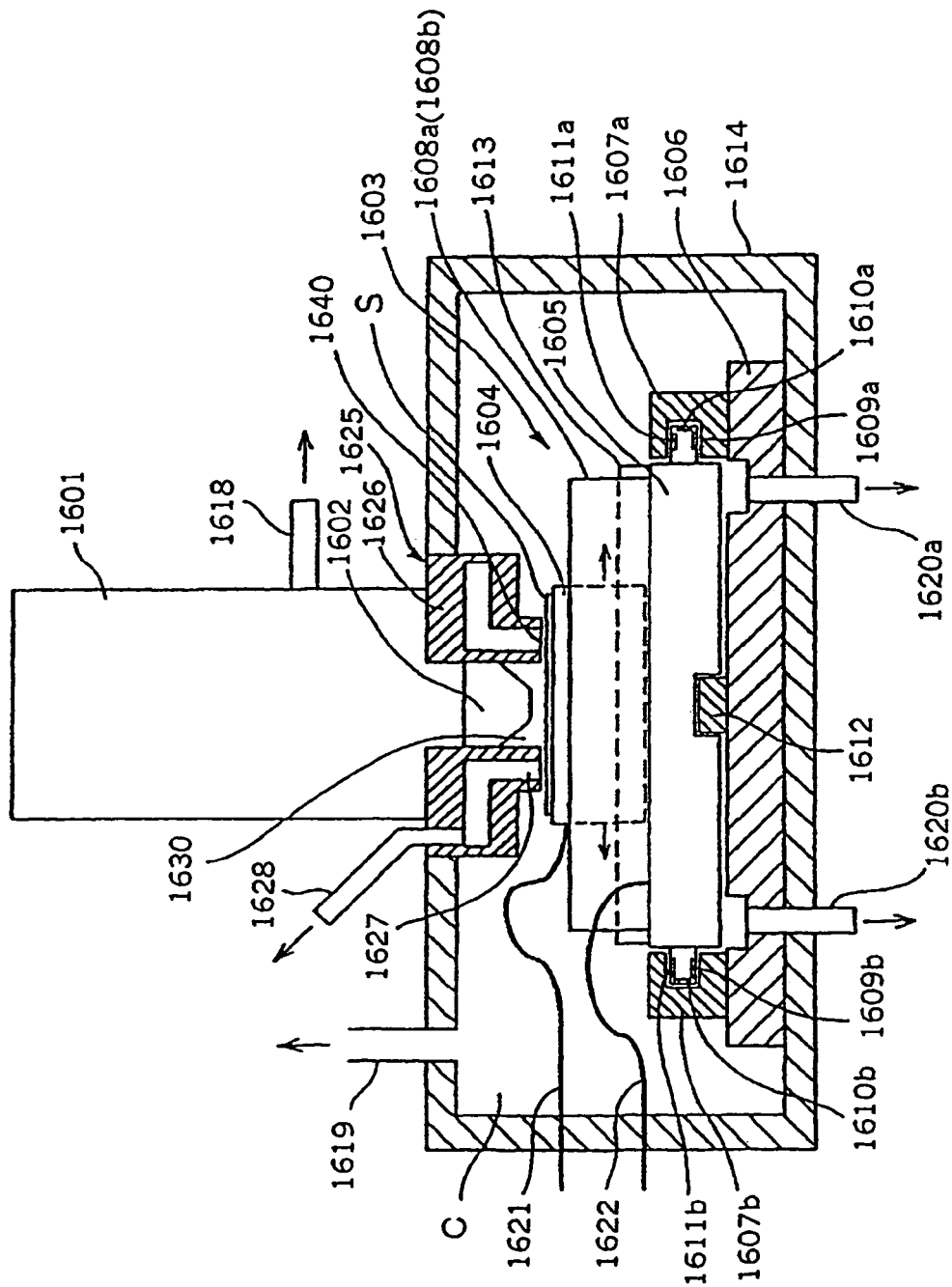
FIG. 44 is a diagram illustrating a vacuum chamber and an XY stage in a tenth embodiment of the charged particle beam apparatus according to the present invention.

In the following, the tenth embodiment of the present invention will be described with reference to the drawings. In FIG. 44, a leading end of a barrel 1601, i.e., an electron beam irradiating tip 1602 for irradiating an electron beam to a sample is attached to a housing 1614 which defines a vacuum chamber C. A sample S carried on a movable table in the X-direction (in the left-to-right direction in FIG. 44) of an XY stage 1603 is positioned beneath the barrel 1601. The sample S can be precisely irradiated with an electron beam at an arbitrary position on the surface of the sample by the highly accurate XY stage 1603.

A pedestal 1606 of the XY stage 1603 is fixed on a bottom wall of the housing 1614, and a Y-table 1605 movable in the Y-direction (in the direction vertical to the sheet in FIG. 24) is carried on the pedestal 1606. On both sides of the Y-table 1605 (on left and right sides in FIG. 24), protrusions are formed protruding into recessed grooves of a pair of Y-direction guides 1607*a* and 1607*b* carried on the pedestal 1606 formed in the sides facing the Y-table. The recessed grooves extend in the Y-direction substantially over the entire length of the Y-direction guides. Static pressure bearings 1611*a*, 1609*a*, 1611*b*, 1609*b* in a known structure are disposed on the top surface, bottom surface and side surfaces of the protrusions protruding into the recessed grooves, respectively. A high pressure gas is blown off through these static pressure bearings to support the Y-table 1605 with respect to the Y-direction guides 1607*a*, 1607*b* in a non-contact manner and to allow the same to smoothly reciprocate in the Y-direction. Also, a linear motor 1612 in a known structure is disposed between the pedestal 1606 and the Y-table 1605 to drive the Y-table 1605 in the Y-direction by means of the linear motor. The Y-table is supplied with a high pressure gas through a flexible pipe 1622 for high pressure gas supply, so that the high pressure gas is supplied to the static pressure bearings 1609*a* to 1611*a* and 1609*b* to 1611*b* through a gas passage (not shown) formed in the Y-table. The high pressure gas supplied to the static pressure bearings blows out into a gap of several microns to several tens of microns formed between opposing guiding surfaces of the Y-direction guide to serve to precisely position the Y-table with respect to the guide surfaces in the X-direction and Z-direction (upward and downward directions in FIG. 44).

An X-table 1604 is carried on the Y-table for movement in the X-direction (in the left-to-right direction in FIG. 44). On the Y-table 1605, a pair of X-direction guides 1608*a*, 1608*b* (only 1608*a* is shown) identical in structure to the Y-direction guides 1607*a*, 1607*b* for the Y-table are disposed with the X-table 1604 interposed therebetween. A recessed groove is also formed in the side of the X-direction guide facing the X-table, and a protrusion is formed in a side portion of the X-table (a side portion facing the X-direction guide), protruding into the recessed groove. The recessed groove extends substantially over the entire length of the X-direction guide. Static pressure bearings (not shown) similar to the static pressure bearings 1611*a*, 1609*a*, 1610*a*, 1611*b*, 1609*b*, 1610*b* are disposed on the top surface, bottom surface and side surfaces of the protrusion of the X-direction table 4 protruding into the recessed groove in similar positioning. Between the Y-table 1605 and the X-table 1604, a linear motor 1613 in a known structure is disposed so that the X-table is driven in the X-direction by means of the linear motor. Then, the X-table 1604 is supplied with a high pressure gas through a flexible pipe 1621 to supply the high pressure gas to the static pressure bearings. The high pressure gas is blown out from the static pressure bearings to the guide surfaces of the X-direction guide to highly accurately support the X-table 1604 with respect to the Y-direction guide in a non-contact manner. The vacuum chamber C is evacuated by vacuum pipes 1619, 1620*a*, 1620*b* connected to a vacuum pump or the like in a known structure. The inlet sides (within the vacuum chamber) of the pipes 1620*a*, 1620*b* extend through the pedestal 1606 and are open near a position at which the high pressure gas is exhausted from the XY stage 1603 on the top surface of the pedestal 1606, to maximally prevent the pressure within the vacuum chamber from rising due to the high pressure gas blown out from the static pressure bearings.

A differential exhaust mechanism 1625 is disposed around the leading end of the barrel 1601, i.e., the electron beam irradiating tip 1602, such that the pressure in the electron beam irradiation space 1630 is held sufficiently low even if the pressure in the vacuum chamber C is high. Specifically, an annular member 1626 of the differential exhaust mechanism 1625 attached around the electron beam irradiating tip 1602 is positioned with respect to the housing 1614 such that a small gap (from several micron to several hundred microns) 1640 is formed between the lower surface (the surface opposing the sample S) and the sample, and an annular groove 1627 is formed on the lower surface thereof. The annular groove 1627 is connected to a vacuum pump or the like, not shown, through an exhaust pipe 1628. Therefore, the small gap 1640 is evacuated through the annular groove 1627 and an exhaust port 1628, so that even if gas molecules attempt to invade from the vacuum chamber C into the space 1630 surrounded by the annular member 1626, they are exhausted. In this way, the pressure within the electron beam irradiation space 1630 can be held low to irradiate an electron beam without problem.

The annular groove may be in a double structure or in a triple structure depending on the pressure within the chamber or the pressure within the electron beam irradiation space 1630.

For the high pressure gas supplied to the static pressure bearings, dry nitrogen is generally used. However, if possible, a highly pure inert gas is further preferable. This is because if impurities such as moisture and oil components are included in the gas, these impurity molecules will attach on the inner surface of the housing which defines the vacuum chamber, and on the surfaces of components of the stage to deteriorate the degree of vacuum, and will attach on the surface of the sample to deteriorate the degree of vacuum in the electron beam irradiation space.

In the foregoing description, the sample S is not generally carried directly on the X-table, but carried on a sample base which has functions of removably holding the sample, and making a slight positional change with respect to the XY stage 1603, and so on. However, since the presence or absence of the sample base, and its structure are not related to the gist of the present invention, they are omitted for simplifying the description.

Since the electron beam apparatus described above can use a static pressure bearing stage mechanism used in the atmosphere as it is, a highly accurate XY stage equivalent to a highly accurate stage for atmosphere used in an exposure apparatus and so on can be implemented in an XY stage for an electron beam apparatus substantially at the same cost and in the same size.

The structure and positioning of the static pressure guides and actuators (linear motors) described above are merely one embodiment in all sense, and any of static pressure guides and actuators can be applied if it is usable in the atmosphere.

Figure 45:
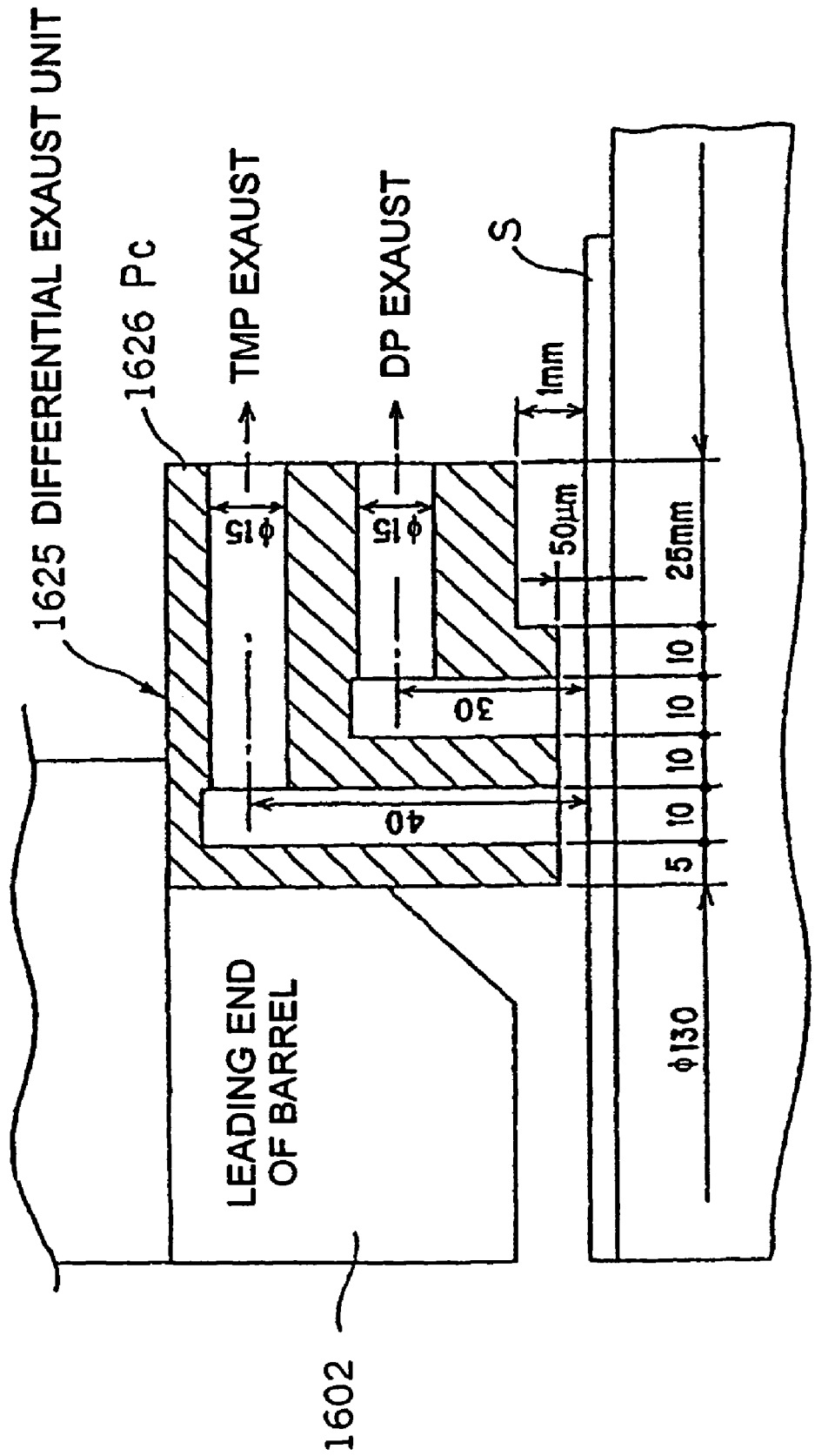
FIG. 45 is a diagram illustrating an example of a differential pumping mechanism disposed in the apparatus illustrated in FIG. 44.

Next, FIG. 45 shows exemplary values for the sizes of the annular member 1626 of the differential exhaust mechanism, and the annular groove formed therein. In this example, the annular groove has a double structure comprised of 1627a and 1627b which are spaced apart in a radial direction. A flow rate of the high pressure gas supplied to the static pressure bearings is generally at about 20 L/min (converted to the atmospheric pressure). Assuming that the vacuum chamber C is evacuated by a dry pump having an exhausting rate of 20000 L/min through a vacuum pipe having an inner diameter of 50 mm and a length of 2 m, the pressure in the vacuum chamber is approximately 160 Pa (approximately 1.2 Torr). In this event, if the dimensions of the annular member 1626 of the differential exhaust mechanism, annular groove and so on are determined as shown in FIG. 45, the pressure in the electron beam irradiation space 1630 can be set at $10^{-4}$ Pa ($10^{-6}$ Torr).

The differential exhaust mechanism is not limited in shape to the concentric shape as in this embodiment, but may be in a rectangular or a polygonal shape, as long as it can maintain the pressure in the electron beam irradiation space 1630 at a predetermined pressure. In addition, it may not be provided over the entire periphery but a portion thereof.

Figure 46:
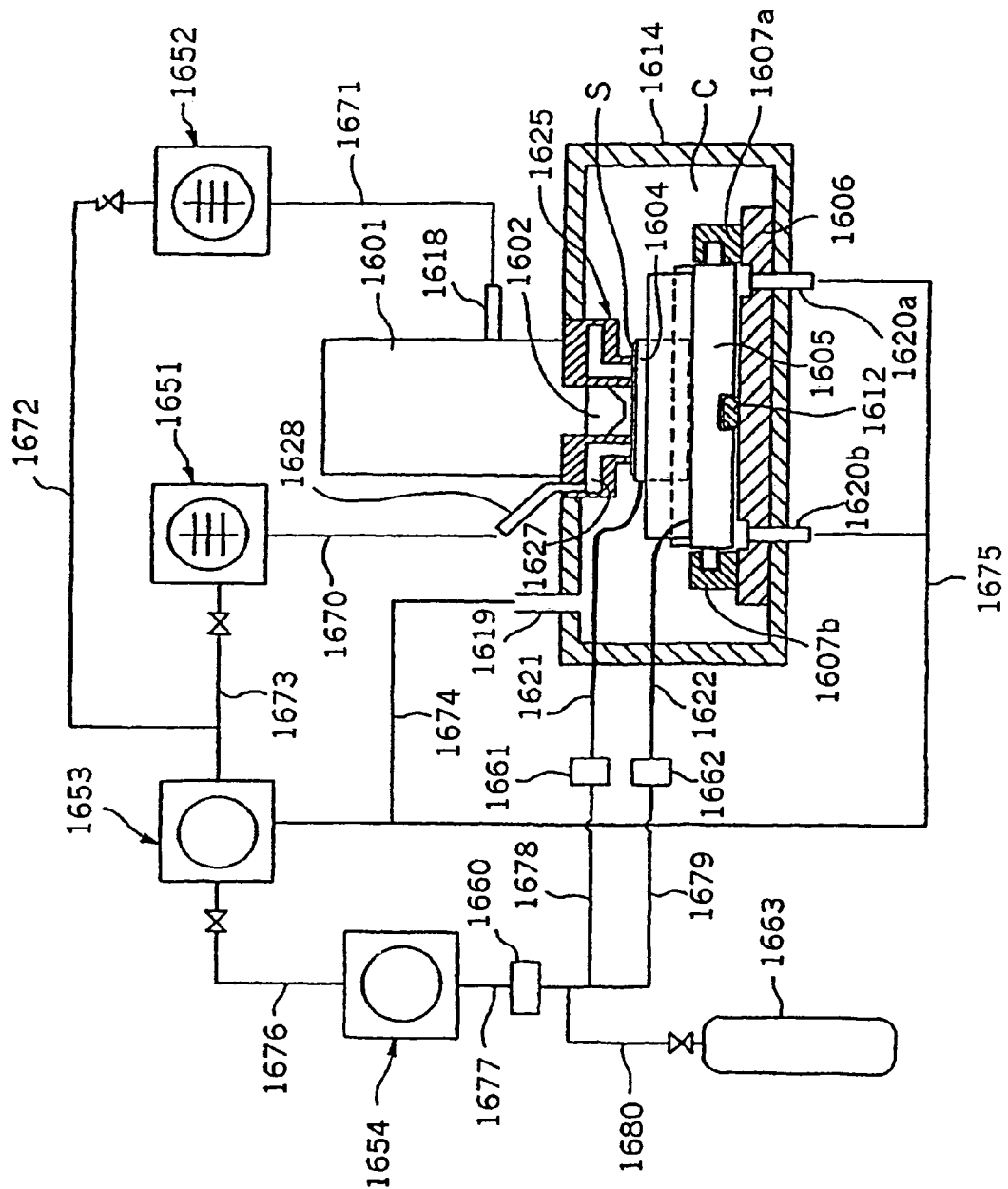
FIG. 46 is a diagram illustrating a gas circulation piping system installed in the apparatus illustrated in FIG. 44.

FIG. 46 illustrates a piping system for the apparatus illustrated in FIG. 44. The vacuum chamber C defined by the housing 1614 is connected to a dry vacuum pump 1653 through vacuum pipes 1674, 1675. Also, the annular grove 1627 of the differential pumping mechanism 1625 is connected to a turbo molecular pump 1651, which is an ultra-high vacuum pump, through a vacuum pipe 1670 connected to the exhaust port 1628. Further, the inside of the barrel 1601 is connected to a turbo molecular pump 1652 through a vacuum pipe 1671 connected to an exhaust port 1618. These turbo molecular pumps 1651, 1652 are connected to the dry vacuum pump 1653 through vacuum pipes 1672, 1673. (While in FIG. 46, a single dry vacuum pump is in double use for a roughing pump as the turbo molecular pump and a vacuum evacuation pump for the vacuum chamber, it is contemplated that separate dry vacuum pumps may be used for evacuation depending on the flow rate of the high pressure gas supplied to the static pressure bearings of the XY stage, the volume and inner surface area of the vacuum chamber, and the inner diameter and length of the vacuum pipe.)

The static pressure bearing of the XY stage 1603 are supplied with highly pure inert gas ($N_2$ gas, Ar gas or the like) through the flexible pipes 1621, 1622. The gas molecules blown out from the static pressure bearings diffuse in the vacuum chamber, and are exhausted by the dry vacuum pump 2353 through the exhaust ports 1619, 1620a, 1620b. Also, the gas molecules introducing into the differential exhaust mechanism and the electron beam irradiation space are sucked from the annular groove 1627 or the leading end of the barrel 1601, exhausted by the turbo molecular pumps 1651 and 1652 through the exhaust ports 1628 and 1618, and exhausted by the dry vacuum pump 1653 after they have been exhausted by the turbo molecular pump.

In this way, the highly pure inert gas supplied to the static pressure bearings is collected and exhausted by the dry vacuum pump.

On the other hand, the dry vacuum pump 1653 has an exhaust port connected to a compressor 1654 through a pipe 1676, while the compressor 2316 has an exhaust port connected to the flexible pipes 1621, 1622 through pipes 1677, 1678, 1679 and regulators 1661, 1662. Therefore, the highly pure inert gas exhausted from the dry vacuum pipe 1653 is again pressurized by the compressor 1654, regulated to a proper pressure by the regulators 1661, 1662, and again supplied to the static pressure bearings of the XY-table.

As described above, the gas supplied to the static pressure bearings must be purified as high as possible to maximally exclude moisture and oil components, so that the turbo molecular pumps, dry pump and compressor are required to have structures which prevent moisture and oil components from introducing into gas flow paths. It is also effective to provide a cold trap, a filter or the like (1660) in the middle of the discharge side pipe 1677 of the compressor to trap impurities such as moisture and oil components mixed in a circulating gas such that they are not supplied to the static pressure bearings.

In this way, since the highly pure inert gas can be circulated for reuse, the highly pure inert gas can be saved. In addition, since the inert gas is not supplied in an uncontrolled manner into a chamber in which the apparatus is installed, the possibility of accidents such as suffocation by the inert gas can be eliminated.

The circulating pipe system is connected to a highly pure inert gas supply system 1663 which serves to fill the highly pure inert gas into the entire circulating system including the vacuum chamber C, vacuum pipes 1670-1675, and pressurizing pipes 1676-1680, and to supply the shortage if the flow rate of the circulating gas is reduced by some cause.

It is also possible to use a single pump as the dry vacuum pump 1653 and the compressor 1654 by providing the dry vacuum pump 1653 with a function of compressing to the atmospheric pressure or higher.

Further, the ultra-high vacuum pump for use in evacuating the barrel may be implemented by a pump such as an ion pump, a getter pump instead of the turbo molecular pump. However, when such an entrapment vacuum pump is used, a circulating piping system cannot be build in this portion.

Also, a dry pump of another configuration such as a diaphragm dry pump may of course be used instead of the dry vacuum pump.

Similarly to the ninth embodiment, the tenth embodiment described with reference to FIGS. 44-46 comprises the optical system and the detection system described in FIG. 43. In the tenth embodiment, the description on FIG. 43 is incorporated herewith by reference. Also, as described in the ninth embodiment, When the tenth embodiment of the present invention is used in the testing process (G) or the exposure process (c) in the device manufacturing method described with reference to FIGS. 3 and 4(*a*), 4(*b*), miniature patterns can be stably tested or exposed at a high accuracy, thereby making it possible to improve the yield rate of products and prevent defective products from being shipped. In this regard, the description related to FIG. 3 and FIGS. 4(*a*), 4(*b*) is incorporated herewith by reference and is omitted herein.

Embodiment Relating to Lenses in Optical System
(Eleventh Embodiment)

An eleventh embodiment of the present invention relates to an electron beam apparatus for evaluating patterns and so on formed on the surface of a sample, and a device manufacturing method for evaluating a sample in the middle of a process or at the end of the process using the electron beam apparatus, and more particularly, to an electron beam apparatus which is capable of performing a variety of evaluations for testing a device on a sample or the like for defects on patterns having a minimum line width of 0.1 micron or less, CD measurement, potential contrast measurement, high time resolution potential measurement, and so on at a high throughput and high reliability, and a device manufacturing method for evaluating a sample in the middle of a process or at the end of the process using such an electron beam apparatus.

A variety of techniques have been reported on apparatuses for observing a sample including an insulating material for evaluation. Among these techniques, stating about a scanning electron microscope, a known apparatus has a charging sensing function of measuring a beam current of a primary beam, a current absorbed into a sample, the amount of electron beam reflected from an irradiating apparatus, the amount of emitted secondary electron beam, and so on to evaluate a charging state.

However, since the conventional scanning electron microscope as mentioned above scans a fine electron beam, i.e., a beam on the surface of a sample, it has a problem of significantly degraded throughput for evaluating a sample having a large area. Also, the known charging sensing function is required to measure a variety of currents at a high time resolution, so that the charging state-cannot be correctly detected at all times.

The eleventh embodiment of the present invention, for solving the above problem, provides an electron beam apparatus which improves the structure of lenses in an optical system to reduce the size of the optical system; an electron beam apparatus which improves a throughput as well as improves the charging sensing function to have a higher reliability for evaluation, and a device manufacturing method which is capable of evaluating a sample in the middle of a process or at the end of the process at a high manufacturing yield rate, using an electron beam apparatus as mentioned above.

Figure 47:
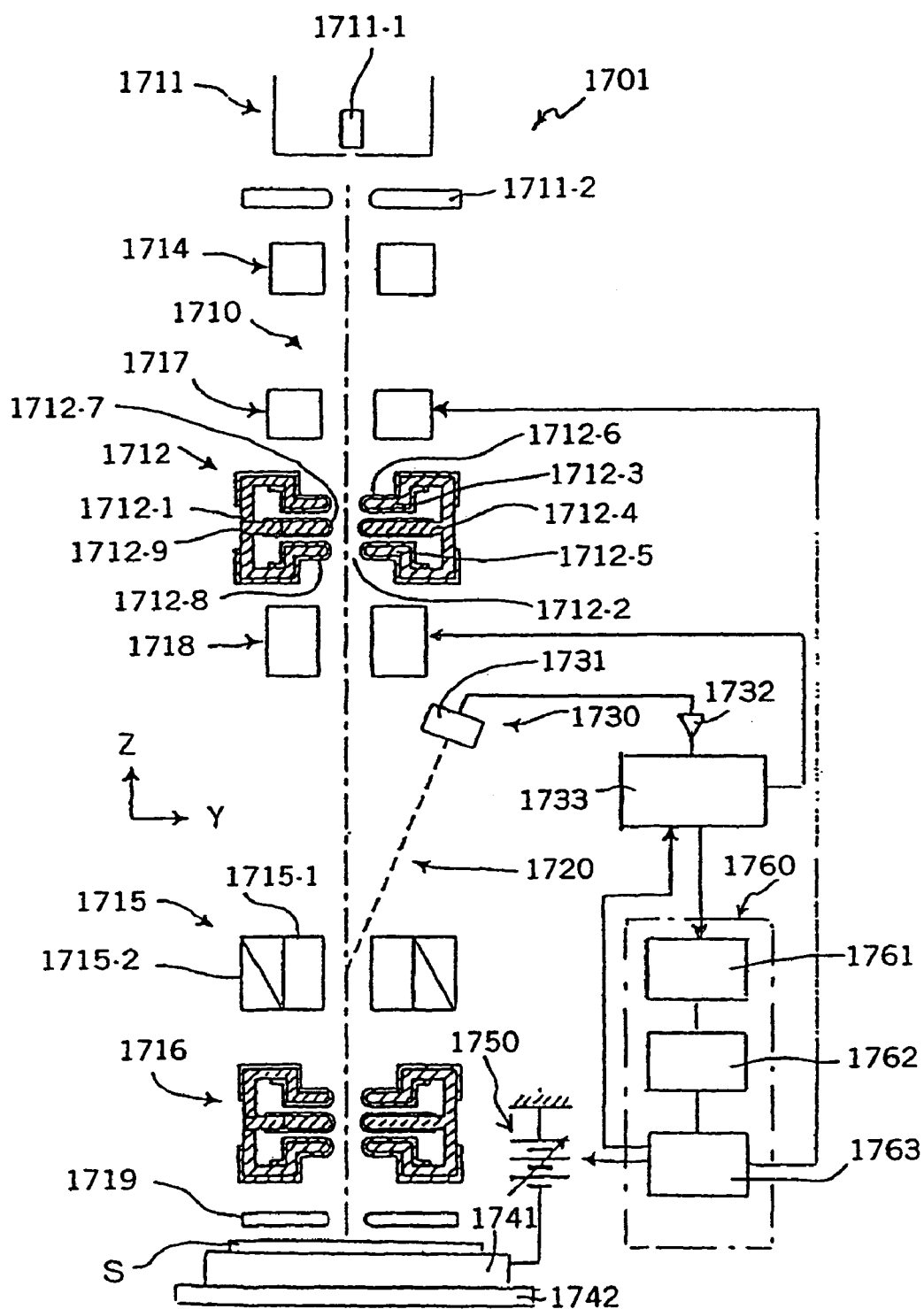
FIG. 47 is a schematic diagram of an optical system in an eleventh embodiment of the charged electron beam apparatus according to the present invention.
Figure 48:
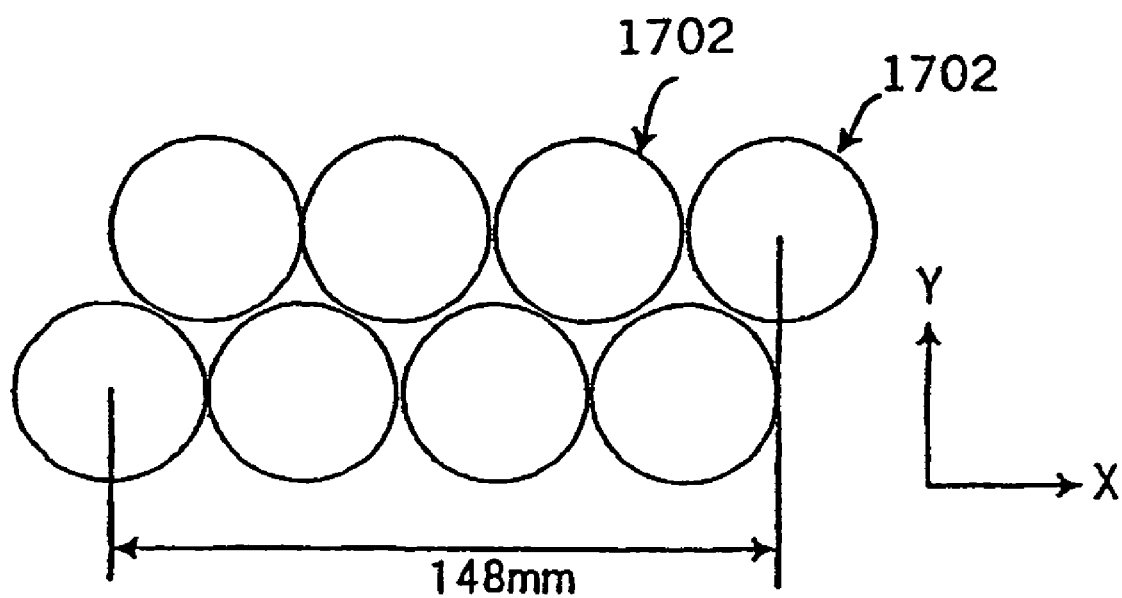
FIG. 48 is a diagram illustrating a state of arrayed barrels of the electron beam apparatus illustrated in FIG. 47.

In the following, the eleventh embodiment of the electron beam apparatus according to the present invention will be described with reference to the drawings. In FIG. 47, an electron beam apparatus 1701 comprises a primary electron-optical system (hereinafter simply called the "primary optical system") 1710, a secondary electron-optical system (hereinafter simply called the "secondary optical system") 1720, and a detecting system 1730. The primary optical system 1710, which is an optical system for irradiating an electron beam to the surface of an object under evaluation (hereinafter called the "sample") S such as a wafer, comprises an electron beam source 1711 for emitting an electron beam, i.e., an electron beam; a condenser lens 1712 for converging a primary electron beam emitted from the electron beam source 1711; a Wien filter 1715; and an objective lens 1716. These are positioned as illustrated in FIG. 48. Reference numerals 1714 and 1717 designate aligners for aligning the primary electron beam; 1718 a deflector for scanning the primary electron beam; and 1719 an axially symmetric electrode.

The secondary optical system 1720 is positioned along an optical axis which is oblique with respect to the optical axis of the primary optical system. Though not shown in FIG. 47, the secondary optical system may comprise at least one lens. The detecting system 1730 comprises a detector 1731, and an image forming unit 1733 connected to the detector 1731 through an amplifier 1732.

The sample S is removably supported by a holder 1741 on an XY stage 1740 by a known method, and is supported by the XY stage 1740 for movements in two orthogonal axial directions (in the left and right directions and the direction vertical to the sheet in FIG. 47).

The electron beam apparatus 1701 comprises a retarding voltage applying unit (hereinafter called the "applying unit") 1750 electrically connected to the holder 1741; and a charging checking and landing energy determining system (hereinafter called the "checking/determining system") 1760. The checking/determining system 1760 comprises a monitor 1761 electrically connected to the image forming unit 1733; an operator 1762 connected to the monitor 1761; and a CPU 1763 connected to the operator 1762. The CPU 1763 supplies signals to the applying unit 1750 and the deflector 1717.

In the eleventh embodiment, since a condenser lens 1712 is substantially identical in structure to an objective lens 1716, the condenser lens 1712 will be described in detail, taken as an example. The condenser lens 1712, which is an electrostatic axially symmetric lens, is formed by cutting a ceramics bulk such that an axial cross-section thereof has a shape as shown in FIG. 47. Specifically, the condenser lens 1712 includes a body 1712-1 made of ceramics. This body 1712-1 is formed with a planar shape in an annular configuration to define a circular hole 1712-2 in a central portion, and the inner peripheral side is partitioned into three plate-shaped portions 1712-3 to 1712-5 separated in the vertical direction (the direction along the optical axis) in FIG. 47. The outer periphery of the body 1712-1 made of ceramics, particularly, surroundings of the plate-shaped portions 1712-3 to 1712-5 are coated with metal coating films 1712-6 to 1712-8. These coating films 1712-6 to 1712-8 function as electrodes (an upper electrode 1712-6, an intermediate electrode 1712-7, and a lower electrode 1712-8), respectively. The coating films, i.e., upper and lower electrodes 1712-6 and 1712-8 are applied with a voltage close to the ground, while the middle coating film, i.e., intermediate electrode 1712-7 is applied with a positive or negative high voltage having a large absolute value by an electrode fitting 1712-9 disposed in the body 1712-1, thereby acting as a lens. Such a lens has a high working accuracy since a ceramics bulk is cut and simultaneously worked, and can be reduced in the dimension of outer diameter.

Since the electron beam apparatus in this embodiment can reduce the outer diameter of the lens, the barrel containing the electron beam apparatus can also be reduced in the outer diameter. Therefore, for a sample such as a wafer having a large diameter, a plurality of column can be arranged for a single wafer. For example, assuming that the outer diameter (diameter) of the lens is chosen to be 40 mm, a total of eight barrels 1702, arranged in four in the X-direction and two in the Y-direction, as illustrated in FIG. 48, can be arranged for one sample. Then, the stage (not shown), which holds the sample S, is sequentially moved in the Y-direction while the sample is scanned by the respective barrels in the X-direction for evaluation, thereby achieving a throughput seven or eight times as high as the evaluation using only one electron beam.

In the electron beam apparatus described above, a primary electron beam, i.e., a beam emitted from the cathode 1711-1 of the electron beam source 1711 in the primary optical system 1710 is accelerated by the anode 1711-2. A crossover image of the electron beam source created by the primary electron beam is reduced by the condenser lens 1712 and the objective lens 1716 into a thin beam of approximately 50 nm which is scanned on the sample S for irradiation. A secondary electron beam emitted from the sample by the irradiation of the primary electron beam is attracted by the axially symmetric electrode 1719 toward the objective lens. As the secondary electron beam is passed toward the objective lens 1716 or returned to the sample side by the axially symmetric electrode 1719, a potential contrast can be produced for a sample pattern.

The secondary electron beam passing through the objective lens is separated from the primary optical system 1710 by the Wien filter 1715, introduced into the secondary electron-optical system (hereinafter simply called the "secondary optical system") 1720, and detected by the detector 1731 in the detecting system 1730. The detector 1731 transduces the detected secondary electron beam image into an electric signal indicative of the intensity thereof. The electric signal output from each detector in this way is amplified by the corresponding amplifier 1732, input to the image forming unit 1733, and converted into image data in this image forming unit. Since the image forming unit 1733 is further supplied with a scanning signal for deflecting the primary electron beam, the image forming unit displays an image which represents the surface of the sample S. By comparing this image with a reference pattern, defects on the sample S can be detected. While this embodiment uses a single electron beam, a plurality of beams may be preferred to the single beam in view of an improvement in throughput.

The image data converted by the image forming unit 1733 is displayed as an image by the display device 1761 of the checking/determining apparatus 1760, and the image is evaluated by the operator 1762. The operator 1762 executes a charging checking function in this embodiment. Also, the operator 1762 can check a charge-up state based on the image. Then, the result is input to the CPU 1763, and a landing energy is set to an optimal value. The CPU 1763 constitutes a landing energy determining unit in this embodiment.

More specifically, as shown in FIG. 49[A], evaluation is made on a location of a sample under evaluation vulnerable to the influence of charging, i.e., a corner region of a memory cell 1771 in a chip 1770 formed on the surface of a wafer as a sample. Specifically, (1) the amounts of distortions in patterns 1773, 1774 are measured on a memory cell boundary 1772 in the corner region, or (2) the contrasts of signal strengths produced when the corner region of the memory cell was scanned so as to cross the pattern (as indicated by arrows A1 and A2) may be displayed as solid lines 1775 and 1777 in FIG. 49[B], for comparison with contrasts 1776 and 1778 (both indicated by broken lines in FIG. 49[B]) of signal strengths produced when patterns were scanned along arrows A3, A4 in a central region of the chip.

The retarding voltage applying unit 1750 was applied with a plurality of values of voltages, and the amounts of distortions 1773 and 1774 or the contrasts 1775, 1777 and 1776, 1778 were measured each time a voltage was applied. A less amount of distortion 1773, 1774 is evaluated as being less affected by the charge-up. Also, the value of contrast 1775, 1777 in the corner region closer to the value of contrast in the central region is evaluated as being less affected by the charge-up.

When a retarding voltage is found with a satisfactory charge-up state, this value is applied to the applying unit 1750 through the CPU 1763, or if values of optimal beam currents are found, the sample or wafer is evaluated with these values.

The eleventh embodiment of the present invention can be used in the testing process (G) in the device manufacturing method described with reference to FIGS. 3 and 4(*a*), 4(*b*). In this way, semiconductor devices even having fine patterns can be tested at a high throughput, so that a total inspection can also be conducted, thereby making it possible to improve the yield rate of products and prevent defective products from being shipped. In this regard, the description related to FIG. 3 and FIGS. 4(*a*), 4(*b*) is incorporated herewith by reference and is omitted herein.

Embodiment Relating to Detection of Defects
(Twelfth Embodiment)

A twelfth embodiment of the present invention relates to a defect testing apparatus for testing a sample such as a semiconductor wafer for defects by comparing an image of the sample with a previously prepared reference image, and a semiconductor device manufacturing method for manufacturing semiconductor devices using such a defect testing apparatus.

Conventionally, a defect testing apparatus has been utilized in semiconductor manufacturing processes and so on for testing a sample such as a semiconductor wafer for defects by detecting a secondary electron beam generated by irradiating the sample with a primary electron beam. Such a defect testing apparatus involves a technique which applies an image recognition technique to automate the testing for defects and improve the efficiency thereof. This technique causes a computer to match pattern image data of a region under testing on the surface of a sample acquired by detecting a secondary electron with previously stored reference image data of the surface of the sample to automatically determine the presence or absence of defects on the sample based on the result of processing.

Recently, increasingly higher definitions are required for patterns, particularly in the field of semiconductor manufacturing, so that the need for detecting fine defects has been increased. Under such a circumstance, a further improvement in recognition accuracy is required as well for the defect testing apparatus which applies the image recognition technique as mentioned above.

However, the aforementioned prior art experiences a problem of discrepancy in position between an image of a secondary electron beam captured by irradiating a primary electron beam to a region under testing on the surface of the sample and a previously prepared reference image to degrade the accuracy of detecting defects. This discrepancy in position constitutes a grave problem particularly when an irradiating area of the primary electron beam shifts with respect to the wafer so that a portion of a pattern under testing is lost from a detected image of the secondary electron beam. This problem cannot be addressed only by a technique for simply optimizing a matching region within a detected image (see Japanese Patent Publication No. 6-95340). This can be a critical disadvantage, particularly, in testing for high definition patterns.

The twelfth embodiment of the present invention, to solve the problem mentioned above, provides a defect testing apparatus for preventing a degraded defect testing accuracy due to the discrepancy in position between an image under testing and a reference image; and a semiconductor manufacturing method for improving the yield rate for device products and preventing defective products from being shipped by testing a sample for defects using a defect testing apparatus as mentioned above in a semiconductor device manufacturing process.

Figure 50:
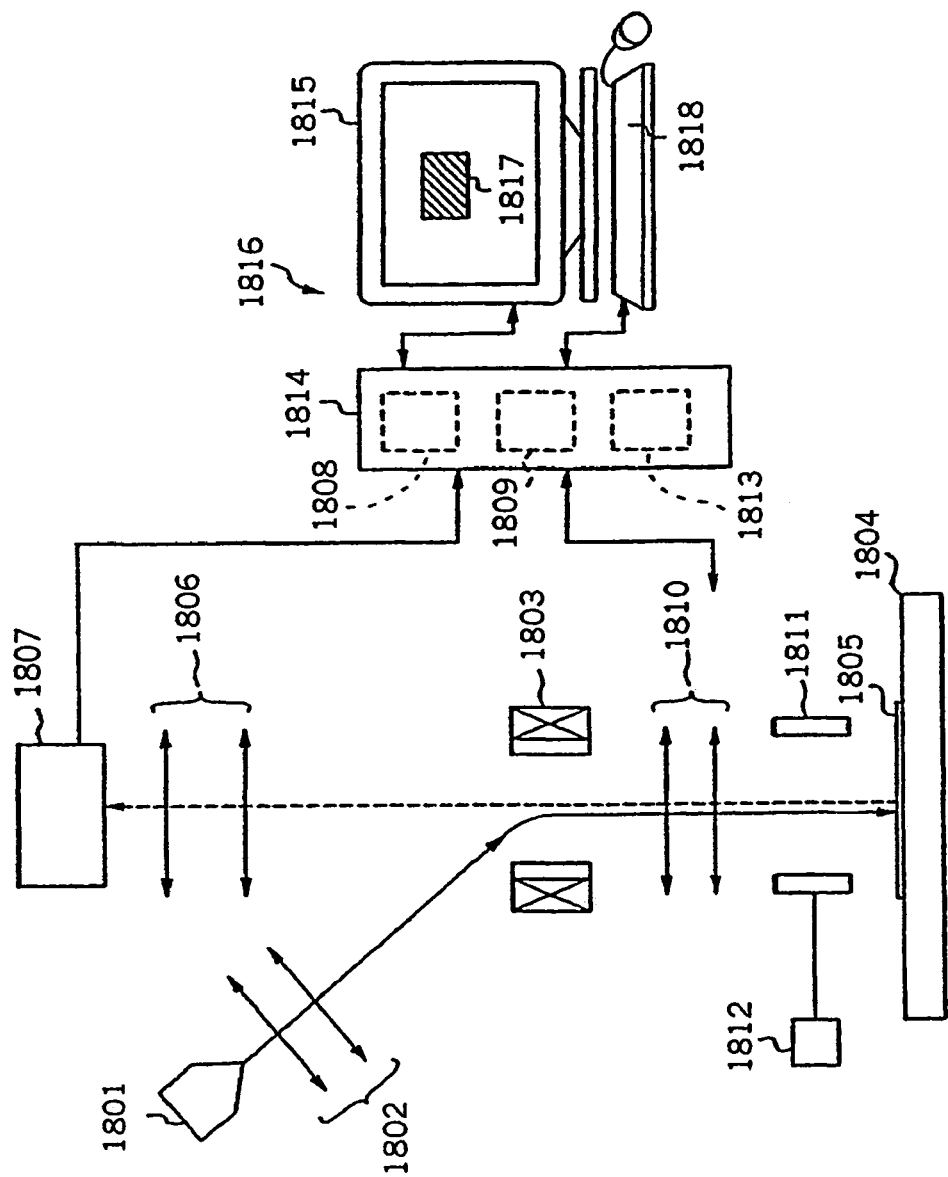
FIG. 50 is a schematic configuration diagram of a defect testing apparatus which is a twelfth embodiment of the charged particle beam apparatus according to the present invention.

FIG. 50 illustrates a general configuration of the defect testing apparatus according to the twelfth embodiment of the present invention. This defect testing apparatus comprises an electron beam source 1801 for emitting a primary electron beam; an electrostatic lens 1802 for deflecting and reshaping the emitted primary electron beam; a Wien filter 1803 for deflecting the reshaped primary electron beam in a field in which an electric field E and a magnetic field B are orthogonal to each other such that the primary electron beam impinges substantially perpendicularly to a semiconductor wafer 1805; an objective lens 1810 for focusing the deflected primary electron beam on the wafer 1805; a stage 1804 disposed in a sample chamber, not shown, which can be evacuated to vacuum and is movable in a horizontal plane with the wafer 1805 carried thereon; an electrostatic lens 21806 of a image projection system for imaging and projecting a secondary electron beam emitted from the wafer 1805 by the irradiation of the primary electron beam and/or a reflected electron beam at a predetermined magnification to form an image; detector 1807 for detecting the formed image as a secondary electron beam image of the wafer; and a controller 1816 for controlling the overall apparatus and executing the processing for detecting defects on the wafer 1805 based on the secondary electron beam image detected by the detector 1807. The secondary electron beam image includes a contribution by reflected electrons as well as a contribution by the secondary electron beam.

In addition, between the objective lens 1810 and the wafer 1805, a deflecting electrode 1811 is interposed for deflecting an incident angle of the primary electron beam to the wafer 1805 by an electric field or the like. The deflecting electrode 1811 is connected to a deflection controller 1812 for controlling the electric field of the deflecting electrode. This deflection controller 1812 is connected to the controller 1816 to control the deflecting electrode to generate an electric field in response to an instruction from the controller 1816 by the deflecting electrode 1811. The deflection controller 1812 can be implemented as a voltage controller for controlling a voltage applied to the deflecting electrode 1811.

Figure 55:
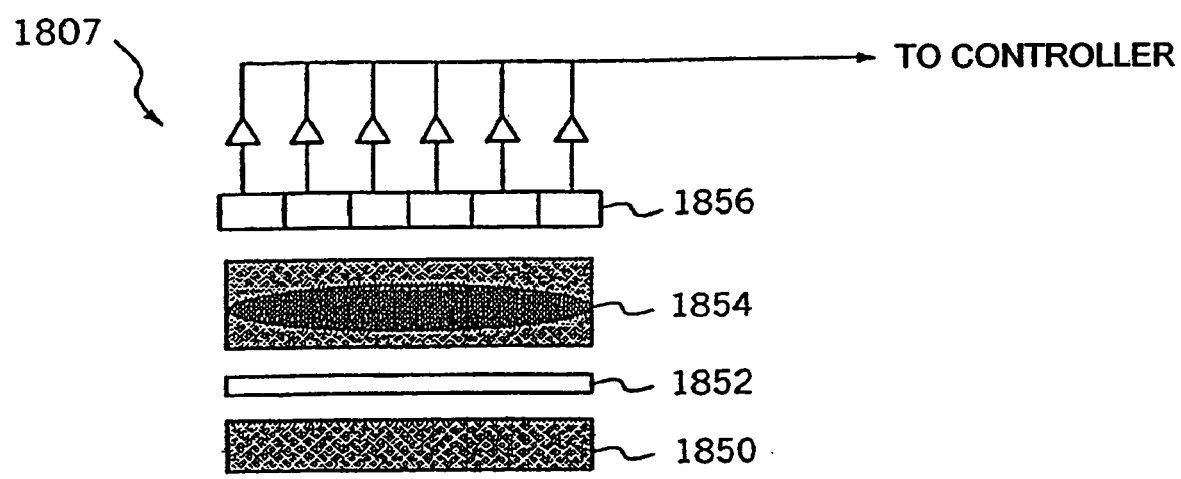
FIG. 55 is a diagram illustrating a specific example of the configuration of a detector in the defect testing apparatus in FIG. 50.

The detector 1807 may be in an arbitrary configuration as long as it can transduce a secondary electron beam image formed by the electrostatic lens 1806 into a signal available for post-processing. For example, as illustrated in detail in FIG. 55, the detector 1807 comprises a multi-channel plate 1850; a fluorescent screen 1852; a relay lens 1854; and an imager sensor 1856 comprised of a large number of CCD devices. The multi-channel plate 1850 comprises a large number of channels within the plate to generate a larger number of electrons while the secondary electrons focused by the electrostatic lens 1806 pass through the channels. In other words, the secondary electron beam is amplified. The fluorescent screen 1852 generates fluorescent light by the amplified secondary electron beam to transduce the secondary electron beam into light. The relay lens 1854 introduces this fluorescent light into the CCD imager sensor 1856, and the CCD imager sensor 1856 converts an intensity distribution of secondary electrons on the surface of the wafer 1805 into an electric signal per device, i.e., digital image signal which is output to the controller 1816.

As illustrated in FIG. 50, the controller 1816 may comprise a general-purpose personal computer or the like. This computer comprises a controller body 1814 for executing a variety of control and operational processing in accordance with predetermined programs; a CRT 1815 for displaying results of processing by the body 1814; and an input device 1818 such as a keyboard and a mouse for the operator to enter instructions. Of course, the controller 1816 may be built by hardware dedicated to the defect testing apparatus, a workstation, or the like.

The controller body 1814 comprises a CPU, RAM, ROM, a hard disk, all not shown, a variety of control boards such as a video board, and so on. On a memory such as RAM and hard disk, a secondary electron beam image storage region 1808 is allocated for storing an electric signal received from the detector 1807, i.e., digital image data representing a secondary electron beam image of the wafer 1805. Also, on the hard disk, a reference image storage 1813 exists for previously storing reference image data of the wafer which is free from defects. Further, the hard disk stores a defect detecting program 1809 for reading the secondary electron beam image data from the storage region 1808 to automatically detect defects on the wafer 1805 in accordance with a predetermined algorithm based on the image data, in addition to a control program for controlling the overall defect testing apparatus. This defect detecting program 1809, details of which will be described later, has functions of matching a reference image read from the reference image storage 1813 with an actually detected secondary electron beam image to automatically detect a defective portion, and displaying a warning to the operator upon determining that defects are found. In this event, a secondary excessive current generated image 1817 may be displayed on a display screen of the CRT 1815.

Next, the action of the defect testing apparatus illustrated in FIG. 50 will be described, by way of example, with reference to flow charts illustrated in FIGS. 52-54. First, as illustrated in a flow of a main routine of FIG. 52, the wafer 1805, under testing, is set on the stage 1804 (step 1900). This may be in a manner in which a large number of wafers 1805 stored in a loader, not shown, are automatically set one by one on the stage 1804.

Figure 51:
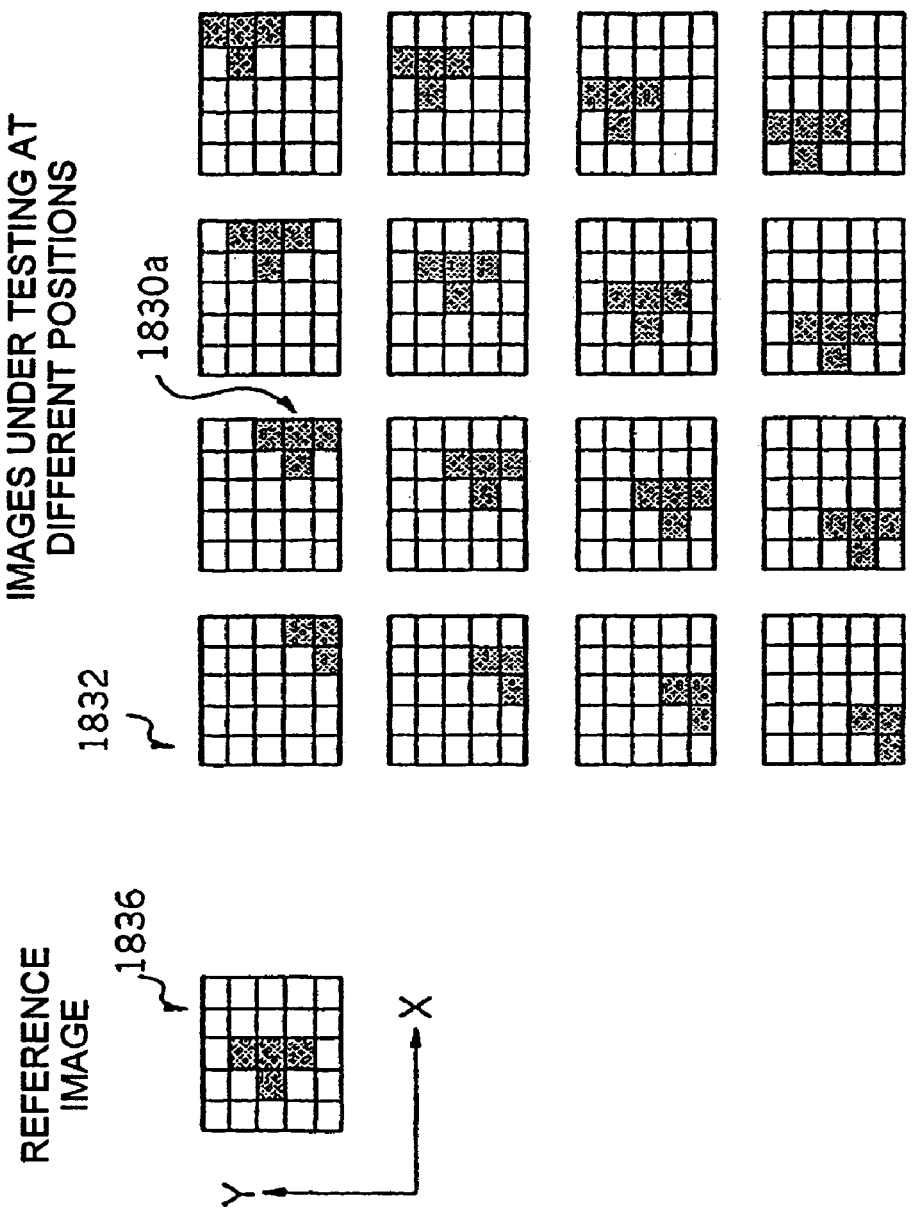
FIG. 51 is a diagram illustrating examples of a plurality of images under testing captured by the defect testing apparatus of FIG. 50 and a reference image.
Figure 56:
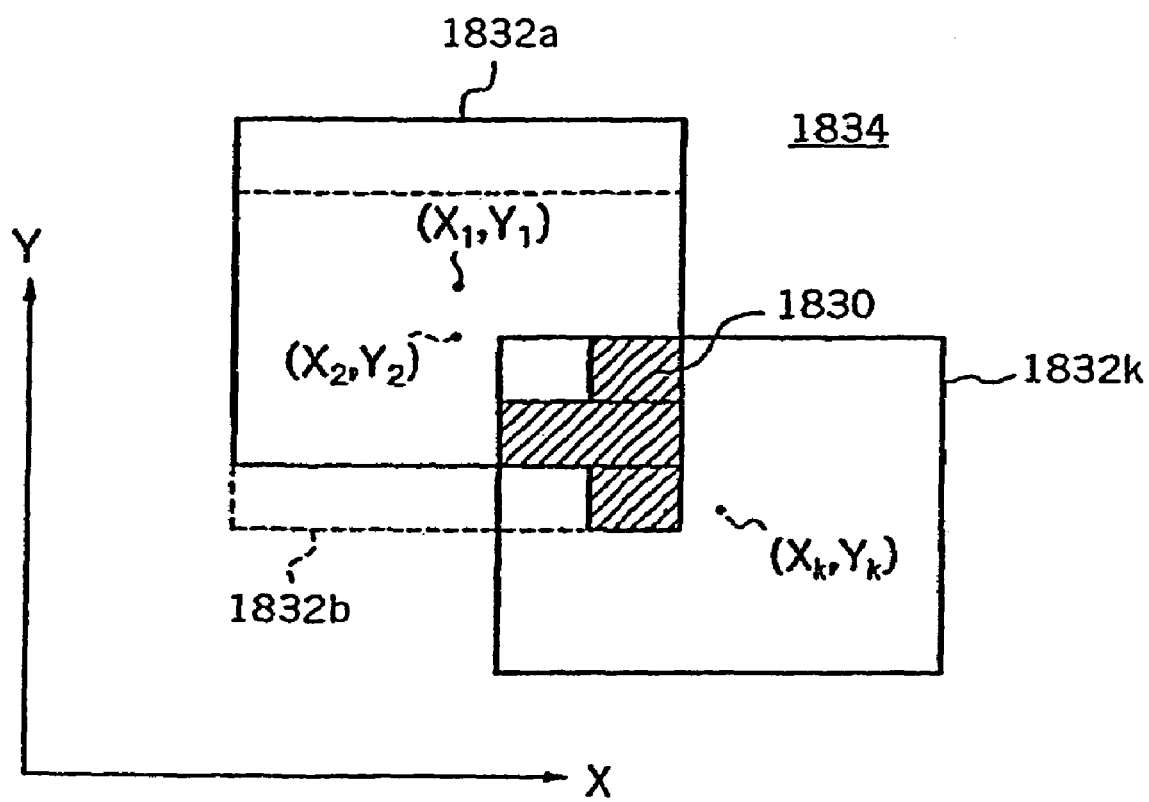
FIG. 56 is a diagram conceptually illustrating a plurality of regions under testing which are shifted in position from one another while partially overlapping with one another on the surface of a semiconductor wafer.

Next, each of a plurality of images of regions under testing, partially overlapping and displaced from one another on the XY plane of the surface of the wafer 1805 is captured (step 1904). The plurality of regions under testing, the images of which should be captured, refer to rectangular regions designated by reference numerals 1832a, 1832b, ..., 1832k, ..., for example, on the surface 1834 under testing of the wafer, as illustrated in FIG. 56. It can be seen that these are shifted in position, while partially overlapping, about a testing pattern 1830 of the wafer. For example, as illustrated in FIG. 51, 16 images 1832 (images under testing) in the regions under testing are captured. Here, in the images illustrated in FIG. 51, a rectangular cell corresponds to one pixel (alternatively, may be a block unit larger than a pixel), wherein a black painted cell corresponds to an image portion of the pattern on the wafer 1805. Details on this step 1904 will be described later with reference to a flow chart of FIG. 53.

Next, the image data of the plurality of regions under testing captured at step 1904 is compared one by one with the reference image data stored in the storage 1813 (step 1908 in FIG. 52) to determine whether or not any defect is found on the tested surface of the wafer covered by the plurality of regions under testing. In this step, so-called matching between image data is executed, details of which will be described later with reference to a flow chart of FIG. 54.

If it is determined from the result of comparison at step 1908 that any defect is found on the tested surface of the wafer covered by the plurality of regions under testing (determined as affirmative at step 1912), the existence of defect is warned to the operator (step 1918). As a method of warning, for example, a message notifying the existence of defect may be displayed on the display screen of the CRT 1815, or an enlarged image 1817 of the pattern including the defect may be displayed simultaneously with this. Such a defective wafer may be immediately removed from the sample chamber 1803, and stored in another storage place separately from defect-free wafers (step 1919).

If it is determined as the result of comparison at step 1908 that the wafer 1805 is free of defect (determined as negative at step 1912), it is determined whether or not more regions to be tested still remain on the wafer 1805 currently under testing (step 1914). If any region to be tested remains (determined as affirmative at step 1914), the stage 1804 is driven to move the wafer 1805 such that another region to be tested from now on enters the irradiating region of the primary electron beam (step 1916). Subsequently, the flow returns to step 1902, from which similar processing is repeated for the other region under testing.

If no region to be tested remains (determined as negative at step 1914), or after a defective wafer removing step (step 1919), it is determined whether or not the wafer 1805 currently under testing is the last wafer, i.e., whether or not untested wafers remain in the loader, not shown (step 1920). If not the last wafer (determined as negative at step 1920), the tested wafer is stored in a predetermined storage place, and a new untested wafer is set on the stage 1804 instead (step 1922). Subsequently, the flow returns to step 1902, from which similar processing is performed on this wafer. If the last wafer (determined as affirmative at step 1920), the tested wafer is stored in a predetermined storage place, followed by termination of the while process.

Next, a flow of the processing at step 1904 will be described along a flow chart of FIG. 53. In FIG. 53, an image number i is first set to an initial value 1 (step 1930). This image number is an identification number sequentially allocated to each of the plurality of image regions under testing. Next, an image position $(X_i, Y_i)$ is determined for a region under testing designated the set image number i (step 1932). This image position is defined as a particular position in the region, for example, a central position in the region for defining a region under testing. At the present time, since i=1, the image position is indicated by $(X_1, Y_1)$ which corresponds to the central position of the region under testing 1832a illustrated in FIG. 16, by way of example. The image positions of all image regions under testing have been previously determined and stored, for example, on the hard disk in the controller 1816 from which it is read at step 1932.

Figure 53:
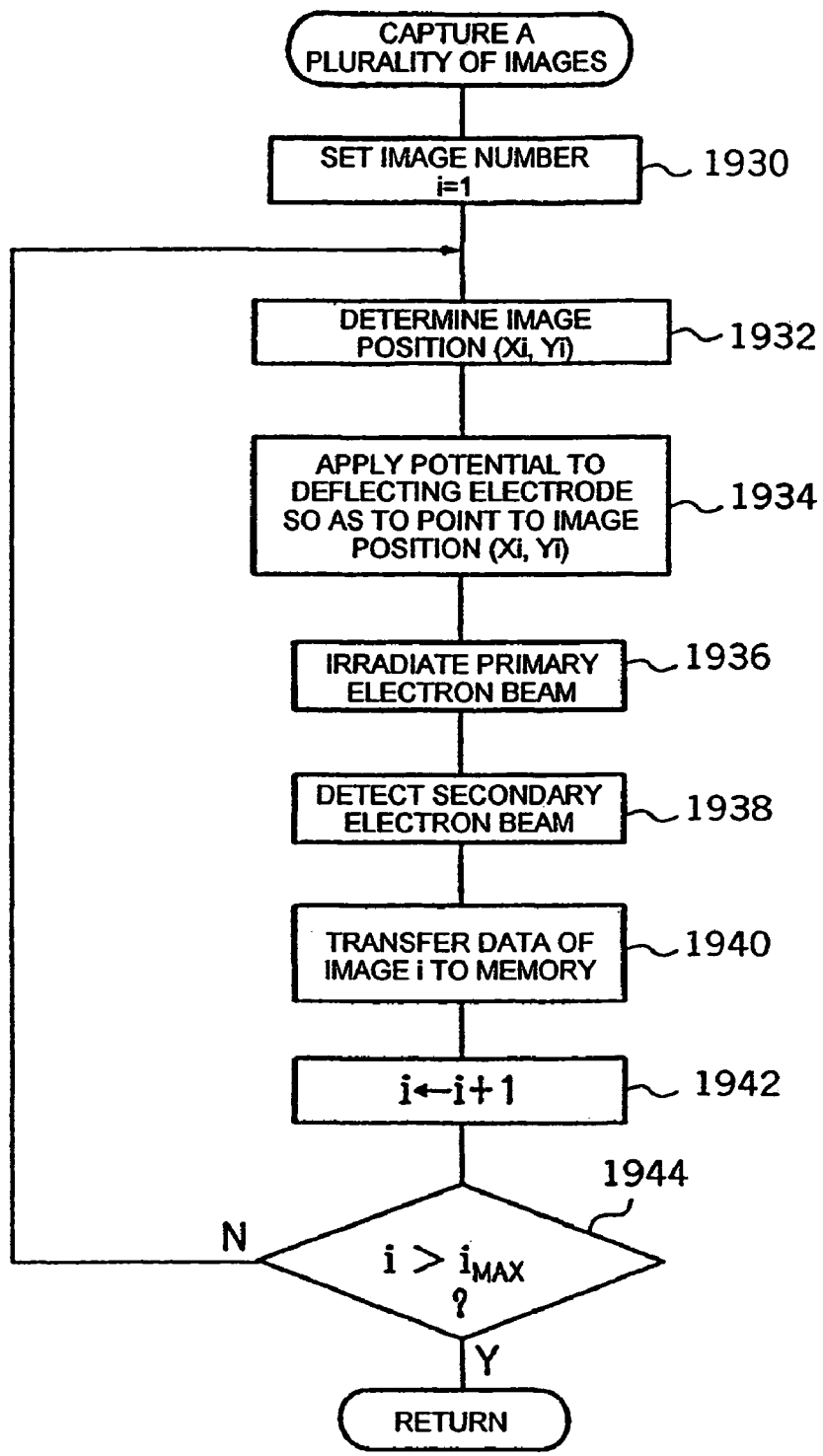
FIG. 53 is a flow chart illustrating in detail the flow of a subroutine for a step of acquiring data on a plurality of images under testing (step 1904) in FIG. 52.
Figure 54:
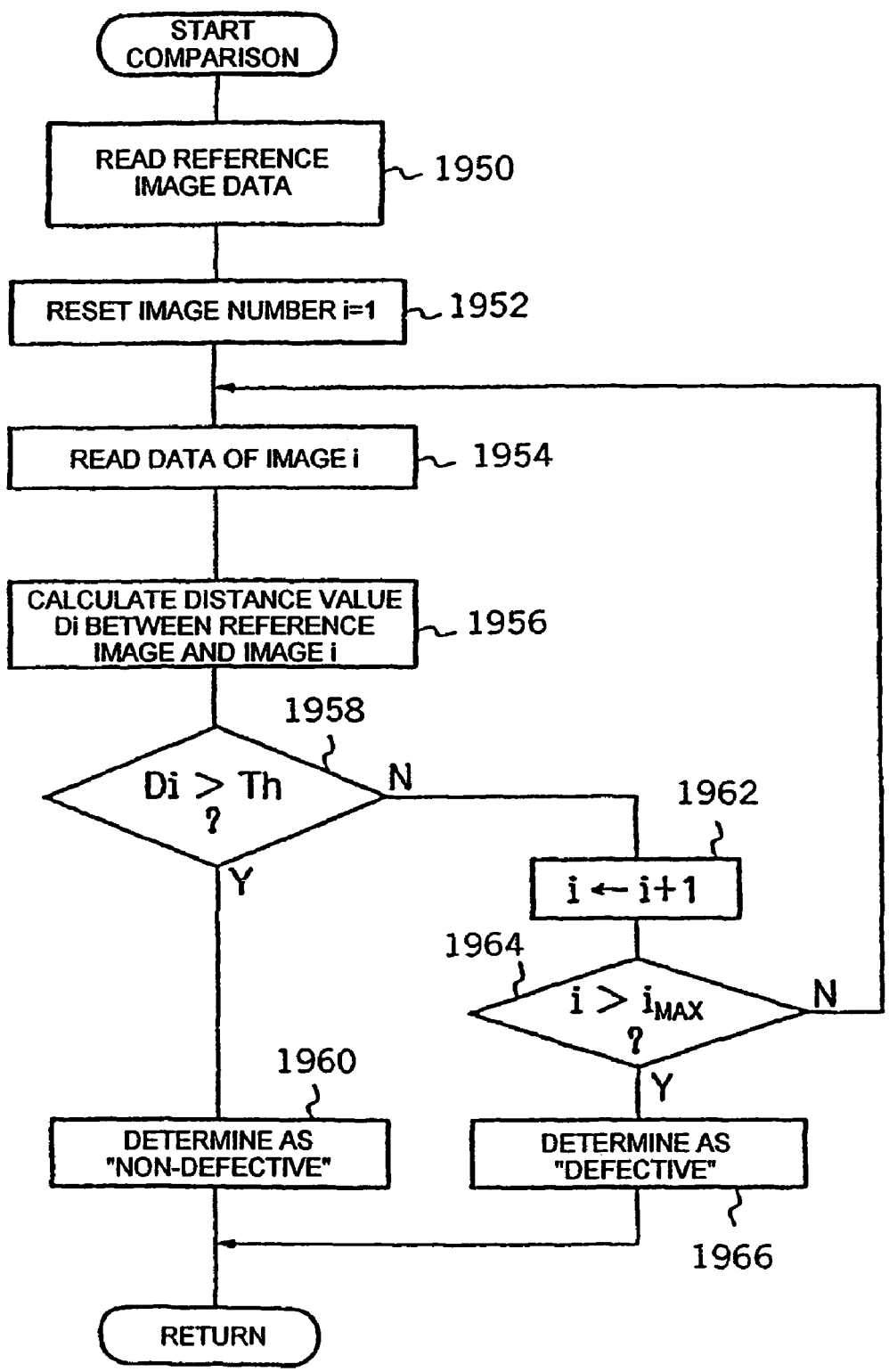
FIG. 54 is a flow chart illustrating in detail the flow of a subroutine for a comparing step (step 1908) in FIG. 52.

Next, the deflection controller 1812 applies a potential to the deflecting electrode 1811 such that the primary electron beam passing through the deflecting electrode 1811 in FIG. 50 is irradiated to an image region under testing at the image position $(X_i, Y_i)$ determined at step 1932 (step 1934 in FIG. 53). Next, a primary electron beam is emitted from an electron beam source 2501, passes through the electrostatic lens 1802, Wien filter 1803, objective lens 1810 and deflecting electrode 1811, and is irradiated on the surface of the set wafer 1805 (step 1936). In this event, the primary electron beam is deflected by an electric field created by the deflecting electrode 1811, and is irradiated over the entire image region under testing at the image position $(X_i, Y_i)$ on the surface 1834 under testing of the wafer. When the image number i=1, a region under testing is indicated by 1832a.

From the region under testing irradiated with the primary electron beam, a secondary electron beam and/or a reflected electron beam (hereinafter, the two are collectively called the "secondary electron beam") are emitted. Then, the generated secondary electron beam is focused on the detector 1807 at a predetermined magnification provided by the electrostatic lens 1806 in the enlargement projection system. The detector 1807 detects the focused secondary electron beam, and transduces it into an electric signal per detector device, i.e., digital image data which is then output (step 1938). Next, the detected digital image data designated the image number i is transferred to the secondary electron beam image storage region 1808 (step 1940).

Next, the image number i is incremented by one (step 1942), and it is determined whether or not the incremented image number (i+1) exceeds a constant value $i_{MAX}$ (step 1944). This $i_{MAX}$ indicates the number of image under testing to be captured, and is "16" in the aforementioned example of FIG. 51.

If the image number i does not exceed the constant value $i_{MAX}$ (determined as negative at step 1944), the flow returns again to step 1932, where an image position $(X_{i+1}, Y_{i+1})$ is again determined for the incremented image number (i+1). This image position indicates a position shifted from the image position $(X_i, Y_i)$ determined in the preceding routine by a predetermined distance $(\Delta X_i, \Delta Y_i)$ in the X-direction and/or Y-direction. In the example of FIG. 56, the region under testing is located at a position $(X_2, Y_2)$ shifted from $(X_1, Y_1)$ only in the Y-direction, and covers a rectangular region 1832b indicated by a broken line. The values $(\Delta X_i, \Delta Y_i)$ (i=1, 2, . . . , $i_{MAX}$) can have been empirically determined as appropriate from data on how much the pattern 1830 on the surface 1834 under testing of the wafer actually shifts from the field of view of the detector 1807, and the number and area of regions under testing.

Then, the processing at steps 1932-1942 is repeatedly executed in sequence for $i_{MAX}$ regions under testing. As illustrated in FIG. 56, these regions under testing are shifted in position, while partially overlapping, on the surface 1834 under testing of the wafer, such that an image position $(X_k, Y_k)$ after shifted k times indicates an image region under testing 1832k. In this way, 16 image data under testing illustrated in FIG. 51 are stored in the image storage region 1808. It can be seen that the plurality of captured images 1832 (images under testing) of the plurality of regions under testing have partially or completely captured over the image 1830a of the pattern 1830 on the surface 1834 under testing on the wafer, as illustrated in FIG. 56.

Figure 52:
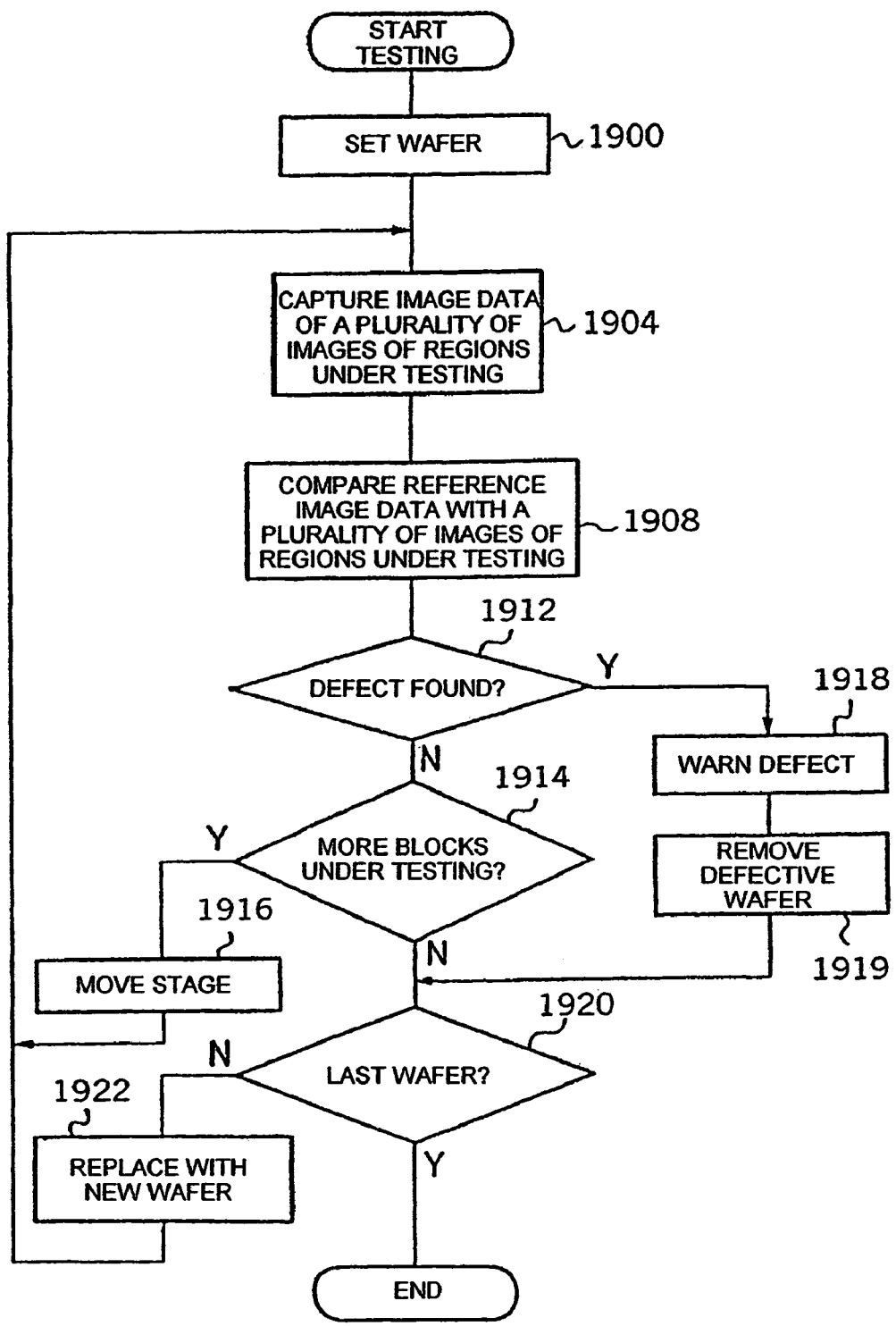
FIG. 52 is a flow chart illustrating the flow of a main routine of wafer testing in the defect testing apparatus of FIG. 50.

If the incremented image number i exceeds $i_{MAX}$ (determined as affirmative at step 1944), this subroutine is returned to proceed to the comparison step (step 1908) in the main routine of FIG. 52.

The image data transferred to the memory at step 1940 is comprised of the intensity value (so-called beta data) of secondary electrons per pixel detected by the detector 1807. For matching with the reference image at the later comparison step (step 1908 in FIG. 52), they may be stored in a storage region 8 after applied with a variety of operational processing. Such operational processing includes, for example, normalization for fitting the size and/or concentration of image data to the size and/or concentration of reference image data; processing for removing a group of isolated pixels below a predetermined number of pixels as noise; and so on. Further, rather than simple unprocessed data, image data may have been compress converted into a feature matrix which extracts features of a detected pattern to the extent of avoiding a degradation in the detection accuracy of the high definition pattern. Such a feature matrix may be an m×n feature matrix or the like, which has a total sum of secondary electron beam intensity values of pixels included in each of m×n blocks (m<M, n<N) divided, for example, from a two-dimensional region under testing comprised of M×pixels (or a normalized value derived by dividing the total sum value by the total number of pixels over the entire region under testing) as each matrix component. In this event, the reference image data is stored in the same representation as well. The image data referred to in the eleventh embodiment encompasses feature extracted image data by an arbitrary algorithm in this manner, not mention to simple unprocessed data.

Next, a flow of the processing at step 1908 will be described along a flow chart of FIG. 54. First, the CPU in the controller 1816 reads the reference image data from the reference image storage 1813 (FIG. 50) onto a working memory such as RAM (step 1950). This reference image is designated by reference numeral 1836 in FIG. 51. Then, the image number i is reset to 1 (step 1952), and image data under testing designated the image number i is read onto the working memory from the storage region 1808 (step 1954).

Next, the read reference image data is matched with data of an image i to calculate a distance value $D_i$ between both (step 1956). This distance value $D_i$ represents the similarity between the reference image and the image i under testing, and a larger distance value indicates a larger difference between the reference image and the image under testing. Any arbitrary value may be employed as the distance value $D_i$ as long as it is an amount representative of the similarity. For example, when image data is comprised of M×N pixels, a secondary electron beam intensity (or feature amount) of each pixel is regarded as each position vector component of an M×N-dimensional space, and a Euclidean distance or correlation coefficient may be calculated between a reference image vector and a vector of the image i on this M×N-dimensional space. Of course, a distance other than the Euclidean distance, for example, a so-called urban distance or the like may be calculated. Further, as a large number of pixels require an immense amount of operations, the distance value between respective image data represented by m×n feature vectors may be calculated as described above.

Next, it is determined whether or not the calculated distance value $D_i$ is smaller than a predetermined threshold Th (step 1958). The threshold Th can be empirically found as a reference for determining sufficient matching between the reference image and an image under testing.

If the distance value $D_i$ is smaller than the predetermined threshold Th (determined as affirmative at step 1958), "non-defective" is determined for the tested surface 1834 on the wafer 1805 (step 1960), followed by returning the subroutine. Specifically, "non-defective" is determined if any one of images under testing substantially matches the reference image. In this way, all images under testing need not be matched with the reference image, so that the determination can be made at a high speed. In the example of FIG. 51, it can be seen that an image under testing at the third row, third column substantially matches the reference image without discrepancy in position.

If the distance value $D_i$ is equal to or larger than the predetermined threshold Th (determined as negative at step 1958), the image number i is incremented by one (step 1962), ad it is determined whether or not the incremented image number (i+1) exceeds the constant value $i_{MAX}$ (step 1964). If the image number i does not exceed the constant value $i_{MAX}$ (determined as negative at step 1964), the flow again returns to step 1954, where image data designated by the incremented image number (i+1) is read, and similar processing is repeated.

If the image number i exceeds the constant value $i_{MAX}$ (determined as affirmative at step 1964), "defective" is determined for the surface 1834 under testing on the wafer 1805 (step 1966), followed by returning the subroutine. Specifically, "defective" is determined unless all images under testing substantially match the reference image.

The defect testing apparatus according to the twelfth embodiment of the present invention can be used in the testing process (G) in the device manufacturing method described with reference to FIGS. 3 and 4(*a*), 4(*b*). In this event, semiconductor devices even having fine patterns can be tested for defects at a high accuracy without image fault on the secondary electron image, thereby making it possible to improve the yield rate of products and prevent defective products from being shipped. In this regard, the description related to FIG. 3 and FIGS. 4(*a*), 4(*b*) is incorporated herewith by reference and is omitted herein.

The twelfth embodiment of the present invention is not limited to those items so far described, but may be arbitrarily modified. For example, while the semiconductor device 1805 has been presented as an example of a sample under testing, samples under testing directed by the present invention are not limited thereto, but any arbitrary one can be selected as long as defects thereon can be detected by an electron beam. For example, a mask formed with a pattern for exposure to a wafer, and so on may be subjected to the testing.

Also, the twelfth embodiment of the present invention can be applied to an arbitrary apparatus which can capture an image which can be tested for defects on a sample.

Further, the deflecting electrode 1811 can be placed at an arbitrary position, not limited to the position between the objective lens 1810 and the wafer, as long as it can change an irradiating region of the primary electron beam. For example, it may be placed between the Wien filter 1803 and the objective lens 1810, between the electron beam source 1801 and the Wien filter 1803, and so on. Furthermore, the deflecting direction may be controlled by controlling the field generated by the Wien filter 1803. In other words, the Wien filter 1803 may be provided with the function of the deflecting electrode 1811.

Also, when image data are matched in the twelfth embodiment, either pixels or feature vectors are matched. Alternatively, both may be combined. For example, a high speed matching is conducted with feature vectors which require a less amount of operations, and as a result, for an image under testing exhibiting a high similarity, more detailed pixel data are matched. By such two-step processing, a high speed and accuracy can be simultaneously provided.

Also, in the twelfth embodiment of the present invention, discrepancy in position of an image under testing is accommodated only by shifting the position of the irradiating region of the primary electron beam. Alternatively, it is also possible to combine the processing for searching image data for an optimal matching region thereon (for example, regions having high correlation coefficients are detected for matching) with the present invention before or during the matching. In this way, large discrepancy in position of an image under testing can be accommodated by shifting the irradiating region of the primary electron beam in accordance with the present invention, while relatively small discrepancy in position can be absorbed by the digital image processing at a later step, thereby making it possible to improve the accuracy in detecting defects.

Further, while the configuration in FIG. 50 has been illustrated as the electron beam apparatus for testing for defects, the electron-optical system and so on can be arbitrarily modified. For example, while the electron beam irradiating means (1801, 1802, 1803) of the illustrated defect detecting apparatus is of the type that directs the primary electron beam to the surface of the wafer 1805 vertically from above, the Wien filter 1803 may be omitted so that the primary electron beam is directed obliquely to the surface of the wafer 1805.

Also, the processing according to the flow chart of FIG. 52 is not limited to that described in the figure. For example, while a sample determined as defective at step 1912 is not subjected to the testing of the remaining regions for defects, the flow of the processing may be changed to detect defects over the entire region. Also, if the entire tested region of a sample can be covered by one irradiation by expanding the irradiating region of the primary electron beam, step 1914 and step 1916 may be omitted.

While the first embodiment through twelfth embodiment of the present invention have been described in detail, a term "predetermined voltage" is assumed to mean a voltage at which a measurement such as testing is conducted in any embodiment.

Also, while a variety of embodiments so far described employ electron beams as charge particle beams, the present invention is not limited to this, but charged particle beams other than electron beams, and non-charged particle beams such as neutron having no charge, laser light, and electromagnetic waves may be used.

As the charged particle beam apparatus according to the present invention operates, a target object floats and is attracted to a high voltage region by a proximity interaction (charging of particles near a surface), so that organic substances are deposited on a variety of electrodes used for formation and deflection of charged particle beams. The organic substance gradually deposited by the charged surface adversely affects the mechanisms for forming and deflecting the charged particle beams, so that such a deposited organic substance must be periodically removed. Here, for periodically removing the deposited organic substance, preferably, an electrode near a region on which the organic substance is deposited is utilized to create a plasma of hydrogen, oxygen or fluorine, and substitutes including them such as HF, $H_2O$, CMFN in a vacuum to maintain a plasma potential within the space at a potential at which the sputtering occurs on the surface of the electrode (several kV, for example 20V-5 kV) to remove only the organic substance through oxidization, hydrogenization and fluoridization.

INDUSTRIAL AVAILABILITY

As will be understood from the first embodiment, the present invention can significantly improve the throughput as compared with the prior art by providing a testing apparatus based on a charge particle beam.

As will be understood from the second embodiment, the present invention produces distinct effects as follows.

1. The general configuration can be established for a testing apparatus in accordance with an electron beam based imaging projection scheme using charged particle beams, which can process objects under testing at a high throughput.

2. A clean gas is forced to flow to an object under testing within the mini-environment chamber to prevent dust from attaching to the object under testing, and a sensor is provided for observing the cleanliness, thereby making it possible to test the object under testing while monitoring dust within the space.

3. Since the loading chamber and the working chamber are integrally supported through a vibration isolator, an object under testing can be supplied to the stage device and tested thereon without affected by the external environment.

4. Since the precharge unit is provided, a wafer made of an insulating material will not either be affected by charging.

As will be understood from the third embodiment, the present invention produces distinct effects as follow.

1. Since the charged particle beam source is separated from the electron-optical system by a partition wall, a required degree of vacuum can be achieved independently for each section.

2. Since the charged particle beam source is coupled to the electron-optical system through holes of small conductance, a large pressure difference can be taken between the charged particle beam source and the electron-optical system.

3. Since the partition wall is formed with holes at positions away from the optical axes of the respective charged particle beam sources, even if positive ions return along the optical axis from the sample or the electron-optical system to the cathode of the charged particle beam source, they are blocked by the partition wall, so that the cathode will not be damaged by positive ions.

As will be understood from the fourth embodiment, the present invention produces distinct effects as follows.

1. Since the electrodes or portions of the electrodes are coated with a metal having a work function of 5 eV or higher, secondary charged particle beam will hardly be emitted from the electrodes, so that a discharge is less likely to occur between electrodes, and a breakdown between electrodes is reduced.

2. Since the electrodes or portions of the electrodes are coated with platinum (work function: 5.3 [eV]) or an alloy which contains platinum as a main material, secondary charged particle beam will hardly be emitted from the electrodes, so that a discharge is less likely to occur between electrodes, and a breakdown between electrodes is reduced.

3. Even if the sample is a semiconductor wafer, attachment of platinum coated on the electrodes onto a pattern of the semiconductor wafer, if any, would not deteriorate the performance of a resulting device, so that the present invention is preferable for testing a semiconductor wafer.

4. The electrodes are supported by an insulating material, so that a discharge between electrodes, and hence a breakdown between electrodes hardly occur.

5. At least one of electrodes is shaped to have a step between a first electrode surface and a second electrode surface and these electrode surfaces, so that the surface of the insulating material need not be formed with crimps, resulting in a lower manufacturing cost.

6. Since the minimum creeping distance of the insulating material between electrodes is substantially equal to the distance between electrodes in a supported electrode portion, the surface of the insulating material is substantially free from ruggedness between the electrodes, and a gas exhausted from the insulating material will not be increased, so that the degree of vacuum will not be lowered in a beam path of the apparatus.

As will be understood from the fifth embodiment, the present invention produces a distinct effect in that the influence of chromatism produced by the ExB separator can be reduced due to an energy distribution of the primary charged particle beam or second charged particle beam.

As will be understood from the sixth embodiment, the present invention produces distinct effects as follows.

1. Since no optical sensor is required for measuring the level of the surface of a sample, the designing can be optimally accomplished between the objective lens and the sample only with the electron-optical system.

2. Since the charge particle beam scanning/detecting system can be focused only by adjusting a low voltage, a settling time can be reduced. In other words, the focusing can be performed in a short time.

3. Astigmatism can also be corrected in a short time during the focusing operation as required.

4. Since a sample in the middle of a process can be evaluated in a short time, it is possible to increase the yield rate of the device manufacturing.

As will be understood from the seventh embodiment, the present invention produces distinct effects as follows.

1. A piezoelectric element is attached to a mechanical construction such that it receives a force from vibrations of the mechanical construction, and a vibration attenuating circuit is electrically connected to the piezoelectric element for attenuating electric energy output from the piezoelectric element, so that unwanted vibrations due to the resonance of the construction for aligning the beam can be appropriately attenuated so as to highly accurately maintain the alignment of the beam without necessarily increasing the rigidity of the construction.

2. It is therefore possible to realize mitigation of constraints on the design, reduction in size and weight of the apparatus, and improvement on the economy.

3. Highly efficient manufacturing, testing, working, observation and so on of semiconductor devices can be achieved by using the charged particle beam apparatus as described above in a semiconductor device manufacturing process.

As will be understood from the eighth embodiment, the present invention produces distinct effects as follows.

1. By an electrostatic chuck and a combination of a wafer and the electrostatic chuck, a voltage required to suck and hold the wafer is applied associated with a voltage applied to the wafer, so that the wafer can be sucked and held without fail until the wafer has been tested.

2. Even with a wafer centrally bowed in concave toward the electrostatic chuck, the front surface of the wafer can be securely sucked and held. Also, a discharge imprint formed on the wafer is reduced to a minimally required size, and an extremely small amount of particles occur during a discharge.

3. By using the electrostatic chuck of the present invention and a combination of a wafer and the electrostatic chuck in a device manufacturing method to securely suck and hold the wafer on the electrostatic chuck on a moving stand during testing, semiconductor devices even having fine patterns can be tested at a high throughput, so that a total inspection can also be conducted, thereby making it possible to improve the yield rate of products and prevent defective products from being shipped.

As will be understood from the ninth embodiment, the present invention produces distinct effects as follows.

1. The stage device can demonstrate highly accurate positioning performance in vacuum, and the pressure at a charged particle beam irradiated position is hardly increased. In other words, a sample can be highly accurately processed by a charged particle beam;

2. A gas released from the static pressure bearings can hardly pass through the partition into the charged particle beam irradiating region. This can further stabilize the degree of vacuum at the charged particle beam irradiated position.

3. An exhausted gas is difficult to pass to the charge particle beam irradiating region, thereby facilitating to stably hold the degree of vacuum at the charged particle beam irradiated position.

4. The vacuum chamber is divided into the charged particle beam irradiation chamber, a static pressure bearing chamber, and an intermediate chamber through a small conductance, and a vacuum evacuation system is configured to set lower pressures from the charged particle beam irradiation chamber to intermediate chamber and to static pressure bearing chamber in this order, fluctuations in pressure to the intermediate chamber are suppressed by the partition, while fluctuations in pressure to the charge particle beam irradiation chamber is further reduced by another partition, thereby making it possible to reduce the fluctuations in pressure to a level at which substantially no problem arises.

5. An increase in pressure can be suppressed when the stage is moved;

6. An increase in pressure can be further suppressed to when the stage is moved.

7. Since a testing apparatus which provides highly accurate stage positioning performance and a stable degree of vacuum in a charged particle beam irradiating region can be realized, it is possible to provide a testing apparatus which is high in testing performance and free from fear of contaminating the sample.

8. Since an exposure apparatus which provides highly accurate stage positioning performance and a stable degree of vacuum in a charged particle beam irradiating region can be realized, it is possible to provide an exposure apparatus which is high in exposure accuracy and free from fear of contaminating the sample.

9. Fine semiconductor circuits can be formed by manufacturing semiconductors using an apparatus which provides highly accurate stage positioning performance and a stable degree of vacuum in a charged particle beam irradiating region.

As will be understood from the tenth embodiment, the present invention produces distinct effects as follows.

1. A sample on the stage can be stably processed by means of a charged particle beam using the stage having a similar structure to a static pressure bearing type stage which is generally used in the atmosphere (a static pressure bearing stage having no differential pumping mechanism).

2. The influence on the degree of vacuum in the charge particle beam irradiating region can be minimized, so that the sample can be stably processed by means of the charged particle beam;

3. It is possible to provide a testing apparatus which provides highly accurate stage positioning performance and a stable degree of vacuum in a charged particle beam irradiating region;

4. It is possible to provide an exposure apparatus which provides highly accurate stage positioning performance and a stable degree of vacuum in a charged particle beam irradiating region; and 5. Fine semiconductor circuits can be formed by manufacturing semiconductors using an apparatus which provides highly accurate stage positioning performance and a stable degree of vacuum in a charged particle beam irradiating region.

As will be understood from the eleventh embodiment, the present invention produces distinct effects as follows:

1. The throughput can be improved by an integer multiple proportional to the number of optical systems.

2. Highly reliable evaluation can be made since a wafer is evaluated with the least charging state.

3. Since the charging performance is not evaluated by measuring a variety of currents but with actual images, more correct evaluation results can be provided.

As will be understood from the twelfth embodiment, the present invention produces distinct effects as follows.

1. Since a sample is tested for defects by capturing each of images of a plurality of regions under testing on the sample which are displaced from one another while partially overlapping, and comparing these images of the regions under testing with a reference image, it is possible to prevent a degraded defect testing accuracy due to discrepancy in position between the images under testing and the reference image.

2. Since a sample is tested for defects using the defect testing apparatus as described above, it is possible to improve the yield rate of products and prevent defective products from being shipped.

What is claimed is:

1. A method of sucking and holding a wafer having at least one surface coated with an insulating film, comprising the steps of:
providing the wafer on an electrostatic chuck;
applying a voltage to at least one surface of the wafer through a contact having a knife edge shaped metal portion by braking the insulating film, the contact being operable to contact with a side surface of the wafer; and
chucking the wafer by applying a voltage to the contact, a first voltage to a first electrode and a second voltage to a second electrode, respectively, the first electrode and the second electrode being disposed below an insulating layer on which the wafer is disposed.

2. The method according to claim 1, wherein the step of applying the first voltage and the step of applying the second voltage are performed in sequence.

3. The method according to claim 1, wherein the first electrode has a central portion.

4. The method according to claim 3, wherein the second electrode has a peripheral portion.

5. The method according to claim 1, wherein the first voltage and the second voltage gradually reduce so that gradually reduced voltage is applied to the first electrode and the second electrode.

6. A method of evaluating a wafer having at least one surface thereof coated with an insulating film, comprising the steps of:
providing the wafer on an electrostatic chuck;
applying a voltage to at least one surface of the wafer through a contact having a knife edge shaped metal portion by braking the insulating film, the contact being operable to contact with a side surface of the wafer; and
chucking the wafer by applying a voltage to the contact, a first voltage to a first electrode and a second voltage to a second electrode, respectively, the first electrode and the second electrode being disposed below an insulating layer on which the wafer is disposed;
emitting an electron beam to the wafer;
detecting a secondary electron beam to capture an image on the wafer;
evaluating the wafer based on the image on the wafer; and
reducing the voltage across the wafer to zero and removing the wafer from the electrostatic chuck.

7. An electrostatic chuck for sucking and holding a wafer having at least one surface coated with an insulating film, comprising:
a first electrode plate disposed below the wafer for holding the wafer and applying a first voltage to the wafer;
a second electrode plate disposed below the wafer for holding the wafer and applying a second voltage to the wafer;
an insulating layer disposed between the wafer and said first and second electrode plates;
a contact having a knife edge shaped metal portion and operable to contact with a side surface of the wafer for breaking the insulating film to make a conduction to the wafer; and
a power supply connected to the contact, the first electrode plate and the second electrode plate through a resistor.

8. The electrostatic chuck according to claim 7, wherein the first electrode plate has a central portion.

9. The electrostatic chuck according to claim 7, wherein the second electrode plate has a peripheral portion.

10. The electrostatic chuck according to claim 7, wherein the first voltage and the second voltage are applied to the first electrode plate and the second electrode plate, respectively.

11. The electrostatic chuck according to claim 10, wherein the first voltage and the second voltage gradually reduce so that gradually reduced voltages are applied to the first electrode plate and the second electrode plate.

12. An electron beam apparatus, comprising:
an electron beam source for emitting an electron beam to a wafer;
a detector for detecting a secondary electron beam to capture an image on the wafer; and
a carrier unit for carrying and placing, on a stage device, a wafer having at least one surface coated with an insulating film, wherein the stage device comprises:
a first electrode plate disposed below the wafer for holding and applying a first voltage to the wafer;
a second electrode plate disposed below the wafer for holding the wafer and applying a second voltage to the wafer;
an insulating layer disposed between the wafer and said first and second electrode plates;
a contact having a knife edge shaped metal portion and operable to contact with the surface of the wafer for breaking the insulating film and making a conduction to the wafer; and
a power supply connected to the contact, the first electrode plate and the second electrode plate.

13. The electron beam apparatus according to claim 12, wherein the first electrode plate has a central portion.

14. The electron beam apparatus according to claim 12, wherein said second electrode plate has a peripheral portion.

15. The electron beam apparatus according to claim 12, wherein the first voltage and the second voltage are applied to the first electrode plate and the second electrode plate.

16. The electron beam apparatus according to claim 12, wherein the first voltage and the second voltage gradually reduce so that gradually reduced voltages are applied to the first electrode plate and the second electrode plate.

17. A beam testing apparatus, comprising:
a testing chamber having a stage for holding an object under test, wherein the stage has an electrostatic chuck for sucking the object;
a beam generator for generating a rectangular or elliptic electron beam as a primary electron beam;
an electro-optical system for guiding the primary electron beam in one direction and for guiding a secondary electron beam generated from the object in the opposite direction, the stage being movable relative to the electro-optical system;
an image processing system for displaying or storing information of the object; and a transport mechanism for transporting the object into and out of the testing chamber and comprising a mini-environment chamber for supplying a clean gas to the object to prevent dust from attaching to the object and a sensor provided within the mini-environment chamber for observing the cleanliness of the mini-environment chamber, wherein the pressure in the mini-environment chamber being equal to atmosphere pressure;

wherein the electrostatic chuck comprises:

a first electrode plate disposed below the object for holding the object and applying a first voltage to the object;

a second electrode plate disposed below the object for holding the object and applying a second voltage to the object;

an insulatiua layer disposed between the wafer and said first and second electrode plates;

a contact having knife edge shaped metal portion and operable to contact with a side surface of the object for breaking the insulating film and making a conduction to the object; and a power supply connected to the contact, the first electrode plate and the second electrode plate through a resistor.

18. The beam testing apparatus according to claim 17, wherein the first voltage and the second voltage gradually reduce so that gradually reduced voltages are applied to the first electrode plate and the second electrode plate.

* * * * *